(12) United States Patent
delCardayre et al.

(10) Patent No.: US 6,326,204 B1
(45) Date of Patent: Dec. 4, 2001

(54) EVOLUTION OF WHOLE CELLS AND ORGANISMS BY RECURSIVE SEQUENCE RECOMBINATION

(75) Inventors: Stephen delCardayre, Los Gatos; Matthew Tobin, San Jose; William P. C. Stemmer, Los Gatos; Jon E. Ness, Sunnyvale; Jeremy Minshull, Menlo Park; Phillip Patten, Mountain View; Venkiteswatan Subramanian, Danville; Linda Castle, Mountain View; Steve Bass, Hillsborough, all of CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/116,188

(22) Filed: Jul. 15, 1998

Related U.S. Application Data

(63) Continuation-in-part of application No. PCT/US98/00852, filed on Jan. 16, 1998.
(60) Provisional application No. 60/035,054, filed on Jan. 17, 1997.

(51) Int. Cl.⁷ ............................ C12N 15/00; C07H 21/02; C07H 21/04
(52) U.S. Cl. ................... 435/440; 536/23.1; 536/24.3; 935/76; 935/77; 935/78
(58) Field of Search .................... 435/6, 172.3, 91.2, 435/440; 536/23.1, 24.3; 935/76, 77, 78

(56) References Cited

U.S. PATENT DOCUMENTS

| | | |
|---|---|---|
| 4,368,263 | 1/1983 | Ball et al. . |
| 4,729,951 | 3/1988 | Ferenczy et al. . |
| 4,940,834 | 7/1990 | Hurley et al. . |
| 5,376,543 | 12/1994 | Chee et al. . |
| 5,470,725 | 11/1995 | Borriss et al. . |
| 5,512,463 | 4/1996 | Stemmer . |
| 5,514,588 | 5/1996 | Varadaraj . |
| 5,521,077 | 5/1996 | Khosia et al. ............... 435/172.3 |
| 5,574,205 | 11/1996 | Kucherlapati et al. . |
| 5,578,461 | 11/1996 | Sherwin et al. . |
| 5,605,793 | 2/1997 | Stemmer . |
| 5,605,820 | 2/1997 | Timberlake et al. . |
| 5,643,745 | 7/1997 | Stuart . |
| 5,683,899 | 11/1997 | Stuart . |
| 5,695,975 | 12/1997 | Zimmerman et al. . |
| 5,721,367 | 2/1998 | Kay et al. . |
| 5,723,323 | 3/1998 | Kauffman et al. . |
| 5,763,192 | 6/1998 | Kauffman et al. . |
| 5,763,239 | 6/1998 | Short et al. . |
| 5,763,240 | 6/1998 | Zarling et al. . |
| 5,773,221 | 6/1998 | Carlson et al. . |
| 5,783,431 | 7/1998 | Peterson et al. . |
| 5,789,228 | 8/1998 | Lam et al. . |
| 5,811,238 | 9/1998 | Stemmer et al. . |
| 5,814,473 | 9/1998 | Warren et al. . |
| 5,814,476 | 9/1998 | Kauffman et al. . |
| 5,817,483 | 10/1998 | Kauffman et al. . |
| 5,824,469 | 10/1998 | Horwitz et al. . |
| 5,824,485 | 10/1998 | Thompson et al. . |
| 5,824,514 | 10/1998 | Kauffman et al. . |
| 5,830,696 | 11/1998 | Short . |
| 5,830,721 | 11/1998 | Stemmer et al. . |
| 5,834,252 | 11/1998 | Stemmer et al. . |
| 5,837,458 | 11/1998 | Minushull et al. . |
| 5,837,470 | 11/1998 | Carlson et al. . |
| 5,843,643 | 12/1998 | Ratner . |
| 5,866,363 | 2/1999 | Pieczenik . |
| 5,869,718 | 2/1999 | Julien et al. . |
| 5,876,997 | 3/1999 | Kretz . |
| 5,877,402 | 3/1999 | Maliga et al. . |
| 5,908,765 | 6/1999 | Carlson et al. . |

(List continued on next page.)

FOREIGN PATENT DOCUMENTS

| | | |
|---|---|---|
| 0229046B1 | 5/1994 | (EP) . |
| 0911396A2 | 4/1999 | (EP) . |
| 0911396A3 | 5/1999 | (EP) . |
| 0934999A1 | 8/1999 | (EP) . |
| WO 93/22443 | 11/1993 | (WO) . |
| WO 97/07205 | 2/1997 | (WO) . |
| WO 97/20078 | 6/1997 | (WO) . |
| WO 97/21806 | 6/1997 | (WO) . |
| WO 97/25410 | 7/1997 | (WO) . |
| WO 97/35957 | 10/1997 | (WO) . |
| WO 97/35966 | 10/1997 | (WO) . |
| WO 97/44361 | 11/1997 | (WO) . |
| WO 97/48416 | 12/1997 | (WO) . |
| WO 97/48717 | 12/1997 | (WO) . |
| WO 97/48794 | 12/1997 | (WO) . |
| WO 98/00526 | 1/1998 | (WO) . |

(List continued on next page.)

OTHER PUBLICATIONS

Allard, R.W., (1960) *Principles of Plant Breeding*, John Wiley and Sons, Inc., New York, Chapter 23 *Recurrent Selection*, pp. 282–302.

William P.C. Stemmer, "DNA Shuffling by Random Fragmentation and Reassembly in vitro Recombination for Molecular Evolution", *Proc. natl. Acad. Sci*, 91:10747–10751 (10/94).

William P.C. Stemmer, "Rapid Evolution of a Protein in vitro by DNA Shuffling", *Nature* 370:389–391 (Aug. 4, 1994).

(List continued on next page.)

Primary Examiner—Ethan Whisenant
(74) Attorney, Agent, or Firm—Norman J. Kruse; Jonathan Alan Quine; Law Offices of Jonathan Alan Quine

(57) ABSTRACT

The invention provides methods employing iterative cycles of recombination and selection/screening for evolution of whole cells and organisms toward acquisition of desired properties. Examples of such properties include enhanced recombinogenicity, genome copy number, and capacity for expression and/or secretion of proteins and secondary metabolites.

49 Claims, 35 Drawing Sheets

U.S. PATENT DOCUMENTS

| | | |
|---|---|---|
| 5,925,749 | 7/1999 | Mathur et al. . |
| 5,928,905 | 7/1999 | Stemmer et al. . |
| 5,929,250 | 8/1999 | Short . |
| 5,939,250 | 8/1999 | Short . |
| 5,939,300 | 8/1999 | Robertson et al. . |
| 5,942,430 | 8/1999 | Robertson et al. . |
| 5,948,666 | 9/1999 | Callen et al. . |
| 5,958,672 | 9/1999 | Short . |
| 5,958,751 | 9/1999 | Murphy et al. . |
| 5,962,258 | 10/1999 | Mathur et al. . |
| 5,962,283 | 10/1999 | Warren et al. . |
| 5,965,408 | 10/1999 | Short . |
| 5,965,415 | 10/1999 | Radman et al. . |
| 5,976,862 | 11/1999 | Kauffman et al. . |
| 5,985,646 | 11/1999 | Murphy et al. . |
| 6,001,574 | 12/1999 | Short et al. . |
| 6,004,788 | 12/1999 | Short . |
| 6,030,779 | 2/2000 | Short . |
| 6,051,409 | 4/2000 | Hansen et al. . |
| 6,054,267 | 4/2000 | Short . |
| 6,057,103 | 5/2000 | Short . |
| 6,071,889 | 6/2000 | Weiss et al. . |
| 6,074,853 | 6/2000 | Pati et al. . |
| 6,087,177 | 7/2000 | Wohlstadter . |
| 6,093,873 | 7/2000 | Chambon et al. . |
| 6,096,548 | 8/2000 | Stemmer . |
| 6,117,679 | 9/2000 | Stemmer . |
| 6,132,970 | 10/2000 | Stemmer . |
| 6,159,687 | 12/2000 | Vind . |
| 6,159,688 | 12/2000 | Borchert et al. . |
| 6,165,793 | 12/2000 | Stemmer . |
| 6,168,919 | 1/2001 | Short . |
| 6,171,820 | 1/2001 | Short . |
| 6,173,410 | 1/2001 | Bondi et al. . |
| 6,174,673 | 1/2001 | Short et al. . |
| 6,180,406 | 1/2001 | Stemmer . |

FOREIGN PATENT DOCUMENTS

| | | |
|---|---|---|
| WO 98/01581 | 1/1998 | (WO) . |
| WO 98/13485 | 4/1998 | (WO) . |
| WO 98/13487 | 4/1998 | (WO) . |
| WO 98/24799 | 6/1998 | (WO) . |
| WO 98/27230 | 6/1998 | (WO) . |
| WO 98/28416 | 7/1998 | (WO) . |
| WO 98/31837 | 7/1998 | (WO) . |
| WO 98/36080 | 8/1998 | (WO) . |
| WO 98/41622 | 9/1998 | (WO) . |
| WO 98/41623 | 9/1998 | (WO) . |
| WO 98/41653 | 9/1998 | (WO) . |
| WO 98/42727 | 10/1998 | (WO) . |
| WO 98/42832 | 10/1998 | (WO) . |
| WO 98/48034 | 10/1998 | (WO) . |
| WO 98/58085 | 12/1998 | (WO) . |
| WO 99/07837 | 2/1999 | (WO) . |
| WO 99/08539 | 2/1999 | (WO) . |
| WO 99/10472 | 3/1999 | (WO) . |
| WO 99/10539 | 3/1999 | (WO) . |
| WO 99/14312 | 3/1999 | (WO) . |
| WO 99/19518 | 4/1999 | (WO) . |
| WO 99/21979 | 5/1999 | (WO) . |
| WO 99/23107 | 5/1999 | (WO) . |
| WO 99/23236 | 5/1999 | (WO) . |
| WO 99/27072 | 6/1999 | (WO) . |
| WO 99/41368 | 8/1999 | (WO) . |
| WO 99/41369 | 8/1999 | (WO) . |
| WO 99/41383 | 8/1999 | (WO) . |
| WO 99/41402 | 8/1999 | (WO) . |
| WO 99/45154 | 9/1999 | (WO) . |
| WO 99/57128 | 11/1999 | (WO) . |
| WO 99/65927 | 12/1999 | (WO) . |

OTHER PUBLICATIONS

Edited by Gardner et al., Principles of Genetics, 1981, pp. 9–40, Sixth Edition. John Wiley & Sons, New York, New York.

Stemmer, W.P.C. et al., (1995), Single–step assembly of a gene and entire plasmid form large numbers of oligodeoxyribonucleotides, *Gene*, 164:49–53.

Stemmer, W.P.C., (1995), Searching Sequence Space, *Bio/Technology* 13:549–553.

Stemmer, W.P.C., (1995), The Evolution of Molecular Computation, *Science* 270:1510.

Crameri, A. and Stemmer, W.P.C. (1995), Combinatorial multiple cassette mutagenesis creates all the permutations of mutant and wild–type cassettes, *Biotechniques* 18:194–195.

Stemmer, W.P.C. (1996), Sexual PCR and Assembly PCR. In: The Encyclopedia of Molecular Biology, VCH Publishers, New York. pp. 447–457.

Gates, C.M. et al., (1996), Affinity selective isolation of ligands from peptide libraries through display on a lac repressor 'headpiece dimer', *Journal of Molecular Biology* 255:373–386.

Crameri, A., et al., (1996), Improve green fluorescent protein by molecular evolution using DNA shuffling, *Nature Biotechnology* 14:315–319.

Crameri, A., et al., (1996), Construction and evolution of antibody–phage libraries by DNA shuffling, *Nature Medicine* 2:100–103.

Zhang, J., et al., (1997), Directed evolution of fucosidase from a galactosidase by DNA shuffling and screening, *Proceedings of the National Academy of Sciences, U.S.A.* 94:4504–4509.

Patten, P.A., et al., (1997), Applications of DNA Shuffling to Pharmaceuticals and Vaccines, *Current Opinion in Biotechnology* 8:724–733.

Crameri, A., et al., (1997), Molecular evolution of an arsenate detoxification pathway by DNA shuffling, *Nature Biotechnology* 15:436–438.

Gerritse, Gijs, et. al., (1998), The phenoltype enhancement method identifies the Xcp outer membrane secretion machinery from *Pseudomonas alcaligenes* as a bottleneck for lipase production. Journal of Biotechnology 24:23–38.

Crameri, A., et al., (1998), DNA shuffling of a family of genes from diverse species accelerates directed evolution, *Nature* 391:288–291.

Christians, F.C., et al. (1999), Directed evolution of thymidine kinase for AZT phosphorylation using DNA family shuffling, Nature Biotechnology 14:259–264.

Minshull, J., et al., (1999), Protein evolution by molecular breeding, *Current Opinion in Chemical Biology* 3:284–290.

Stemmer, W.P.C., et al., (1999) Molecular breeding of viruses for targeting and other clinical properties. *Tumor Targeting* 4:1–4.

Alder, Jeffrey, "Determining the Therapeutic Potential of Experimental Antibacterial Agents: The Use of Animal Models" *Current Pharm. Design* 1997, 3: 143–158.

Hopwood, et al., "Factors Affecting Recombinant Frequency in Protoplast Fusions of Streptomyces coeilcolor" *J. of General Microbiology* (1979) 111, 137–143.

Lavery et al. (1990) Properties of recA441 Protein–catalyzed DNA Strand Exchange Can Be Attributed to an Enhanced Ability to Compete with SSB Protein *Journal of Biological Chemistry* 265(7): 4004–4010.

Sipiczki et al., "Enzymic Methods for Enrichment of Fungal Mutants . . . " *Mutation Research* (1978) 50:163–173.

Chang, et al., "Evilution of a cytokine using DNA family shuffling" *Nature Biology* vol. 17 (1999) pp. 793–797.

Crameri & Stemmer "$10_{20}$–Fold aptamer library amplification without gel purification" *Nucleic Acid Research* (1993) vol. 21 No. 18, pp. 4410.

Ness et al., "DNA Shuffling of Subgenomic sequences of subtilisin" *Nature Biotechnology* vol. 17 (1999) pp. 893–896.

```
                                                                            ━   ━
                    ----------------------------------------AGAGGCCAGAGAAGCCTGTCGGCACGGT
                             10        20        30        40        50        60        70
    New Minshall   GGGATTTTGGTCATGAGATTATCAAAAAGCGGCCGCGGCCTAAGAGGCCAGAGAAGCCTGTCGGCACGGT  70
    New Clone 2    ------------------------------------------------------------TGTTGGCACGGT  12
    New Clone 4    ----------------------------------------AGAGGCCAGAGAAGCCTGTCGGCACGGT  28
    New Clone 5    -----------------------------------------------------------CGGCAGGGT   9
    New Clone 6    ----------------------------------------AGAGGCCAGAGAAGCCAGTTGGCACGGT  28
    complete 13    G---------------------------------------AGGCCAGAGAAGCCTGTCGGCTTGGT    27

━━  ━━  ━━  ━━  ━━  ━━  ━━  ━━  ━━  ━━  ━━  ━━  ━━  ━━  ━━
                   CTGGTTTGCTTTTGCCACTGCCCGCGGTGAAGGCATTACCCGGCGGGAATGCTTCAGCGGCGACCGTGAT
                             80        90       100       110       120       130       140
    New Minshall   CTGGTTTGCTTTTGCCACTGCCCGCGGTGAAGGCATTACCCGGCGGGA-TGCTTCAGCGGCGACCGTGAT 139
    New Clone 2    CTGGCTTGCTTTTGCCACTGCCCGCGGTGAAGGCATTACCCGGCGGGAATGCTTCAACGGCGACCGTGAT  82
    New Clone 4    CTGGTTTGCCTTTGCCACTGCCCGCGGTGAATGCATTACTCGGCGGGAATGCTTCAGTGGCGACCGTGAT  98
    New Clone 5    CTGGTTTGCTTTTGCCACTGCCCGCGGTGAAGGCATTATCCGGCGGGAATGCTTCAGCGGCGGCCGTGAT  79
    New Clone 6    CTGGTTTGCTTTTGCCACTGCCCGGGGTGAGGGCATTACCCGGCGGGAATGCTTCAGCGGCGACCGTGAT  98
    complete 13    CTGGTTTGCTTTTACCATTGCCCGCGGTGAAGGCATTACCCGGCGGGAATGCTTCAGCGGCGACCGTGAT  97

━━━━  ━━  ━━  ━━  ━━  ━━  ━━  ━━  ━━  ━━  ━━  ━━  ━━  ━━
                   GCGGTGCGTCGTCAGGCTACTGCGTATGCATTGCAGACCTTGTGGCAACAATTTCTACAAAACACCTGAT
                             150       160       170       180       190       200       210
    New Minshall   GCGGTGCGTCGTCAGGCTACTGCGTATGCATTGCAGACCTTGTGGCAACAATTTCTACAAAACACTTGAT 209
    New Clone 2    GCGGTGCGTCGTCAGGCTACTGCGTATGCATTGCAGACCTTGTGGCAACAATTTCTACAAAACACCTGAT 152
    New Clone 4    GCGGTGCGTCGTCAGGCTACTGCGTATGCATTGCAGACCTTGTGGCAACAATTTCTACAAAACACCTGAT 168
    New Clone 5    GCGGTGCGTCGTCAGGCTACTGCGTATGCATTGCAGACCTTGTGGCAACAATTTCTACAAAACACCTGAT 149
    New Clone 6    GCGGTGCGTCGTCAGGCTACTGCGTATGCACTGCAGACCTTGTGGCAACAATTTCTACAAAACACCTGTT 168
    complete 13    GCGGTGCGTCGTCAGGCTACTGTGTATGCACTGCAGACCTTGTGGCAACGATTTCTACAAAACACTCGAT 167

━━  ━━  ━━  ━━  ━━  ━━  ━━  ━━  ━━  ━━  ━━  ━━  ━━
                   ACTGTATGAGCATACAGTATAATTGCTTCAACAGAACATATTGACTATCCGGTATTACCCGGCATGACAG
                             220       230       240       250       260       270       280
    New Minshall   ACTGTATGAGCATACAGTATAATTGCTTCAACAGAACATATTGACTATCCGGTATTACCCGGCATGACAG 279
    New Clone 2    ACTGTATGAGCATACAGTATAATTGCTTCAACAGAACATATTGACTATCCGGTATTACCCGGCATGACAG 222
    New Clone 4    ACTGTATGAGCATACAGTATAATTGCTTCAACAGAACATATTGACTATCCGGTATTACCCGGCATGACAG 238
    New Clone 5    ACTGTATGAGCATACAGTATAATTGCTTCAACAGAACATATTGACTATCCGGTATTACCCGGCATGACAG 219
    New Clone 6    ACTGTATGAGCATGCAGTATAATTGCTTCAACAGAACATATTGACTATCCGGTATTACCCGGCATGACAG 238
    complete 13    ACCGTATGAGCACACAGTATAATCGCTTCGACAGAACTTATTGACTATCCGGTATTACCCGGCATGACAG 237

━━  ━━  ━━━━  ━━  ━━  ━━  ━━  ━━  ━━  ━━  ━━
                   GAGTAAAAATGGCTATTGACGAAAACAAACAGAAAGCGTTGGCGGCAGCACTGGGCCAGATTGAGAAACA
                             290       300       310       320       330       340       350
    New Minshall   GAGTAAAAATGGCTATCGACGAAAACAAACAGAAAGCGTTGGCGGCAGCACTGGGCCAGATTGAGAAACA 349
    New Clone 2    GAGTAAAAATGGCTATTGACGAAAACAAACAGAAAGCGTTGGCGACAGCACTGGGCCAGATTGAGAAACA 292
    New Clone 4    GAGTAAACATGGCTATCGACGAAAACAAACAGAAAGCGTTAGCGGCAGCACTGGGCCAGATTGAGAAACA 308
    New Clone 5    GAGTAAAAATGGCTATCGACGAAACAAACAGAAAGCGTTGGCGGCAGCACTGGGCCAGATTGAGAAACA 289
    New Clone 6    GAGTAAAAATGGCTATTGACGAAAACAAACAGAAAGCGTTGGCGGCAGCACTGGGCCAGATTGAGAAACA 308
    complete 13    GAGTAAAAATGGCTATTGACGAAAACAAACAGAAAGCGTTGGCGGCAGCACTGGGCCAGATTGAGAAACA 307

━━  ━━  ━━  ━━  ━━  ━━  ━━  ━━  ━━  ━━  ━━━━
                   ATTTGGTAAAGGCTCCATCATGCGCCTGGGTGAAGACCGTTCCATGGATGTGGAAACCATCTCTACCGGT
                             360       370       380       390       400       410       420
    New Minshall   ATTTGGTAAAGGCTCCATCATGCGCCTGGGTGAAGACCGTTCCATGGATGTGGAAACCATCTCTACCGGT 419
    New Clone 2    ATTTGGTAAAGGCTCCATCATGCGCCTGGGTGAAGACCGTTCCATGGATGTGGAAACCATCTCTACCGGT 362
    New Clone 4    ATTTGGTAAAGGCTCCATCATGCGCCTGGGTGAAGACCGTTCCATGGATGTGGAAACCATCTCCACCGGT 378
    New Clone 5    ATTTGGTAAAGGCTCCATCATGCGCCTGGGTGAAGACCGTTCCATGGATGTGGAAACCATCTCTACCGGT 359
    New Clone 6    ATTTGGTAAAGGCTCCATCATGCGCCTGGGTGAAGACCGTTCCATGGATGTGGAAACCATCTCTACTGGT 378
    complete 13    GTTTGGTAAAGGCTCCATCATGCGCCTGGGGGAAGACCGTTCCATGGATGTGGAAACCATCTCTACCGGT 377
```

FIG. 12A

```
              TCGCTTTCACTGGATATCGCGCTTGGGGCAGGTGGTCTGCCGATGGGCCGTATCGTCGAAATCTACGGAC
              |   430   |   440   |   450   |   460   |   470   |   480   |   490
New Minshall  TCGCTTTCACTGGATATCGCGCTTGGGGCAGGTGGTCTGCCGATGGGCCGTATCGTCGAAATCTACGGAC 489
New Clone 2   TCGCTTTCACTGGATATCGCGCTTGGGGCAGGTGGTCTGCCGATGGGCCGTATCGTCGAAATCTACGGAC 432
New Clone 4   TCGCTTTCACTGGATATCGCACTTGGGGCAGGTGGTCTGCCGATGGGCCGTATCGTCGAAATCTACGGAC 448
New Clone 5   TCGCTTTCACTGGATATCGCGCTTGGGGCAGGTGGTCTGCCGATGGGCCGTATCGTCGAAATCTACGGAC 429
New Clone 6   TCGCTTTCACTGGATATCGCGCTTGGGGCAGGTGGTCTGCCGATGGGCCGTATCGTCGAAATCTATGGAC 448
complete 13   TCGCTTTCACTGGATATCGCGCTTGGGGCAGGTGGTCTGCCGATGGGCCGTATCGTCGAAATCTACGGAC 447

CGGAATCTTCCGGTAAAACCACGCTGACGCTGCAGGTGATCGCCGCAGCGCAGCGTGAAGGTAAAACCTG
              |   500   |   510   |   520   |   530   |   540   |   550   |   560
New Minshall  CGGAATCTTCCGGTAAAACCACGCTGACGCTGCAGGTGATCGCCGCAGCGCAGCGTGAAGGTAAAACCTG 559
New Clone 2   CGGAATCTTCCGGTAAAACCACACTGACGCTGCAGGTGATCGCCGCAGCGCAGCGTGAAGGTAAAACCTG 502
New Clone 4   CGGAATCTTCCGGTAAAACCACGCTGACGCTGCAGGTGATCGCCGCAGCGCAGCGTGAAGGTAAAACCTG 518
New Clone 5   CGGAATCTTCCGGTAAAACCACACTGACGCTGCAGGTGATCGCCGCAGCGCAGCGTGAAGGTAAAACCTG 499
New Clone 6   CGGAATCTTCCGGTAAAACCACACTGACGCTGCAGGTGATCGCCGCAGCGCAGCGTGAGGGTAAAACCTG 518
complete 13   CGGAATCTTCCGGTAAAACCACGCTGACGCTGCAGGTGATCGCCGCAGCGCAGCGTGAAGGTAAAACCTG 517

T-GCGTTTATCGATGCTGAACACGCGCTGGACCCAATCTACGCACGTAAACTGGGCGTCGATATCGACAA
              |   570   |   580   |   590   |   600   |   610   |   620   |   630
New Minshall  T-GCGTTTATCGATGCTGAACACGCGCTGGACCCAATCTACGCACGTAAACTGGGCGTCGATATCGACAA 628
New Clone 2   T-GCGTTTATCGATGCCGAACACGCGCTGGACCCAATCTACGCACGCAAACTGGGCGTCGATATCGACAA 571
New Clone 4   T-GCGTTTATCGATGCTGAACACGCGCTGGACCCAATCTACGCACGTAAACTGGGCGTCGATATCGACAA 587
New Clone 5   TTGCGTTTATCGATGCTGAACACGCGCTAGACCCAATCTACGCACGTAAACTGGGCGTCGATATCGACAA 569
New Clone 6   T-GCGTTTATCGATGCTGAACACGCGCTGGACCCAATCTACGCACGTAAACTGGGCGTCGATATCGACAA 587
complete 13   T GCGTTTATCGATGCTGAACACGCGCTGGACCCGATCTACGCACGTAAACTGGGCGTCGATATCGACAA 586

CCTGCTGTGCTCCCAGCCGGACACCGGCGAGCAGGCACTGGAAATCTGTGACGCCCTGGCGCGTTCTGGC
              |   640   |   650   |   660   |   670   |   680   |   690   |   700
New Minshall  CCTGCTGTGCTCCCAGCCGGACACCGGCGAGCAGGCACTGGAAATCTGTGACGCCCTGGCGCGTTCTGGC 698
New Clone 2   CCTGCTGTGCTCCCAGCCGGACACCGGCGAGCAGGCACTGGAAATCTGTGACGCCCTGGCGCGTTCTGGC 641
New Clone 4   CCTGCTGTGCTCCCAGCCGGACACCGGCGAGCAGGCACTGGAAATCTGTGACGCCCTGGCGCGTTCTGGC 657
New Clone 5   CCTGCTGTGCTCCCAGCCGGACACCGGCGAGCAGGCACTGGAAATCTGTGACGCCCTGGCGCGTTCTGGC 639
New Clone 6   CCTGCTGTGCTCCCAGCCGGACACCGGCGAGCAGGCACTGGAAATCTGTGACGCCCTGGCGCGTTCTGGC 657
complete 13   CCTGCTGTGCTCCCAGCCGGACACCGGCGAGCAGGCACTGGAAATCTGTGACGCCCTGGCGCGCTCTGGC 656

GCAGTAGACGTTATCGTCGTTGACTCCGTGGCGGCACTGACGCCGAAAGCGGAAATCGAAGGCGAAATCG
              |   710   |   720   |   730   |   740   |   750   |   760   |   770
New Minshall  GCAGTAGACGTTATCGTCGTTGACTCCGTGGCGGCACTGACGCCGAAAGCGGAAATCGAAGGCGAAATCG 768
New Clone 2   GCAGTAGACGTTATCGTCGTTGACTCCGTGGCGGCACTGACGCCGAAAGCGGAAATCGAAGGCGAAATCG 711
New Clone 4   GCGGTAGACGTTATCGTCGTTGACTCCGTGGCGGCACTGACGCCGAAAGCGGAAATCGAAGGCGAAATCG 727
New Clone 5   GCAGTAGACGTTATCGTCGTTGACTCCG*AGCGGCACTGACGCCGAAAGCGGAAATCGAAGGCGAAATCG 709
New Clone 6   GCTGTAGACGTTATCGTCGTTGACTCCGTGGCGGCACTGTCGCCGAAAGCGGAAATCGAAGGCGAAATCG 727
complete 13   GCAGTGGACGTTATCGTCGTTGACTCCGTGGCGGCACTGACGCCGAAAGCGGAAATCGAAGGCGAAATCG 726

GCGACTCTCACATGGGCCTTGCGGCACGTATGATGAGCCAGGCGATGCGTAAGCTGGCGGGTAACCTGAA
              |   780   |   790   |   800   |   810   |   820   |   830   |   840
New Minshall  GCGACTCTCACATGGGCCTTGCGGCACGTATGATGAGCCAGGCGATGCGTAAGCTGGCGGGTAACCTGAA 838
New Clone 2   GCGACTCTCACATGGGCCTTGCGGCACGTATGATGAGCCAGGCGATGCGCAAGCTGGCGGGTAACCTGAA 781
New Clone 4   GCGACTCTCACATGGGCCTTGCGGCACGTATGATGAGCCAGGCGATGCGTAAGCTGGCGGGTAACCTGAA 797
New Clone 5   GCGACTCTCACATGGGCCTTGCGGCACGTATGATGAGCCAGGCGATGCGTAAGCTGGCGGGTAACCTGAA 779
New Clone 6   GCGACTCTCACATGGGCCTTGCGGCACGTATGATGAGCCAGGCAATGCGTAAGCTGGCGGGTAACCTGAA 797
complete 13   GCGACTCTCACATGGGCCTTGCAGCACGTATGATGAGCCAGGCGATGCGTAAGCTGGCGGGTAACCTGAA 796
```

FIG. 12B

```
                        GCAGTCCAACACGCTGCTGATCTTCATCAACCAGATCCGTATGAAAATTGGTGTGATGTTCGGTAACCCG
                        |         |         |         |         |         |         |
                        850       860       870       880       890       900       910
New Minshall            GCAGTCCAACACGCTGCTGATCTTCATCAACCAGATCCGTATGAAAATTGGTGTGATGTTCGGTAACCCG 908
New Clone 2             GCAGTCCAACACGCTGCTGATCTTCATTAACCAGATCCGTATGAAAATTGGTGTGATGTTCGGTAACCCG 851
New Clone 4             GCAGTCCAACACGCTGCTGATCTTCATCAACCAGATCCGTATGAAAATTGGTGTGATGTTCGGTAACCCG 867
New Clone 5             GTTGTCCAACACGCTGCTGATCTTTATCAACCAGATCCGTATGAAAATTGGCGTGATGTTCGGTAACCCG 849
New Clone 6             GCAGTCCAACACGCTGCTGATCTTCATCAACCAGATCCGTATGAAAATTGGTGTGATGTTCGGTAACCCG 867
complete 13             GCAGTCCAACACGCTGCTGATCTTCATCAACCAGATCCGTATGAAAATTGGTGTGATGTTCGGTAACCCG 866

GAAACCACTACCGGTGGTAACGCGCTGAAATTCTACGCCTCTGTTCGTCTCGACATCCGTCGTATCGGCG
                        |         |         |         |         |         |         |
                        920       930       940       950       960       970       980
New Minshall            GAAACCACCACCGGTGGTAACGCGCTGAAATTCTACGCCTCTGTTCGTCTCGACATCCGTCGTATCGGCG 978
New Clone 2             GAAACCACTACCGGTGGTAACGCGCTGAAATTCTACGCCTCTGTTCGTCTCGACATCCGTCGTATCGGCG 921
New Clone 4             GAAACCACTACCGGTGGTAACGCGCTGAAATTCTACGCCTCTGTTCGTCTCGACATCCGTCGTATCGGCG 937
New Clone 5             GAAACCACCACCGGTGGTAACGCGCTGAAATTCTACGCCTCTGTTCGTCTCGACATCCGTCGTATCGGCG 919
New Clone 6             GAAACCACCACCGGTGGTAACGCGCTGAAATTCTACGCCTCTGTTCGTCTCGACATCCGTCGTATCGGCG 937
complete 13             GAAACCACTACCGGTGGTAACGCGCTGAAATTCTACGCCTCTGTTCGTCTCGACATCCGTCGTATCGGCG 936

CGGTGAAAGAGGGCGAAAACGTGGTGGGTAGCGAAACCCGCGTGAAAGTGGTGAAGAACAAAATCGCTGC
                        |         |         |         |         |         |         |
                        990       1000      1010      1020      1030      1040      1050
New Minshall            CGGTGAAAGAGGGCGAAAACGTGGTGGGTAGCGAAACCCGCGTGAAAGTGGTGAAGAACAAAATCGCTGC 1048
New Clone 2             CGGTGAAAGAGGGCGAAAACGTGGTGGGTAGCGAAACCCGCGTGAAAGTGGTGAAGAACAAAATCGCTGC 991
New Clone 4             CGGTGAAAGAGGGCGAAAACGTGGTGGGTAGCGAAACCCGCGTGAAAGTGGTGAAGAACAAAATCGCTGC 1007
New Clone 5             CGGTGAAAGAGGGCGAAAACGTGGTGGGTAGCGAAACCCGCGTGAAAGTGGTGAAGAACAAAATCGCTGC 989
New Clone 6             CAGTGAAAGAGGGCGAAAACGTGGTGGGTAGCGAAACCCGCGTGAAAGTGGTGAAGAACAAAATCGCTGC 1007
complete 13             CGGTGAAAGAGGGCGAAAACGTGGTGGGTAGCGAAACCCGCGTGAAAGTGGTGAAGAACAAAATCGCTGC 1006

GCCGTTTAAACAGGCTGAATTCCAGATCCTCTACGGCGAAGGTATCAACTTCTACGGCGAACTGGTTGAC
                        |         |         |         |         |         |         |
                        1060      1070      1080      1090      1100      1110      1120
New Minshall            GCCGTTTAAACAGGCTGAATTCCAGATCCTCTACGGCGAAGGTATCAACTTCTACGGCGAACTGGTTGAC 1118
New Clone 2             GCCGTTTAAACAGGCTGAATTCCAGGTCCTCTACGGCGAAGGTATCAACTTCTACGGCGAACTGGTTGAC 1061
New Clone 4             GCCGTTTAAACAGGCTGAATTCCAGATCCTCTACGGCGAAGGTATCAACTTCTACGGCGAACTGGTTGAC 1077
New Clone 5             GCCGTTTAAACAGGCTGAATTCCAGATCCTCTACGGCGAAGGTATCAACTTCTACGGCGAACTGGTTGAC 1059
New Clone 6             GCCGTTTAAACAGGCTGAATTCCAGATCCTCTACGGCGAAGGTATCAACTTCTACGGCGAACTGGTTGAC 1077
complete 13             GCCGTTTAAACAGGCTGAATTCCAAATCCTCTACGACGAAGGTATCAACTTCTACGGCGAACTGGTTGAC 1076

CTGGGCGTAAAAGAGAAGCTGATCGAGAAAGCAGGCGCGTGGTACAGCTACAAAGGTGAGAAGATCGGTC
                        |         |         |         |         |         |         |
                        1130      1140      1150      1160      1170      1180      1190
New Minshall            CTGGGCGTAAAAGAGAAGCTGATCGAGAAAGCAGGCGCGTGGTACAGCTACAAAGGTGAGAAGATCGGTC 1188
New Clone 2             CTGGGCGTAAAAGAGAAGCTGATCGAGAAAGCAGGCGCGTGGTACAGCTACAAAGGAGAGAAGATTGGTC 1131
New Clone 4             CTGGGCGTAAAAGAGAAGCTGATCGAGAAAGCAGGCGCGTGGTACAGCTACAAAGGTGAGAAGATCGGTC 1147
New Clone 5             CTGGGCGTAAAAGAGAAGCTGATCGAGAAAGCAGGCGCGTGGTACAGCTACAAAGGTGAGAAGATCGGTC 1129
New Clone 6             CTGGGCGTAAAAGAGAAGCTGATCGAGAAAGCAGGCGCGTGGTACAGCTACAAAGGTGAGAAGGTTGGTC 1147
complete 13             CTGGGCGTAAAAGAGAAGCTGATCGAGAAAGCAGGCGCGTGGTACAGCTACAAAGGTGAGAAGGCCGGTC 1146

AGGGTAAAGCGAATGCGACTGCCTGGCTGAAAGATAACCCGGAAACCGCGAAAGAGATCGAGAAGAAAGT
                        |         |         |         |         |         |         |
                        1200      1210      1220      1230      1240      1250      1260
New Minshall            AGGGTAAAGCGAATGCGACTGCCTGGCTGAAAGATAACCCGGAAACCGCGAAAGAGATCGAGAAGAAAGT 1258
New Clone 2             AGGGTAAAGCGAACGCGACTGCCTGGCTGAAAGATAATCCGGAAACCGCGAAAGAGATTGAGAAGAAAGT 1201
New Clone 4             AGGGTAAAGCGAATGCGACTGCCTGGCTGAAAGATAACCCGGAAACCGCGAAAGAGATCGAGAAGAAAGT 1217
New Clone 5             AGGGTAAAGCGAATGCGGCTGCCTGGCTGAAAGATAACCCGGAAACCGCGAAAGAGATCGAGAAGAAAGT 1199
New Clone 6             AGGGTAAAGCGAATGCGACTGCCTGGCTGAAAGATAACCCGGAAACCGCGAAAGAGATCGAGAAGAAAGT 1217
complete 13             AGGGTAAAGCGAATGCGACTGCCTGGCTGAAAGATAACCCGGAAACCGCGAAAGAGATCGAGAAGAAAGT 1216
```

FIG. 12C

```
                    ACGTGAGTTGCTGCTGAGCAACCCGAACTCAACGCCGGATTTCTCTGTAGATGATAGCGAAGGCGTAGCA
                    |         |         |         |         |         |         |
                   1270      1280      1290      1300      1310      1320      1330
New Minshall       ACGTGAGTTGCTGCTGAGCAACCCGAACTCAACGCCGGATTTCTCTGTAGATGATAGCGAAGGCGTAGCA 1328
New Clone 2        ACGTGAGTTGCTGCTGAGCAACCCGAACTCAACGCCGGATTTCTCTGGAGATGATAGCGAAGGCGTAGCA 1271
New Clone 4        ACGTGAGTTGCTGCTGAGTAACCCGAACTCAACGCCGGATTTCTCTAGAGATGATAGCGAAGGCGTAGCA 1287
New Clone 5        ACGTGAGTTGCTGCTGAGCAACCCGAACTCAACGCCGGATTTCTCTGTAGATGATAGCGAAGGCGTAGCA 1269
New Clone 6        ACGTGAGTTGCTGCTGAGCAACCCGAACTCAACGCCGGATTTCTCTGTAGATGATAGCGAAGGCGTAGCA 1287
complete 13        ACGTGAGTTGCTGCTGAGCAACCCGAACTCAACGCCGGATTTCTCTGTAGATGATAGCGAAGGCGTAGCA 1286

GAAACTAACGAAGATTTTTAATCGTCTTGTTTGATACACAAGGGTCGCATCTGCGGCCCTTTTGCTTTTT
                    |         |         |         |         |         |         |
                   1340      1350      1360      1370      1380      1390      1400
New Minshall       GAAACTAACGAAGATTTTTAATCGTCTTGTTTGATACACAAGGGTCGCATCTGCGGCCCTTTTGCTTTTT 1398
New Clone 2        GAAACTAACGAAGATTTTTAATCGTCTTGTTTGATACACAAGGGTCGCATCTGCGGCCCTTTTGCTTTTT 1341
New Clone 4        GGAACTAACGAAGATTTTTAATCGTCTTGTTTGATACACAAGGGTCGCATCTGCGGCCCTTTTGCTTTTT 1357
New Clone 5        GAAACTAACGAAGATTTTTAATCGTCTTGTTTAATACACGAGGGTCGCATCTGCGGCCCTTTTGCTTTTT 1339
New Clone 6        GAAACTAACGAAGATTTTTAATCGTCTTGTTTGATACACAAGGGTCGCATCTGCGGCCCTTTTGCTTTTT 1357
complete 13        GAAACTAACGAAGATTTTTAATCGTCTTGTTTGATACACAAGGGTCGCATCTGCGGCCCTTTTGCTTTTT 1356

TAAGTTGTAAGGATATGCCATGACAGAATCAACATCCCGTCXXXXXXXXXXXXXXXXXXXXXXXXXXXXX
                    |         |         |         |         |         |         |
                   1410      1420      1430      1440      1450      1460      1470
New Minshall       TAAGTTGTAAGGATATGCCATGACAGAATCAACATCCCGTCGGCCTGGTAGGCCATTTTTTGGATCTTCA 1468
New Clone 2                                                                          1382
New Clone 4        TAAGTTGTAGGGATATGCCATGACAGAATCAACATCCCGTCGGCCTGGTAGGCCATTTTTTGGATCTTCA 1427
New Clone 5        TAAGTTGTAAGGATATGCCATGACAGAATCAACATCCAGTC                             1380
New Clone 6                                                                          1343
complete 13        TAAGTTGTAAGGATATGCCATGA                                              1379

XXXXXXXXXXXXXXXXX
                         |
                        1480
New Minshall       CCTAGATCCTTTTAAAT                                                  1485
New Clone 2                                                                          1382
New Clone 4        CCT                                                                1430
New Clone 5                                                                          1380
New Clone 6                                                                          1343
complete 13                                                                          1379
```

FIG. 12D

```
              MTGVKMAIDENKQKALAAALGQIEKQFGKGSIMRLGEDRSMDVETISTGSLSLDIALGAGGLPMGRIVEI
                       10        20        30        40        50        60        70
orig prot     MTGVKMAIDENKQKALAAALGQIEKQFGKGSIMRLGEDRSMDVETISTGSLSLDIALGAGGLPMGRIVEI 70
clone 2 prot  MTGVKMAIDENKQKALATALGQIEKQFGKGSIMRLGEDRSMDVETISTGSLSLDIALGAGGLPMGRIVEI 70
clone 4 prot  MTGVNMAIDENKQKALAAALGQIEKQFGKGSIMRLGEDRSMDVETISTGSLSLDIALGAGGLPMGRIVEI 70
clone 5 prot  MTGVKMAIDENKQKALAAALGQIEKQFGKGSIMRLGEDRSMDVETISTGSLSLDIALGAGGLPMGRIVEI 70
clone 6 prot  MTGVKMAIDENKQKALAAALGQIEKQFGKGSIMRLGEDRSMDVETISTGSLSLDIALGAGGLPMGRIVEI 70
clone 13 prot MTGVKMAIDENKQKALAAALGQIEKQFGKGSIMRLGEDRSMDVETISTGSLSLDIALGAGGLPMGRIVEI 70

YGPESSGKTTLTLQVIAAAQREGKTCAFIDAEHALDPIYARKLGVDIDNLLCSQPDTGEQALEICDALAR
                       80        90       100       110       120       130       140
orig prot     YGPESSGKTTLTLQVIAAAQREGKTCAFIDAEHALDPIYARKLGVDIDNLLCSQPDTGEQALEICDALAR 140
clone 2 prot  YGPESSGKTTLTLQVIAAAQREGKTCAFIDAEHALDPIYARKLGVDIDNLLCSQPDTGEQALEICDALAR 140
clone 4 prot  YGPESSGKTTLTLQVIAAAQREGKTCAFIDAEHALDPIYARKLGVDIDNLLCSQPDTGEQALEICDALAR 140
clone 5 prot  YGPESSGKTTLTLQVIAAAQREGKTCAFIDAEHALDPIYARKLGVDIDNLLCSQPDTGEQALEICDALAR 140
clone 6 prot  YGPESSGKTTLTLQVIAAAQREGKTCAFIDAEHALDPIYARKLGVDIDNLLCSQPDTGEQALEICDALAR 140
clone 13 prot YGPESSGKTTLTLQVIAAAQREGKTCAFIDAEHALDPIYARKLGVDIDNLLCSQPDTGEQALEICDALAR 140

SGAVDVIVVDSVAALTPKAEIEGEIGDSHMGLAARMMSQAMRKLAGNLKQSNTLLIFINQIRMKIGVMFG
                      150       160       170       180       190       200       210
orig prot     SGAVDVIVVDSVAALTPKAEIEGEIGDSHMGLAARMMSQAMRKLAGNLKQSNTLLIFINQIRMKIGVMFG 210
clone 2 prot  SGAVDVIVVDSVAALTPKAEIEGEIGDSHMGLAARMMSQAMRKLAGNLKQSNTLLIFINQIRMKIGVMFG 210
clone 4 prot  SGAVDVIVVDSVAALTPKAEIEGEIGDSHMGLAARMMSQAMRKLAGNLKQSNTLLIFINQIRMKIGVMFG 210
clone 5 prot  SGAVDVIVVDSVAALTPKAEIEGEIGDSHMGLAARMMSQAMRKLAGNLKLSNTLLIFINQIRMKIGVMFG 210
clone 6 prot  SGAVDVIVVDSVAALTSKAEIEGEIGDSHMGLAARMMSQAMRKLAGNLKQSNTLLIFINQIRMKIGVMFG 210
clone 13 prot SGAVDVIVVDSVAALTPKAEIEGEIGDSHMGLAARMMSQAMRKLAGNLKQSNTLLIFINQIRMKIGVMFG 210

NPETTTGGNALKFYASVRLDIRRIGAVKEGENVVGSETRVKVVKNKIAAPFKQAEFQILYGEGINFYGEL
                      220       230       240       250       260       270       280
orig prot     NPETTTGGNALKFYASVRLDIRRIGAVKEGENVVGSETRVKVVKNKIAAPFKQAEFQILYGEGINFYGEL 280
clone 2 prot  NPETTTGGNALKFYASVRLDIRRIGAVKEGENVVGSETRVKVVKNKIAAPFKQAEFQVLYGEGINFYGEL 280
clone 4 prot  NPETTTGGNALKFYASVRLDIRRIGAVKEGENVVGSETRVKVVKNKIAAPFKQAEFQILYGEGINFYGEL 280
clone 5 prot  NPETTTGGNALKFYASVRLDIRRIGAVKEGENVVGSETRVKVVKNKIAAPFKQAEFQILYGEGINFYGEL 280
clone 6 prot  NPETTTGGNALKFYASVRLDIRRIGAVKEGENVVGSETRVKVVKNKIAAPFKQAEFQILYGEGINFYGEL 280
clone 13 prot NPETTTGGNALKFYASVRLDIRRIGTVKEGENVVGSETRVKVVKNKIAAPFKQAEFQILYDEGINFYGEL 280

VDLGVKEKLIEKAGAWYSYKGEKIGQGKANATAWLKDNPETAKEIEKKVRELLLSNPNSTPDFSVDDSEG
                      290       300       310       320       330       340       350
orig prot     VDLGVKEKLIEKAGAWYSYKGEKIGQGKANATAWLKDNPETAKEIEKKVRELLLSNPNSTPDFSVDDSEG 350
clone 2 prot  VDLGVKEKLIEKAGAWYSYKGEKIGQGKANATAWLKDNPETAKEIEKKVRELLLSNPNSTPDFSGDDSEG 350
clone 4 prot  VDLGVKEKLIEKAGAWYSYKGEKIGQGKANATAWLKDNPETAKEIEKKVRELLLSNPNSTPDFSVDDSEG 350
clone 5 prot  VDLGVKEKLIEKAGAWYSYKGEKIGQGKANAAAWLKGNPETAKEIEKKVRELLLSNPNSTPDFSRDDSEG 350
clone 6 prot  VDLGVKEKLIEKAGAWYSYKGEKVGQGKANATAWLKDNPETAKEIEKKVRELLLSNPNSTPDFSVDDSEG 350
clone 13 prot VDMGVKEKLIEKAGAWYSYKGEKAGQGKANATAWLKDNPETAKEIEKKVRELLLSNPNSTPDFSVDDSEG 350

VAETNEDF
orig prot     VAETNEDF  358
New Clone 2   VAETNEDF  358
New Clone 4   VAGTNEDF  358
New Clone 5   VAETNEDF  358
New Clone 6   VAETNEDF  358
complete 13   VAETNEDF  358
```

FIG. 13

Protoplast Formation
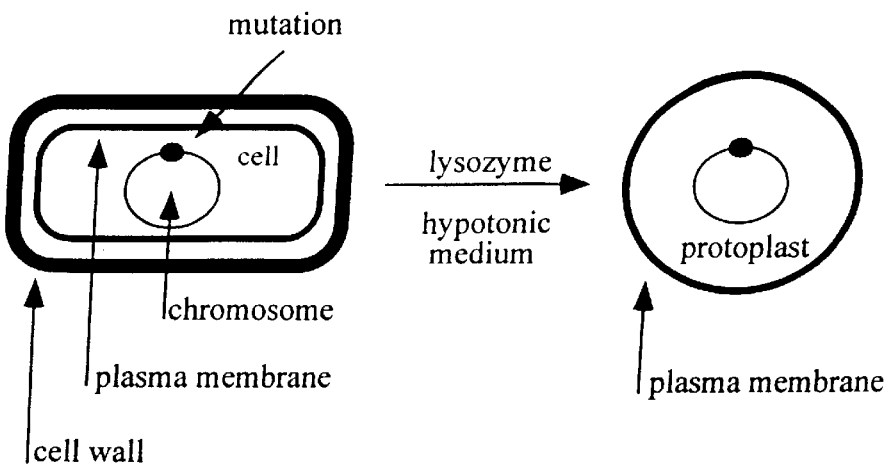
Protoplast Fusion
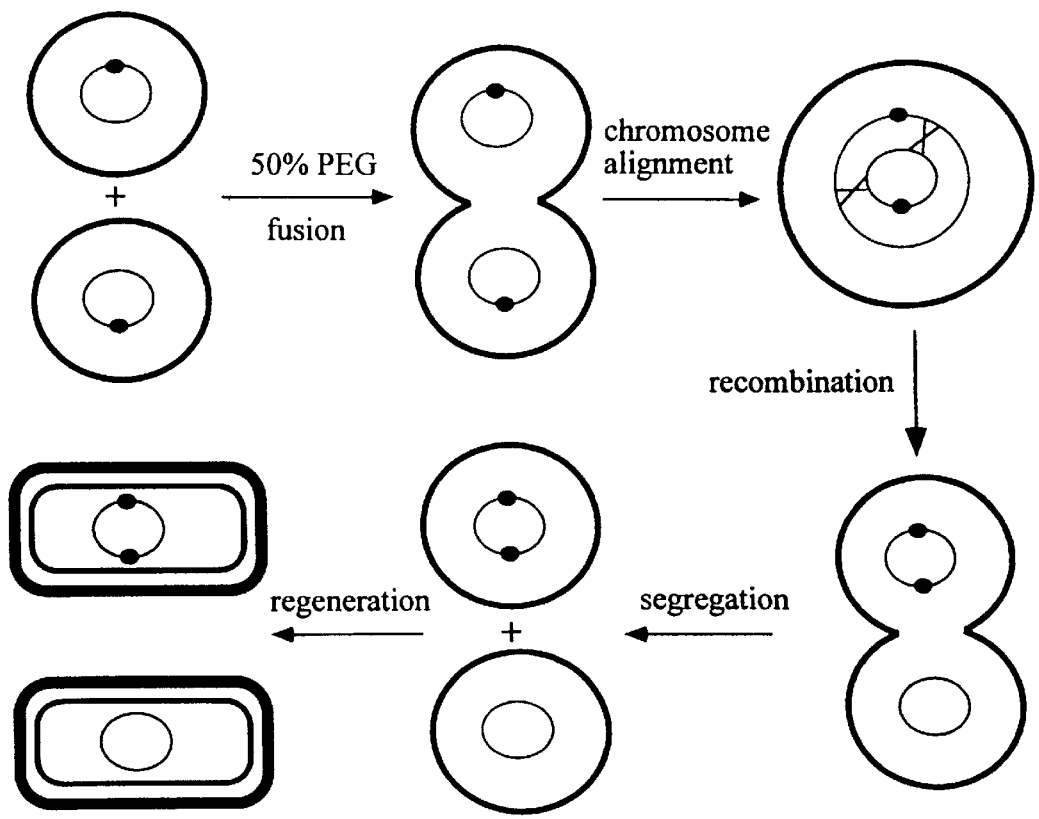
Fig. 26

EVOLUTION OF WHOLE CELLS AND ORGANISMS BY RECURSIVE SEQUENCE RECOMBINATION

CROSS-REFERENCE TO RELATED APPLICATION

Pursuant to 37 C.F.R 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

This application claims priority to U.S. Ser. No. 60/035,054, filed Jan. 17, 1997, which is incorporated by reference in its entirety for all purposes. This application also claims priority to PCT/US/98/00852 filed Jan. 16, 1998, designating the U.S., which is also incorporated by reference in its entirety for all purposes.

TECHNICAL FIELD

The invention applies the technical field of molecular genetics to evolve the genomes of cells and organisms to acquire new and improved properties.

BACKGROUND

Cells have a number of well-established uses in molecular biology. For example, cells are commonly used as hosts for manipulating DNA in processes such as transformation and recombination. Cells are also used for expression of recombinant proteins encoded by DNA transformed into the cells. Some types of cells are also used as progenitors for generation of transgenic animals and plants. Although all of these processes are now routine, in general, the genomes of the cells used in these processes have evolved little from the genomes of natural cells, and particularly not toward acquisition of new or improved properties for use in the above processes.

The traditional approach to artificial or forced molecular evolution focuses on optimization of individual genes having discrete and selectable phenotypes. The strategy is to clone a gene, identify a discrete function for the gene and an assay by which it can be selected, mutate selected positions in the gene (e.g., by error-prone PCR or cassette mutagenesis) and select variants of the gene for improvement in the known function of the gene. A variant having improved function can then be expressed in a desired cell type. This approach has a number of limitations. First, it is only applicable to genes that have been isolated and functionally characterized. Second, the approach is usually only applicable to genes that have a discrete function. In other words, multiple genes that cooperatively confer a single phenotype cannot usually be optimized in this manner—and many genes have cooperative functions. Finally, this approach can only explore a very limited number of the total number of permutations even for a single gene. For example, varying even ten positions in a protein with every possible amino acid would generate $20^{10}$ variants, which is more than can be accommodated by existing methods of transfection and screening.

In view of these limitations, traditional approaches are inadequate for improving cellular genomes in many useful properties. For example, to improve a cell's capacity to express a recombinant protein might require modification in any or all of a substantial number of genes, known and unknown, having roles in transcription, translation, post-translational modification, secretion or proteolytic degradation, among others. Attempting individually to optimize even all the known genes having such functions would be a virtually impossible task, let alone optimizing hitherto unknown genes which may contribute to expression in manners not yet understood.

For example, one area where traditional methods are used extensively is in the fermentation industry. The primary goal of current strain improvement programs (SIPs) in fermentation is typically an increase in product titre. State-of-the-art mutagenesis and screening is practiced by large fermentation companies, such as those in the pharmaceutical and chemical industries. Parent strains are mutated and individual fermentations of 5,000–40,000 mutants are screened by high-throughput methods for increases in product titre. For a well developed strain, an increase in yield of 10% per year (i.e., one new parent strain per year) is achieved using these methods. In general, cells are screened for titre increases significantly above that of the parent, with the detection sensitivity of most screens being ~5% increase due to variation in growth conditions. Only those that "breed true" during scale up make it to production and become the single parent of the next round of random mutagenesis.

Employing optimal mutation conditions one mutant out of 5,000–40,000 typically has a titre increase of 10%. However, a much higher percentage has slightly lower titre increases, 4–6%. These are generally not pursued, since experience has demonstrated that a higher producer can be isolated and that a significant percent of the lower producers actually are no better than the parent strain. The key to finding high producers using current strategies is to screen very large numbers of mutants per round of mutagenesis and to have a stable and sensitive assay. For these reasons, R&D to advance this field are in the automation and the screening capacity of the SIPs. Unfortunately, this strategy is inherently limited by the value of single mutations to strain improvement and the growth rate of the target organisms.

The present invention overcomes the problems noted above, providing, inter alia, novel methods for evolving the genome of whole cells and organisms.

SUMMARY OF THE INVENTION

In one aspect, the invention provides methods of evolving a cell to acquire a desired function. Such methods entail, e.g., introducing a library of DNA fragments into a plurality of cells, whereby at least one of the fragments undergoes recombination with a segment in the genome or an episome of the cells to produce modified cells. The modified cells are then screened for modified cells that have evolved toward acquisition of the desired function. DNA from the modified cells that have evolved toward the desired function is then recombined with a further library of DNA fragments, at least one of which undergoes recombination with a segment in the genome or the episome of the modified cells to produce further modified cells. The further modified cells are then screened for further modified cells that have further evolved toward acquisition of the desired function. Steps of recombination and screening/selection are repeated as required until the further modified cells have acquired the desired function.

In some methods, the library or further library of DNA fragments is coated with recA protein to stimulate recombination with the segment of the genome. In some methods, the library of fragments is denatured to produce single-stranded DNA, the single-stranded DNA are annealed to produce duplexes some of which contain mismatches at points of variation in the fragments, and duplexes containing mismatches are selected by affinity chromatography to immobilized MutS.

In some methods, the desired function is secretion of a protein, and the plurality of cells further comprises a construct encoding the protein. The protein is inactive unless secreted and further modified cells are selected for protein function. Optionally, the protein is toxic to the plurality of cells unless secreted. In this case, the modified or further modified cells which evolve toward acquisition of the desired function are screened by propagating the cells and recovering surviving cells.

In some methods, the desired function is enhanced recombination. In such methods, the library of fragments sometimes comprises a cluster of genes collectively conferring recombination capacity. Screening can be achieved using cells carrying a gene encoding a marker whose expression is prevented by a mutation removable by recombination. The cells are screened by their expression of the marker resulting from removal of the mutation by recombination.

In some methods, the plurality of cells are plant cells and the desired property is improved resistance to a chemical or microbe. The modified or further modified cells (or whole plants) are exposed to the chemical or microbe and modified or further modified cells having evolved toward the acquisition of the desired function are selected by their capacity to survive the exposure.

In some methods, the plurality of cells are embryonic cells of an animal, and the method further comprises propagating the transformed cells to transgenic animals.

The invention further provides methods for performing in vivo recombination. At least first and second segments from at least one gene are introduced into a cell, the segments differing from each other in at least two nucleotides, whereby the segments recombine to produce a library of chimeric genes. A chimeric gene is selected from the library having acquired a desired function.

The invention further provides methods of predicting efficacy of a drug in treating a viral infection. Such method entail recombining a nucleic acid segment from a virus, whose infection is inhibited by a drug, with at least a second nucleic acid segment from the virus, the second nucleic acid segment differing from the nucleic acid segment in at least two nucleotides, to produce a library of recombinant nucleic acid segments. Host cells are then contacted with a collection of viruses having genomes including the recombinant nucleic acid segments in a media containing the drug, and progeny viruses resulting from infection of the host cells are collected.

A recombinant DNA segment from a first progeny virus recombines with at least a recombinant DNA segment from a second progeny virus to produce a further library of recombinant nucleic acid segments. Host cells are contacted with a collection of viruses having genomes including the further library or recombinant nucleic acid segments, in media containing the drug, and further progeny viruses are produced by the host cells. The recombination and selection steps are repeated, as necessary, until a further progeny virus has acquired a desired degree of resistance to the drug, whereby the degree of resistance acquired and the number of repetitions needed to acquire it provide a measure of the efficacy of the drug in treating the virus. Viruses are optionally adapted to grow on particular cell lines.

The invention further provides methods of predicting efficacy of a drug in treating an infection by a pathogenic microorganism. These methods entail delivering a library of DNA fragments into a plurality of microorganism cells, at least some of which undergo recombination with segments in the genome of the cells to produce modified microorganism cells. Modified microorganisms are propagated in a media containing the drug, and surviving microorganisms are recovered. DNA from surviving microorganisms is recombined with a further library of DNA fragments at least some of which undergo recombination with cognate segments in the DNA from the surviving microorganisms to produce further modified microorganisms cells. Further modified microorganisms are propagated in media containing the drug, and further surviving microorganisms are collected. The recombination and selection steps are repeated as needed, until a further surviving microorganism has acquired a desired degree of resistance to the drug. The degree of resistance acquired and the number of repetitions needed to acquire it provide a measure of the efficacy of the drug in killing the pathogenic microorganism.

The invention further provides methods of evolving a cell to acquire a desired function. These methods entail providing a populating of different cells. The cells are cultured under conditions whereby DNA is exchanged between cells, forming cells with hybrid genomes. The cells are then screened or selected for cells that have evolved toward acquisition of a desired property. The DNA exchange and screening/selecting steps are repeated, as needed, with the screened/selected cells from one cycle forming the population of different cells in the next cycle, until a cell has acquired the desired property.

Mechanisms of DNA exchange include conjugation, phage-mediated transduction, protoplast fusion, and sexual recombination of the cells. Optionally, a library of DNA fragments can be transformed or electroporated into the cells.

As noted, some methods of evolving a cell to acquire a desired property are effected by protoplast-mediated exchange of DNA between cells. Such methods entail forming protoplasts of a population of different cells. The protoplasts are then fused to form hybrid protoplasts, in which genomes from the protoplasts recombine to form hybrid genomes. The hybrid protoplasts are incubated under conditions promoting regeneration of cells. The next step is to select or screen to isolate regenerated cells that have evolved toward acquisition of the desired property. DNA exchange and selection/screening steps are repeated, as needed, with regenerated cells in one cycle being used to form protoplasts in the next cycle until the regenerated cells have acquired the desired property. Industrial microorganisms are a preferred class of organisms for conducting the above methods. Some methods further comprise a step of selecting or screening for fused protoplasts free from unfused protoplasts of parental cells. Some methods further comprise a step of selecting or screening for fused protoplasts with hybrid genomes free from cells with parental genomes. In some methods, protoplasts are provided by treating individual cells, mycelia or spores with an enzyme that degrades cell walls. In some methods, the strain is a mutant that is lacking capacity for intact cell wall synthesis, and protoplasts form spontaneously. In some methods, protoplasts are formed by treating growing cells with an inhibitor of cell wall formation to generate protoplasts.

In some methods, the desired property is expression and/or secretion of a protein or secondary metabolite, such as an industrial enzyme, a therapeutic protein, a primary metabolite such as lactic acid or ethanol, or a secondary metabolite such as erythromycin cyclosporin A or taxol. In other methods it is the ability of the cell to convert compounds provided to the cell to different compounds. In yet other methods, the desired property is capacity for meiosis. In some methods, the desired property is compatibility to form a heterokaryon with another strain.

The invention further provides methods of evolving a cell toward acquisition of a desired property. These methods entail providing a population of different cells. DNA is isolated from a first subpopulation of the different cells and encapsulated in liposomes. Protoplasts are formed from a second subpopulation of the different cells. Liposomes are fused with the protoplasts, whereby DNA from the liposomes is taken up by the protoplasts and recombines with the genomes of the protoplasts. The protoplasts are incubated under regenerating conditions. Regenerating or regenerated cells are then selected or screened for evolution toward the desired property.

The invention further provides methods of evolving a cell toward acquisition of a desired property using artificial chromosomes. Such methods entail introducing a DNA fragment library cloned into an artificial chromosome into a population of cells. The cells are then cultured under conditions whereby sexual recombination occurs between the cells, and DNA fragments cloned into the artificial chromosome homologously recombines with corresponding segments of endogenous chromosomes of the populations of cells, and endogenous chromosomes recombine with each other. Cells that have evolved toward acquisition of the desired property are then selected or screened. The method is then repeated with cells that have evolved toward the desired property in one cycle forming the population of different cells in the next cycle.

The invention further provides methods of evolving a DNA segment cloned into an artificial chromosome for acquisition of a desired property. These methods entail providing a library of variants of the segment, each variant cloned into separate copies of an artificial chromosome. The copies of the artificial chromosome are introduced into a population of cells. The cells are cultured under conditions whereby sexual recombination occurs between cells and homologous recombination occurs between copies of the artificial chromosome bearing the variants. Variants are then screened or selected for evolution toward acquisition of the desired property.

The invention further provides hyperrecombinogenic recA proteins. Examples of such proteins are from clones 2, 4, 5, 6 and 13 shown in FIG. 13.

BRIEF DESCRIPTION OF THE DRAWING

FIGS. 12: (A, B, C and D) DNA sequences of a wildtype recA protein and five hyperrecombinogenic variants thereof.

FIG. 13: Amino acid sequences of a wildtype recA protein and five hyperrecombinogenic variants thereof.

FIG. 20, panel B: schematic for selectable/counterselectable marker strategy for Rec A.

FIG. 26: Schematic of protoplast fusion.

DEFINITIONS

Figure 1:
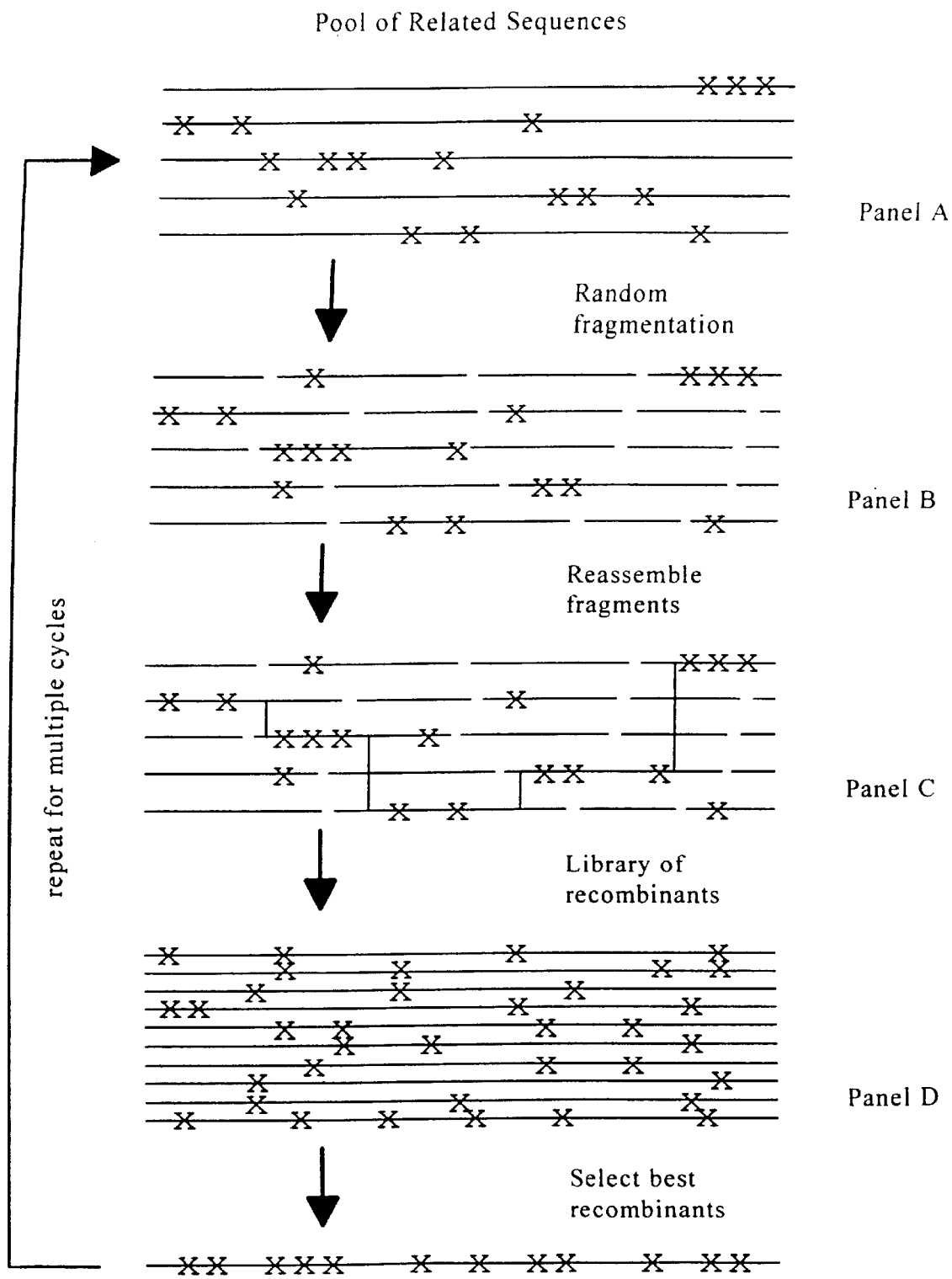
FIG. 1, panels A–D: Scheme for in vitro shuffling of genes.

The term cognate refers to a gene sequence that is evolutionarily and functionally related between species. For example, in the human genome, the human CD4 gene is the cognate gene to the mouse CD4 gene, since the sequences and structures of these two genes indicate that they are homologous and that both genes encode a protein which functions in signaling T-cell activation through MHC class II-restricted antigen recognition.

Screening is, in general, a two-step process in which one first determines which cells do and do not express a screening marker or phenotype (or a selected level of marker or phenotype), and then physically separates the cells having the desired property. Selection is a form of screening in which identification and physical separation are achieved simultaneously by expression of a selection marker, which, in some genetic circumstances, allows cells expressing the marker to survive while other cells die (or vice versa). Screening markers include luciferase, β-galactosidase, and green fluorescent protein. Selection markers include drug and toxin resistance genes.

An exogenous DNA segment is one foreign (or heterologous) to the cell or homologous to the cell but in a position within the host cell nucleic acid in which the element is not ordinarily found. Exogenous DNA segments can be expressed to yield exogenous polypeptides.

The term gene is used broadly to refer to any segment of DNA associated with a biological function. Thus, genes include coding sequences and/or the regulatory sequences required for their expression. Genes also include nonexpressed DNA segments that, for example, form recognition sequences for other proteins.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of algorithms GAP, BESTFIT, FASTA, and TFASTA in the Wisconsin Genetics Software Package Release 7.0, Genetics Computer Group, 575 Science Dr., Madison, Wis.

Another example of a useful alignment algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

The term "naturally-occurring" is used to describe an object that can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

Asexual recombination is recombination occurring without the fusion of gametes to form a zygote.

A "mismatch repair deficient strain" can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. Impairment can be of the genes noted, or of homologous genes in any organism.

Detailed Description

I. General

A. The Basic Approach

The invention provides methods for artificially evolving cells to acquire a new or improved property by recursive sequence recombination. Briefly, recursive sequence recombination entails successive cycles of recombination to generate molecular diversity and screening/selection to take advantage of that molecular diversity. That is, a family of nucleic acid molecules is created showing substantial sequence and/or structural identity but differing as to the presence of mutations. These sequences are then recombined in any of the described formats so as to optimize the diversity of mutant combinations represented in the resulting recombined library. Each recombination cycle is followed by at least one cycle of screening or selection for molecules having a desired characteristic. The molecule(s) selected in one round form the starting materials for generating diversity in the next round.

The cells to be evolved can be bacteria, archaebacteria, or eukaryotic cells and can constitute a homogeneous cell line or mixed culture. Suitable cells for evolution include the bacterial and eukaryotic cell lines commonly used in genetic engineering, protein expression, or the industrial production or conversion of proteins, enzymes, primary metabolites, secondary metabolites, fine, specialty or commodity chemicals. Suitable mammalian cells include those from, e.g., mouse, rat, hamster, primate, and human, both cell lines and primary cultures. Such cells include stem cells, including embryonic stem cells and hemopoietic stem cells, zygotes, fibroblasts, lymphocytes, Chinese hamster ovary (CHO), mouse fibroblasts (NIH3T3), kidney, liver, muscle, and skin cells. Other eukaryotic cells of interest include plant cells, such as maize, rice, wheat, cotton, soybean, sugarcane, tobacco, and arabidopsis; fish, algae, fungi (penicillium, aspergillus, podospora, neurospora, saccharomyces), insect (e.g., baculo lepidoptera), yeast (picchia and saccharomyces, *Schizosaccharomyces pombe*). Also of interest are many bacterial cell types, both gram-negative and gram-positive, such as *Bacillus subtilis, B. licehniformis, B. cereus, Escherichia coli*, Streptomyces, Pseudomonas, Salmonella, Actinomycetes and Erwinia. The complete genome sequences of *E. coli* and *Bacillus subtilis* are described by Blattner et al., *Science* 277, 1454–1462 (1997); Kunst et al., *Nature* 390, 249–256 (1997)).

Evolution commences by generating a population of variant cells. Typically, the cells in the population are of the same type but represent variants of a progenitor cell. In some instances, the variation is natural as when different cells are obtained from different individuals within a species, from different species or from different genera. In other instances, variation is induced by mutagenesis of a progenitor cell. Mutagenesis can be effected by subjecting the cell to mutagenic agents, or if the cell is a mutator cell (e.g., has mutations in genes involved in DNA replication, recombination and/or repair which favor introduction of mutations) simply by propagating the mutator cells. Mutator cells can be generated from successive selections for simple phenotypic changes (e.g., acquisition of rifampicin-resistance, then nalidixic acid resistance then lac– to lac+ (see Mao et al., *J. Bacteriol.* 179, 417–422 (1997)), or mutator cells can be generated by exposure to specific inhibitors of cellular factors that result in the mutator phenotype. These could be inhibitors of mutS, mutL, mutD, recD, mutY, mutM, dam, uvrD and the like.

More generally, mutations are induced in cell populations using any available mutation technique. Common mechanisms for inducing mutations include, but are not limited to the use of strains comprising mutations such as those involved in mismatch repair e.g. mutations in mutS, mutT, mutL and mutH; exposure to U.V. light; Chemical mutagenesis, e.g. use of inhibitors of MMR, DNA damage inducible genes, or SOS inducers; overproduction/underproduction/mutation of any component of the homologous recombination complex/pathway, eg. RecA, ssb, etc.; overproduction/underproduction/mutation of genes involved in DNA synthesis/homeostasis; overproduction/underproduction/mutation of recombination-stimulating genes from bacteria, phage (eg. Lambda Red function), or other organisms; addition of chi sites into/flanking the donor DNA fragments; coating the DNA fragments with RecA/ssb and the like.

Figure 20A:
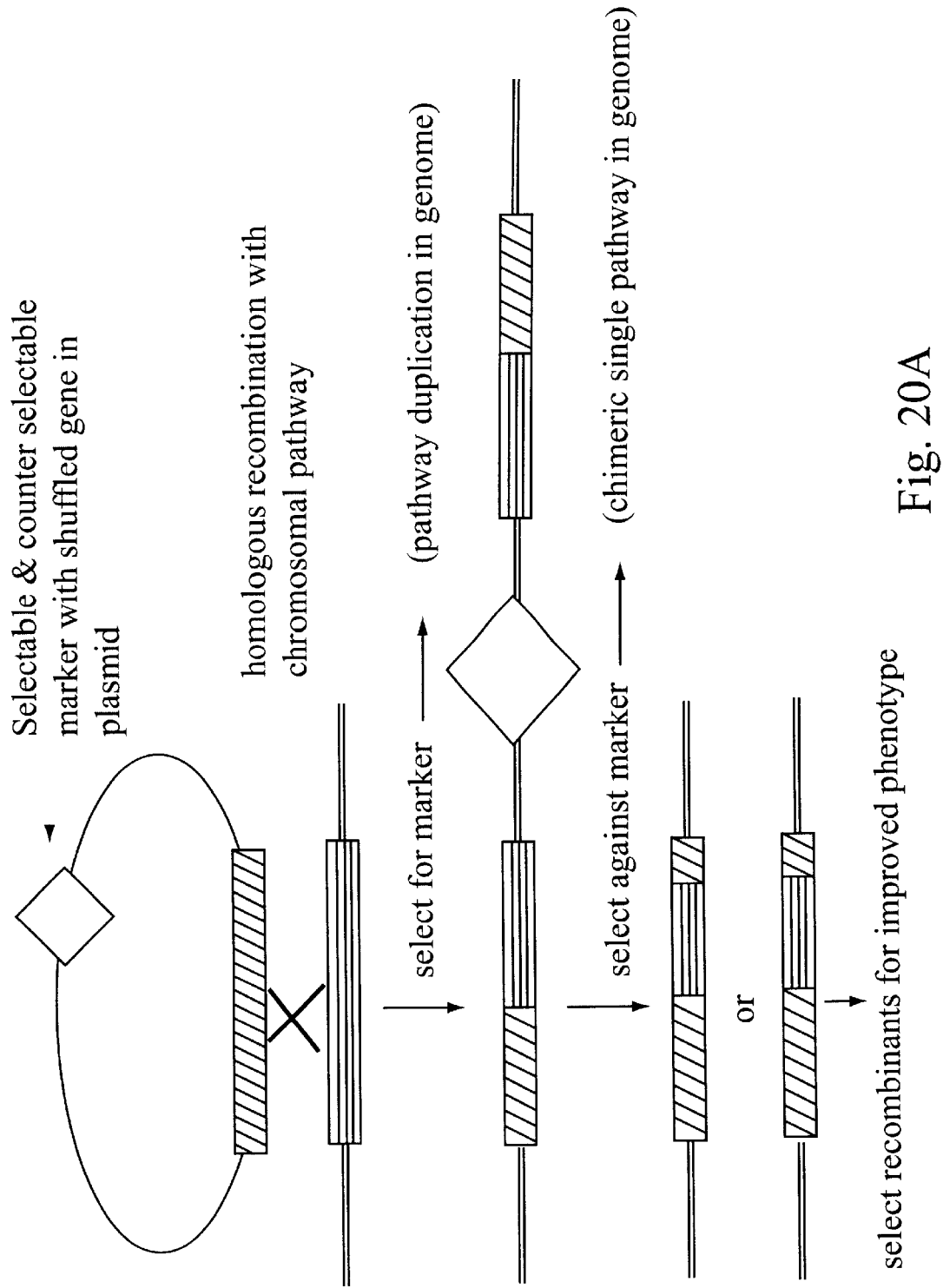
FIG. 20, panel A: schematic for selectable/counterselectable marker strategy.

In other instances, variation is the result of transferring a library of DNA fragments into the cells (e.g., by conjugation, protoplast fusion, transformation, transduction or natural competence). At least one, and usually many of the fragments in the library, show some, but not complete, sequence or structural identity with a cognate or allelic gene within the cells sufficient to allow homologous recombination to occur. For example, in one embodiment, homologous integration of a plasmid carrying a shuffled gene or metabolic pathway leads to insertion of the plasmid-borne sequences adjacent to the genomic copy. Optionally, a counter-selectable marker strategy is used to select for recombinants in which recombination occurred between the homologous sequences, leading to elimination of the counter-selectable marker. This strategy is illustrated in FIG. 20A. A variety of selectable and counter selectable markers are amply illustrated in the art. For a list of useful markers, see, Berg and Berg (1996), *Transposable element tools for microbial genetics. Escherichia coli and Salmonella* Neidhardt. Washington, D.C., ASM Press. 2:2588–2612; La Rossa, ibid., 2527–2587.

The library of fragments can derive from one or more sources. One source of fragments is a genomic library of fragments from a different species, cell type, organism or individual from the cells being transfected. In this situation, many of the fragments in the library have a cognate or allelic gene in the cells being transformed but differ from that gene due to the presence of naturally occurring species variation, polymorphisms, mutations, and the presence of multiple copies of some homologous genes in the genome. Alternatively, the library can be derived from DNA from the same cell type as is being transformed after that DNA has been subject to induced mutation, by conventional methods, such as radiation, error-prone PCR, growth in a mutator organism or cassette mutagenesis. Alternatively, the library can derive from a genomic library of fragments generated from the pooled genomic DNA of a population of cells having the desired characteristics. Alternatively, the library can derive from a genomic library of fragments generated from the pooled-genomic DNA of a population of cells having desired characteristics.

In any of these situations, the genomic library can be a complete genomic library or subgenomic library deriving, for example, from a selected chromosome, or part of a chromosome or an episomal element within a cell. As well as, or instead of these sources of DNA fragments, the library can contain fragments representing natural or selected variants of selected genes of known function (i.e., focused libraries).

The number of fragments in a library can vary from a single fragment to about $10^{10}$, with libraries having from $10^3$ to $10^8$ fragments being common. The fragments should be sufficiently long that they can undergo homologous recombination and sufficiently short that they can be introduced into a cell, and if necessary, manipulated before introduction. Fragment sizes can range from about 10 b to about 20 mb. Fragments can be double- or single-stranded.

The fragments can be introduced into cells as whole genomes or as components of viruses, plasmids, YACS, HACs or BACs or can be introduced as they are, in which case all or most of the fragments lack an origin of replication. Use of viral fragments with single-stranded genomes offer the advantage of delivering fragments in single stranded form, which promotes recombination. The fragments can also be joined to a selective marker before introduction. Inclusion of fragments in a vector having an origin of replication affords a longer period of time after introduction into the cell in which fragments can undergo recombination with a cognate gene before being degraded or selected against and lost from the cell, thereby increasing the proportion of cells with recombinant genomes. Optionally, the vector is a suicide vector capable of a longer existence than an isolated DNA fragment but not capable of permanent retention in the cell line. Such a vector can transiently express a marker for a sufficient time to screen for or select a cell bearing the vector (e.g., because cells transduced by the vector are the target cell type to be screened in subsequent selection assays), but is then degraded or otherwise rendered incapable of expressing the marker. The use of such vectors can be advantageous in performing optional subsequent rounds of recombination to be discussed below. For example, some suicide vectors express a long-lived toxin which is neutralized by a short-lived molecule expressed from the same vector. Expression of the toxin alone will not allow vector to be established. Jense & Gerdes, *Mol. Microbiol.*, 17, 205–210 (1995); Bernard et al., *Gene* 162, 159–160. Alternatively, a vector can be rendered suicidal by incorporation of a defective origin of replication (e.g. a temperature-sensitive origin of replication) or by omission of an origin of replication. Vectors can also be rendered suicidal by inclusion of negative selection markers, such as ura3 in yeast or sacB in many bacteria. These genes become toxic only in the presence of specific compounds. Such vectors can be selected to have a wide range of stabilities. A list of conditional replication defects for vectors which can be used, e.g., to render the vector replication defective is found, e.g., in Berg and Berg (1996), "Transposable element tools for microbial genetics" *Escherichia coli* and Salmonella Neidhardt. Washington, D.C., ASM Press. 2: 2588–2612. Similarly, a list of counterselectable markers, generally applicable to vector selection is also found in Berg and Berg, id. See also, LaRossa (1996) "Mutant selections linking physiology, inhibitors, and genotypes" *Escherichia coli* and Salmonella F. C. Neidhardt. Washington, D.C., ASM Press. 2: 2527–2587.

After introduction into cells, the fragments can recombine with DNA present in the genome, or episomes of the cells by homologous, nonhomologous or site-specific recombination. For present purposes, homologous recombination makes the most significant contribution to evolution of the cells because this form of recombination amplifies the existing diversity between the DNA of the cells being transfected and the DNA fragments. For example, if a DNA fragment being transfected differs from a cognate or allelic gene at two positions, there are four possible recombination products, and each of these recombination products can be formed in different cells in the transformed population. Thus, homologous recombination of the fragment doubles the initial diversity in this gene. When many fragments recombine with corresponding cognate or allelic genes, the diversity of recombination products with respect to starting products increases exponentially with the number of mutations. Recombination results in modified cells having modified genomes and/or episomes.

The variant cells, whether the result of natural variation, mutagenesis, or recombination are screened or selected to identify a subset of cells that have evolved toward acquisition of a new or improved property. The nature of the screen, of course, depends on the property and several examples will be discussed below. Optionally, the screening is repeated before performing subsequent cycles of recombination. Stringency can be increased in repeated cycles of screening.

The subpopulation of cells surviving screening are optionally subjected to a further round of recombination. In some instances, the further round of recombination is effected by propagating the cells under conditions allowing exchange of DNA between cells. For example, protoplasts can be formed from the cells, allowed to fuse, and regenerated. Cells with recombinant genomes are propagated from the fused protoplasts. Alternatively, exchange of DNA can be promoted by propagation of cells or protoplasts in an electric field. For cells having a conjugative transfer apparatus, exchange of DNA can be promoted simply by propagating the cells.

Figure 19:
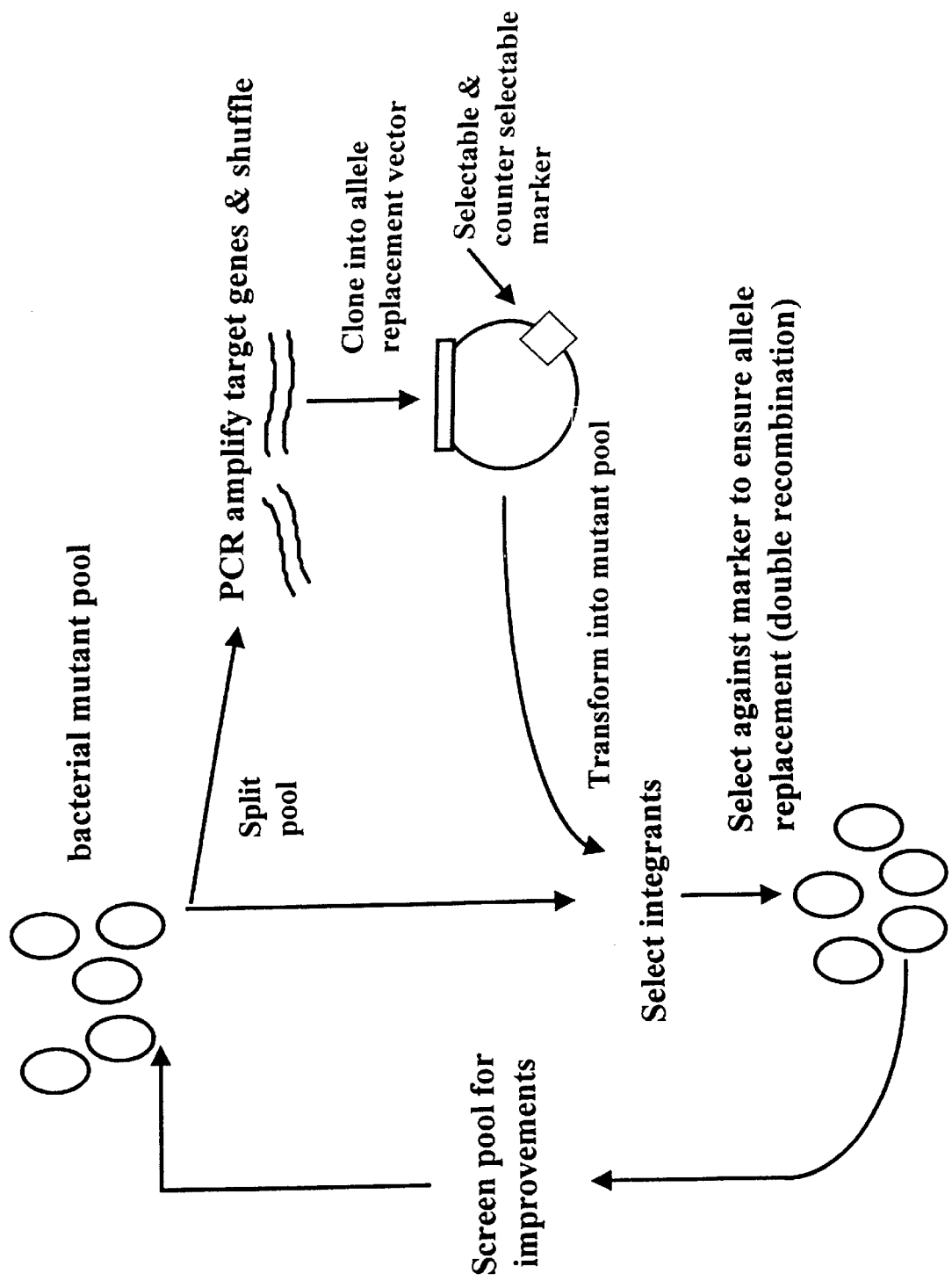
FIG. 19: Schematic for split and pool strategy.

In other methods, the further round of recombination is performed by a split and pool approach. That is, the surviving cells are divided into two pools. DNA is isolated from one pool, and if necessary amplified, and then transformed into the other pool. Accordingly, DNA fragments from the first pool constitute a further library of fragments and recombine with cognate fragments in the second pool resulting in further diversity. An example of this strategy is illustrated in FIG. 19. As shown, a pool of mutant bacteria with improvements in a desired phenotype is obtained and split. Genes are obtained from one half, e.g., by PCR or by cloning of random genomic fragments. These are then shuffled, or simply cloned into an allele replacement vector (e.g., one carrying selectable and counter-selectable markers). The gene pool is then transformed into the other half of the original mutant pool and recombinants are selected and screened for further improvements in phenotype. These best variants are used as the starting point for then next cycle.

In other methods, some or all of the cells surviving screening are transfected with a fresh library of DNA fragments, which can be the same or different from the library used in the first round of recombination. In this situation, the genes in the fresh library undergo recombination with cognate genes in the surviving cells. If genes are introduced as components of a vector, compatibility of this vector with any vector used in a previous round of transfection should be considered. If the vector used in a previous round was a suicide vector, there is no problem of incompatibility. If, however, the vector used in a previous round was not a suicide vector, a vector having a different incompatibility origin should be used in the subsequent round. In all of these formats, further recombination generates additional diversity in the DNA component of the cells resulting in further modified cells.

The further modified cells are subjected to another round of screening/selection according to the same principles as the first round. Screening/selection identifies a subpopulation of further modified cells that have further evolved toward acquisition of the property. This subpopulation of cells can be subjected to further rounds of recombination and screening according to the same principles, optionally with the stringency of screening being increased at each round. Eventually, cells are identified that have acquired the desired property.

B. Variations

1. Coating Fragments with recA Protein

The frequency of homologous recombination between library fragments and cognate endogenous genes can be increased by coating the fragments with a recombinogenic protein before introduction into cells. See Pati et al., *Molecular Biology of Cancer* 1, 1 (1996); Sena & Zarling, *Nature Genetics* 3, 365 (1996); Revet et al., *J. Mol. Biol.* 232, 779–791 (1993); Kowalczkowski & Zarling in *Gene Targeting* (CRC 1995), Ch. 7. The recombinogenic protein promotes homologous pairing and/or strand exchange. The best characterized recA protein is from *E. coli* and is available from Pharmacia (Piscataway, N.J.). In addition to the wild-type protein, a number of mutant recA-like proteins have been identified (e.g., recA803). Further, many organisms have recA-like recombinases with strand-transfer activities (e.g., Ogawa et al., *Cold Spring Harbor Symposium on Quantitative Biology* 18, 567–576 (1993); Johnson & Symington, *Mol. Cell. Biol.* 15, 4843–4850 (1995); Fugisawa et al., *Nucl. Acids Res.* 13, 7473 (1985); Hsieh et al., *Cell* 44, 885 (1986); Hsieh et al., *J. Biol. Chem.* 264, 5089 (1989); Fishel et al., *Proc. Natl. Acad. Sci. USA* 85, 3683 (1988); Cassuto et al., *Mol. Gen. Genet.* 208, 10 (1987); Ganea et al., *Mol. Cell Biol.* 7, 3124 (1987); Moore et al., *J. Biol. Chem.* 19, 11108 (1990); Keene et al., *Nucl. Acids Res.* 12, 3057 (1984); Kimiec, *Cold Spring Harbor Symp.* 48, 675 (1984); Kimeic, *Cell* 44, 545 (1986); Kolodner et al., *Proc. Natl. Acad. Sci. USA* 84, 5560 (1987); Sugino et al., *Proc. Natl. Acad. Sci. USA* 85, 3683 (1985); Halbrook et al., *J. Biol. Chem.* 264, 21403 (1989); Eisen et al., *Proc. Natl. Acad. Sci. USA* 85, 7481 (1988); McCarthy et al., *Proc. Natl. Acad. Sci. USA* 85, 5854 (1988); Lowenhaupt et al., *J. Biol. Chem.* 264, 20568 (1989). Examples of such recombinase proteins include recA, recA803, uvsX, (Roca, A. I., *Crit. Rev. Biochem. Molec. Biol.* 25, 415 (1990)), sep1 (Kolodner et al., *Proc. Natl. Acad. Sci.* (U.S.A.) 84, 5560 (1987); Tishkoff et al., *Molec. Cell. Biol.* 11, 2593), RuvC (Dunderdale et al., *Nature* 354, 506 (1991)), DST2, KEM1, XRN1 (Dykstra et al., *Molec. Cell. Biol.* 11, 2583 (1991)), STPα/DST1 (Clark et al., *Molec. Cell. Biol.* 11, 2576 (1991)), HPP-1 (Moore et al., *Proc. Natl. Acad. Sci.* (U.S.A.) 88, 9067 (1991)), other eukaryotic recombinases (Bishop et al., Cell 69, 439 (1992); Shinohara et al., *Cell* 69, 457.

RecA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA to be shuffled and can form complexes with both single-stranded and double-stranded DNA in procaryotic and eukaryotic cells.

Before contacting with recA or other recombinase, fragments are often denatured, e.g., by heat-treatment. RecA protein is then added at a concentration of about 1–10 $\mu$M. After incubation, the recA-coated single-stranded DNA is introduced into recipient cells by conventional methods, such as chemical transformation or electroporation. The fragments undergo homologous recombination with cognate endogenous genes. Because of the increased frequency of recombination due to recombinase coating, the fragments need not be introduced as components of vectors.

Fragments are sometimes coated with other nucleic acid binding proteins that promote recombination, protect nucleic acids from degradation, or target nucleic acids to the nucleus. Examples of such proteins includes Agrobacterium virE2 (Durrenberger et al., *Proc. Natl. Acad. Sci. USA* 86, 9154–9158 (1989)). Alternatively, the recipient strains are deficient in RecD activity. Single stranded ends can also be generated by 3'–5' exonuclease activity or restriction enzymes producing 5' overhangs.

2. MutS Selection

The *E. coli* mismatch repair protein MutS can be used in affinity chromatography to enrich for fragments of double-stranded DNA containing at least one base of mismatch. The MutS protein recognizes the bubble formed by the individual strands about the point of the mismatch. See, e.g., Hsu & Chang, WO9320233. The strategy of affinity enriching for partially mismatched duplexes can be incorporated into the present methods to increase the diversity between an incoming library of fragments and corresponding cognate or allelic genes in recipient cells.

Figure 2:
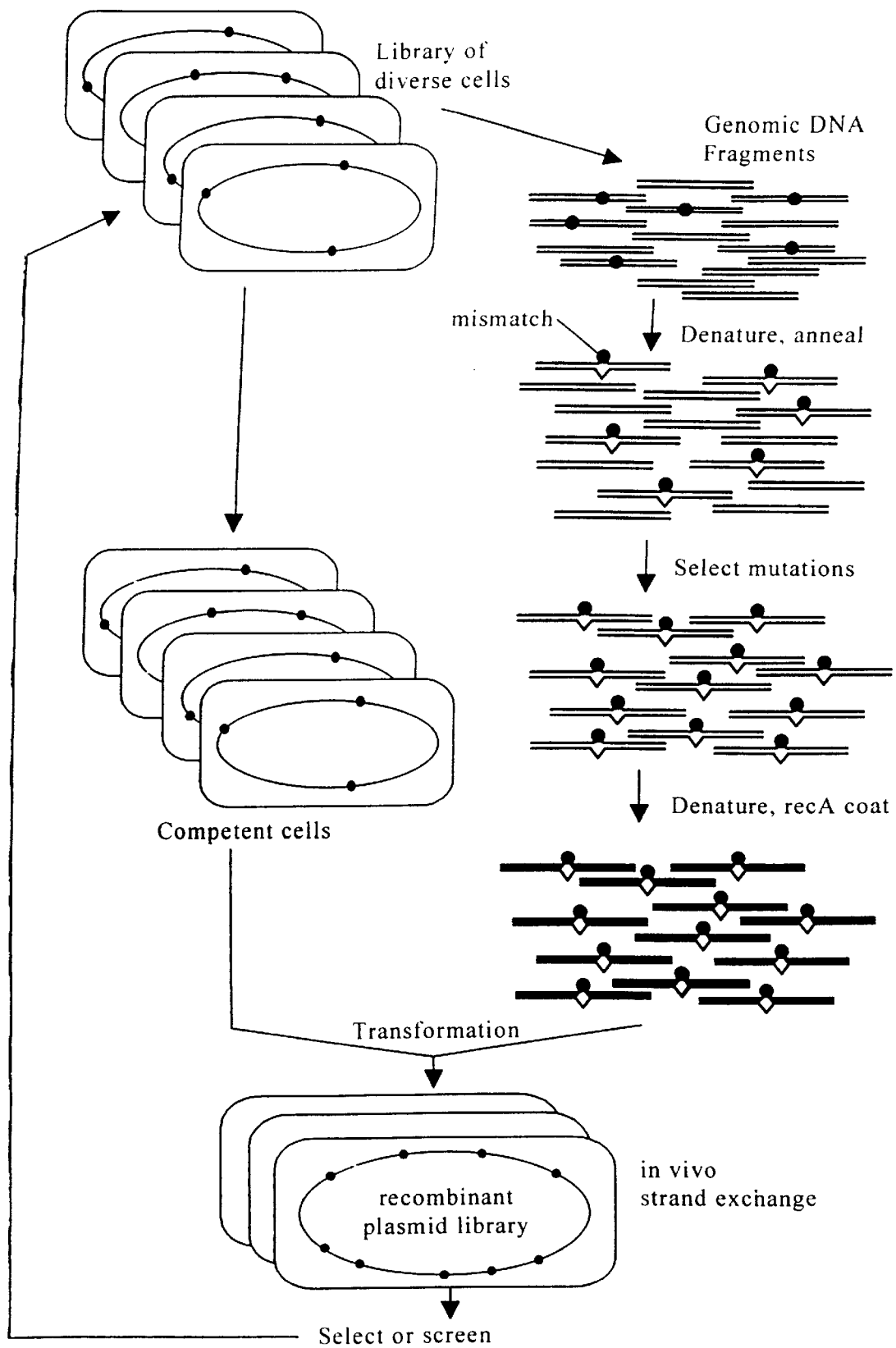
FIG. 2: Scheme for enriching for mismatched sequences using MutS.

FIG. 2 shows one scheme in which MutS is used to increase diversity. The DNA substrates for enrichment are substantially similar to each other but differ at a few sites. For example, the DNA substrates can represent complete or partial genomes (e.g., a chromosome library) from different individuals with the differences being due to polymorphisms. The substrates can also represent induced mutants of a wildtype sequence. The DNA substrates are pooled, restriction digested, and denatured to produce fragments of single-stranded DNA. The single-stranded DNA is then allowed to reanneal. Some single-stranded fragments reanneal with a perfectly matched complementary strand to generate perfectly matched duplexes. Other single-stranded fragments anneal to generate mismatched duplexes. The mismatched duplexes are enriched from perfectly matched duplexes by MutS chromatography (e.g., with MutS immobilized to beads). The mismatched duplexes recovered by chromatography are introduced into recipient cells for recombination with cognate endogenous genes as described above. MutS affinity chromatography increases the proportion of fragments differing from each other and the cognate endogenous gene. Thus, recombination between the incoming fragments and endogenous genes results in greater diversity.

Figure 3:
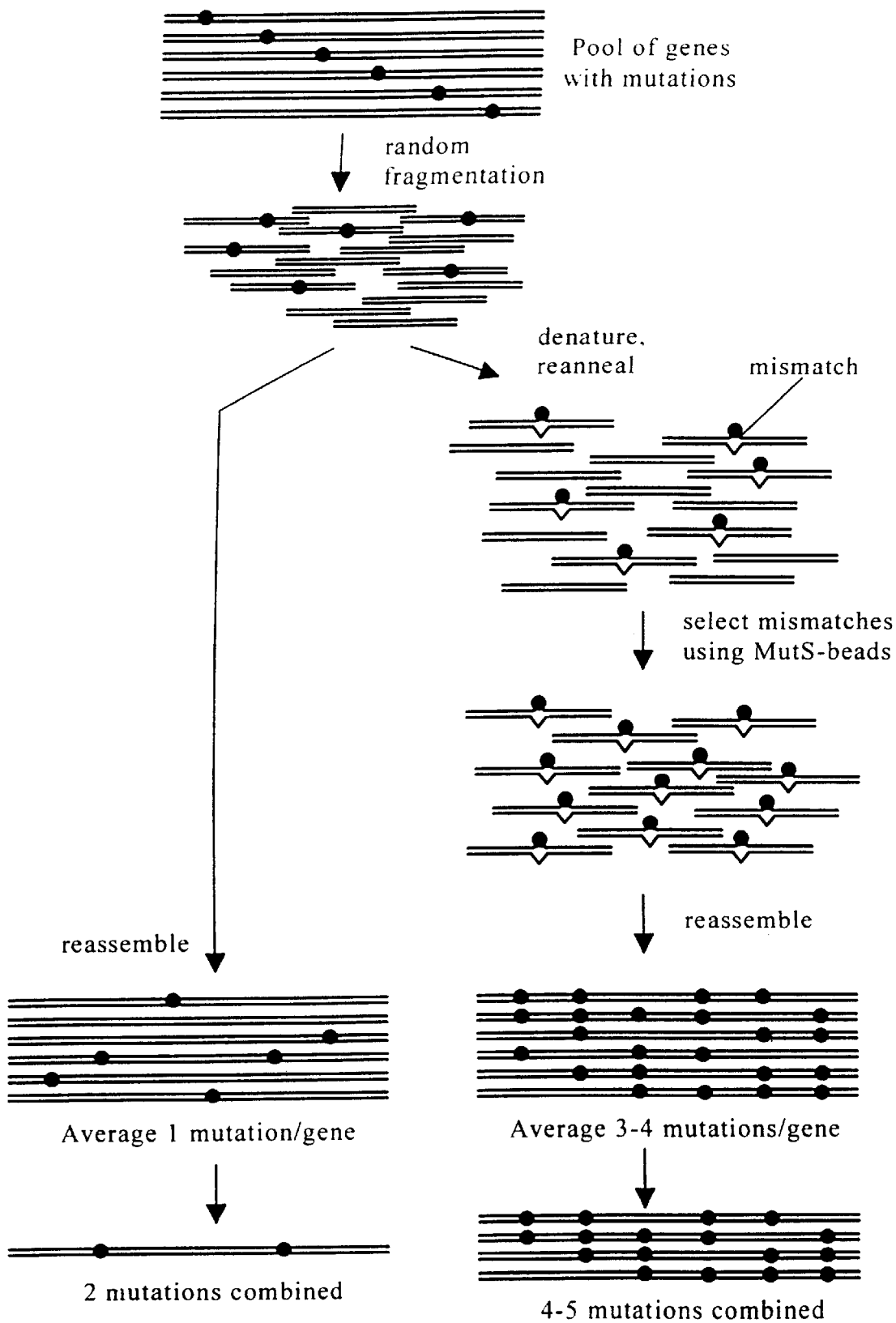
FIG. 3: Alternative scheme for enriching for mismatched sequences using MutS.

FIG. 3 shows a second strategy for MutS enrichment. In this strategy, the substrates for MutS enrichment represent variants of a relatively short segment, for example, a gene or cluster of genes, in which most of the different variants differ at no more than a single nucleotide. The goal of MutS enrichment is to produce substrates for recombination that contain more variations than sequences occurring in nature. This is achieved by fragmenting the substrates at random to produce overlapping fragments. The fragments are denatured and reannealed as in the first strategy. Reannealing generates some mismatched duplexes which can be separated from perfectly matched duplexes by MutS affinity chromatography. As before, MutS chromatography enriches for duplexes bearing at least a single mismatch. The mismatched duplexes are then reassembled into longer fragments. This is accomplished by cycles of denaturation, reannealing, and chain extension of partially annealed duplexes (see Section V). After several such cycles, fragments of the same length as the original substrates are achieved, except that these fragments differ from each other at multiple sites. These fragments are then introduced into cells where they undergo recombination with cognate endogenous genes.

3. Positive Selection For Allelic Exchange

The invention further provides methods of enriching for cells bearing modified genes relative to the starting cells. This can be achieved by introducing a DNA fragment library (e.g., a single specific segment or a whole or partial genomic library) in a suicide vector (i.e., lacking a functional replication origin in the recipient cell type) containing both positive and negative selection markers. Optionally, multiple fragment libraries from different sources (e.g., *B. subtilis, B. licheniformis* and *B. cereus*) can be cloned into different vectors bearing different selection markers. Suitable positive selection markers include $neo^R$, $kanamycin^R$, hyg, hisD, gpt, ble, $tet^R$, hprt SacB and ura3. Suitable negative selection markers include hsv-tk, hprt, gpt, and cytosine deaminase. A variety of examples of conditional replication vectors, mutations affecting vector replication, limited host range vectors, and counterselectable markers are found in Berg and Berg, supra, and LaRossa, ibid. and the references therein.

In one example, a plasmid with R6K and f1 origins of replication, a positively selectable marker (beta-lactamase), and a counterselectable marker (B. subtilis sacB) was used. M13 transduction of plasmids containing cloned genes were efficiently recombined into the chromosomal copy of that gene in a rep mutant *E. coli* strain.

Another strategy for applying negative selection is to include a wildtype rpsL gene (encoding ribosomal protein S12) in a vector for use in cells having a mutant rpsL gene conferring streptomycin resistance. The mutant form of rpsL is recessive in cells having wildtype rpsL. Thus, selection for Sm resistance selects against cells having a wildtype copy of rpsL. See Skorupski & Taylor, *Gene* 169, 47–52 (1996). Alternatively, vectors bearing only a positive selection marker can be used with one round of selection for cells expressing the marker, and a subsequent round of screening for cells that have lost the marker (e.g., screening for drug sensitivity). The screen for cells that have lost the positive selection marker is equivalent to screening against expression of a negative selection marker. For example, Bacillus can be transformed with a vector bearing a CAT gene and a sequence to be integrated. See Harwood & Cutting, *Molecular Biological Methods for Bacillus,* at pp. 31–33. Selection for chloramphenicol resistance isolates cells that have taken up vector. After a suitable period to allow recombination, selection for CAT sensitititvity isolates cells which have lost the CAT gene. About 50% of such cells will have undergone recombination with the sequence to be integrated.

Suicide vectors bearing a positive selection marker and optionally, a negative selection marker and a DNA fragment can integrate into host chromosomal DNA by a single crossover at a site in chromosomal DNA homologous to the fragment. Recombination generates an integrated vector flanked by direct repeats of the homologous sequence. In some cells, subsequent recombination between the repeats results in excision of the vector and either acquisition of a desired mutation from the vector by the genome or restoration of the genome to wildtype.

In the present methods, after transfer of the gene library cloned in a suitable vector, positive selection is applied for expression of the positive selection marker. Because nonintegrated copies of the suicide vector are rapidly eliminated from cells, this selection enriches for cells that have integrated the vector into the host chromosome. The cells surviving positive selection can then be propagated and subjected to negative selection, or screened for loss of the positive selection marker. Negative selection selects against cells expressing the negative selection marker. Thus, cells that have retained the integrated vector express the negative marker and are selectively eliminated. The cells surviving both rounds of selection are those that initially integrated and then eliminated the vector. These cells are enriched for cells having genes modified by homologous recombination with the vector.

4. Individualized Optimization of Genes

In general, the above methods do not require knowledge of the number of genes to be optimized, their map location or their function. However, in some instances, where this information is available for one or more gene, it can be exploited. For example, if the property to be acquired by evolution is enhanced recombination of cells, one gene likely to be important is recA, even though many other genes, known and unknown, may make additional contributions. In this situation, the recA gene can be evolved, at least in part, separately from other candidate genes. The recA gene can be evolved by any of the methods of recursive recombination described in Section V. Briefly, this approach entails obtaining diverse forms of a recA gene, allowing the forms to recombine, selecting recombinants having improved properties, and subjecting the recombinants to further cycles of recombination and selection. At any point in the individualized improvement of recA, the diverse forms of recA can be pooled with fragments encoding other genes in a library to be used in the general methods described herein. In this way, the library is seeded to contain a higher proportion of variants in a gene known to be important to the property sought to be acquired than would otherwise be the case.

Figure 20B:
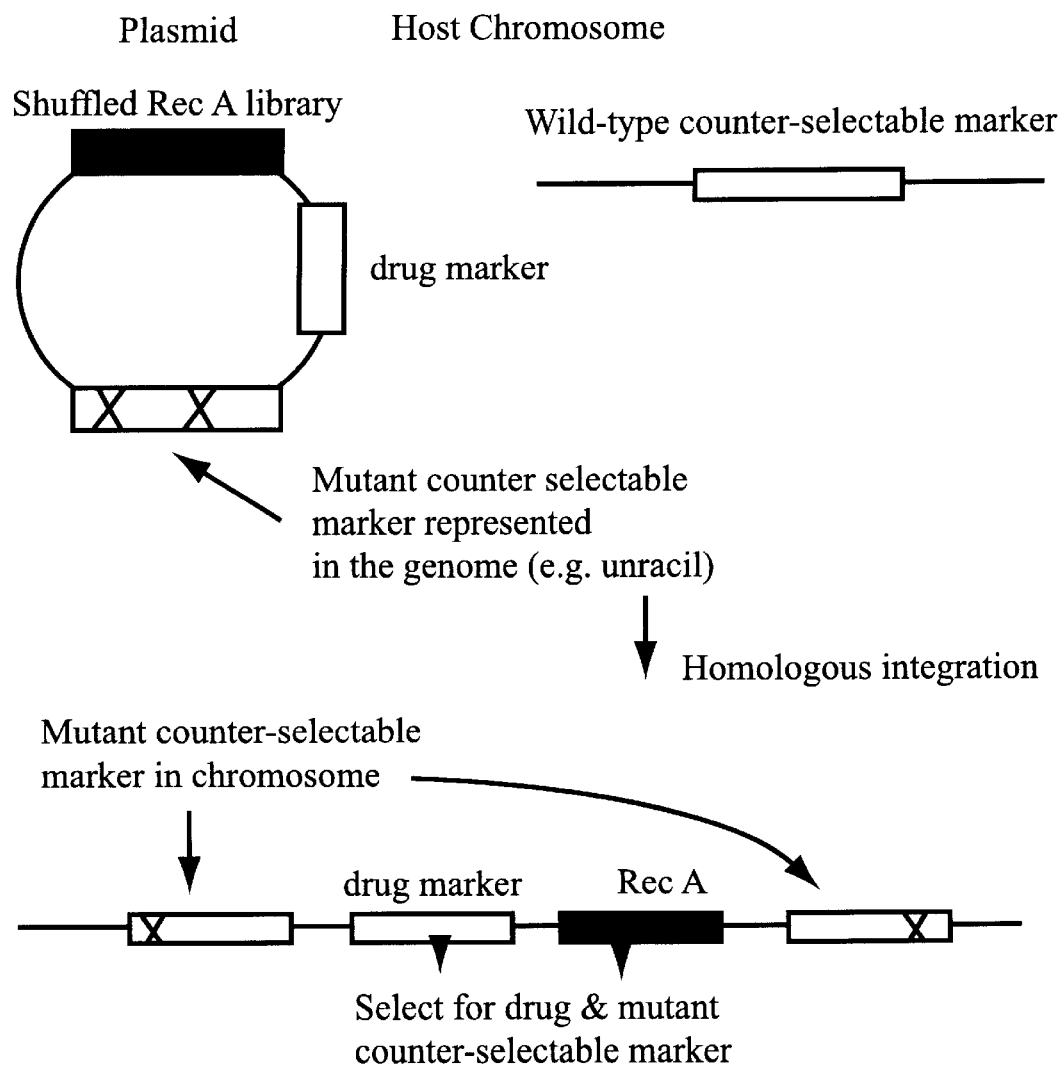

In one example (illustrated in FIG. 20B), a plasmid is constructed carrying a non-functional (mutated) version of a chromosomal gene such as URA3, where the wild-type gene confers sensitivity to a drug (in this case 5-fluoroorotic acid). The plasmid also carries a selectable marker (resistance to another drug such as kanamycin), and a library of recA variants. Transformation of the plasmid into the cell results in expression of the recA variants, some of which will catalyze homologous recombination at an increased rate. Those cells in which homologous recombination occurred are resistant to the selectable drug on the plasmid, and to 5-fluoroorotic acid because of the disruption of the chromosomal copy of this gene. The recA variants which give the highest rates of homologous recombination are the most highly represented in a pool of homologous recombinants. The mutant recA genes can be isolated from this pool by PCR, re-shuffled, cloned back into the plasmid and the process repeated. Other sequences can be inserted in place of recA to evolve other components of the homologous recombination system.

5. Harvesting DNA Substrates for Shuffling

In some shuffling methods, DNA substrates are isolated from natural sources and are not easily manipulated by DNA modifying or polymerizing enzymes due to recalcitrant impurities, which poison enzymatic reactions. Such difficulties can be avoided by processing DNA substrates through a harvesting strain. The harvesting strain is typically a cell type with natural competence and a capacity for homologous recombination between sequences with substantial diversity (e.g., sequences exhibiting only 75% sequence identity). The harvesting strain bears a vector encoding a negative selection marker flanked by two segments respectively complementary to two segments flanking a gene or other region of interest in the DNA from a target organism. The harvesting strain is contacted with fragments of DNA from the target organism. Fragments are taken up by natural competence, or other methods described herein, and a fragment of interest from the target organism recombines with the vector of the harvesting strain causing loss of the negative selection marker. Selection against the negative marker allows isolation of cells that have taken up the fragment of interest. Shuffling can be carried out in the harvester strain or vector can be isolated from the harvester strain for in vitro shuffling or transfer to a different cell type for in vivo shuffling. Alternatively, the vector can be transferred to a different cell type by conjugation, protoplast fusion or electrofusion. An example of a suitable harvester strain is *Acinetobacter calcoaceticus mutS*. Young et al., 97th ASM Meeting Abstracts. This strain is naturally competent and takes up DNA in a nonsequence-specific manner. Also, because of the mutS mutation, this strain is capable of homologous recombinatin of sequences showing only 75% sequence identity.

III. Applications

A. Recombinogenicity

One goal of whole cell evolution is to generate cells having improved capacity for recombination. Such cells are useful for a variety of purposes in molecular genetics including the in vivo formats of recursive sequence recombination described in Section V. Almost thirty genes (e.g., recA, recB, reC, recD, recE, recF, recG, recO, recQ, recR, recT, ruvA, ruvB, ruvC, sbcB, ssb, topA, gyrA and B, lig, polA, uvrD, E, recL, mutD, mutH, mutL, mutT, mutU, helD) and DNA sites (e.g., chi, recN, sbcC) involved in genetic recombination have been identified in *E. coli*, and cognate forms of several of these genes have been found in other organisms (e.g., rad51, rad55-rad57, Dmc1 in yeast (see Kowalczykowski et al., Microbiol. Rev. 58, 401–465 (1994); Kowalczkowski & Zarling, supra) and human homologs of Rad51 and Dmc1 have been identified (see Sandler et al., *Nucl. Acids Res.* 24, 2125–2132 (1996)). At least some of the *E. coli* genes, including recA are functional in mammalian cells, and can be targeted to the nucleus as a fusion with SV40 large T antigen nuclear targeting sequence (Reiss et al., *Proc. Natl. Acad. Sci. USA,* 93, 3094–3098 (1996)). Further, mutations in mismatch repair genes, such as mutL, mutS, mutH, mutT relax homology requirements and allow recombination between more diverged sequences (Rayssiguier et al., *Nature* 342, 396–401 (1989)). The extent of recombination between divergent strains can be enhanced by impairing mismatch repair genes and stimulating SOS genes. Such can be achieved by use of appropriate mutant strains and/or growth under conditions of metabolic stress, which have been found to stimulate SOS and inhibit mismatch repair genes. Vulic et al., *Proc. Natl. Acad. Sci. USA* 94 (1997). In addition, this can be achieved by impairing the products of mismatch repair genes by exposure to selective inhibitors.

Starting substrates for recombination are selected according to the general principles described above. That is, the substrates can be whole genomes or fractions thereof containing recombination genes or sites. Large libraries of essentially random fragments can be seeded with collections of fragments constituting variants of one or more known recombination genes, such as recA. Alternatively, libraries can be formed by mixing variant forms of the various known recombination genes and sites.

The library of fragments is introduced into the recipient cells to be improved and recombination occurs, generating modified cells. The recipient cells preferably contain a marker gene whose expression has been disabled in a manner that can be corrected by recombination. For example, the cells can contain two copies of a marker gene bearing mutations at different sites, which copies can recombine to generate the wildtype gene. A suitable marker gene is green fluorescent protein. A vector can be constructed encoding one copy of GFP having stopcodons near the N-terminus, and another copy of GFP having stopcodons near the C-terminus of the protein. The distance between the stop codons at the respective ends of the molecule is 500 bp and about 25% of recombination events result in active GFP. Expression of GFP in a cell signals that a cell is capable of homologous recombination to recombine in between the stop codons to generate a contiguous coding sequence. By screening for cells expressing GFP, one enriches for cells having the highest capacity for recombination. The same type of screen can be used following subsequent rounds of recombination. However, unless the selection marker used in previous round(s) was present on a suicide vector, subsequent round(s) should employ a second disabled screening marker within a second vector bearing a different origin of replication or a different positive selection marker to vectors used in the previous rounds.

B. Multigenomic Copy Number—Gene Redundancy

The majority of bacterial cells in stationary phase cultures grown in rich media contain two, four or eight genomes. In minimal medium the cells contain one or two genomes. The number of genomes per bacterial cell thus depends on the growth rate of the cell as it enters stationary phase. This is because rapidly growing cells contain multiple replication forks, resulting in several genomes in the cells after termination. The number of genomes is strain dependent, although all strains tested have more than one chromosome in stationary phase. The number of genomes in stationary phase cells decreases with time. This appears to be due to fragmentation and degradation of entire chromosomes, similar to apoptosis in mammalian cells. This fragmentation of genomes in cells containing multiple genome copies results in massive recombination and mutagenesis. Useful mutants may find ways to use energy sources that will allow them to continue growing. Multigenome or gene-redundant cells are much more resistant to mutagenesis and can be improved for a selected trait faster.

Some cell types, such as *Deinococcus radians* (Daly and Minton *J. Bacteriol.* 177, 5495–5505 (1995)) exhibit polyploidy throughout the cell cycle. This cell type is highly radiation resistant due to the presence of many copies of the genome. High frequency recombination between the genomes allows rapid removal of mutations induced by a variety of DNA damaging agents.

A goal of the present methods is to evolve other cell types to have increased genome copy number akin to that of *Deinoccocus radians*. Preferably, the increased copy number is maintained through all or most of its cell cycle in all or most growth conditions. The presence of multiple genome copies in such cells results in a higher frequency of homologous recombination in these cells, both between copies of a gene in different genomes within the cell, and between a genome within the cell and a transfected fragment. The increased frequency of recombination allows the cells to be evolved more quickly to acquire other useful characteristics.

Starting substrates for recombination can be a diverse library of genes only a few of which are relevant to genomic copy number, a focused library formed from variants of gene(s) known or suspected to have a role in genomic copy number or a combination of the two. As a general rule one would expect increased copy number would be achieved by evolution of genes involved in replication and cell septation such that cell septation is inhibited without impairing replication. Genes involved in replication include tus, xerC, xerD, dif, gyrA, gyrB, parE, parC, dif, TerA, TerB, TerC, TerD, TerE, TerF, and genes influencing chromosome partitioning and gene copy number include minD, mukA (tolC), mukB, mukC, mukD, spoOJ, spoIIIE (Wake & Errington, *Annu. Rev. Genet.* 29, 41–67 (1995)). A useful source of substrates is the genome of a cell type such as *Deinoccocus radians* known to have the desired phenotype of multigenomic copy number. As well as, or instead of, the above substrates, fragments encoding protein or antisense RNA inhibitors to genes known to be involved in cell septation can also be used.

In nature, the existence of multiple genomic copies in a cell type would usually not be advantageous due to the greater nutritional requirements needed to maintain this copy number. However, artificial conditions can be devised to select for high copy number. Modified cells having recombinant genomes are grown in rich media (in which conditions, multicopy number should not be a disadvantage) and exposed to a mutagen, such as ultraviolet or gamma irradiation or a chemical mutagen, e.g., mitomycin, nitrous acid, photoactivated psoralens, alone or in combination, which induces DNA breaks amenable to repair by recombination. These conditions select for cells having multicopy number due to the greater efficiency with which mutations can be excised. Modified cells surviving exposure to mutagen are enriched for cells with multiple genome copies. If desired, selected cells can be individually analyzed for genome copy number (e.g., by quantitative hybridization with appropriate controls). Some or all of the collection of cells surviving selection provide the substrates for the next round of recombination. In addition, individual cells can be sorted using a cell sorter for those cells containing more DNA, e.g., using DNA specific fluorescent compounds or sorting for increased size using light dispersion. Eventually cells are evolved that have at least 2, 4, 6, 8 or 10 copies of the genome throughout the cell cycle.

C. Secretion

The protein (or metabolite) secretion pathways of bacterial and eukaryotic cells can be evolved to export desired molecules more efficiently, such as for the manufacturing of protein pharmaceuticals, small molecule drugs or specialty chemicals. Improvements in efficiency are particularly desirable for proteins requiring multisubunit assembly (such as antibodies) or extensive posttranslational modification before secretion.

The efficiency of secretion may depend on a number of genetic sequences including a signal peptide coding sequence, sequences encoding protein(s) that cleave or otherwise recognize the coding sequence, and the coding sequence of the protein being secreted. The latter may affect folding of the protein and the ease with which it can integrate into and traverse membranes. The bacterial secretion pathway in *E. coli* include the SecA, SecB, SecE, SecD and SecF genes. In *Bacillus subtilis,* the major genes are secA, secD, secE, secF, secY, ffh, ftsY together with five signal peptidase genes (sipS, sipT, sipU, sipV and sipW) (Kunst et al, supra). For proteins requiring posttranslational modification, evolution of genes effecting such modification may contribute to improved secretion. Likewise genes with expression products having a role in assembly of multisubunit proteins (e.g., chaperonins) may also contribute to improved secretion.

Selection of substrates for recombination follows the general principles discussed above. In this case, the focused libraries referred to above comprise variants of the known secretion genes. For evolution of procaryotic cells to express eukaryotic proteins, the initial substrates for recombination are often obtained at least in part from eukaryotic sources. Incoming fragments can undergo recombination both with chromosomal DNA in recipient cells and with the screening marker construct present in such cells (see below). The latter form of recombination is important for evolution of the signal coding sequence incorporated in the screening marker construct. Improved secretion can be screened by the inclusion of marker construct in the cells being evolved. The marker construct encodes a marker gene, operably linked to expression sequences, and usually operably linked to a signal peptide coding sequence. The marker gene is sometimes expressed as a fusion protein with a recombinant protein of interest. This approach is useful when one wants to evolve the recombinant protein coding sequence together with secretion genes.

In one variation, the marker gene encodes a product that is toxic to the cell containing the construct unless the product is secreted. Suitable toxin proteins include diphtheria toxin and ricin toxin. Propagation of modified cells bearing such a construct selects for cells that have evolved to improve secretion of the toxin. Alternatively, the marker gene can encode a ligand to a known receptor, and cells bearing the ligand can be detected by FACS using labelled receptor. Optionally, such a ligand can be operably linked to a phospholipid anchoring sequence that binds the ligand to the cell membrane surface following secretion. (See commonly owned, copending Ser. No. 08/309,345). In a further variation, secreted marker protein can be maintained in proximity with the cell secreting it by distributing individual cells into agar drops. This is done, e.g., by droplet formation of a cell suspension. Secreted protein is confined within the agar matrix and can be detected by e.g., FACS. In another variation, a protein of interest is expressed as a fusion protein together with b-lactamase or alkaline phosphatase. These enzymes metabolize commercially available chromogenic substrates (e.g., X-gal), but do so only after secretion into the periplasm. Appearance of colored substrate in a colony of cells therefore indicates capacity to secrete the fusion protein and the intensity of color is related to the efficiency of secretion.

The cells identified by these screening and selection methods have the capacity to secrete increased amounts of protein. This capacity may be attributable to increased secretion and increased expression, or from increased secretion alone.

D. Expression

Cells can also be evolved to acquire increased expression of a recombinant protein. The level of expression is, of course, highly dependent on the construct from which the recombinant protein is expressed and the regulatory sequences, such as the promoter, enhancer(s) and transcription termination site contained therein. Expression can also be affected by a large number of host genes having roles in transcription, posttranslational modification and translation. In addition, host genes involved in synthesis of ribonucleotide and amino acid monomers for transcription and translation may have indirect effects on efficiency of expression. Selection of substrates for recombination follows the general principles discussed above. In this case, focused libraries comprise variants of genes known to have roles in expression. For evolution of procaryotic cells to express eukaryotic proteins, the initial substrates for recombination are often obtained, at least in part, from eukaryotic sources; that is eukaryotic genes encoding proteins such as chaperonins involved in secretion and/assembly of proteins. Incoming fragments can undergo recombination both with chromosomal DNA in recipient cells and with the screening marker construct present in such cells (see below).

Screening for improved expression can be effected by including a reporter construct in the cells being evolved. The reporter construct expresses (and usually secretes) a reporter protein, such as GFP, which is easily detected and nontoxic. The reporter protein can be expressed alone or together with a protein of interest as a fusion protein. If the reporter gene is secreted, the screening effectively selects for cells having either improved secretion or improved expression, or both.

E. Plant Cells

A further application of recursive sequence recombination is the evolution of plant cells, and transgenic plants derived from the same, to acquire resistance to pathogenic diseases (fungi, viruses and bacteria), insects, chemicals (such as salt, selenium, pollutants, pesticides, herbicides, or the like), including, e.g., atrazine or glyphosate, or to modify chemical composition, yield or the like. The substrates for recombination can again be whole genomic libraries, fractions thereof or focused libraries containing variants of gene(s) known or suspected to confer resistance to one of the above agents. Frequently, library fragments are obtained from a different species to the plant being evolved.

The DNA fragments are introduced into plant tissues, cultured plant cells or plant protoplasts by standard methods including electroporation (From et al., *Proc. Natl. Acad. Sci. USA* 82, 5824 (1985), infection by viral vectors such as cauliflower mosaic virus (CaMV) (Hohn et al., *Molecular Biology of Plant Tumors*, (Academic Press, New York, 1982) pp. 549–560; Howell, U.S. Pat. No. 4,407,956), high velocity ballistic penetration by small particles with the nucleic acid either within the matrix of small beads or particles, or on the surface (Klein et al., *Nature* 327, 70–73 (1987)), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al., *Science* 233, 496–498 (1984); Fraley et al., *Proc. Natl. Acad. Sci. USA* 80, 4803 (1983)).

Diversity can also be generated by genetic exchange between plant protoplasts according to the same principles described below for fungal protoplasts. Procedures for formation and fusion of plant protoplasts are described by Takahashi et al., U.S. Pat. No. 4,677,066; Akagi et al., U.S. Pat. No. 5,360,725; Shimamoto et al., U.S. Pat. No. 5,250,433; Cheney et al., U.S. Pat. No. 5,426,040.

After a suitable period of incubation to allow recombination to occur and for expression of recombinant genes, the plant cells are contacted with the agent to which resistance is to be acquired, and surviving plant cells are collected. Some or all of these plant cells can be subject to a further round of recombination and screening. Eventually, plant cells having the required degree of resistance are obtained.

These cells can then be cultured into transgenic plants. Plant regeneration from cultured protoplasts is described in Evans et al., "Protoplast Isolation and Culture," *Handbook of Plant Cell Cultures* 1, 124–176 (MacMillan Publishing Co., New York, 1983); Davey, "Recent Developments in the Culture and Regeneration of Plant Protoplasts," *Protoplasts*, (1983) pp. 12–29, (Birkhauser, Basal 1983); Dale, "Protoplast Culture and Plant Regeneration of Cereals and Other Recalcitrant Crops," *Protoplasts* (1983) pp. 31–41, (Birkhauser, Basel 1983); Binding, "Regeneration of Plants," *Plant Protoplasts*, pp. 21–73, (CRC Press, Boca Raton, 1985).

In a variation of the above method, one or more preliminary rounds of recombination and screening can be performed in bacterial cells according to the same general strategy as described for plant cells. More rapid evolution can be achieved in bacterial cells due to their greater growth rate and the greater efficiency with which DNA can be introduced into such cells. After one or more rounds of recombination/screening, a DNA fragment library is recovered from bacteria and transformed into the plants. The library can either be a complete library or a focused library. A focused library can be produced by amplification from primers specific for plant sequences, particularly plant sequences known or suspected to have a role in conferring resistance.

Example: Concatemeric Assembly of Atrazine-Catabolizing Plasmid

Pseudomonas atrazine catabolizing genes AtzA and AtzB were subcloned from pMD1 (deSouza et al., *Appl. Environ. Microbiol.* 61, 3373–3378 (1995); de Souza et al., *J. Bacteriol.* 178, 4894–4900 (1996)) into pUC18. A 1.9 kb AvaI fragment containing AtzA was end-filled and inserted into an AvaI site of pUC18. A 3.9 kb ClaI fragment containing AtzB was end-filled and cloned into the HincII site of pUC18. AtzA was then excised from pUC18 with EcoRI and BamHI, AzB with BamHI and HindIII, and the two inserts were co-ligated into pUC18 digested with EcoRI and HindIII. The result was a 5.8 kb insert containing AtzA and AtzB in pUC18 (total plasmid size 8.4 kb).

Recursive sequence recombination was performed as follows. The entire 8.4 kb plasmid was treated with DNaseI in 50 mM Tris-Cl pH 7.5, 10 mM $MnCl_2$ and fragments between 500 and 2000 bp were gel purified. The fragments were assembled in a PCR reaction using Tth-XL enzyme and buffer from Perkin Elmer, 2.5 mM MgOAc, 400 µM dNTPs and serial dilutions of DNA fragments. The assembly reaction was performed in an MJ Research "DNA Engine" programmed with the following cycles: 1) 94° C., 20 seconds; 2) 94° C., 15 seconds; 3) 40° C., 30 seconds; 4) 72° C., 30 seconds+2 seconds per cycle; 5) go to step 2, 39 more times; 6) 4° C.

We were unable to amplify the AtzA and AtzB genes from the assembly reaction using the polymerase chain reaction, so instead we purified DNA from the reaction by phenol extraction and ethanol precipitation, then digested the assembled DNA with a restriction enzyme that linearized the plasmid (KpnI: the KpnI site in pUC18 was lost during subcloning, leaving only the KpnI site in AtzA). Linearized plasmid was gel-purified, self-ligated overnight and transformed into *E. coli* strain NM522. (The choice of host strain was important: very little plasmid of poor quality was obtained from a number of other commercially available strains including TG1, DH10B, DH12S.)

Serial dilutions of the transformation reaction were plated onto LB plates containing 50 µg/ml ampicillin, the remainder of the transformation was made 25% in glycerol and frozen at −80° C. Once the transformed cells were titered, the frozen cells were plated at a density of between 200 and 500 on 150 mm diameter plates containing 500 μg/ml atrazine and grown at 37° C.

Atrazine at 500 μg/ml forms an insoluble precipitate. The products of the AtzA and AtzB genes transform atrazine into a soluble product. Cells containing the wild type AtzA and AtzB genes in pUC18 will thus be surrounded by a clear halo where the atrazine has been degraded. The more active the AtzA and AtzB enzymes, the more rapidly a clear halo will form and grow on atrazine-containing plates. Positives were picked as those colonies that most rapidly formed the largest clear zones. The (approximately ) 40 best colonies were picked, pooled, grown in the presence of 50 μg/ml ampicillin and plasmid prepared from them. The entire process (from DNase-treatment to plating on atrazine plates) was repeated 4 times with 2000–4000 colonies/cycle.

A modification was made in the fourth round. Cells were plated on both 500 μg/ml atrazine, and 500 μg/ml of the atrazine analogue terbutylazine, which was undegradable by the wild type AtzA and AtzB genes. Positives were obtained that degraded both compounds. The atrazine chlorohydrolase (product of AtzA gene) was 10–100 fold higher than that produced by the wildtype gene.

F. Plant Genome Shuffling

Plant genome shuffling allows recursive cycles to be used for the introduction and recombination of genes or pathways that confer improved properties to desired plant species. Any plant species, including weeds and wild cultivars, showing a desired trait, such as herbicide resistance, salt tolerance, pest resistance, or temperature tolerance, can be used as the source of DNA that is introduced into the crop or horticultural host plant species.

Genomic DNA prepared from the source plant is fragmented (e.g. by DNaseI, restriction enzymes, or mechanically) and cloned into a vector suitable for making plant genomic libraries, such as pGA482 (An. G., 1995, Methods Mol. Biol. 44:47–58). This vector contains the *A. tumefaciens* left and right borders needed for gene transfer to plant cells and antibiotic markers for selection in *E. coli*, Agrobacterium, and plant cells. A multicloning site is provided for insertion of the genomic fragments. A cos sequence is present for the efficient packaging of DNA into bacteriophage lambda heads for transfection of the primary library into *E. coli*. The vector accepts DNA fragments of 25–40 kb.

The primary library can also be directly electroporated into an *A. tumefaciens* or *A. rhizogenes* strain that is used to infect and transform host plant cells (Main, GD et al., 1995, Methods Mol. Biol. 44:405–412). Alternatively, DNA can be introduced by electroporation or PEG-mediated uptake into protoplasts of the recipient plant species (Bilang et al. (1994) *Plant Mol. Biol Manual,* Kluwer Academic Publishers, A1:1–16) or by particle bombardment of cells or tissues (Christou, ibid, A2:1–15). If necessary, antibiotic markers in the T-DNA region can be eliminated, as long as selection for the trait is possible, so that the final plant products contain no antibiotic genes.

Stably transformed whole cells acquiring the trait are selected on solid or liquid media containing the agent to which the introduced DNA confers resistance or tolerance. If the trait in question cannot be selected for directly, transformed cells can be selected with antibiotics and allowed to form callus or regenerated to whole plants and then screened for the desired property.

The second and further cycles consist of isolating genomic DNA from each transgenic line and introducing it into one or more of the other transgenic lines. In each round, transformed cells are selected or screened for incremental improvement. To speed the process of using multiple cycles of transformation, plant regeneration can be eliminated until the last round. Callus tissue generated from the protoplasts or transformed tissues can serve as a source of genomic DNA and new host cells. After the final round, fertile plants are regenerated and the progeny are selected for homozygosity of the inserted DNAs. Ultimately, a new plant is created that carries multiple inserts which additively or synergistically combine to confer high levels of the desired trait.

In addition, the introduced DNA that confers the desired trait can be traced because it is flanked by known sequences in the vector. Either PCR or plasmid rescue is used to isolate the sequences and characterize them in more detail. Long PCR (Foord, OS and Rose, EA, 1995, *PCR Primer: A Laboratory Manual,* CSHL Press, pp 63–77) of the full 25–40 kb insert is achieved with the proper reagents and techniques using as primers the T-DNA border sequences. If the vector is modified to contain the *E. coli* origin of replication and an antibiotic marker between the T-DNA borders, a rare cutting restriction enzyme, such as NotI or SfiI, that cuts only at the ends of the inserted DNA is used to create fragments containing the source plant DNA that are then self-ligated and transformed into *E. coli* where they replicate as plasmids. The total DNA or subfragment of it that is responsible for the transferred trait can be subjected to in vitro evolution by DNA shuffling. The shuffled library is then introduced into host plant cells and screened for improvement of the trait. In this way, single and multigene traits can be transferred from one species to another and optimized for higher expression or activity leading to whole organism improvement.

Example: Acquisition of Salt Tolerance

Figure 21:
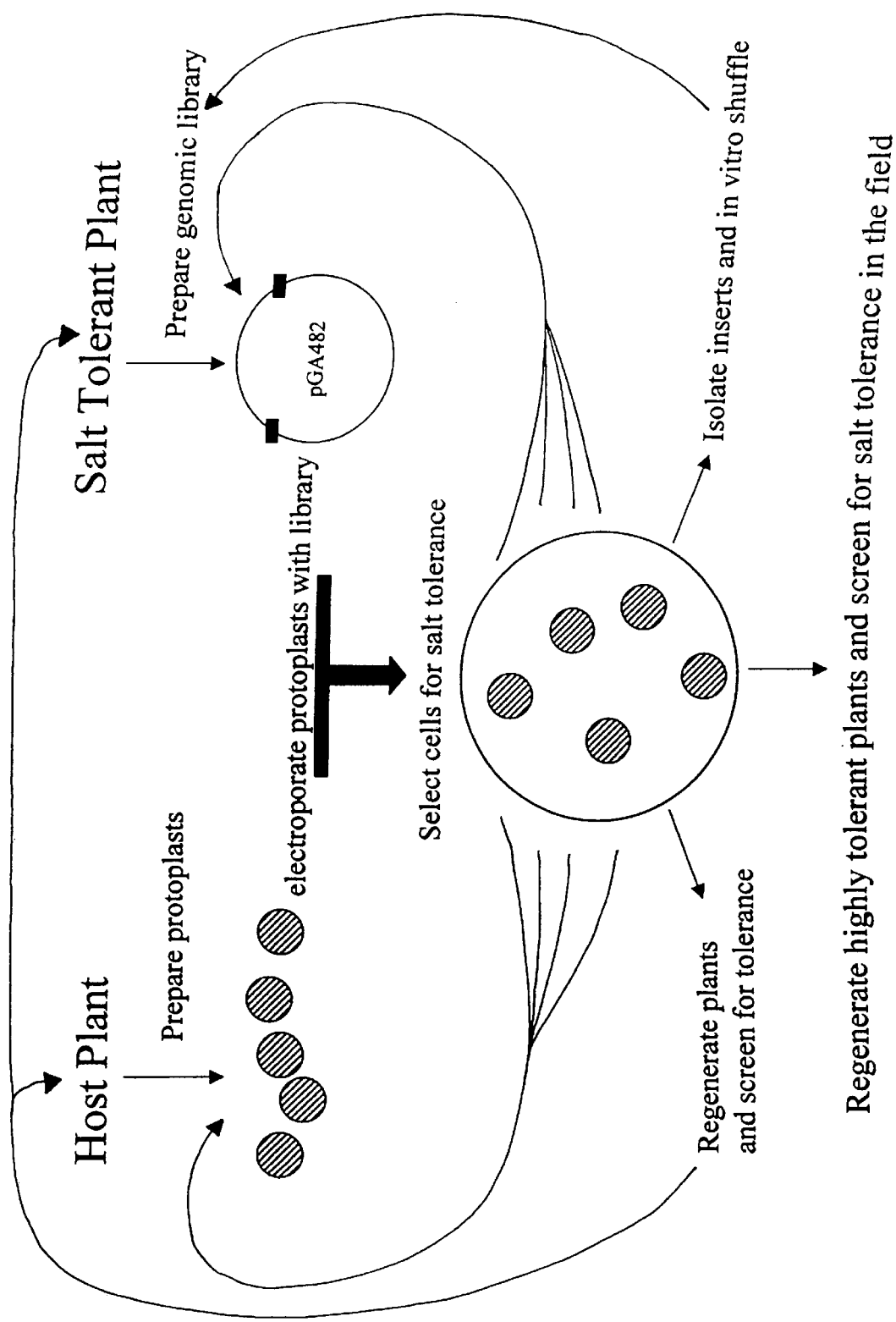
FIG. 21: plant regeneration strategy for regenerating salt-tolerant plants.

As depicted in FIG. 21, DNA from a salt tolerant plant is isolated and used to create a genomic library. Protoplasts made from the recipient species are electroporated with the genomic library. Cells are selected on media with a normally inhibitory level of NaCl. Only the cells with newly acquired salt tolerance will grow into callus tissue. The best lines are chosen and genomic libraries are made from their pooled DNA. These libraries are electroporated into protoplasts made from the first round transformed calli. Again, cells are selected on increased salt concentrations. After the desired level of salt tolerance is achieved, the callus tissue can be induced to regenerate whole plants. Progeny of these plants are typically analyzed for homozygosity of the inserts to ensure stability of the acquired trait. At the indicated steps, plant regeneration or isolation and shuffling of the introduced genes can be added to the overall protocol.

G. Transgenic Animals

1. Transgenic Optimization

One goal of transgenesis is to produce transgenic animals, such as mice, rabbits, sheep, pigs, goats, and cattle, secreting a recombinant protein in the milk. A transgene for this purpose typically comprises in operable linkage a promoter and an enhancer from a milk-protein gene (e.g., α, β, or γ casein, β-lactoglobulin, acid whey protein or α-lactalbumin), a signal sequence, a recombinant protein coding sequence and a transcription termination site. Optionally, a transgene can encode multiple chains of a multichain protein, such as an immunoglobulin, in which case, the two chains are usually individually operably linked to sets of regulatory sequences. Transgenes can be optimized for expression and secretion by recursive sequence recombination. Suitable substrates for recombination include regulatory sequences such as promoters and enhancers from milk-protein genes from different species or individual animals. Cycles of recombination can be performed in vitro or in vivo by any of the formats discussed in Section V. Screening is performed in vivo on cultures of mammary-gland derived cells, such as HCll or MacT, transfected with transgenes and reporter constructs such as those discussed above. After several cycles of recombination and screening, transgenes resulting in the highest levels of expression and secretion are extracted from the mammary gland tissue culture cells and used to transfect embryonic cells, such as zygotes and embryonic stem cells, which are matured into transgenic animals.

2. Whole Animal Optimization

In this approach, libraries of incoming fragments are transformed into embryonic cells, such as ES cells or zygotes. The fragments can be variants of a gene known to confer a desired property, such as growth hormone. Alternatively, the fragments can be partial or complete genomic libraries including many genes.

Fragments are usually introduced into zygotes by microinjection as described by Gordon et al., *Methods Enzymol.* 101, 414 (1984); Hogan et al., *Manipulation of the Mouse Embryo: A Laboratory Manual* (C.S.H.L. N.Y., 1986) (mouse embryo); and Hammer et al., *Nature* 315, 680 (1985) (rabbit and porcine embryos); Gandolfi et al., *J. Reprod. Fert.* 81, 23–28 (1987); Rexroad et al., *J. Anim. Sci.* 66, 947–953 (1988) (ovine embryos) and Eyestone et al., *J. Reprod. Fert.* 85, 715–720 (1989); Camous et al.,*J. Reprod. Fert.* 72, 779–785 (1984); and Heyman et al., *Theriogenology* 27, 5968 (1987) (bovine embryos) by reference in their entirety for all purposes). Zygotes are then matured and introduced into recipient female animals which gestate the embryo and give birth to a transgenic offspring.

Alternatively, transgenes can be introduced into embryonic stem cells (ES). These cells are obtained from preimplantation embryos cultured in vitro. Bradley et al., *Nature* 309, 255–258 (1984). Transgenes can be introduced into such cells by electroporation or microinjection. Transformed ES cells are combined with blastocysts from a nonhuman animal. The ES cells colonize the embryo and in some embryos form the germ line of the resulting chimeric animal. See Jaenisch, *Science,* 240, 1468–1474 (1988).

Regardless whether zygotes or ES are used, screening is performed on whole animals for a desired property, such as increased size and/or growth rate. DNA is extracted from animals having evolved toward acquisition of the desired property. This DNA is then used to transfect further embryonic cells. These cells can also be obtained from animals that have acquired toward the desired property in a split and pool approach. That is, DNA from one subset of such animals is transformed into embryonic cells prepared from another subset of the animals. Alternatively, the DNA from animals that have evolved toward acquisition of the desired property can be transfected into fresh embryonic cells. In either alternative, transfected cells are matured into transgenic animals, and the animals subjected to a further round of screening for the desired property.

Figure 4:
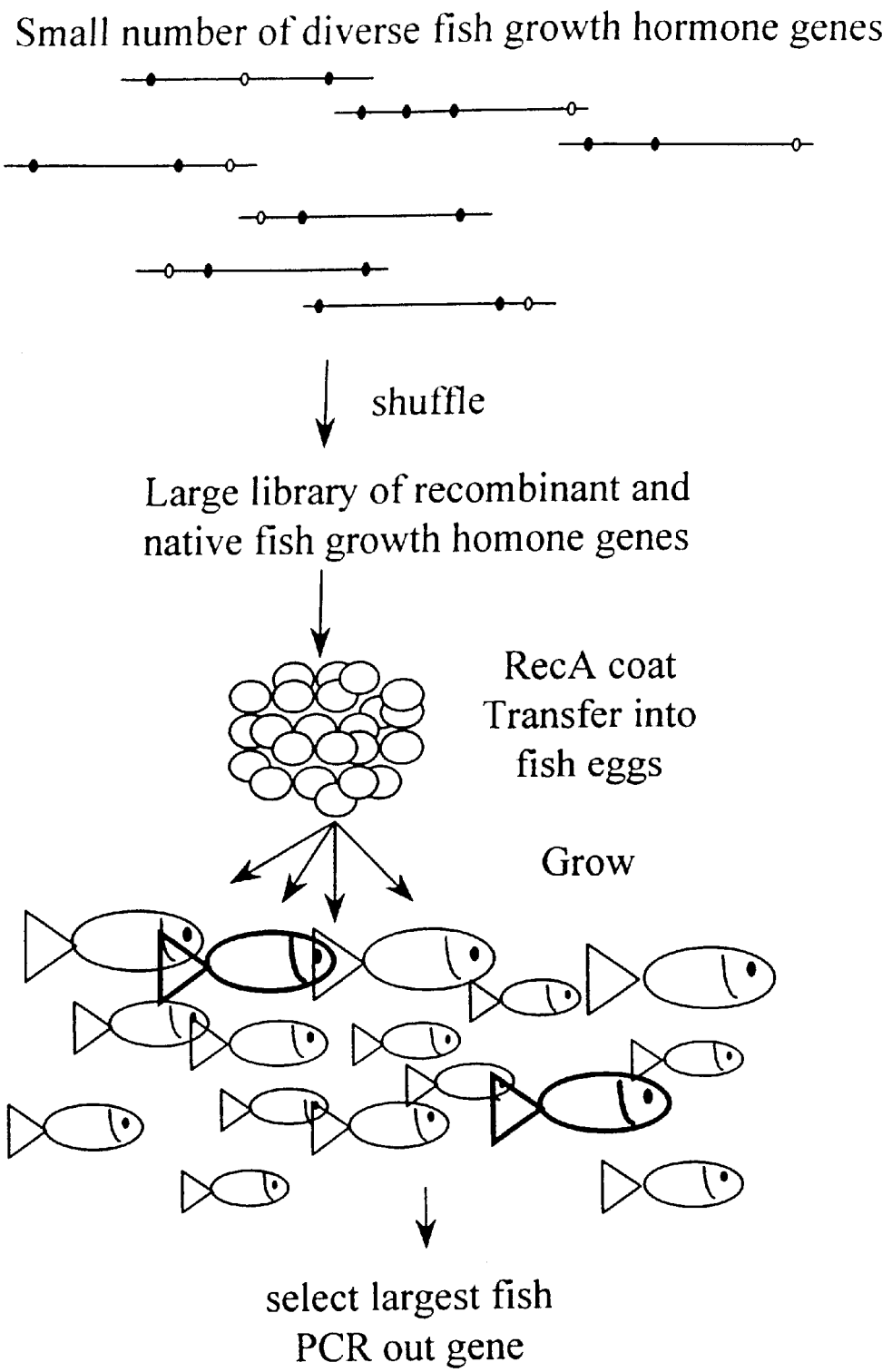
FIG. 4: Scheme for evolving growth hormone genes to produce larger fish.

FIG. 4 shows the application of this approach for evolving fish toward a larger size. Initially, a library is prepared of variants of a growth hormone gene. The variants can be natural or induced. The library is coated with recA protein and transfected into fertilized fish eggs. The fish eggs then mature into fish of different sizes. The growth hormone gene fragment of genomic DNA from large fish is then amplified by PCR and used in the next round of recombination. Alternatively, fish α-IFN is evolved to enhance resistance to viral infections as described below.

3. Evolution of Improved Hormones for Expression in Transgenic Animals (e.g., Fish) to Create Animals with Improved Traits Hormones and cytokines are key regulators of size, body weight, viral resistance and many other commercially important traits. DNA shuffling is used to rapidly evolve the genes for these proteins using in vitro assays. This was demonstrated with the evolution of the human alpha interferon genes to have potent antiviral activity on murine cells. Large improvements in activity were achieved in two cycles of family shuffling of the human IFN genes.

In general, a method of increasing resistance to virus infection in cells can be performed by first introducing a shuffled library comprising at least one shuffled interferon gene into animal cells to create an initial library of animal cells or animals. The initial library is then challenged with the virus. Animal cells or animals are selected from the initial library which are resistant to the virus and a plurality of transgenes from a plurality of animal cells or animals which are resistant to the virus are recovered. The plurality of transgenes is recovered to produce an evolved library of animal cells or animals which is again challenged with the virus. Cells or animals are selected from the evolved library the which are resistant to the virus.

For example, genes evolved with in vitro assays are introduced into the germplasm of animals or plants to create improved strains. One limitation of this procedure is that in vitro assays are often only crude predictors of in vivo activity. However, with improving methods for the production of transgenic plants and animals, one can now marry whole organism breeding with molecular breeding. The approach is to introduce shuffled libraries of hormone genes into the species of interest. This can be done with a single gene per transgenic or with pools of genes per transgenic. Progeny are then screened for the phenotype of interest. In this case, shuffled libraries of interferon genes (alpha IFN for example) are introduced into transgenic fish. The library of transgenic fish are challenged with a virus. The most resistant fish are identified (i.e. either survivors of a lethal challenge; or those that are deemed most 'healthy' after the challenge). The IFN transgenes are recovered by PCR and shuffled in either a poolwise or a pairwise fashion. This generates an evolved library of IFN genes. A second library of transgenic fish is created and the process is repeated. In this way, IFN is evolved for improved antiviral activity in a whole organism assay.

This procedure is general and can be applied to any trait that is affected by a gene or gene family of interest and which can be quantitatively measured.

Fish interferon sequence data is available for the Japanese flatfish (*Paralichthys olivaceus*) as mRNA sequence (Tamai et al. (1993) "Cloning and expression of flatfish (*Paralichthys olivaceus*) interferon cDNA." *Biochem. Biophys. Acta* 1174, 182–186; see also, Tami et al. (1993) "Purification and characterization of interferon-like antiviral protein derived from flatfish (*Paralichthys olivaceus*) lymphocytes immortalized by oncogenes." *Cytotechnology* 1993; 1 1 (2):121–131). This sequence can be used to clone out IFN genes from this species. This sequence can also be used as a probe to clone homologous interferons from additional species of fish. As well, additional sequence information can be utilized to clone out more species of fish interferons. Once a library of interferons has been cloned, these can be family shuffled to generate a library of variants.

A Protein sequence of flatfish interferon is:
MIRSTNSNKS DILMNCHHLIIR YDDNSAPSGGSL
FRKMIMLLKL LKLITFGQLRVV ELFVKSNTSKTS

TVLSIDGSNLISL LDAPKDILDKPSCNSF QLD-LLLASSAWTLLT ARLLNYPYPA VLLSAGVASVV-LVQVP.

In one embodiment, BHK-21 (A fibroblast cell line from hamster) can be transfected with the shuffled IFN-expression plasmids. Active recombinant IFN is produced and then purified by WGA agarose affinity chromatography (Tamai, et al. 1993 Biochim Ciophys Acta. supra). The antiviral activity of IFN can be measured on fish cells challenged by rhabdoviurs. Tami et al. (1993) "Purification and characterization of interferon-like antiviral protein derived from flatfish (*Paralichthys olivaceus*) lymphocytes immortalized by oncogenes." *Cytotechnology* 1993; 1 1 (2):121–131).

H. Rapid Evolution as a Predictive Tool

Recursive sequence recombination can be used to simulate natural evolution of pathogenic microorganisms in response to exposure to a drug under test. Using recursive sequence recombination, evolution proceeds at a faster rate than in natural evolution. One measure of the rate of evolution is the number of cycles of recombination and screening required until the microorganism acquires a defined level of resistance to the drug. The information from this analysis is of value in comparing the relative merits of different drugs and in particular, in predicting their long term efficacy on repeated administration.

The pathogenic microorganisms used in this analysis include the bacteria that are a common source of human infections, such as *chlamydia,* rickettsial bacteria, *mycobacteria, staphylococci, streptocci, pneumonococci, meningococci* and *conococci, klebsiella, proteus, serratia, pseudomonas, legionella, diphtheria, salmonella, bacilli, cholera, tetanus, botulism, anthrax, plague, leptospirosis,* and Lymes disease bacteria. Evolution is effected by transforming an isolate of bacteria that is sensitive to a drug under test with a library of DNA fragments. The fragments can be a mutated version of the genome of the bacteria being evolved. If the target of the drug is a known protein or nucleic acid, a focused library containing variants of the corresponding gene can be used. Alternatively, the library can come from other kinds of bacteria, especially bacteria typically found inhabiting human tissues, thereby simulating the source material available for recombination in vivo. The library can also come from bacteria known to be resistant to the drug. After transformation and propagation of bacteria for an appropriate period to allow for recombination to occur and recombinant genes to be expressed, the bacteria are screened by exposing them to the drug under test and then collecting survivors. Surviving bacteria are subject to further rounds of recombination. The subsequent round can be effected by a split and pool approach in which DNA from one subset of surviving bacteria is introduced into a second subset of bacteria. Alternatively, a fresh library of DNA fragments can be introduced into surviving bacteria. Subsequent round(s) of selection can be performed at increasing concentrations of drug, thereby increasing the stringency of selection.

A similar strategy can be used to simulate viral acquisition of drug resistance. The object is to identify drugs for which resistance can be acquired only slowly, if at all. The viruses to be evolved are those that cause infections in humans for which at least modestly effective drugs are available. Substrates for recombination can come from induced mutants, natural variants of the same viral strain or different viruses. If the target of the drug is known (e.g., nucleotide analogs which inhibit the reverse transcriptase gene of HIV), focused libraries containing variants of the target gene can be produced. Recombination of a viral genome with a library of fragments is usually performed in vitro. However, in situations in which the library of fragments constitutes variants of viral genomes or fragments that can be encompassed in such genomes, recombination can also be performed in vivo, e.g., by transfecting cells with multiple substrate copies (see Section V). For screening, recombinant viral genomes are introduced into host cells susceptible to infection by the virus and the cells are exposed to a drug effective against the virus (initially at low concentration). The cells can be spun to remove any noninfected virus. After a period of infection, progeny viruses can be collected from the culture medium, the progeny viruses being enriched for viruses that have acquired at least partial resistance to the drug. Alternatively, virally infected cells can be plated in a soft agar lawn and resistant viruses isolated from plaques. Plaque size provides some indication of the degree of viral resistance.

Progeny viruses surviving screening are subject to additional rounds of recombination and screening at increased stringency until a predetermined level of drug resistance has been acquired. The predetermined level of drug resistance may reflect the maximum dosage of a drug practical to administer to a patient without intolerable side effects. The analysis is particularly valuable for investigating acquisition of resistance to various combination of drugs, such as the growing list of approved anti-HIV drugs (e.g., AZT, ddI, ddC, d4T, TIBO 82150, nevaripine, 3TC, crixivan and ritonavir).

I. Fermentation

The fermentation of microorganisms for the production of natural products is the oldest and most sophisticated application of biocatalysis. Industrial microorganisms effect the multistep conversion of renewable feedstocks to high value chemical products in a single reactor and in so doing catalyze a multi-billion dollar industry. Fermentation products range from fine and commodity chemicals such as ethanol, lactic acid, amino acids and vitamins, to high value small molecule pharmaceuticals, protein pharmaceuticals, and industrial enzymes. See, e.g., McCoy (1998) *C&EN* 13–19) for an introduction to biocatalysis.

Success in bringing these products to market and success in competing in the market depends on continuous improvement of the whole cell biocatalysts. Improvements include increased yield of desired products, removal of unwanted co-metabolites, improved utilization of inexpensive carbon and nitrogen sources, and adaptation to fermenter conditions, increased production of a primary metabolite, increased production of a secondary metabolite, increased tolerance to acidic conditions, increased tolerance to basic conditions, increased tolerance to organic solvents, increased tolerance to high salt conditions and increased tolerance to high or low temperatures. Shortcomings in any of these areas can result in high manufacturing costs, inability to capture or maintain market share, and failure of bringing promising products to market. For this reason, the fermentation industry invests significant financial and personnel resources in the improvement of production strains.

Current strategies for strain improvement rely on the empirical and iterative modification of fermenter conditions and genetic manipulation of the producing organism. While advances in the molecular biology of established industrial organisms have been made, rational metabolic engineering is information intensive and is not broadly applicable to less characterized industrial strains. The most widely practiced strategy for strain improvement employs random mutagenesis of the producing strain and screening for mutants having improved properties. For mature strains, those subjected to many rounds of improvement, these efforts routinely provide a 10% increase in product titre per year. Although effective, this classic strategy is slow, laborious, and expensive. Technological advances in this area are aimed at automation and increasing sample screening throughput in hopes of reducing the cost of strain improvement. However, the real technical barrier resides in the intrinsic limitation of single mutations to effect significant strain improvement. The methods herein overcome this limitation and provide access to multiple useful mutations per cycle which can be used to complement automation technologies and catalyze strain improvement processes.

The methods herein allow biocatalysts to be improved at a faster pace than conventional methods. Whole genome shuffling can at least double the rate of strain improvement for microorganisms used in fermentation as compared to traditional methods. This provides for a relative decrease in the cost of fermentation processes. New products can enter the market sooner, producers can increase profits as well as market share, and consumers gain access to more products of higher quality and at lower prices. Further, increased efficiency of production processes translates to less waste production and more frugal use of resources. Whole genome shuffling provides a means of accumulating multiple useful mutation per cycle and thus eliminate the inherent limitation of current strain improvement programs (SIPs).

DNA shuffling provides recursive mutagenesis, recombination, and selection of DNA sequences. A key difference between DNA shuffling-mediated recombination and natural sexual recombination is that DNA shuffling effects both the pairwise (two parents) and the poolwise (multiple parents) recombination of parent molecules, as described supra. Natural recombination is more conservative and is limited to pairwise recombination. In nature, pairwise recombination provides stability within a population by preventing large leaps in sequences or genomic structure that can result from poolwise recombination. However, for the purposes of directed evolution, poolwise recombination is appealing since the beneficial mutations of multiple parents can be combined during a single cross to produce a superior offspring. Poolwise recombination is analogous to the crossbreeding of inbred strains in classic strain improvement, except that the crosses occur between many strains at once. In essence, poolwise recombination is a sequence of events that effects the recombination of a population of nucleic acid sequences that results in the generation of new nucleic acids that contains genetic information from more than two of the original nucleic acids.

There are a few general methods for effecting efficient recombination in prokaryotes. Bacteria have no known sexual cycle per se, but there are natural mechanisms by which the genomes of these organisms undergo recombination. These mechanisms include natural competence, phage-mediated transduction, and cell-cell conjugation. Bacteria that are naturally competent are capable of efficiently taking up naked DNA from the environment. If homologous, this DNA undergoes recombination with the genome of the cell, resulting in genetic exchange. *Bacillus subtilis*, the primary production organism of the enzyme industry, is known for the efficiency with which it carries out this process.

In generalized transduction, a bacteriophage mediates genetic exchange. A transducing phage will often package headfulls of the host genome. These phage can infect a new host and deliver a fragment of the former host genome which is frequently integrated via homologous recombination. Cells can also transfer DNA between themselves by conjugation. Cells containing the appropriate mating factors transfer episomes as well as entire chromosomes to an appropriate acceptor cell where it can recombine with the acceptor genome. Conjugation resembles sexual recombination for microbes and can be intraspecific, interspecific, and intergeneric. For example, an efficient means of transforming Streptomyces sp., a genera responsible for producing many commercial antibiotics, is by the conjugal transfer of plasmids from *Echerichia coli*.

For many industrial microorganisms, knowledge of competence, transducing phage, or fertility factors is lacking. Protoplast fusion has been developed as a versatile and general alternative to these natural methods of recombination. Protoplasts are prepared by removing the cell wall by treating cells with lytic enzymes in the presence of osmotic stabilizers. In the presence of a fusogenic agent, such as polyethylene glycol (PEG), protoplasts are induced to fuse and form transient hybrids or "fusants." During this hybrid state, genetic recombination occurs at high frequency allowing the genomes to reassort. The final crucial step is the successful segregation and regeneration of viable cells from the fused protoplasts. Protoplast fusion can be intraspecific, interspecific, and intergeneric and has been applied to both prokaryotes and eukaryotes. In addition, it is possible to fuse more than two cells, thus providing a mechanism for effecting poolwise recombination. While no fertility factors, transducing phages or competency development is needed for protoplast fusion, a method for the formation, fusing, and regeneration of protoplasts is typically optimized for each organism. Protoplast fusion as applied to poolwise recombination is described in more detail, supra.

One key to SIP is having an assay that can be dependably used to identify a few mutants out of thousands that have subtle increases in product yield. The limiting factor in many assay formats is the uniformity of cell growth. This variation is the source of baseline variability in subsequent assays. Inoculum size and culture environment (temperature/humidity) are sources of cell growth variation. Automation of all aspects of establishing initial cultures and state-of-the-art temperature and humidity controlled incubators are useful in reducing variability.

Figure 28:
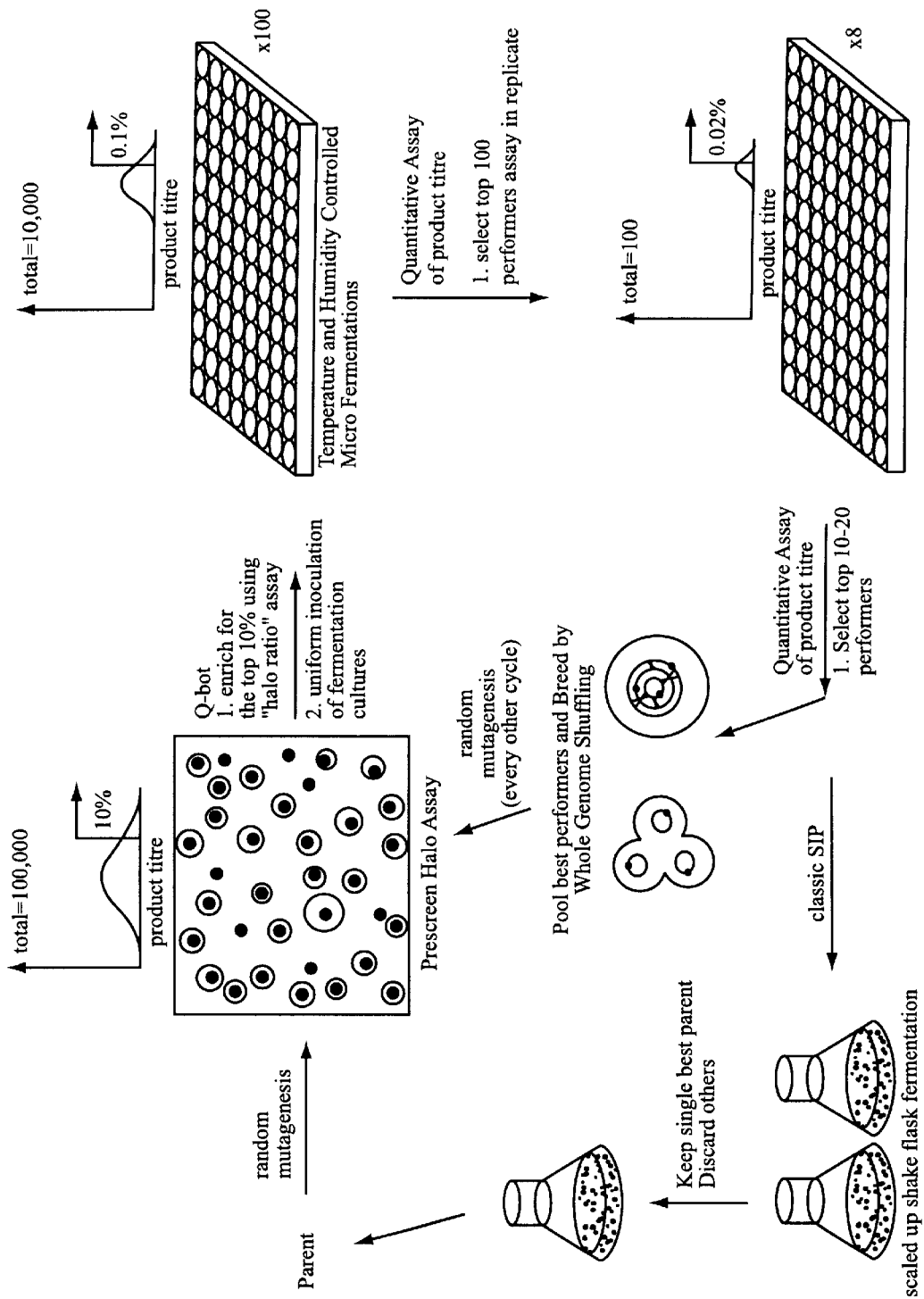
FIG. 28: Schematic of halo assay and integrated system.

Mutant cells or spores are separated on solid media to produce individual sporulating colonies. Using an automated colony picker (Q-bot, Genetix, U.K.), colonies are identified, picked, and 10,000 different mutants inoculated into 96 well microtitre dishes containing two 3 mm glass balls/well. The Q-bot does not pick an entire colony but rather inserts a pin through the center of the colony and exits with a small sampling of cells (or mycelia) and spores. The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls act to promote uniform aeration of cells and the dispersal of mycelial fragments similar to the blades of a fermenter. An embodiment of this procedure is further illustrated in FIG. 28, including an integrated system for the assay.

(a.) Prescreen

The ability to detect a subtle increase in the performance of a mutant over that of a parent strain relies on the sensitivity of the assay. The chance of finding the organisms having an improvement is increased by the number of individual mutants that can be screened by the assay. To increase the chances of identifying a pool of sufficient size a prescreen that increases the number of mutants processed by 10-fold can be used. The goal of the primary screen will be to quickly identify mutants having equal or better product titres than the parent strain(s) and to move only these mutants forward to liquid cell culture.

The primary screen is an agar plate screen is analyzed by the Q-bot colony picker. Although assays can be fundamentally different, many result, e.g., in the production of colony halos. For example, antibiotic production is assayed on plates using an overlay of a sensitive indicator strain, such as *B. subtilis*. Antibiotic production is typically assayed as a zone of clearing (inhibited growth of the indicator organism) around the producing organism. Similarly, enzyme production can be assayed on plates containing the enzyme substrate, with activity being detected as a zone of substrate modification around the producing colony. Product titre is correlated with the ratio of halo area to colony area.

The Q-bot or other automated system is instructed to only pick colonies having a halo ratio in the top 10% of the population i.e. 10,000 mutants from the 100,000 entering the plate prescreen. This increases the number of improved clones in the secondary assay and eliminates the wasted effort of screening knock-out and low producers. This improves the "hit rate" of the secondary assay.

IV. Promotion of Genetic Exchange (1) General

Some methods of the invention effect recombination of cellular DNA by propagating cells under conditions inducing exchange of DNA between cells. DNA exchange can be promoted by generally applicable methods such as electroporation, biolistics, cell fusion, or in some instances, by conjugation, transduction, or agrobacterium mediated transfer and meiosis. For example, Agrobacterium can transform *S. cerevisiae* with T-DNA, which is incorporated into the yeast genome by both homologous recombination and a gap repair mechanism. (Piers et al., *Proc. Natl. Acad. Sci. USA* 93(4), 1613–8 (1996)).

In some methods, initial diversity between cells (i.e., before genome exchange) is induced by chemical or radiation-induced mutagenesis of a progenitor cell type, optionally followed by screening for a desired phenotype. In other methods, diversity is natural as where cells are obtained from different individuals, strains or species.

In some shuffling methods, induced exchange of DNA is used as the sole means of effecting recombination in each cycle of recombination. In other methods, induced exchange is used in combination with natural sexual recombination of an organism. In other methods, induced exchange and/or natural sexual recombination are used in combination with the introduction of a fragment library. Such a fragment library can be a whole genome, a whole chromosome, a group of functionally or genetically linked genes, a plasmid, a cosmid, a mitochondrial genome, a viral genome (replicative and nonreplicative) or specific or random fragments of any of these. The DNA can be linked to a vector or can be in free form. Some vectors contain sequences promoting homologous or nonhomologous recombination with the host genome. Some fragments contain double stranded breaks such as caused by shearing with glass beads, sonication, or chemical or enzymatic fragmentation, to stimulate recombination.

In each case, DNA can be exchanged between cells after which it can undergo recombination to form hybrid genomes. Cells bearing hybrid genomes are screened for a desired phenotype, and cells having this phenotype are isolated. These cells form the starting materials for the next cycle of recombination in a recursive recombination/ selection scheme.

One means of promoting exchange of DNA between cells is by fusion of cells, such as by protoplast fusion. A protoplast results from the removal from a cell of its cell wall, leaving a membrane-bound cell that depends on an isotonic or hypertonic medium for maintaining its integrity. If the cell wall is partially removed, the resulting cell is strictly referred to as a spheroplast and if it is completely removed, as a protoplast. However, here the term protoplast includes spheroplasts unless otherwise indicated.

Protoplast fusion is described by Shaffner et al., *Proc. Natl. Acad. Sci. USA* 77, 2163 (1980) and other exemplary procedures are described by Yoakum et al., U.S. Pat. No. 4,608,339, Takahashi et al., U.S. Pat. No. 4,677,066 and Sambrooke et al., at Ch. 16. Protoplast fusion has been reported between strains, species, and genera (e.g., yeast and chicken erythrocyte).

Protoplasts can be prepared for both bacterial and eukaryotic cells, including mammalian cells and plant cells, by several means including chemical treatment to strip cell walls. For example, cell walls can be stripped by digestion with a cell wall degrading enzyme such as lysozyme in a 10–20% sucrose, 50 mM EDTA buffer. Conversion of cells to spherical protoplasts can be monitored by phase-contrast microscopy. Protoplasts can also be prepared by propagation of cells in media supplemented with an inhibitor of cell wall synthesis, or use of mutant strains lacking capacity for cell wall formation. Preferably, eukaryotic cells are synchronized in G1 phase by arrest with inhibitors such as α-factor, *K. lactis* killer toxin, leflonamide and adenylate cyclase inhibitors. Optionally, some but not all, protoplasts to be fused can be killed and/or have their DNA fragmented by treatment with ultraviolet irradiation, hydroxylamine or cupferon (Reeves et al., *FEMS Microbiol. Lett.* 99, 193–198 (1992)). In this situation, killed protoplasts are referred to as donors, and viable protoplasts as acceptors. Using dead donors cells can be advantageous in subsequently recognizing fused cells with hybrid genomes, as described below. Further, breaking up DNA in donor cells is advantageous for stimulating recombination with acceptor DNA. Optionally, acceptor and/or fused cells can also be briefly, but nonlethally, exposed to uv irradiation further to stimulate recombination.

Once formed, protoplasts can be stabilized in a variety of osmolytes and compounds such as sodium chloride, potassium chloride, sodium phosphate, potassium phosphate, sucrose, sorbitol in the presence of DTT. The combination of buffer, pH, reducing agent, and osmotic stabilizer can be optimized for different cell types. Protoplasts can be induced to fuse by treatment with a chemical such as PEG, calcium chloride or calcium propionate or electrofusion (Tsoneva, *Acta Microbiologica Bulgaria* 24, 53–59 (1989)). A method of cell fusion employing electric fields has also been described. See Chang U.S. Pat. No. 4,970,154. Conditions can be optimized for different strains.

The fused cells are heterokaryons containing genomes from two component protoplasts. Fused cells can be enriched from unfused parental cells by sucrose gradient sedimentation or cell sorting. The two nuclei in the heterokaryons can fuse (karyogamy) and homologous recombination can occur between the genomes. The chromosomes can also segregate asymmetrically resulting in regenerated protoplasts that have lost or gained whole chromosomes. The frequency of recombination can be increased by treatment with ultraviolet irradiation or by use of strains overexpressing recA or other recombination genes, or the yeast rad genes, and cognate variants thereof in other species, or by the inhibition of gene products of MutS, MutL, or MutD.

Overexpression can be either the result of introduction of exogenous recombination genes or the result of selecting strains, which as a result of natural variation or induced mutation, overexpress endogenous recombination genes. The fused protoplasts are propagated under conditions allowing regeneration of cell walls, recombination and segregation of recombinant genomes into progeny cells from the heterokaryon and expression of recombinant genes. After, or occasionally before or during, recovery of fused cells, the cells are screened or selected for evolution toward a desired property.

Thereafter a subsequent round of recombination can be performed by preparing protoplasts from the cells surviving selection/screening in a previous round. The protoplasts are fused, recombination occurs in fused protoplasts, and cells are regenerated from the fused protoplasts. Protoplasts, regenerated or regenerating cells are subject to further selection or screening.

Alternatively, a subsequent round of recombination can be performed on a split pool basis as described above. That is, a first subpopulation of cells surviving selection/screening from a previous round are used for protoplast formation. A second subpopulation of cells surviving selection/screening from a previous round are used as a source for DNA library preparation. The DNA library from the second subpopulation of cells is then transformed into the protoplasts from the first subpopulation. The library undergoes recombination with the genomes of the protoplasts to form recombinant genomes. Cells are regenerated from protoplasts, and selection/screening is applied to regenerating or regenerated cells. In a further variation, a fresh library of nucleic acid fragments is introduced into protoplasts surviving selection/screening from a previous round.

Figure 5:
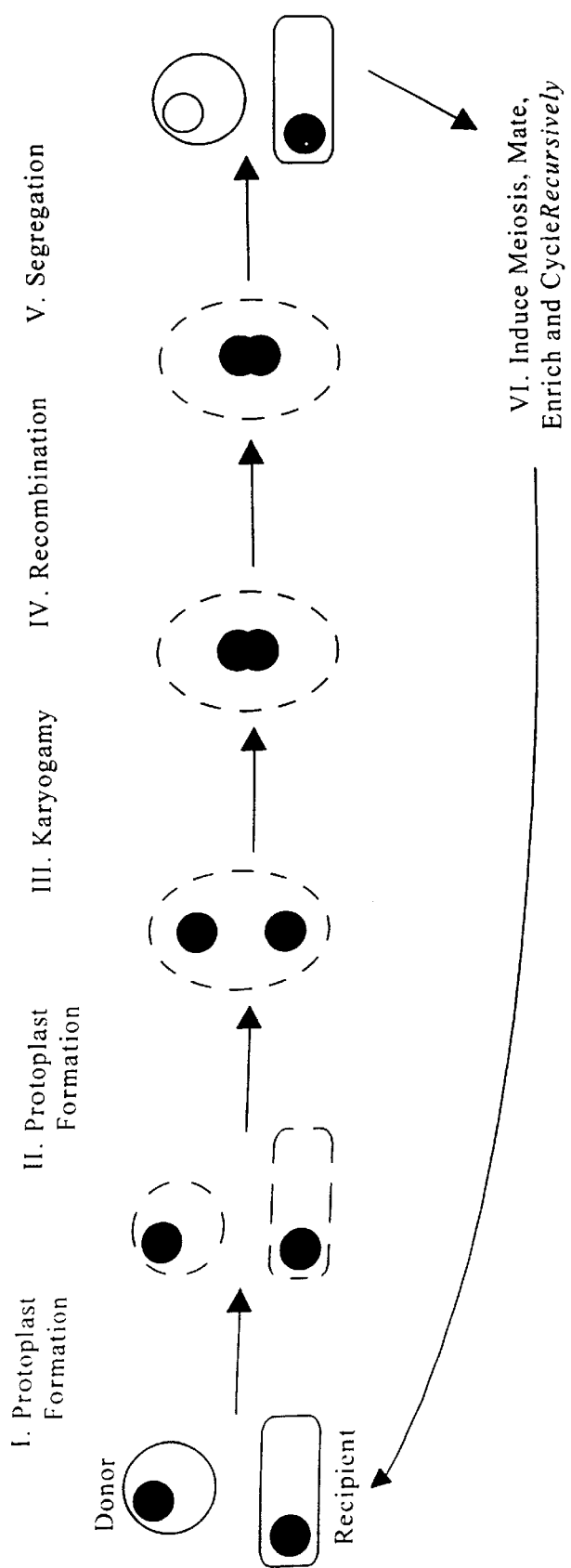
FIG. 5: Scheme for shuffling prokaryotes by protoplast fusion.

An exemplary format for shuffling using protoplast fusion is shown in FIG. 5. The figure shows the following steps: protoplast formation of donor and recipient strains, heterokaryon formation, karyogamy, recombination, and segregation of recombinant genomes into separate cells. Optionally, the recombinant genomes, if having a sexual cycle, can undergo further recombination with each other as a result of meiosis and mating. Cells are then screened or selected for a desired property. Cells surviving selection/screening are then used as the starting materials in a further cycle of protoplasting.

2. Selection For Hybrid Strains

The invention provides selection strategies to identify cells formed by fusion of components from parental cells from two or more distinct subpopulations. Selection for hybrid cells is usually performed before selecting or screening for cells that have evolved (as a result of genetic exchange) to acquisition of a desired property. A basic premise of most such selection schemes is that two initial subpopulations have two distinct markers. Cells with hybrid genomes can thus be identified by selection for both markers.

In one such scheme, at least one subpopulation of cells bears a selective marker attached to its cell membrane. Examples of suitable membrane markers include biotin, fluorescein and rhodamine. The markers can be linked to amide or thiol groups or through more specific derivatization chemistries, such as iodo-acetates, iodoacetamides, maleimides. For example, a marker can be attached as follows. Cells or protoplasts are washed with a buffer (e.g., PBS), which does not interfere with the chemical coupling of a chemically active ligand which reacts with amino groups of lysines or N-terminal aminogroups of membrane proteins. The ligand is either amine reactive itself (e.g., isothiocyanates, succinimidyl esters, sulfonyl chlorides) or is activated by a heterobifunctional linker (e.g. EMCS, SIAB, SPDP, SMB) to become amine reactive. The ligand is a molecule which is easily bound by protein derivatized magnetic beads or other capturing solid supports. For example, the ligand can be succinimidyl activated biotin (Molecular probes: B-1606, B-2603, S-1515, S-1582). This linker is reacted with aminogroups of proteins residing in and on the surface of a cell. The cells are then washed to remove excess labelling agent before contacting with cells from the second subpopulation bearing a second selective marker.

The second subpopulation of cells can also bear a membrane marker, albeit a different membrane marker from the first subpopulation. Alternatively, the second subpopulation can bear a genetic marker. The genetic marker can confer a selective property such as drug resistance or a screenable property, such as expression of green fluorescent protein.

After fusion of first and second subpopulations of cells and recovery, cells are screened or selected for the presence of markers on both parental subpopulations. For example, fusants are enriched for one population by adsorbtion to specific beads and these are then sorted by FACS for those expressing a marker. Cells surviving both screens for both markers are those having undergone protoplast fusion, and are therefore more likely to have recombined genomes. Usually, the markers are screened or selected separately. Membrane-bound markers, such as biotin, can be screened by affinity enrichment for the cell membrane marker (e.g., by panning fused cells on an affinity matrix). For example, for a biotin membrane label, cells can be affinity purified using streptavidin-coated magnetic beads (Dynal). These beads are washed several times to remove the non-fused host cells. Alternatively, cells can be panned against an antibody to the membrane marker. In a further variation, if the membrane marker is fluorescent, cells bearing the marker can be identified by FACS. Screens for genetic markers depend on the nature of the markers, and include capacity to grow on drug-treated media or FACS selection for green fluorescent protein. If first and second cell populations have fluorescent markers of different wavelengths, both markers can be screened simultaneously by FACS sorting.

In a further selection scheme for hybrid cells, first and second populations of cells to be fused express different subunits of a heteromultimeric enzyme. Usually, the heteromultimeric enzyme has two different subunits, but heteromultimeric enzymes having three, four or more different subunits can be used. If an enzyme has more than two different subunits, each subunit can be expressed in a different subpopulation of cells (e.g., three subunits in three subpopulations), or more than one subunit can be expressed in the same subpopulation of cells (e.g., one subunit in one subpopulation, two subunits in a second subpopulation). In the case where more than two subunits are used, selection for the poolwise recombination of more than two protoplasts can be achieved.

Hybrid cells representing a combination of genomes of first, second or more subpopulation component cells can then be recognized by an assay for intact enzyme. Such an assay can be a binding assay, but is more typically a functional assay (e.g., capacity to metabolize a substrate of the enzyme). Enzymatic activity can be detected for example by processing of a substrate to a product with a fluorescent or otherwise easily detectable emission spectrum. The individual subunits of a heteromultimeric enzyme used in such an assay preferably have no enzymic activity in dissociated form, or at least have significantly less activity in dissociated form than associated form. Preferably, the cells used for fusion lack an endogenous form of the heteromultimeric enzyme, or at least have significantly less endogenous activity than results from heteromultimeric enzyme formed by fusion of cells.

Penicillin acylase enzymes, cephalosporin acylase and penicillin acyltransferase are examples of suitable heteromultimeric enzymes. These enzymes are encoded by a single gene, which is translated as a proenzyme and cleaved by posttranslational autocatalytic proteolysis to remove a spacer endopeptide and generate two subunits, which associate to form the active heterodimeric enzyme. Neither subunit is active in the absence of the other subunit. However, activity can be reconstituted if these separated gene portions are expressed in the same cell by co-transformation. Other enzymes that can be used have subunits that are encoded by distinct genes (e.g., faoA and faoB genes encode 3-oxoacyl-CoA thiolase of *Pseudonmonas fragi* (*Biochem. J* 328, 815–820 (1997)).

An exemplary enzyme is penicillin G acylase from *Escherichia coli*, which has two subunits encoded by a single gene. Fragments of the gene encoding the two subunits operably linked to appropriate expression regulation sequences are transfected into first and second subpopulations of cells, which lack endogenous penicillin acylase activity. A cell formed by fusion of component cells from the first and second subpopulations expresses the two subunits, which assemble to form functional enzyme, e.g., penicillin acylase. Fused cells can then be selected on agar plates containing penicillin G, which is degraded by penicillin acylase.

In another variation, fused cells are identified by complementation of auxotrophic mutants. Parental subpopulations of cells can be selected for known auxotrophic mutations. Alternatively, auxotrophic mutations in a starting population of cells can be generated spontaneously by exposure to a mutagenic agent. Cells with auxotrophic mutations are selected by replica plating on minimal and complete media. Lesions resulting in auxotrophy are expected to be scattered throughout the genome, in genes for amino acid, nucleotide, and vitamin biosynthetic pathways. After fusion of parental cells, cells resulting from fusion can be identified by their capacity to grow on minimal media. These cells can then be screened or selected for evolution toward a desired property. Further steps of mutagenesis generating fresh auxotrophic mutations can be incorporated in subsequent cycles of recombination and screening/selection.

In variations of the above method, de novo generation of auxotrophic mutations in each round of shuffling can be avoided by reusing the same auxotrophs. For example, auxotrophs can be generated by transposon mutagenesis using a transposon bearing selective marker. Auxotrophs are identified by a screen such as replica plating. Auxotrophs are pooled, and a generalized transducing phage lysate is prepared by growth of phage on a population of auxotrophic cells. A separate population of auxtrophic cells is subjected to genetic exchange, and complementation is used to selected cells that have undergone genetic exchange and recombination. These cells are then screened or selected for acquisition of a desired property. Cells surviving screening or selection then have auxotrophic markers regenerated by introduction of the transducing transposon library. The newly generated auxotrophic cells can then be subject to further genetic exchange and screening/selection.

In a further variation, auxotrophic mutations are generated by homologous recombination with a targeting vector comprising a selective marker flanked by regions of homology with a biosynthetic region of the genome of cells to be evolved. Recombination between the vector and the genome inserts the positive selection marker into the genome causing an auxotrophic mutation. The vector is in linear form before introduction of cells. Optionally, the frequency of introduction of the vector can be increased by capping its ends with self-complementarity oligonucleotides annealed in a hair pin formation. Genetic exchange and screening/selection proceed as described above. In each round, targeting vectors are reintroduced regenerating the same population of auxotrophic markers.

In another variation, fused cells are identified by screening for a genomic marker present on one subpopulation of parental cells and an episomal marker present on a second subpopulation of cells. For example, a first subpopulation of yeast containing mitochondria can be used to complement a second subpopulation of yeast having a petite phenotype (i.e., lacking mitochondria).

In a further variation, genetic exchange is performed between two subpopulations of cells, one of which is dead. Cells are preferably killed by brief exposure to DNA fragmenting agents such as hydroxylamine, cupferon, or irradiation. Viable cells are then screened for a marker present on the dead parental subpopulation.

3. Liposome-mediated Transfers

In the methods noted above, in which nucleic acid fragment libraries are introduced into protoplasts, the nucleic acids are sometimes encapsulated in liposomes to facilitate uptake by protoplasts. Lipsome-mediated uptake of DNA by protoplasts is described in Redford et al., *Mol. Gen. Genet.* 184, 567–569 (1981). Liposomes can efficiently deliver large volumes of DNA to protoplasts (see Deshayes et al., *EMBO J.* 4, 2731–2737 (1985)). See also, Philippot and Schuber (eds) (1995) *Liposomes as Tools in Basic Research and Industry* CRC press, Boca Raton, e.g., Chapter 9, Remy et al. "Gene Transfer with Cationic Amphiphiles." Further, the DNA can be delivered as linear fragments, which are often more recombinogenic that whole genomes. In some methods, fragments are mutated prior to encapsulation in liposomes. In some methods, fragments are combined with RecA and homologs, or nucleases (e.g., restriction endonucleases) before encapsulation in liposomes to promote recombination.

4. Shuffling Filamentous Fungi

Filamentous fungi are particularly suited to performing the shuffling methods described above. Filamentous fungi are divided into four main classifications based on their structures for sexual reproduction: Phycomycetes, Ascomycetes, Basidiomycetes and the *Fungi Imperfecti*. Phycomycetes (e.g., Rhizopus, Mucor) form sexual spores in sporangium. The spores can be uni or multinucleate and often lack septated hyphae (coenocytic). Ascomycetes (e.g., Aspergillus, Neurospora, Penicillum) produce sexual spores in an ascus as a result of meiotic division. Asci typically contain 4 meiotic products, but some contain 8 as a result of additional mitotic division. Basidiomycetes include mushrooms, and smuts and form sexual spores on the surface of a basidium. In holobasidiomycetes, such as mushrooms, the basidium is undivided. In hemibasidiomycetes, such as ruts (Uredinales) and smut fungi (Ustilaginales), the basidium is divided. *Fungi imperfecti*, which include most human pathogens, have no known sexual stage.

Fungi can reproduce by asexual, sexual or parasexual means. Asexual reproduction, involves vegetative growth of mycelia, nuclear division and cell division without involvement of gametes and without nuclear fusion. Cell division can occur by sporulation, budding or fragmentation of hyphae.

Sexual reproduction provides a mechanism for shuffling genetic material between cells. A sexual reproductive cycle is characterized by an alteration of a haploid phase and a diploid phase. Diploidy occurs when two haploid gamete nuclei fuse (karyogamy). The gamete nuclei can come from the same parental strains (self-fertile), such as in the homothallic fungi. In heterothallic fungi, the parental strains come from strains of different mating type.

A diploid cell converts to haploidy via meiosis, which essentially consists of two divisions of the nucleus accompanied by one division of the chromosomes. The products of one meiosis are a tetrad (4 haploid nuclei). In some cases, a mitotic division occurs after meiosis, giving rise to eight product cells. The arrangement of the resultant cells (usually enclosed in spores) resembles that of the parental strains. The length of the haploid and diploid stages differs in various fungi: for example, the Basidiomycetes and many of the Ascomycetes have a mostly hapolid life cycle (that is, meiosis occurs immediately after karyogamy), whereas others (e.g., *Saccharomyces cerevisiae*) are diploid for most of their life cycle (karyogamy occurs soon after meiosis). Sexual reproduction can occur between cells in the same strain (selfing) or between cells from different strains (outcrossing).

Sexual dimorphism (dioecism) is the separate production of male and female organs on different mycelia. This is a rare phenomenon among the fungi, although a few examples are known. Heterothallism (one locus-two alleles) allows for outcrossing between crosscompatable strains which are self-incompatable. The simplest form is the two allele-one locus system of mating types/factors, illustrated by the following organisms:

A and a in Neurospora
a and α in Saccharomyces
plus and minus in Schizzosaccharomyces and Zygomycetes
$a_1$ and $a_2$ in Ustilago Multiple-allelomorph heterothallism is exhibited by some of the higher Basidiomycetes (e.g. Gasteromycetes and Hymenomycetes), which are heterothallic and have several mating types determined by multiple alleles. Heterothallism in these organisms is either bipolar with one mating type factor, or tetrapolar with two unlinked factors, A and B. Stable, fertile heterokaryon formation depends on the presence of different A factors and, in the case of tetrapolar organisms, of different B factors as well. This system is effective in the promotion of outbreeding and the prevention of self-breeding. The number of different mating factors may be very large (i.e. thousands) (Kothe, *FEMS Microbiol. Rev.* 18, 65–87 (1996)), and non-parental mating factors may arise by recombination.

Parasexual reproduction provides a further means for shuffling genetic material between cells. This process allows recombination of parental DNA without involvement of mating types or gametes. Parasexual fusion occurs by hyphal fusion giving rise to a common cytoplasm containing different nuclei. The two nuclei can divide independently in the resulting heterokaryon but occasionally fuse. Fusion is followed by haploidization, which can involve loss of chromosomes and mitotic crossing over between homologous chromosomes. Protoplast fusion is a form of parasexual reproduction.

Within the above four classes, fungi are also classified by vegetative compatibility group. Fungi within a vegetative compatibility group can form heterokaryons with each other.

Thus, for exchange of genetic material between different strains of fungi, the fungi are usually prepared from the same vegetative compatibility group. However, some genetic exchange can occur between fungi from different incompatibility groups as a result of parasexual reproduction (see Timberlake et al., U.S. Pat. No. 5,605,820). Further, as discussed elsewhere, the natural vegetative compatibility group of fungi can be expanded as a result of shuffling.

Several isolates of *Aspergillus nidulans, A. flavus, A. fumigatus, Penicillium chrysogenum, P. notatum, Cephalosporium chrysogenum, Neurospora crassa, Aureobasidium pullulans* have been karyotyped. Genome sizes generally range between 20 and 50 Mb among the Aspergilli. Differences in karyotypes often exist between similar strains and are also caused by transformation with exogenous DNA. Filamentous fungal genes contain introns, usually ~50–100 bp in size, with similar consensus 5' and 3' splice sequences. Promotion and termination signals are often cross-recognizable, enabling the expression of a gene/pathway from one fungus (e.g. *A. nidulans*) in another (e.g. *P. chrysogenum*).

The major components of the fungal cell wall are chitin (or chitosan), β-glucan, and mannoproteins. Chitin and β-glucan form the scaffolding, mannoproteins are interstitial components which dictate the wall's porosity, antigenicity and adhesion. Chitin synthetase catalyzes the polymerization of β-(1,4)-linked N-acetylglucosamine (GIcNAc) residues, forming linear strands running antiparallel; β-(1,3)-glucan synthetase catalyze the homopolymerization of glucose.

One general goal of shuffling is to evolve fungi to become useful hosts for genetic engineering, in particular for the shuffling of unrelated genes. *A. nidulans* is generally the fungal organism of choice to serve as a host for such manipulations because of its sexual cycle and well-established use in classical and molecular genetics. Another general goal is to improve the capacity of fungi to make specific compounds (e.g. antibacterials (penicillins, cephalosporins), antifungals (e.g. echinocandins, aureobasidins), and wood-degrading enzymes). There is some overlap between these general goals, and thus, some desired properties are useful for achieving both goals.

Figure 6:
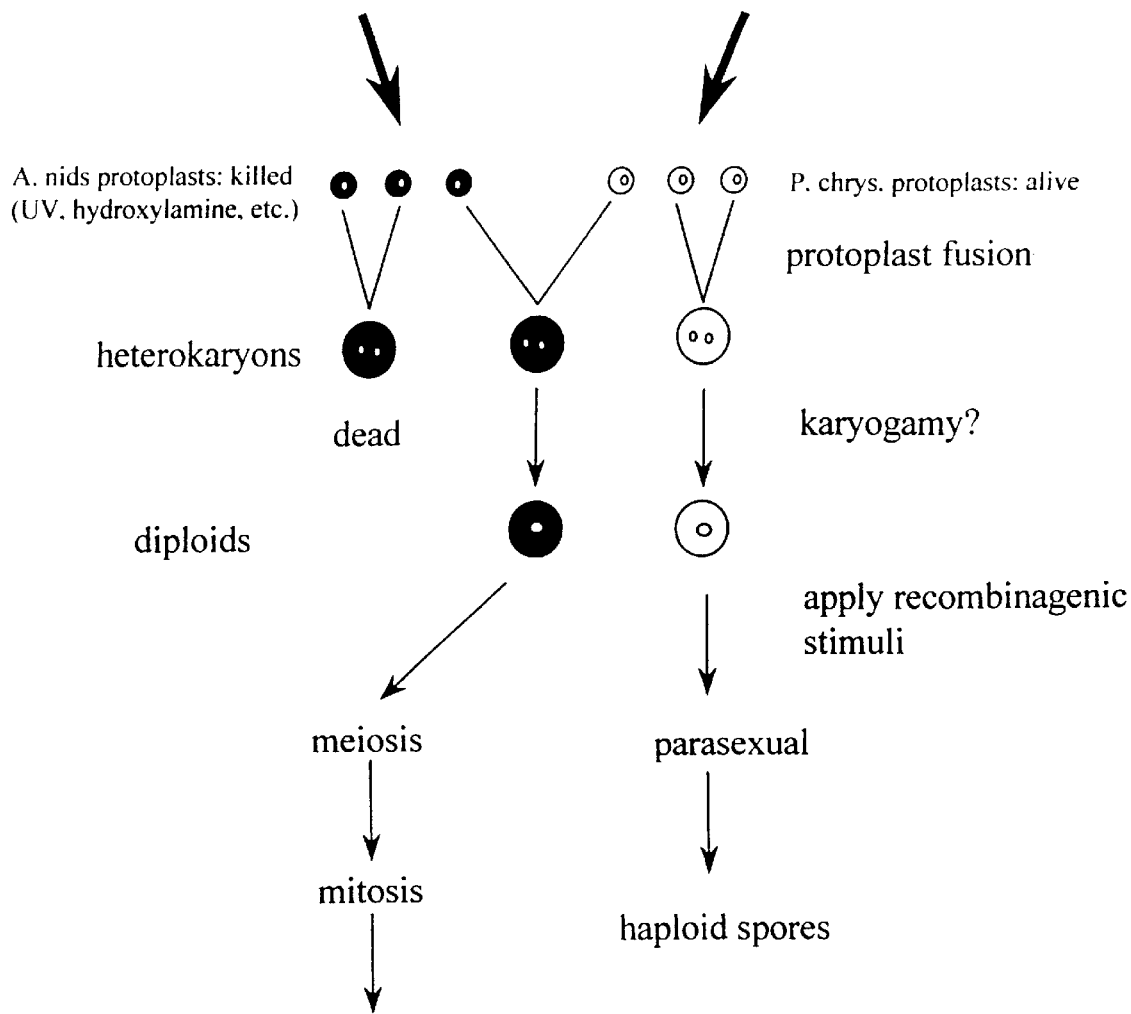
FIG. 6: Scheme for introducing a sexual cycle into fungi previously incapable of sexual reproduction.

One desired property is the introduction of meiotic apparatus into fungi presently lacking a sexual cycle (see Sharon et al., *Mol. Gen. Genet.* 251, 60–68 (1996)). A scheme for introducing a sexual cycle into the fungi *P. chrysogenum* (a fungus imperfecti) is shown in FIG. 6. Subpopulations of protoplasts are formed from *A. nidulans* (which has a sexual cycle) and *P. chrysogenum,* which does not. The two strains preferably bear different markers. The *A. nidulans* protoplasts are killed by treatment with uv or hydroxylamine. The two subpopulations are fused to form heterokaryons. In some heterokaryons, nuclei fuse, and some recombination occurs. Fused cells are cultured under conditions to generate new cell walls and then to allow sexual recombination to occur. Cells with recombinant genomes are then selected (e.g., by selecting for complementation of auxotrophic markers present on the respective parent strains). Cells with hybrid genomes are more likely to have acquired the genes necessary for a sexual cycle. Protoplasts of cells can then be crossed with killed protoplasts of a further population of cells known to have a sexual cycle (the same or different as the previous round) in the same manner, followed by selection for cells with hybrid genomes.

Another desired property is the production of a mutator strain of fungi. Such a fungus can be produced by shuffling a fungal strain containing a marker gene with one or more mutations that impair or prevent expression of a functional product. Shufflants are propagated under conditions that select for expression of the positive marker (while allowing a small amount of residual growth without expression). Shufflants growing fastest are selected to form the starting materials for the next round of shuffling.

Another desired property is to expand the host range of a fungus so it can form heterokaryons with fungi from other vegetative compatibility groups. Incompatability between species results from the interactions of specific alleles at different incompatability loci (such as the "het" loci). If two strains undergo hyphal anastomosis, a lethal cytoplasmic incompatability reaction may occur if the strains differ at these loci. Strains must carry identical loci to be entirely compatible. Several of these loci have been identified in various species, and the incompatibility effect is somewhat additive (hence, "partial incompatibility" can occur). Some tolerant and het-negative mutants have been described for these organisms (e.g. Dales & Croft, *J. Gen. Microbiol.* 136, 1717–1724 (1990)). Further, a tolerance gene (tol) has been reported, which suppresses mating-type heterokaryon incompatibility. Shuffling is performed between protoplasts of strains from different incompatibility groups. A preferred format uses a live acceptor strain and a UV-irradiated dead acceptor strain. The UV irradiation serves to introduce mutations into DNA inactivating het genes. The two strains should bear different genetic markers. Protoplasts of the strain are fused, cells are regenerated and screened for complementation of markers. Subsequent rounds of shuffling and selection can be performed in the same manner by fusing the cells surviving screening with a protoplasts of a fresh population of donor cells.

Another desired property is the introduction of multiple-allelomorph heterothallism into Ascomycetes and *Fungi imperfecti,* which do not normally exhibit this property. This mating system allows outbreeding without self-breeding. Such a mating system can be introduced by shuffling Ascomycetes and *Fungi imperfecti* with DNA from Gasteromycetes or Hymenomycetes, which have such a system.

Another desired property is spontaneous formation of protoplasts to facilitate use of a fungal strain as a shuffling host. Here, the fungus to be evolved is typically mutagenized. Spores of the fungus to be evolved are briefly treated with a cell-wall degrading agent for a time insufficient for complete protoplast formation, and are mixed with protoplasts from other strain(s) of fungi. Protoplasts formed by fusion of the two different subpopulations are identified by genetic or other selection/or screening as described above. These protoplasts are used to regenerate mycelia and then spores, which form the starting material for the next round of shuffling. In the next round, at least some of the surviving spores are treated with cell-wall removing enzyme but for a shorter time than the previous round. After treatment, the partially stripped cells are labelled with a first label. These cells are then mixed with protoplasts, which may derive from other cells surviving selection in a previous round, or from a fresh strain of fungi. These protoplasts are physically labelled with a second label. After incubating the cells under conditions for protoplast fusion fusants with both labels are selected. These fusants are used to generate mycelia and spores for the next round of shuffling, and so forth. Eventually, progeny that spontaneously form protoplasts (i.e., without addition of cell wall degrading agent) are identified.

Another desired property is the acquisition and/or improvement of genes encoding enzymes in biosynthetic pathways, genes encoding transporter proteins, and genes encoding proteins involved in metabolic flux control. In this situation, genes of the pathway can be introduced into the fungus to be evolved either by genetic exchange with another strain of fungus possessing the pathway or by introduction of a fragment library from an organism possessing the pathway. Genetic material of these fungi can then be subjected to further shuffling and screening/selection by the various procedures discussed in this application. Shufflant strains of fungi are selected/screened for production of the compound produced by the metabolic pathway or precursors thereof.

Another desired property is increasing the stability of fungi to extreme conditions such as heat. In this situation, genes conferring stability can be acquired by exchanging DNA with or transforming DNA from a strain that already has such properties. Alternatively, the strain to be evolved can be subjected to random mutagenesis. Genetic material of the fungus to be evolved can be shuffled by any of the procedures described in this application, with shufflants being selected by surviving exposure to extreme conditions.

Another desired property is capacity of a fungus to grow under altered nutritional requirements (e.g., growth on particular carbon or nitrogen sources). Altering nutritional requirements is particularly valuable, e.g., for natural isolates of fungi that produce valuable commercial products but have esoteric and therefore expensive nutritional requirement. The strain to be evolved undergoes genetic exchange and/or transformation with DNA from a strain that has the desired nutritional requirements. The fungus to be evolved can then optionally be subjected to further shuffling as described in this application and with recombinant strains being selected for capacity to grow in the desired nutritional circumstances. Optionally, the nutritional circumstances can be varied in successive rounds of shuffling starting at close to the natural requirements of the fungus to be evolved and in subsequent rounds approaching the desired nutritional requirements.

Another desired property is acquisition of natural competence in a fungus. The procedure for acquisition of natural competence by shuffling is generally described in PCT/US97/04494. The fungus to be evolved typically undergoes genetic exchange or transformation with DNA from a bacterial strain or fungal strain that already has this property. Cells with recombinant genomes are then selected by capacity to take up a plasmid bearing a selective marker. Further rounds of recombination and selection can be performed using any of the procedures described above.

Another desired property is reduced or increased secretion of proteases and DNase. In this situation, the fungus to be evolved can acquire DNA by exchange or transformation from another strain known to have the desired property. Alternatively, the fungus to be evolved can be subject to random mutagenesis. The fungus to be evolved is shuffled as above. Before selection/screening isolates, pooled isolates of fungi are typically lysed to release proteases or DNase to the surrounding media. The presence of such enzymes, or lack thereof, can be assayed by contacting the media with a fluorescent molecule tethered to a support via a peptide or DNA linkage. Cleavage of the linkage releases detectable fluorescence to the media.

Another desired property is producing fungi with altered transporters (e.g., MDR). Such altered transporters are useful, for example, in fungi that have been evolved to produce new secondary metabolites, to allow entry of precursors required for synthesis of the new secondary metabolites into a cell, or to allow efflux of the secondary metabolite from the cell. Transporters can be evolved by introduction of a library of transporter variants into a fungal cells and allowing the cells to recombine by sexual or parasexual recombination. To evolve a transporter with capacity to transport a precursor into the cells, cells are propagated in the present of precursor, and cells are then screened for production of metabolite. To evolve a transporter with capacity to export a metabolite, cells are propagated under conditions supporting production of the metabolite, and screened for export of metabolite to culture medium.

Figure 7:
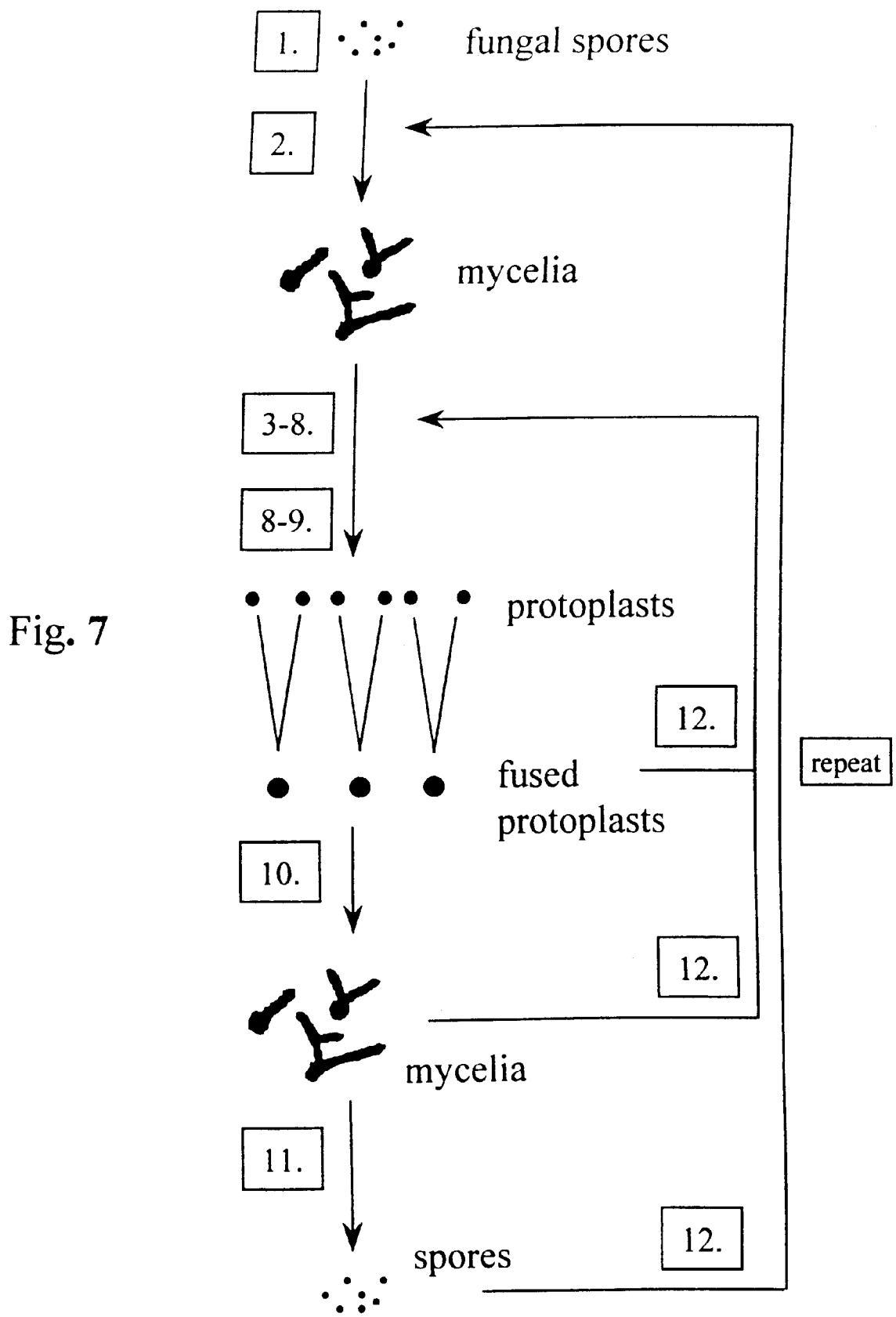
FIG. 7: General scheme for shuffling of fungi by protoplast fusion.

A general method of fungal shuffling is shown in FIG. 7. Spores from a frozen stock, a lyophilized stock, or fresh from an agar plate are used to inoculate suitable liquid medium (1). Spores are germinated resulting in hyphal growth (2). Mycelia are harvested, and washed by filtration and/or centrifugation. Optionally the sample is pretreated with DTT to enhance protoplast formation (3). Protoplasting is performed in an osmotically stabling medium (e.g., 1 m NaCl/20 mM MgSO4, pH 5.8) by the addition of cell wall-degrading enzyme (e.g., Novozyme 234) (4). Cell wall degrading enzyme is removed by repeated washing with osmotically stabilizing solution (5). Protoplasts can be separated from mycelia, debris and spores by filtration through miracloth, and density centrifugation (6). Protoplasts are harvested by centrifugation and resuspended to the appropriate concentration. This step may lead to some protoplast fusion (7). Fusion can be stimulated by addition of PEG (e.g., PEG 3350), and/or repeated centrifugation and resuspension with or without PEG. Electrofusion can also be performed (8). Fused protoplasts can optionally be enriched from unfused protoplasts by sucrose gradient sedimentation (or other methods of screening described above). Fused protoplasts can optionally be treated with ultraviolet irradiation to stimulate recombination (9). Protoplasts are cultured on osmotically stabilized agar plates to regenerate cell walls and form mycelia (10). The mycelia are used to generate spores (11), which are used as the starting material in the next round of shuffling (12). Selection for a desired property can be performed either on regenerated mycelia or spores derived therefrom.

Figure 8:
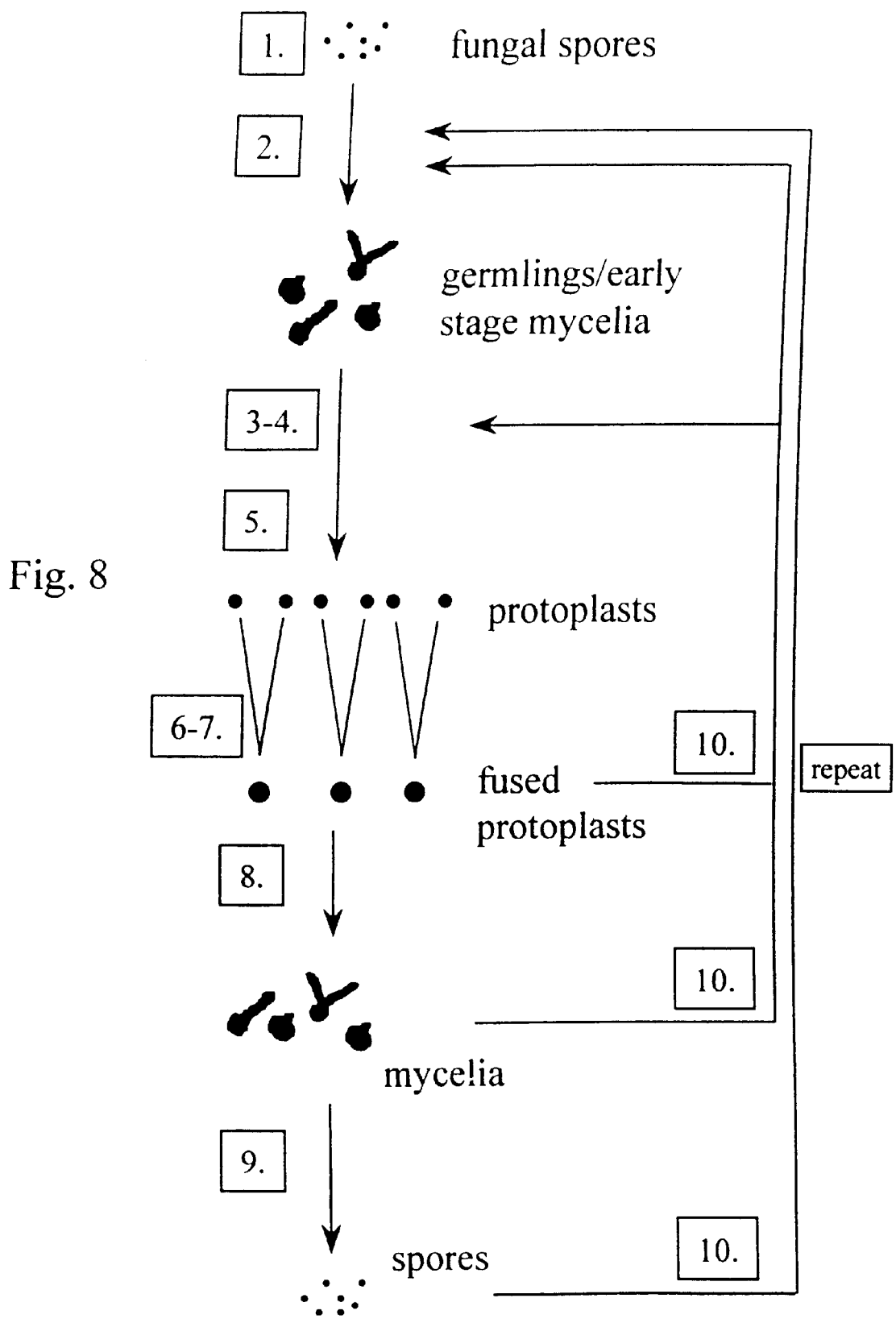
FIG. 8: Shuffling fungi by protoplast fusion with protoplasts generated by use of inhibitors of enzymes responsible for cell wall formation.

In an alternative method, protoplasts are formed by inhibition of one or more enzymes required for cell wall synthesis (see FIG. 8). The inhibitor should be fungistatic rather than fungicidal under the conditions of use. Examples of inhibitors include antifungal compounds described by (e.g., Georgopapadakou & Walsh, *Antimicrob. Ag. Chemother.* 40, 279–291 (1996); Lyman & Walsh, *Drugs* 44, 9–35 (1992)). Other examples include chitin synthase inhibitors (polyoxin or nikkomycin compounds) and/or glucan synthase inhibitors (e.g. echinocandins, papulocandins, pneumocandins). Inhibitors should be applied in osmotically stabilized medium. Cells stripped of their cell walls can be fused or otherwise employed as donors or hosts in genetic transformation/strain development programs. A possible scheme utilizing this method reiteratively is outlined in FIG. 8.

Figure 9:
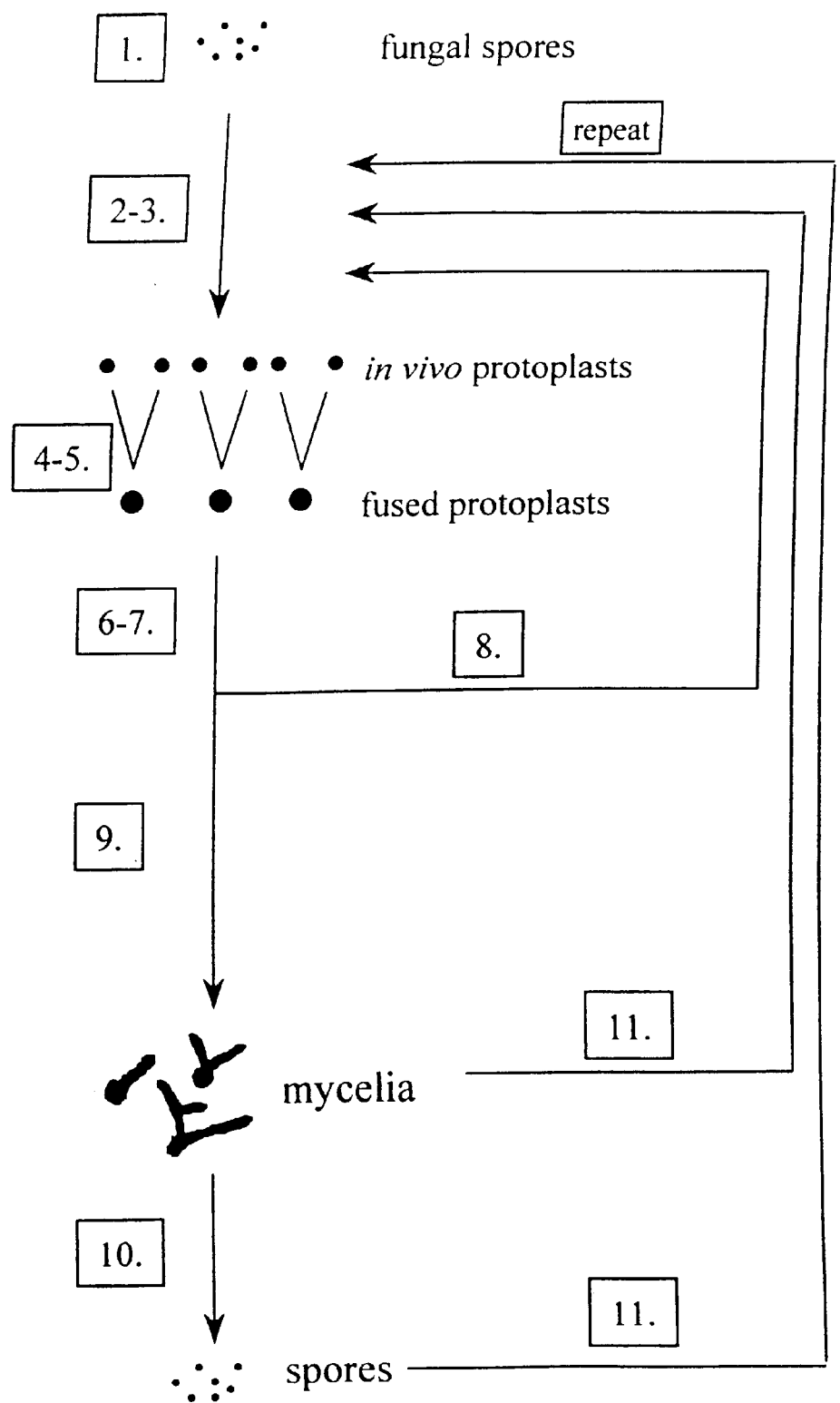
FIG. 9: Shuffling fungi by protoplast fusion using fungal strains deficient in cell-wall synthesis that spontaneously form protoplasts.

In a further variation, protoplasts are prepared using strains of fungi, which are genetically deficient or compromised in their ability to synthesize intact cell walls (see FIG. 9). Such mutants are generally referred to as fragile, osmotic-remedial, or cell wall-less, and are obtainable from strain depositories. Examples of such strains include *Neurospora crassa* os mutants (Selitrennikoff, *Antimicrob. Agents. Chemother.* 23, 757–765 (1983)). Some such mutations are temperature-sensitive. Temperature-sensitive strains can be propagated at the permissive temperature for purposes of selection and amplification and at a nonpermissive temperature for purposes of protoplast formation and fusion. A temperature sensitive strain *Neurospora crassa* os strain has been described which propagates as protoplasts when growth in osmotically stabilizing medium containing sorbose and polyoxin at nonpermissive temperature but generates whole cells on transfer to medium containing sorbitol at a permissive temperature. See U.S. Pat. No. 4,873,196.

Other suitable strains can be produced by targeted mutagenesis of genes involved in chitin synthesis, glucan synthesis and other cell wall-related processes. Examples of such genes include CHT1, CHT2 and CALI (or CSD2) of *Saccharomyces cerevisiae* and *Candida* spp. (Georgopapadakou & Walsh 1996); ETGI/FKSI/CNDI/ CWH53/PB RI and homologs in *S. cerevisiae, Candida albicans, Cryptococcus neoformans, Aspergillus fumigatus,* ChvAINdvA Agrobacterium and Rhizobium. Other examples are MA, orlB, orlC, MD, tsE, and bimG of *Aspergillus nidulans* (Borgia, *J. Bacteriol.* 174, 377–389 (1992)). Strains of *A. nidulans* containing OrlA1 or tse1 mutations lyse at restrictive temperatures. Lysis of these strains may be prevented by osmotic stabilization, and the mutations may be complemented by the addition of N-acetylglucosimine (GlcNac). BimG11 mutations are ts for a type 1 protein phosphatase (germlines of strains carrying this mutation lack chitin, and condia swell and lyse). Other suitable genes are chsA, chsB, chsC, chsD and chsE of *Aspergillus fumigatus;* chs1 and chs2 of *Neurospora crassa; Phycomyces blakesleeanus* MM and chs1, 2 and 3 of *S. cerevisiae.* Chs1 is a non-essential repair enzyme; chs2 is involved in septum formation and chs3 is involved in cell wall maturation and bud ring formation.

Other useful strains include *S. cerevisiae* CLY (cell lysis) mutants such as ts strains (Paravicini et al., *Mol. Cell Biol.* 12, 4896–4905 (1992)), and the CLY 15 strain which harbors a PKC 1 gene deletion. Other useful strains include strain VY 1160 containing a ts mutation in srb (encoding actin) (Schade et al. *Acta Histochem. Suppl.* 41, 193–200 (1991)), and a strain with an ses mutation which results in increased sensitivity to cell-wall digesting enzymes isolated from snail gut (Metha & Gregory, *Appl. Environ. Microbiol.* 41, 992–999 (1981)). Useful strains of *C. albicans* include those with mutations in chs1, chs2, or chs3 (encoding chitin synthetases), such as osmotic remedial conditional lethal mutants described by Payton & de Tiani, *Curr. Genet.* 17, 293–296 (1990); *C. utilis* mutants with increased sensitivity to cell-wall digesting enzymes isolated from snail gut (Metha & Gregory, 1981, supra); and *N. crassa* mutants os-1, os-2, os-3, os-4, os-5, and os-6. See, Selitrennikoff, *Antimicrob. Agents Chemother.* 23, 757–765 (1983). Such mutants grow and divide without a cell wall at 37° C., but at 22° C. produce a cell wall.

Targeted mutagenesis can be achieved by transforming cells with a positive-negative selection vector containing homologous regions flanking a segment to be targeted, a positive selection marker between the homologous regions and a negative selection marker outside the homologous regions (see Capecchi, U.S. Pat. No. 5,627,059). In a variation, the negative selection marker can be an antisense transcript of the positive selection marker (see U.S. Pat. No. 5,527,674).

Other suitable cells can be selected by random mutagenesis or shuffling procedures in combination with selection. For example, a first subpopulation of cells are mutagenized, allowed to recover from mutagenesis, subjected to incomplete degradation of cell walls and then contacted with protoplasts of a second subpopulation of cells. Hybrids cells bearing markers from both subpopulations are identified (as described above) and used as the starting materials in a subsequent round of shuffling. This selection scheme selects both for cells with capacity for spontaneous protoplast formation and for cells with enhanced recombinogenicity.

In a further variation, cells having capacity for spontaneous protoplast formation can be crossed with cells having enhanced recombinogenicity evolved using other methods of the invention. The hybrid cells are particularly suitable hosts for whole genome shuffling.

Cells with mutations in enzymes involved in cell wall synthesis or maintenance can undergo fusion simply as a result of propagating the cells in osmotic-protected culture due to spontaneous protoplast formation. If the mutation is conditional, cells are shifted to a nonpermissive condition. Protoplast formation and fusion can be accelerated by addition of promoting agents, such as PEG or an electric field (See Philipova & Venkov, *Yeast* 6, 205–212 (1990); Tsoneva et al., *FEMS Microbiol. Lett.* 51, 61–65 (1989)).

5. Shuffling Methods in Yeast

Yeasts are subspecies of fungi that grow as single cells. Yeasts are used for the production of fermented beverages and leavening, for production of ethanol as a fuel, low molecular weight compounds, and for the heterologous production of proteins and enzymes (see accompanying list of yeast strains and their uses). Commonly used strains of yeast include *Saccharomyces cerevisiae*, Pichia sp., Canidia sp. and *Schizosaccharomyces pombe*.

Several types of vectors are available for cloning in yeast including integrative plasmid (YIp), yeast replicating plasmid (YRp, such as the 2μ circle based vectors), yeast episomal plasmid (YEp), yeast centromeric plasmid (YCp), or yeast artificial chromosome (YAC). Each vector can carry markers useful to select for the presence of the plasmid such as LUE2, URA3, and H1S3, or the absence of the plasmid such as URA3 (a gene that is toxic to cells grown in the presence of 5-fluoro orotic acid.

Many yeasts have a sexual cycle and asexual (vegetative) cycles. The sexual cycle involves the recombination of the whole genome of the organism each time the cell passes through meiosis. For example, when diploid cells of *S. cerevisiae* are exposed to nitrogen and carbon limiting conditions, diploid cells undergo meiosis to form asci. Each ascus holds four haploid spores, two of mating type "a" and two of mating type "α." Upon return to rich medium, haploid spores of opposite mating type mate to form diploid cells once again. Asci of opposite mating type can mate within the ascus, or if the ascus is degraded, for example with zymolase, the haploid cells can mate with spores from other asci. This sexual cycle provides a format to shuffle endogenous genomes of yeast and/or exogenous fragment libraries inserted into yeast vectors. This process results in swapping or accumulation of hybrid genes, and for the shuffling of homologous sequences shared by mating cells.

Yeast strains having mutations in several known genes have properties useful for shuffling. These properties include increasing the frequency of recombination and increasing the frequency of spontaneous mutations within a cell. These properties can be the result of mutation of a coding sequence or altered expression (usually overexpression) of a wildtype coding sequence. The HO nuclease effects the transposition of HMLa/α and HMRa/α to the MAT locus resulting in mating type switching. Mutants in the gene encoding this enzyme do not switch their mating type and can be employed to force crossing between strains of defined genotype, such as ones that harbor a library or have a desired phenotype and to prevent in breeding of starter strains. PMS1, MLH1, MSH2, MSH6 are involved in mismatch repair. Mutations in these genes all have a mutator phenotype (Chambers et al., *Mol. Cell. Biol.* 16, 6110–6120 (1996)). Mutations in TOP3 DNA topoisomerase have a 6-fold enhancement of interchromosomal homologous recombination (Bailis et al., *Molecular and Cellular Biology* 12, 4988–4993 (1992)). The RAD50–57 genes confer resistance to radiation. Rad3 functions in excision of pyrimidine dimers. RAD52 functions in gene conversion. RAD50, MRE11, XRS2 function in both homologous recombination and illegitimate recombination. HOP1, RED1 function in early meiotic recombination (Mao-Draayer, *Genetics* 144, 71–86) Mutations in either HOP1 or RED1 reduce double stranded breaks at the HIS2 recombination hotspot. Strains deficient in these genes are useful for maintaining stability in hyper recombinogenic constructs such as tandem expression libraries carried on YACs. Mutations in HPR 1 are hyperrecombinogenic. HDF1 has DNA end binding activity and is involved in double stranded break repair and V(D)J recombination. Strains bearing this mutation are useful for transformation with random genomic fragments by either protoplast fusion or electroporation. Kar-1 is a dominant mutation that prevents karyogamy. Kar-1 mutants are useful for the directed transfer of single chromosomes from a donor to a recipient strain. This technique has been widely used in the transfer of YACs between strains, and is also useful in the transfer of evolved genes/chromosomes to other organisms (Markie, *YAC Protocols*, (Humana Press, Totowa, N.J., 1996). HOT1 is an *S. cerevisiae* recombination hotspot within the promoter and enhancer region of the rDNA repeat sequences. This locus induces mitotic recombination at adjacent sequences—presumably due to its high level transcription. Genes and/or pathways inserted under the transcriptional control of this region undergo increased mitotic recombination. CDC2 encodes polymerase δ and is necessary for mitotic gene conversion. Overexpression of this gene can be used in a shuffler or mutator strain. A temperature sensitive mutation in CDC4 halts the cell cycle at G1 at the restrictive temperature and could be used to synchronize protoplasts for optimized fusion and subsequent recombination.

As with filamentous fungi, the general goals of shuffling yeast include improvement in yeast as a host organism for genetic manipulation, and as a production apparatus for various compounds. One desired property in either case is to improve the capacity of yeast to express and secrete a heterologous protein. The following example describes the use of shuffling to evolve yeast to express and secrete increased amounts of RNase A.

RNase A catalyzes the cleavage of the P—$O_5$, bond of RNA specifically after pyrimidine nucleotides. The enzyme is a basic 124 amino acid polypeptide that has 8 half cystine residues, each required for catalysis. YEpWL-RNase A is a vector that effects the expression and secretion of RNaseA from the yeast *S. cerevisiae*, and yeast harboring this vector secrete 1–2 mg of recombinant RNase A per liter of culture medium (delCardayré et al., *Protein Engineering* 8(3):26, 1–273 (1995)). This overall yield is poor for a protein heterologously expressed in yeast and can be improved at least 10–100 fold by shuffling. The expression of RNaseA is easily detected by several plate and microtitre plate assays (delCardayré & Raines, *Biochemistry* 33, 6031–6037 1994)). Each of the described formats for whole genome shuffling can be used to shuffle a strain of *S. cerevisiae* harboring YEpWL.RNase A, and the resulting cells can be screened for the increased secretion of RNase A into the medium. The new strains are cycled recursively through the shuffling format, until sufficiently high levels of RNase A secretion is observed. The use of RNase A is particularly useful since it not only requires proper folding and disulfide bond formation but also proper glycosylation. Thus numerous components of the expression, folding, and secretion systems can be optimized. The resulting strain is also evolved for improved secretion of other heterologous proteins.

Another goal of shuffling yeast is to increase the tolerance of yeast to ethanol. Such is useful both for the commercial production of ethanol, and for the production of more alcoholic beers and wines. The yeast strain to be shuffled acquires genetic material by exchange or transformation with other strain(s) of yeast, which may or may not be know to have superior resistance to ethanol. The strain to be evolved is shuffled and shufflants are selected for capacity to survive exposure to ethanol. Increasing concentrations of ethanol can be used in successive rounds of shuffling. The same principles can be used to shuffle baking yeasts for improved osmotolerance.

Another desired property of shuffling yeast is capacity to grow under desired nutritional conditions. For example, it is useful to yeast to grow on cheap carbon sources such as methanol, starch, molases, cellulose, cellobiose, or xylose depending on availability. The principles of shuffling and selection are similar to those discussed for filamentous fungi.

Another desired property is capacity to produce secondary metabolites naturally produced by filamentous fungi or bacteria. Examples of such secondary metabolites are cyclosporin A, taxol, and cephalosporins. The yeast to be evolved undergoes genetic exchange or is transformed with DNA from organism(s) that produce the secondary metabolite. For example, fungi producing taxol include *Taxomyces andreanae* and *Pestalotopis microspora* (Stierle et al., *Science* 260, 214– 216 (1993); Strobel et al., *Microbiol.* 142, 435–440 (1996)). DNA can also be obtained from trees that naturally produce taxol, such as *Taxus brevifolia*. DNA encoding one enzyme in the taxol pathway, taxadiene synthase, which it is believed catalyzes the commited step in taxol biosynthesis and may be rate limiting in overal taxol production, has been cloned (Wildung & Croteau, *J. Biol. Chem.* 271, 9201–4 (1996). The DNA is then shuffled, and shufflants are screened/selected for production of the secondary metabolite. For example, taxol production can be monitored using antibodies to taxol, by mass spectroscopy or uv spectrophotometry. Alternatively, production of intermediates in taxol synthesis or enzymes in the taxol synthetic pathway can be monitored. Concetti & Ripani, *Biol. Chem. Hoppe Seyler* 375, 419–23 (1994). Other examples of secondary metabolites are polyols, amino acids, polyketides, non-ribosomal polypeptides, ergosterol, and the like.

Another desired property is to increase the flocculence of yeast to facilitate separation in preparation of ethanol. Yeast can be shuffled by any of the procedures noted above with selection for shuffled yeast forming the largest clumps.

Exemplary Procedure for Yeast Protoplasting

Protoplast preparation in yeast is reviewed by Morgan, in *Protoplasts* (Birkhauser Verlag, Basel, 1983). Fresh cells (~$10^8$) are washed with buffer, for example 0.1 M potassium phosphate, then resuspended in this same buffer containing a reducing agent, such as 50 mM DTT, incubated for 1 h at 30° C. with gentle agitation, and then washed again with buffer to remove the reducing agent. These cells are then resuspended in buffer containing a cell wall degrading enzyme, such as Novozyme 234 (1 mg/mL), and any of a variety of osmotic stabilizers, such as sucrose, sorbitol, NaCl, KCl, $MgSO_4$, $MgCl_2$, or $NH_4Cl$ at any of a variety of concentrations. These suspensions are then incubated at 30° C. with gentle shaking (~60 rpm) until protoplasts are released. To generate protoplasts that are more likely to produce productive fusants several strategies are possible.

Protoplast formation can be increased if the cell cycle of the protoplasts have been synchronized to be halted at G1. In the case of *S. cerevisiae* this can be accomplished by the addition of mating factors, either a or α (Curran & Carter, *J. Gen. Microbiol.* 129, 1589–1591 (1983)). These peptides act as adenylate cyclase inhibitors which by decreasing the cellular level of cAMP arrest the cell cycle at G1. In addition, sex factors have been shown to induce the weakening of the cell wall in preparation for the sexual fusion of a and α cells (Crandall & Brock, *Bacteriol. Rev.* 32, 139–163 (1968); Osumi et al., *Arch. Microbiol.* 97, 27–38 (1974)). Thus in the preparation of protoplasts, cells can be treated with mating factors or other known inhibitors of adenylate cyclase, such as leflunomide or the killer toxin from *K. lactis,* to arrest them at G1 (Sugisaki et al., *Nature* 304, 464–466 (1983)). Then after fusing of the protoplasts (step 2), cAMP can be added to the regeneration medium to induce S-phase and DNA synthesis. Alternatively, yeast strains having a temperature sensitive mutation in the CDC4 gene can be used, such that cells could be synchronized and arrested at G1. After fusion cells are returned to the permissive temperature so that DNA synthesis and growth resumes.

Once suitable protoplasts have been prepared, it is necessary to induce fusion by physical or chemical means. An equal number of protoplasts of each cell type is mixed in phosphate buffer (0.2 M, pH 5.8, $2 \times 10^8$ cells/mL) containing an osmotic stabilizer, for example 0.8 M NaCl, and PEG 6000 (33% w/v) and then incubated at 30° C. for 5 mm while fusion occurs. Polyols, or other compounds that bind water, can be employed. The fusants are then washed and resuspended in the osmotically stabilized buffer lacking PEG, and transferred to osmotically stabilized regeneration medium on/in which the cells can be selected or screened for a desired property.

6. Shuffling Methods Using Artificial Chromosomes

Yeast artificial chromosomes (Yacs) are yeast vectors into which very large DNA fragments (e.g., 50–2000 kb) can be cloned (see, e.g., Monaco & Larin, *Trends. Biotech.* 12(7), 280–286 (1994); Ramsay, *Mol. Biotechnol.* 1(2), 181–201 1994; Huxley, *Genet. Eng.* 16, 65–91 (1994); Jakobovits, *Curr. Biol.* 4(8), 761–3 (1994); Lamb & Gearhart, *Curr. Opin. Genet. Dev.* 5(3), 342–8 (1995); Montoliu et al., *Reprod. Fertil. Dev.* 6, 577–84 (1994)). These vectors have telomeres (Tel), a centromere (Cen), an autonomously replicating sequence (ARS), and can have genes for positive (e.g., TRP1) and negative (e.g., URA3) selection. YACs are maintained, replicated, and segregate as other yeast chromosomes through both meiosis and mitosis thereby providing a means to expose cloned DNA to true meiotic recombination.

YACs provide a vehicle for the shuffling of libraries of large DNA fragments in vivo. The substrates for shuffling are typically large fragments from 20 kb to 2 Mb. The fragments can be random fragments or can be fragments known to encode a desirable property. For example, a fragment might include an operon of genes involved in production of antibiotics. Libraries can also include whole genomes or chromosomes. Viral genomes and some bacterial genomes can be cloned intact into a single YAC. In some libraries, fragments are obtained from a single organism. Other libraries include fragment variants, as where some libraries are obtained from different individuals or species. Fragment variants can also be generated by induced mutation. Typically, genes within fragments are expressed from naturally associated regulatory sequences within yeast. However, alternatively, individual genes can be linked to yeast regulatory elements to form an expression cassette, and a concatemer of such cassettes, each containing a different gene, can be inserted into a YAC.

In some instances, fragments are incorporated into the yeast genome, and shuffling is used to evolve improved yeast strains. In other instances, fragments remain as components of YACs throughout the shuffling process, and after acquisition of a desired property, the YACs are transferred to a desired recipient cell.

a. Methods of Evolving Yeast Strains

Fragments are cloned into a YAC vector, and the resulting YAC library is transformed into competent yeast cells. Transformants containing a YAC are identified by selecting for a positive selection marker present on the YAC. The cells are allowed to recover and are then pooled. Thereafter, the cells are induced to sporulate by transferring the cells from rich medium, to nitrogen and carbon limiting medium. In the course of sporulation, cells undergo meiosis. Spores are then induced to mate by return to rich media. Optionally, asci are lysed o liberate spores, so that the spores can mate with other spores originating from other asci. Mating results in recombination between YACs bearing different inserts, and between YACs and natural yeast chromosomes. The latter can be promoted by irradiating spores with ultra violet light. Recombination can give rise to new phenotypes either as a result of genes expressed by fragments on the YACs or as a result of recombination with host genes, or both.

After induction of recombination between YACs and natural yeast chromosomes, YACs are often eliminated by selecting against a negative selection marker on the YACs. For example, YACs containing the marker URA3 can be selected against by propagation on media containing 5-fluro-orotic acid. Any exogenous or altered genetic material that remains is contained within natural yeast chromosomes. Optionally, further rounds of recombination between natural yeast chromosomes can be performed after elimination of YACs. Optionally, the same or different library of YACs can be transformed into the cells, and the above steps repeated.

After elimination of YACs, yeast are then screened or selected for a desired property. The property can be a new property conferred by transferred fragments, such as production of an antibiotic. The property can also be an improved property of the yeast such as improved capacity to express or secrete an exogenous gene, improved recombinogenicity, improved stability to temperature or solvents, or other property required of commercial or research strains of yeast.

Yeast strains surviving selection/screening are then subject to a further round of recombination. Recombination can be exclusively between the chromosomes of yeast surviving selection/screening. Alternatively, a library of fragments can be introduced into the yeast cells and recombined with endogenous yeast chromosomes as before. This library of fragments can be the same or different from the library used in the previous round of transformation. YACs are eliminated as before, followed by additional rounds of recombination and/or transformation with further YAC libraries. Recombination is followed by another round of selection/screening, as above. Further rounds of recombination/screening can be performed as needed until a yeast strain has evolved to acquire the desired property.

Figure 10:
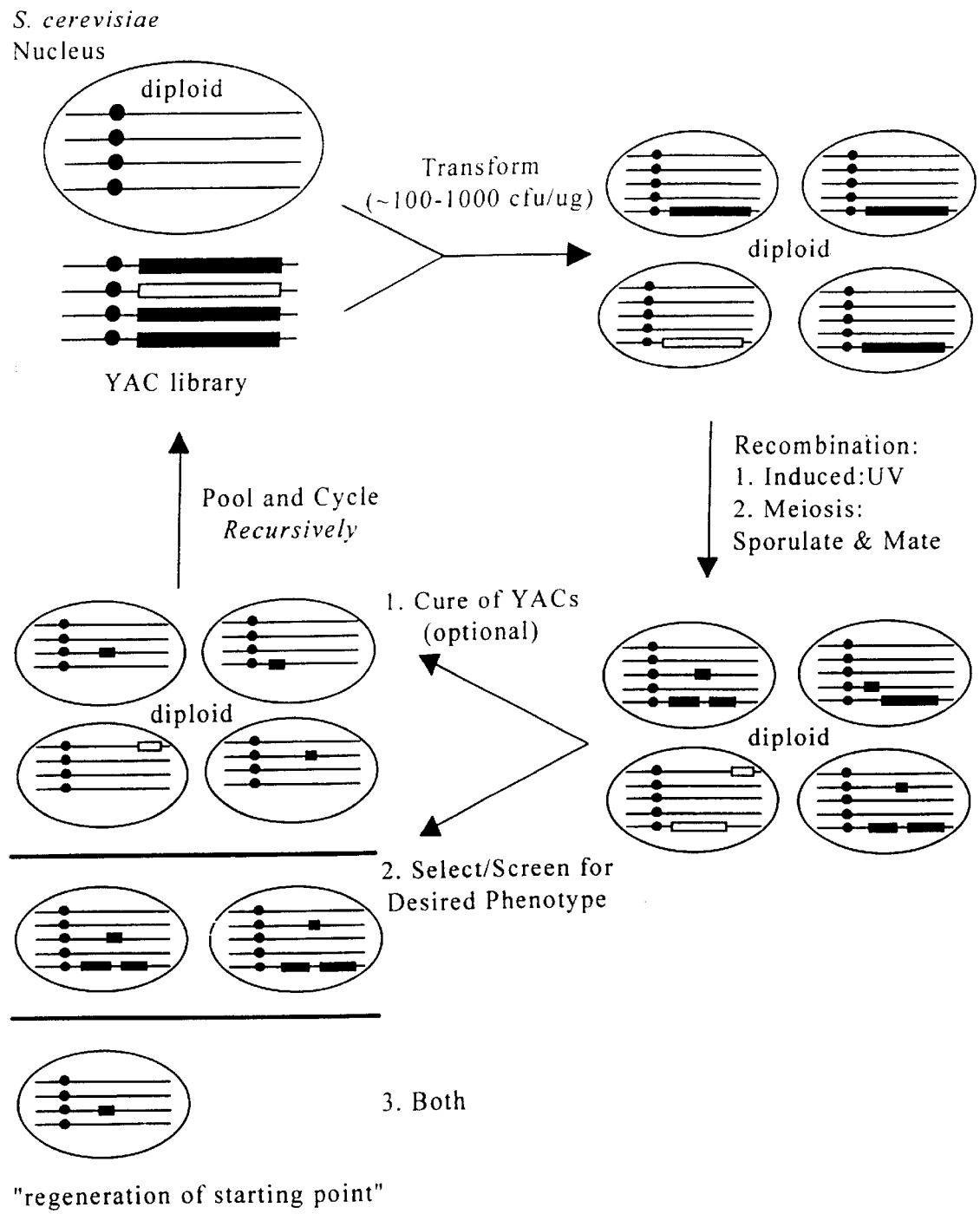
FIG. 10: YAC-mediated whole genome shuffling of Saccharomyces cerevisiae and related organisms.

An exemplary scheme for evolving yeast by introduction of a YAC library is shown in FIG. 10. The first part of the figure shows yeast containing an endogenous diploid genome and a YAC library of fragments representing variants of a sequence. The library is transformed into the cells to yield 100–1000 colonies per $\mu$gDNA. Most transformed yeast cells now harbor a single YAC as well as endogenous chromosomes. Meiosis is induced by growth on nitrogen and carbon limiting medium. In the course of meiosis the YACs recombine with other chromosomes in the same cell. Haploid spores resulting from meiosis mate and regenerated diploid forms. The diploid forms now harbor recombinant chromosomes, parts of which come from endogenous chromosomes and parts from YACs. Optionally, the YACs can now be cured from the cells by selecting against a negative selection marker present on the YACS. Irrespective whether YACS are selected against, cells are then screened or selected for a desired property. Cells surviving selection/screening are transformed with another YAC library to start another shuffling cycle.

b. Method of Evolving YACs for Transfer to Recipient Strain

These methods are based in part on the fact that multiple YACs can be harbored in the same yeast cell, and YAC—YAC recombination is known to occur (Green & Olson, *Science* 250, 94–98 1990)). Inter-YAC recombination provides a format for which families of homologous genes harbored on fragments of >20 kb can be shuffled in vivo.

The starting population of DNA fragments show sequence similarity with each other but differ as a result of for example, induced, allelic or species diversity. Often DNA fragments are known or suspected to encode multiple genes that function in a common pathway.

The fragments are cloned into a Yac and transformed into yeast, typically with positive selection for transformants. The transformants are induced to sporulate, as a result of which chromosomes undergo meiosis. The cells are then mated. Most of the resulting diploid cells now carry two YACs each having a different insert. These are again induced to sporulate and mated. The resulting cells harbor YACs of recombined sequence. The cells can then be screened or selected for a desired property. Typically, such selection occurs in the yeast strain used for shuffling. However, if fragments being shuffled are not expressed in yeast, YACs can be isolated and transferred to an appropriate cell type in which they are expressed for screening. Examples of such properties include the synthesis or degradation of a desired compound, increased secretion of a desired gene product, or other detectable phenotype.

Cells surviving selection/screening are subjected to successive cycles of pooling, sporulation, mating and selection/screening until the desired phenotype has been observed. Recombination can be achieved simply by transferring cells from rich medium to carbon and nitrogen limited medium to induce sporulation, and then returning the spores to rich media to induce mating. Asci can be lysed to stimulate mating of spores originating from different asci.

After YACs have been evolved to encode a desired property they can be transferred to other cell types. Transfer can be by protoplast fusion, or retransformation with isolated DNA. For example, transfer of YACs from yeast to mammalian cells is discussed by Monaco & Larin, *Trends in Biotechnology* 12, 280–286 (1994); Montoliu et al., *Reprod. Fertil. Dev.* 6, 577–84 (1994); Lamb et al., *Curr. Opin. Genet. Dev.* 5, 342–8 (1995).

Figure 11:
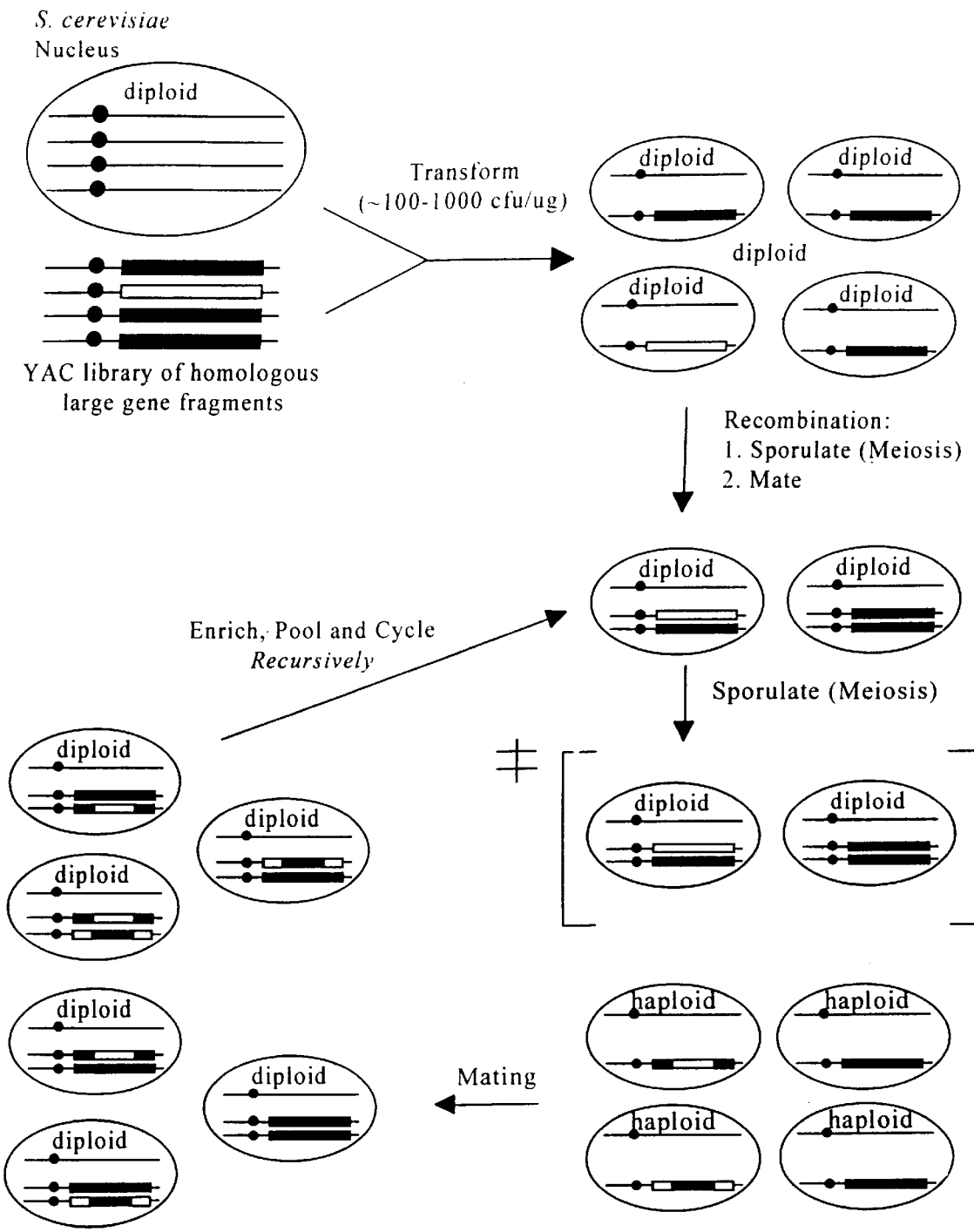
FIG. 11: YAC-mediated shuffling of large DNA fragments.

An exemplary scheme for shuffling a YAC fragment library in yeast is shown in FIG. 11. A library of YAC fragments representing genetic variants are transformed into yeast that have diploid endogenous chromosomes. The transformed yeast continue to have diploid endogenous chromosomes, plus a single YAC. The yeast are induced to undergo meiosis and sporulate. The spores contain haploid genomes, some of which contain only endogenous yeast chromosomes, and some of which contain yeast chromosomes plus a YAC. The spores are induced to mate generating diploid cells. Some of the diploid cells now contain two YAC bearing different inserts as well as diploid endogenous chromosomes. The cells are again induced to undergo meiosis and sporulate. In cells bearing two YACs, recombination occurs between the inserts, and recombinant YACs are segregated to ascoytes. Some ascoytes thus contain haploid endogenous chromosomes plus a YAC chromosome with a recombinant insert. The ascoytes mature to spores, which can mate again generating diploid cells. Some diploid cells now possess a diploid complement of endogenous chromosomes plus two recombinant YACs. These cells can then be taken through further cycles of meiosis, sporulation and mating. In each cycle, further recombination occurs between YAC inserts and further recombinant forms of inserts are generated. After one or several cycles of recombination has occurred, cells can be tested for acquisition of a desired property. Further cycles of recombination, followed by selection, can then be performed in similar fashion.

c. Use of YACs to Clone Unlinked Genes

Shuffling of YACs is particularly amenable to transfer of unlinked but functionally related genes from one species to another, particularly where such genes have not been identified. Such is the case for several commercially important natural products, such as taxol. Transfer of the genes in the metabolic pathway to a different organism is often desirable because organisms naturally producing such compounds are not well suited for mass culturing.

Clusters of such genes can be isolated by cloning a total genomic library of DNA from an organisms producing a useful compound into a YAC library. The YAC library is then transformed into yeast. The yeast is sporulated and mated such that recombination occurs between YACs and/or between YACs and natural yeast chromosomes. Selection/screening is then performed for expression of the desired collection of genes. If the genes encode a biosynthetic pathway, expression can be detected from the appearance of product of the pathway. Production of individual enzymes in the pathway, or intermediates of the final expression product or capacity of cells to metabolize such intermediates indicates partial acquisition of the synthetic pathway. The original library or a different library can be introduced into cells surviving/selection screening, and further rounds of recombination and selection/screening can be performed until the end product of the desired metabolic pathway is produced.

7. Conjugation-Mediated Genetic Exchange

Conjugation can be employed in the evolution of cell genomes in several ways. Conjugative transfer of DNA occurs during contact between cells. See Guiney (1993) in: *Bacterial Conjugation* (Clewell, ed., Plenum Press, New York), pp. 75–104; Reimmann & Haas in *Bacterial Conjugation* (Clewell, ed., Plenum Press, New York 1993), at pp. 137–188 (incorporated by reference in their entirety for all purposes). Conjugation occurs between many types of gram negative bacteria, and some types of gram positive bacteria. Conjugative transfer is also known between bacteria and plant cells (*Agrobacterium tumefaciens*) or yeast. As discussed in copending application attorney docket no. 16528J-014612, the genes responsible for conjugative transfer can themselves be evolved to expand the range of cell types (e.g., from bacteria to mammals) between which such transfer can occur.

Conjugative transfer is effected by an origin of transfer (oriT) and flanking genes (MOB A, B and C), and 15–25 genes, termed tra, encoding the structures and enzymes necessary for conjugation to occur. The transfer origin is defined as the site required in cis for DNA transfer. Tra genes include tra A, B, C, D, E, F, G, H, I, J, K, L, M, N, P, Q, R, S, T, U, V, W, X, Y, Z, virAB (alleles 1–11), C, D, E, G, IHF, and FinOP. Tra genes can be expressed in cis or trans to oriT. Other cellular enzymes, including those of the RecBCD pathway, RecA, SSB protein, DNA gyrase, DNA polI, and DNA ligase, are also involved in conjugative transfer. RecE or recF pathways can substitute for RecBCD.

One structural protein encoded by a tra gene is the sex pilus, a filament constructed of an aggregate of a single polypeptide protruding from the cell surface. The sex pilus binds to a polysaccharide on recipient cells and forms a conjugative bridge through which DNA can transfer. This process activates a site-specific nuclease encoded by a MOB gene, which specifically cleaves DNA to be transferred at oriT. The cleaved DNA is then threaded through the conjugation bridge by the action of other tra enzymes.

Mobilizable vectors can exist in episomal form or integrated into the chromosome. Episomal mobilizable vectors can be used to exchange fragments inserted into the vectors between cells. Integrated mobilizable vectors can be used to mobilize adjacent genes from the chromosome.

a. Use of Integrated Mobilizable Vectors to Promote Exchange of

Genomic DNA

The F plasmid of *E. coli* integrates into the chromosome at high frequency and mobilizes genes unidirectional from the site of integration (Clewell, 1993, supra; Firth et al., in *Escherichia coli and Salmonella Cellular and Molecular Biology* 2, 2377–2401 (1996); Frost et al., *Microbiol. Rev.* 58, 162–210 (1994)). Other mobilizable vectors do not spontaneously integrate into a host chromosome at high efficiency but can be induced to do by growth under particular conditions (e.g., treatment with a mutagenic agent, growth at a nonpermissive temperature for plasmid replication). See Reimann & Haas in *Bacterial Conjugation* (ed. Clewell, Plenum Press, NY 1993), Ch. 6. Of particular interest is the IncP group of conjugal plasmids which are typified by their broad host range (Clewell, 1993, supra.

Donor "male" bacteria which bear a chromosomal insertion of a conjugal plasmid, such as the *E. coli* F factor can efficiently donate chromosomal DNA to recipient "female" enteric bacteria which lack F (F–). Conjugal transfer from donor to recipient is initiated at oriT. Transfer of the nicked single strand to the recipient occurs in a 5' to 3' direction by a rolling circle mechanisms which allows mobilization of tandem chromosomal copies. Upon entering the recipient, the donor strand is discontinuously replicated. The linear, single-stranded donor DNA strand is a potent substrate for initiation of recA-mediated homologous recombination within the recipient. Recombination between the donor strand and recipient chromosomes can result in the inheritance of donor traits. Accordingly, strains which bear a chromosomal copy of F are designated Hfr (for high frequency of recombination) (Low, 1996 in *Escherichia coli and Salmonella Cellular and Molecular Biology* Vol. 2, pp. 2402–2405; Sanderson, in *Escherichia coli and Salmonella Cellular and Molecular Biology* 2, 2406–2412 (1996)).

The ability of strains with integrated mobilizable vector to transfer chromosomal DNA provides a rapid and efficient means of exchanging genetic material between a population of bacteria thereby allowing combination of positive mutations and dilution of negative mutations. Such shuffling methods typically start with a population of strains with an integrated mobilizable vector encompassing at least some genetic diversity. The genetic diversity can be the result of natural variation, exposure to a mutagenic agent or introduction of a fragment library. The population of cells is cultured without selection to allow genetic exchange, recombination and expression of recombinant genes. The cells are then screened or selected for a evolution toward a desired property. The population surviving selection/screening can then be subject to a further round of shuffling by HFR-mediated genetic exchange or otherwise.

The natural efficiency of Hfr and other strains with integrated mob vectors as recipients of conjugal transfer can be improved by several means. The relatively low recipient efficiency of natural HFR strains is attributable to the products of traS and traT genes of F (Clewell, 1993, supra; Firth et al., 1996, supra; Frost et al., 1994, supra; Achtman et al., *J. Mol. Biol.* 138, 779–795 (1980). These products are localized to the inner and outer membranes of F+ strains, respectively, where they serve to inhibit redundant matings between two strains which are both capable of donating DNA. The effects of traS and traT, and cognate genes in other conjugal plasmids, can be eliminated by use of knockout cells incapable of expressing these enzymes or reduced by propagating cells on a carbon-limited source. (Peters et al., *J. Bacteriol.*, 178, 3037–3043 (1996)).

In some methods, the starting population of cells has a mobilizable vector integrated at different genomic sites. Directional transfer from oriT typically results in more frequent inheritance of traits proximal to oriT. This is because mating pairs are fragile and tend to dissociate (particularly when in liquid medium) resulting in the interruption of transfer. In a population of cells having a mobilizable vector integrated at different sites chromosomal exchange occurs in a more random fashion. Kits of Hfr strains are available from the *E. coli.* Genetic Stock Center and the Salmonella Genetic Stock Centre (Frost et al., 1994, supra). Alternatively, a library of strains with oriT at random sites and orientations can be produced by insertion mutagenesis using a transposon which bears oriT. The use of a transposon bearing an oriT [e.g., the Tn5-oriT described by Yakobson E A, et al. *J. Bacteriol.* 1984 October; 160(1): 451–453] provides a quick method of generating such a library. Transfer functions for mobilization from the transposon-borne oriT sites are provided by a helper vector. It is possible to generate similar genetic constructs using other sequences known to one of skill as well.

In one aspect, a recursive scheme for genomic shuffling using Tn-oriT elements is provided. A prototrophic bacterial strain or set of related strains bearing a conjugal plasmid, such as the F fertility factor or a member of the IncP group of broad host range plasmids is mutagenized and screened for the desired properties. Individuals with the desired properties are mutagenized with a Tn-oriT element and screened for acquisition of an auxotrophy (e.g., by replica-plating to a minimal and complete media) resulting from insertion of the Tn-oriT element in any one of many biosynthetic gene scattered across the genome. The resulting auxotrophs are pooled and allowed to mate under conditions promoting male-to-male matings, e.g., during growth in close proximity on a filter membrane. Note that transfer functions are provided by the helper conjugal plasmid present in the original strain set. Recombinant transconjugants are selected on minimal medium and screened for further improvement.

Optionally, strains bearing integrated mobilizable vectors are defective in mismatch repair gene(s). Inheritance of donor traits which arise from sequence heterologies increases in strains lacking the methyl-directed mismatch repair system. Optionally, the gene products which decrease recombination efficiency can be inhibited by small molecules.

Intergenic congual transfer between species such as *E. coli* and *Salmonella typhimurium*, which are 20% divergent at the DNA level, is also possible if the recipient strain is mutH, mutL or mutS (see Rayssiguier et al., *Nature* 342, 396–401 (1989)). Such transfer can be used to obtain recombination at several points as shown by the following example.

The example uses an *S. typhimurium* Hfr donor strain having markers thr557 at map position 0, pyrF2690 at 33 min, serA13 at 62 min and hfrK5 at 43 min. MutS +/−, F− *E. coli* recipient strains had markers pyrD68 at 21 min aroC355 at 51 min, ilv3164 at 85 min and mutS215 at 59 min. The triauxotrophic *S. typhimurium* Hfr donor and isogenic mutS+/−triauxotrophic *E. coli* recipient were inoculated into 3 ml of Lb broth and shaken at 37° C. until fully grown. 100 $\mu$l of the donor and each recipient were mixed in 10 ml fresh LB broth, and then deposited to a sterile Millipore 0.45 $\mu$M HA filter using a Nalgene 250 ml reusable filtration device. The donor and recipients alone were similarly diluted and deposited to check for reversion. The filters with cells were placed cell-side-up on the surface of an LB agar plate which was incubated overnight at 37° C. The filters were removed with the aid of a sterile forceps and placed in a sterile 50 ml tube containing 5 ml of minimal salts broth. Vigorous vortexing was used to wash the cells from the filters. 100 $\mu$l of mating mixtures, as well as donor and recipient controls were spread to LB for viable cell counts and minimal glucose supplemented with either two of the three recipient requirements for single recombinant counts, one of the three requirements for double recombinant counts, or none of the three requirements for triple recombinant counts. The plates were incubated for 48 hr at 37° after which colones were counted.

| Medium Supplements | Recombinant Genotype | Recombinant CFUs/ Total CFUs | | |
|---|---|---|---|---|
| | | mutS$^+$ | mutS$^-$ | mutS$^-$/mutS$^+$ |
| Aro + Iiv | pyr$^+$ aro$^-$ ilv$^-$ | — | — | |
| Aro + Ura | pyr$^-$ aro$^-$ ilv$^+$ | $1.2 \times 10^{-8}$ | $2.5 \times 10^{-6}$ | 208 |
| Ilv + Ura | pyr$^-$ aro$^+$ ilv$^-$ | $2.7 \times 10^{-8}$ | $3.0 \times 10^{-6}$ | 111 |
| Aro | pyr$^+$ aro$^-$ ilv$^+$ | — | — | — |
| Ilv | pyr$^+$ aro$^+$ ilv$^-$ | — | — | — |
| Ura | pyr$^-$ aro$^+$ ilv$^+$ | $<10^{-9}$ | $<10^{-9}$ | |
| nothing | pyr$^+$ aro$^+$ ilv$^+$ | | | |

Aro = aromatic amino acids and vitamins
Ilv = branched chain amino acids
Ura = uracil The data indicate that recombinants can be generated at reasonable frequenceis using Hfr matings. Intergeneric recombination is enhanced 100–200 fold in a recipient that is defective methyl-directed mismatch repair.

b. Introduction of Fragments by Conjugation

Mobilizable vectors can also be used to transfer fragment libraries into cells to be evolved. This approach is particularly useful in situations in which the cells to be evolved cannot be efficiently transformed directly with the fragment library but can undergo conjugation with primary cells that can be transformed with the fragment library.

DNA fragments to be introduced into host cells encompasses diversity relative to the host cell genome. The diversity can be the result of natural diversity or mutagenesis. The DNA fragment library is cloned into a mobilizable vector having an origin of transfer. Some such vectors also contain mob genes although alternatively these functions can also be provided in trans. The vector should be capable of efficient conjugal transfer between primary cells and the intended host cells. The vector should also confer a selectable phenotype. This phenotype can be the same as the phenotype being evolved or can be conferred by a marker, such as a drug resistance marker. The vector should preferably allow self-elimination in the intended host cells thereby allowing selection for cells in which a cloned fragment has undergone genetic exchange with a host homologous host segment rather than duplication. Such can be achieved by use of vector lacking an origin of replication functional in the intended host type or inclusion of a negative selection marker in the vector.

One suitable vector is the broad host range conjugation plasmid described by Simon et al., *Bio/Technology* 1, 784–791 (1983); TrieuCuot et al., *Gene* 102, 99–104 (1991); Bierman et al., *Gene* 116, 43–49 (1992). These plasmids can be transformed into *E. coli* and then force-mated into bacteria that are difficult or impossible to transform by chemical or electrical induction of competence. These plasmids contain the origin of the IncP plasmid, oriT. Mobilization functions are supplied in trans by chromosomally-integrated copies of the necessary genes. Conjugal transfer of DNA can in some cases be assisted by treatment of the recipient (if gram-positive) with sub-inhibitory concentrations of penicillins (Trieu-Cuot et al., 1993 *FEMS Microbiol. Lett.* 109, 19–23).

Cells that have undergone allelic exchange with library fragments can be screened or selected for evolution toward a desired phenotype. Subsequent rounds of recombination can be performed by repeating the conjugal transfer step. the library of fragments can be fresh or can be obtained from some (but not all) of the cells surviving a previous round of selection/screening. Conjugation-mediated shuffling can be combined with other methods of shuffling.

8. Genetic Exchange Promoted by Transducing Phage

Transduction is the transfer, from one cell to another, of nonviral genetic material within a viral coat (Masters, in *Escherichia coli and Salmonella Cellular and Molecular Biology* 2, 2421–2442 (1996). Perhaps the two best examples of generalized transducing phage are bacteriophages P1 and P22 of *E. coli* and *S. typhimurium*, respectively. Generalized transducing bacteriophage particles are formed at a low frequency during lytic infection when viral-genome-sized, doubled-stranded fragments of host (which serves as donor) chromosomal DNA are packaged into phage heads. Promiscuous high transducing (HT) mutants of bacteriophage P22 which efficiently package DNA with little sequence specificity have been isolated. Infection of a susceptible host results in a lysate in which up to 50% of the phage are transducing particles. Adsorption of the generalized transducing particle to a susceptible recipient cell results in the injection of the donor chromosomal fragment. RecA-mediated homologous recombination following injection of the donor fragment can result in the inheritance of donor traits. Another type of phage which achieves quasi random insertion of DNA into the host chromosome is Mu. For an overview of Mu biology, see, Groisman (1991) in *Methods in Enzymology* v. 204. Mu can generate a variety of chromosomal rearrangements including deletions, inversions, duplications and transpositions. In addition, elements which combine the features of P22 and Mu are available, including Mud-P22, which contains the ends of the Mu genome in place of the P22 att site and int gene. See, Berg, supra.

Generalized transducing phage can be used to exchange genetic material between a population of cells encompassing genetic diversity and susceptible to infection by the phage. Genetic diversity can be the result of natural variation between cells, induced mutation of cells or the introduction of fragment libraries into cells. DNA is then exchanged between cells by generalized transduction. If the phage does not cause lysis of cells, the entire population of cells can be propagated in the presence of phage. If the phage results in lytic infection, transduction is performed on a split pool basis. That is, the starting population of cells is divided into two. One subpopulation is used to prepare transducing phage. The transducing phage are then infected into the other subpopulation. Preferably, infection is performed at high multiplicity of phage per cell so that few cells remain uninfected. Cells surviving infection are propagated and screened or selected for evolution toward a desired property. The pool of cells surviving screening/selection can then be shuffled by a further round of generalized transduction or by other shuffling methods.

The efficiency of the above methods can be increased by reducing infection of cells by infectious (nontransducing phage) and by reducing lysogen formation. The former can be achieved by inclusion of chelators of divalent cations, such as citrate and EGTA in culture media. Tail defective transducing phages can be used to allow only a single round of infection. Divalent cations are required for phage absorption and the inclusion of chelating agents therefore provides a means of preventing unwanted infection. Integration defective (int⁻) derivatives of generalized transducing phage can be used to prevent lysogen formation. In a further variation, host cells with defects in mismatch repair gene(s) can be used to increase recombination between transduced DNA and genomic DNA.

9. Use of Locked in Prophages to Facilitate DNA Shuffling

The use of a hybrid, mobile genetic element (locked-in prophages) as a means to facilitate whole genome shuffling of organisms using phage transduction as a means to transfer DNA from donor to recipient is a preferred embodiment. One such element (Mud-P22) based on the temperate Salmonella phage P22 has been described for use in genetic and physical mapping of mutations. See, Youderian et al. (1988) *Genetics* 118:581–592, and Benson and Goldman (1992) *J. Bacteriol.* 174(5):1673–1681. Individual Mud-P22 insertions package specific regions of the Salmonella chromosome into phage P22 particles. Libraries of random Mud-P22 insertions can be readily isolated and induced to create pools of phage particles packaging random chromosomal DNA fragments. These phage particles can be used to infect new cells and transfer the DNA from the host into the recipient in the process of transduction. Alternatively, the packaged chromosomal DNA can be isolated and manipulated further by techniques such as DNA shuffling or any other mutagenesis technique prior to being reintroduced into cells (especially recD cells for linear DNA) by transformation or electroporation, where they integrate into the chromosome.

Either the intact transducing phage particles or isolated DNA can be subjected to a variety of mutagens prior to reintroduction into cells to enhance the mutation rate. Mutator cell lines such as mutD can also be used for phage growth. Either method can be used recursively in a process to create genes or strains with desired properties. *E. coli* cells carrying a cosmid clone of Salmonella LPS genes are infectable by P22 phage. It is possible to develop similar genetic elements using other combinations of transposable elements and bacteriophages or viruses as well.

P22 is a lambdoid phage that packages its DNA into preassembled phage particles (heads) by a "headful" mechanism. Packaging of phage DNA is initiated at a specific site (pac) and proceeds unidirectionally along a linear, double stranded normally concatameric molecule. When the phage head is full (~43 kb), the DNA strand is cleaved, and packaging of the next phage head is initiated. Locked-in or excision-defective P22 prophages, however, initiate packaging at their pac site, and then proceed unidirectionally along the chromosome, packaging successive headfuls of chromosomal DNA (rather than phage DNA). When these transducing phages infect new Salmonella cells they inject the chromosomal DNA from the original host into the recipient cell, where it can recombine into the chromosome by homologous recombination creating a chimeric chromosome. Upon infection of recipient cells at a high multiplicity of infection, recombination can also occur between incoming transducing fragments prior to recombination into the chromosome.

Integration of such locked-in P22 prophages at various sites in the chromosome allows flanking regions to be amplified and packaged into phage particles. The Mud-P22 mobile genetic element contains an excision-defective P22 prophage flanked by the ends of phage/transposon Mu. The entire Mud-P22 element can transpose to virtually any location in the chromosome or other episome (eg. F', BAC clone) when the Mu A and B proteins are provided in trans.

A number of embodiments for this type of genetic element are available. In one example, the locked in prophage are used as generalized transducing phage to transfer random fragments of a donor chromosome into a recipient. The Mud-P22 element acts as a transposon when Mu A and B transposase proteins are provided in trans and integrate copies of itself at random locations in the chromosome. In this way, a library of random chromosomal Mud-P22 insertions can be generated in a suitable host. When the Mud-P22 prophages in this library are induced, random fragments of chromosomal DNA will be packaged into phage particles. When these phages infect recipient cells, the chromosomal DNA is injected and can recombine into the chromosome of the recipient. These recipient cells are screened for a desired property and cells showing improvement are then propagated. The process can be repeated, since the Mud-P22 genetic element is not transferred to the recipient in this process. Infection at a high multiplicity allows for multiple chromosomal fragments to be injected and recombined into the recipient chromosome.

Locked-in prophages can also be used as specialized transducing phage. Individual insertions near a gene of interest can be isolated from a random insertion library by a variety of methods. Induction of these specific prophages results in packaging of flanking chromosomal DNA including the gene(s) of interest into phage particles. Infection of recipient cells with these phages and recombination of the packaged DNA into the chromosome creates chimeric genes that can be screened for desired properties. Infection at a high multiplicity of infection can allow recombination between incoming transducing fragments prior to recombination into the chromosome.

These specialized transducing phage can also be used to isolate large quantities of high quality DNA containing specific genes of interest without any prior knowledge of the DNA sequence. Cloning of specific genes is not required. Insertion of such an element nearby a biosynthetic operon for example allows for large amounts of DNA from that operon to be isolated for use in DNA shuffling (in vitro and/or in vivo), cloning, sequencing, or other uses as set forth herein. DNA isolated from similar insertions in other organisms containing homologous operons are optionally mixed for use in family shuffling formats as described herein, in which homologous genes from different organsims (or different chromosomal locations within a single species, or both).

Phage isolated from insertions in a variety of strains or organisms containing homologous operons are optionally mixed and used to coinfect cells at a high MOI allowing for recombination between incoming transducing fragments prior to recombination into the chromosome.

Locked in prophage are useful for mapping of genes, operons, and/or specific mutations with either desirable or undesirable phenotypes. Locked-in prophages can also provide a means to separate and map multiple mutations in a given host. If one is looking for beneficial mutations outside a gene or operon of interest, then an unmodified gene or operon can be transduced into a mutagenized or shuffled host then screened for the presence of desired secondary mutations. Alternatively, the gene/operon of interest can be readily moved from a mutagenized/shuffled host into a different background to screen/select for modifications in the gene/operon itself.

It is also possible to develop similar genetic elements using other combinations of transposable elements and bacteriophages or viruses as well. Similar systems are set up in other organisms, e.g., that do not allow replication of P22 or P1. Broad host range phages and transposable elements are especially useful. Similar genetic elements are derived from other temperate phages that also package by a headful mechanism. In general, these are the phages that are capable of generalized transduction. Viruses infecting eukaryotic cells may be adapted for similar purposes. Examples of generalized transducing phages that are useful are described in: Green et al., "Isolation and preliminary characterization of lytic and lysogenic phages with wide host range within the streptomycetes", *J. Gen Microbiol* 131(9):2459–2465 (1985); Studdard et al., "Genome structure in Streptomyces spp.: adjacent genes on the *S. coelicolor* A3(2) linkage map have cotransducible analogs in *S. venezuelae*", *J. Bacteriol* 169(8):3814–3816 (1987); Wang et al., "High frequency generalized transduction by miniMu plasmid phage", *Genetics* 116(2):201–206, (1987); Welker, N. E., "Transduction in *Bacillus stearothermophilus*", *J. Bacteriol*, 176(11):3354–3359, (1988); Darzins et al., "Mini-D3112 bacteriophage transposable elements for genetic analysis of *Pseudomonas aeruginosa, J. Bacteriol* 171(7):3909–3916 (1989); Hugouvieux-Cotte-Pattat et al., "Expanded linkage map of *Erwinia chrysanthemi* strain 3937", *Mol Microbiol* 3(5):573–581, (1989); Ichige et al., "Establishment of gene transfer systems for and construction of the genetic map of a marine Vibrio strain", *J. Bacteriol* 171(4):1825–1834 (1989); Muramatsu et al., "Two generalized transducing phages in *Vibrio parahaemolyticus* and *Vibrio alginolyticus*", *Microbiol Immunol* 35(12):1073–1084 (1991); Regue et al., "A generalized transducing bacteriophage for *Serratia marcescens*", *Res Microbiol* 42(1):23–27, (1991); Kiesel et al., "Phage Acm1-mediated transduction in the facultatively methanol-utilizing *Acetobacter methanolicus* MB 58/4", *J. Gen Virol* 74(9):1741–1745 (1993); Blahova et al., "Transduction of imipenem resistance by the phage F-116 from a nosocomial strain of *Pseudomonas aeruginosa* isolated in Slovakia", *Acta Virol* 38(5):247–250 (1994); Kidambi et al., "Evidence for phage-mediated gene transfer among *Pseudomonas aeruginosa* strains on the phylloplane", *Appl Environ Microbiol* 60:(2)496–500 (1994); Weiss et al., "Isolation and characterization of a generalized transducing phage for *Xanthomonas campestris* pv. *campestris", J. Bacteriol* 176(11):3354–3359 (1994); Matsumoto et al., "Clustering of the trp genes in Burkholderia (formerly Pseudomonas) cepacia", *FEMS Microbiol Lett* 134(2–3):265–271 (1995); Schicklmaier et al., "Frequency of generalized transducing phages in natura isolates of the *Salmonella typhimurium* complex", *Appl Environ Microbiol* 61(4): 61(4):1637–1640 (1995); Humphrey et al., "Purification and characterization of VSH-1, a generalized transducing bacteriophase of *Serpulina hyodysenteriae", J Bacteriol* 179(2):323–329 (1997); Willi et al., "Transduction of antibiotic resistance markers among *Actinobacillus actinomycetemcomitans* strains by temperate bacteripphages Aa phi 23", *Cell Mol Life Sci* 53(11–12):904–910 (1997); Jensen et al., "Prevalence of broad-host-range lytic bacteriophages of *Sphaerotilus natans, Escherichia coli,* and *Pseudomonas aeruginosa", Appl Environ Microbiol* 64(2):575–580 (1998), and Nedelmann et al., "Generalized transduction for genetic linkage analysis and transfer of transposon insertions in different *Staphylococcus epidermidis* strains", *Zentiviralalbl Bakteriol* 287(1–2):85–92 (1998).

A Mud-P1/Tn-P1 system comparable to Mud-P22 is developed using phage P1. Phage P1 has an advantage of packaging much larger (~110 kb) fragments per headful. Phage P1 is currently used to create bacterial artificial chromosomes or BAC's. P1-based BAC vectors are designed along these principles so that cloned DNA is packaged into phage particles, rather than the current system, which requires DNA preparation from single-copy episomes. This combines the advantages of both systems in having the genes cloned in a stable single-copy format, whilst allowing for amplification and specific packaging of cloned DNA upon induction of the prophage.

10. Random Placement of Genes or Improved Genes Throughout the Genome for Optimization of Gene Context The placement and orientation of genes in a host chromosome (the "context" of the gene in a chromosome) or episome has large effects on gene expression and activity. Random integration of plasmid or other episomal sequences into a host chromosome by non-homologous recombination, followed by selection or screening for the desired phenotype, is a preferred way of identifing optimal chromosomal positions for expression of a target. This strategy is illustrated in FIG. 18.

A variety of transposon mediated delivery systems can be employed to deliver genes of interest, either individual genes, genomic libraries, or a library of shuffled gene(s) randomly throughout the genome of a host. Thus, in one preferred embodiment, the improvement of a cellular function is achieved by cloning a gene of interest, for example a gene encoding a desired metabolic pathway, within a transposon delivery vehicle.

Such transposon vehicles are available for both Gram-negative and Gram-positive bacteria. De Lorenzo and Timis (1994) *Methods in Enzymology* 235:385–404 describe the analysis and construction of stable phenotypes in gram-negative Bacteria with Tn5- and Tn 10-derived minitransposons. Kleckner et al. (1991) *Methods in Enzymology* 204, chapter 7 describe uses of transposons such as Tn10, including for use in gram positive bacteria. Petit et al. (1990) *Journal of Bacteriology* 172(12):6736–6740 describe Tn10 derived transposons active in *Bacillus Subtilis.* The transposon delivery vehicle is introduced into a cell population, which is then selected for recombinant cells that have incorporated the transposon into the genome.

The selection is typically by any of a variety of drug resistant markers also carried within the transposon. The selected subpopulation is screened for cells having improved expression of the gene(s) of interest. Once cells harboring the genes of interest in the optimal location are isolated, the genes are amplified from within the genome using PCR, shuffled, and cloned back into a similar transposon delivery vehicle which contains a different selection marker within the transposon and lacks the transposon integrase gene.

This shuffled library is then transformed back into the strain harboring the original transposon, and the cells are selected for the presence of the new resistance marker and the loss of the previous selection marker. Selected cells are enriched for those that have exchanged by homologous recombination the original transposon for the new transposon carrying members of the shuffled library. The surviving cells are then screened for further improvements in the expression of the desired phenotype. The genes from the improved cells are then amplified by the PCR and shuffled again. This process is carried out recursively, oscillating each cycle between the different selection markers. Once the gene(s) of interest are optimized to a desired level, the fragment can be amplified and again randomly distributed throughout the genome as described above to identify the optimal location of the improved genes.

Alternatively, the gene(s) conferring a desired property may not be known. In this case the DNA fragments cloned within the transposon delivery vehicle could be a library of genomic fragments originating from a population of cells derived from one or more strains having the desired property(ies). The library is delivered to a population of cells derived from one or more strains having or lacking the desired property(ies) and cells incorporating the transposon are selected. The surviving cells are then screened for acquisition or improvement of the desired property. The fragments contained within the surviving cells are amplified by PCR and then cloned as a pool into a similar transposon delivery vector harboring a different selection marker from the first delivery vector. This library is then delivered to the pool of surviving cells, and the population having acquired the new selective marker is selected. The selected cells are then screened for further acquisition or improvement of the desired property. In this way the different possible combinations of genes conferring or improving a desired phenotype are explored in a combinatorial fashion. This process is carried out repetitively with each new cycle employing an additional selection marker.

Alternatively, the amplified fragments from each improved cell are shuffled independently. The shuffled libraries are then cloned back into a transposon delivery vehicle similar to the original vector but containing a different selection marker and lacking the transposase gene. Selection is then for acquisition of the new marker and loss of the previous marker. Selected cells are enriched for those incorporating the shuffled variants of the amplified genes by homologous recombination. This process is carried out recursively, oscillating each cycle between the two selective markers.

11. Improvement of Overexpressed Genes for a Desired Phenotype

The improvement of a cellular property or phenotype is often enhanced by increasing the copy number or expression of gene(s) participating in the expression of that property. Genes that have such an effect on a desired property can also be improved by DNA shuffling to have a similar effect. A genomic DNA library is cloned into an overexpression vector and transformed into a target cell population such that the genomic fragments are highly expressed in cells selected for the presence of the overexpression vector. The selected cells are then screened for improvement of a desired property. The overexpression vector from the improved cells are isolated and the cloned genomic fragments shuffled. The genomic fragment carried in the vector from each improved isolate is shuffled independently or with identified homologous genes (family shuffling). The shuffled libraries are then delivered back to a population of cells and the selected transformants rescreened for further improvements in the desired property. This shuffling/screening process is cycled recursively until the desired property has been optimized to the desired level.

As stated above, gene dosage can greatly enhance a desired cellular property. One method of increasing gene copy number of unknown genes is using a method of random amplification (see also, Mavingui et. al. (1997) *Nature Biotech,* 15, 564). In this method, a genomic library is cloned into a suicide vector containing a selective marker that also at higher dosage provides an enhanced phenotype. An example of such a marker is the kanamycin resistance gene. At successively higher copy number, resistance to successively higher levels of kanamycin is achieved. The genomic library is delivered to a target cell by any of a variety of methods including transformation, transduction, conjugation, etc. Cells that have incorporated the vector into the chromosome by homologous recombination between the vector and chromosomal copies of the cloned genes can be selected by requiring expression of the selection marker under conditions where the vector does not replicate. This recombination event results in the duplication of the cloned DNA fragment in the host chromosome with a copy of the vector and selection marker separating the two copies. The population of surviving cells are screened for improvement of a desired cellular property resulting form the gene duplication event. Further gene duplication events resulting in additional copies of the original cloned DNA fragments can be generated by further propagating the cells under successively more stringent selective conditions i.e. increased concentrations of kanamycin. In this case selection requires increased copies of the selective marker, but increased copies of the desired gene fragment is also concomitant. Surviving cells are further screened for an improvement in the desired phenotype. The resulting population of cells likely resulted in the amplification of different genes since often many genes effect a given phenotype. To generate a library of the possible combinations of these genes, the original selected library showing phenotypic improvements are recombined, using the methods described herein, e.g., protoplast fusion, split pool transduction, transformation, conjugation, etc.

The recombined cells are selected for increased expression of the selective marker. Survivors are enriched for cells having incorporated additional copies of the vector sequence by homologous recombination, and these cells will be enriched for those having combined duplications of different genes. In other words, the duplication from one cell of enhanced phenotype becomes combined with the duplication of another cell of enhanced phenotype. These survivors are screened for further improvements in the desired phenotype. This procedure is repeated recursively until the desired level of phenotypic expression is achieved.

Alternatively, genes that have been identified or are suspected as being beneficial in increased copy number are cloned in tandem into appropriate plasmid vectors. These vectors are then transformed and propagated in an appropriate host organism. Plasmid-plasmid recombination between the cloned gene fragments result in further duplication of the genes. Resolution of the plasmid doublet can result in the uneven distribution of the gene copies, with some plasmids having additional gene copies and others having fewer gene copies. Cells carrying this distribution of plasmids are then screened for an improvement in the phenotype effected by the gene duplications.

In summary, a method of selecting for increased copy number of a nucleic acid sequence by the above procedure is provided. In the method, a genomic library in a suicide vector comprising a dose-sensitive selectable marker is provided, as noted above. The genomic library is transduced into a population of target cells. The target cells are selected in a population of target cells for increasing doses of the selectable marker under conditions in which the suicide vector does not replicate episomally. A plurality of target cells are selected for the desired phenotype, recombined and reselected. The process is recursively repeated, if desired, until the desired phenotype is obtained.

12. Strategies for Improving Genomic Shuffling via Transformation of Linear DNA Fragments Wild-type members of the Enterobacteriaceae (e.g. *Escherichia coli*) are typically resistant to genetic exchange following transformation of linear DNA molecules. This is due, at least in part, to the Exonuclease V (Exo V) activity of the RecBCD holoenzyme which rapidly degrades linear DNA molecules following transformation. Production of Exo V has been traced to the recD gene, which encodes the D subunit of the holoenzyme. As demonstrated by Russel et al. (1989) *Journal of Bacteriology* 2609–2613, homologous recombination between a transformed linear donor DNA molecule and the chromosome of recipient is readily detected in a strains bearing a loss of function mutation in recD mutant. The use of recD strains provides a simple means for genomic shuffling of the Enterobacteriaceae. For example, a bacterial strain or set of related strains bearing a recD null mutation (e.g., the *E. coli* recD1903::mini-Tet allele) is mutagenized and screened for the desired properties. In a split-pool fashion, Chromosomal DNA prepared on one aliquot could be used to transform (e.g., via electroporation or chemically induce competence) the second aliquot. The resluting transformants are then screened for improvement.

The RecBCD holoezyme plays an important role in initiation of RecA-dependent homologous recombination. Upon recognizing a dsDNA end, the RecBCD enzyme unwinds and degrades the DNA asymmetrically in a 5' to 3' direction until it encounters a chi (or "X")-site (consensus 5'-GCTGGTGG-3') which attenuates the nuclease activity. This results in the generation of ssDNA terminating near the c site with 3'-ssDNA tail that is preferred RecA loading and subsequent invasion of dsDNA for homologous recombination. Accordingly, preprocessing of transforming fragments with 5' to 3' specific ssDNA Exonuclease, such as Lamda ($\lambda$) exonuclease (available, e.g., from Boeringer Mannheim) prior to transformation may serve to stimulate homologous recombination recD strain by providing ssDNA invasive end for RecA loading and subsequent stand invasion.

The addition of DNA sequence encoding chi-sites (consensus 5'-GCTGGTGG-3') to DNA fragments can serve to both attenuate Exonuclease V activity and stimulate homologous recombination, thereby obviating the need for a recD mutation (see also, Kowalczykowski, et al. (1994) "Biochemistry of homologous recombination in *Escherichia coli,*" *Microbiol. Rev.* 358:401–465 and Jessen, et al. (1998) "Modification of bacterial artificial chromosomes through Chi-stimulated homologous recombination and its application in zebrafish transgenesis." *Proc. Natl. Acad. Sci.* 95:5121–5126).

Chi-sites are optionally included in linkers ligated to the ends of transforming fragments or incorporated into the external primers used to generate DNA fragments to be transformed. The use of recombination-stimulatory sequences such as chi is a generally useful approach for evolution of a broad range of cell types by fragment transformation.

Methods to inhibit or mutate analogs of Exo V or other nucleases (such as, Exonucleases I (endA1), III (nth), IV (nfo), VII, and VIII of E. coli) is similarly useful. Inhibition or elimination of nucleases, or modification of ends of transforming DNA fragments to render them resistant to exonuclease activity has applications in evolution of a broad range of cell types.

13. Shuffling to optimize unknown interactions

Many observed traits are the result of complex interactions of multiple genes or gene products. Most such interactions are still uncharacterized. Accordingly, it is often unclear which genes need to optimized to achieve a desired trait, even if some of the genes contributing to the trait are known.

This lack of characterization is not an issue during DNA shuffling, which produces solutions that optimize whatever is selected for. An alternative approach, which has the potential to solve not only this problem, but also anticipated future rate limiting factors, is complementation by overexpression of unknown genomic sequences.

A library of genomic DNA is first made a described, supra. This is transformed into the cell to be optimized and transformants are screened for increases in a desired property. Genomic fragments which result in an improved property are evolved by DNA shuffling to further increase their beneficial effect. This approach requires no sequence information, nor any knowledge or assumptions about the nature of protein or pathway interactions, or even of what steps are rate-limiting; it relies only on detection of the desired phenotype. This sort of random cloning and subsequent evolution by DNA shuffling of positively interacting genomic sequences is extremely powerful and generic. A variety of sources of genomic DNA are used, from isogenic strains to more distantly related species with potentially desirable properties. In addition, the technique is applicable to any cell for which the molecular biology basics of transformation and cloning vectors are available, and for any property which can be assayed (preferably in a high-throughput format).

14. Homologous Recombination within the Chromosome

Homologous recombination within the chromosome is used to circumvent the limitations of plasmid based evolution and size restrictions. The strategy is similar to that described above for shuffling genes within their chromosomal context, except that no in vitro shuffling occurs. Instead, the parent strain is treated with mutagens such a ultraviolet light or nitrosoguanidine, and improved mutants are selected. The improved mutants are pooled and split. Half of the pool is used to generate random genomic fragments for cloning into a homologous recombination vector. Additional genomic fragments are optionally derived from related species with desirable properties. The cloned genomic fragments are homologously recombined into the genomes of the remaining half of the mutant pool, and variants with improved properties are selected. These are subjected to a further round of mutagenesis, selection and recombination. Again this process is entirely generic for the improvement of any whole cell biocatalyst for which a recombination vector and an assay can be developed.

V. Methods for Recursive Sequence Recombination

Some formats and examples for recursive sequence recombination, sometimes referred to as DNA shuffling or molecular breeding, have been described by the present inventors and co-workers in copending application Ser. No. 08/621,859, now U.S. Pat. No. 6,117,679, filed Mar. 25, 1996, PCT/US95/02126 filed Feb. 17, 1995 (published as WO 95/22625); Stemmer, Science 270, 1510 (1995); Stemmer et al., Gene, 164, 49–53 (1995); Stemmer, Bio/Technology, 13, 549–553 (1995); Stemmer, Proc. Natl. Acad. Sci. USA 91, 10747–10751 (1994); Stemmer, Nature 370, 389–391 (1994); Crameri et al., Nature Medicine, 2(1):1–3, (1996), and Crameri et al., Nature Biotechnology 14, 315–319 (1996) (each of which is incorporated by reference in its entirety for all purposes).

Figure 16A:
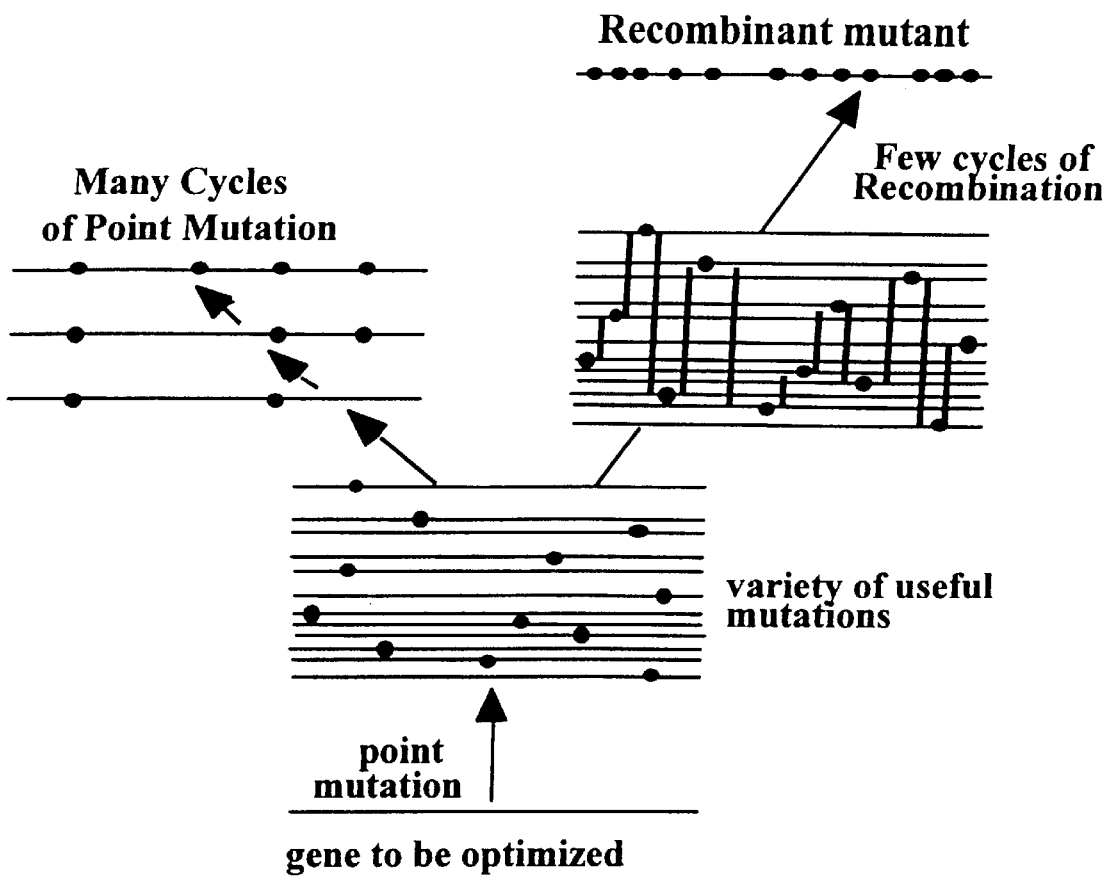
FIG. 16: graph of fitness versus sequence space for three different mutation strategies.
Figure 16B:
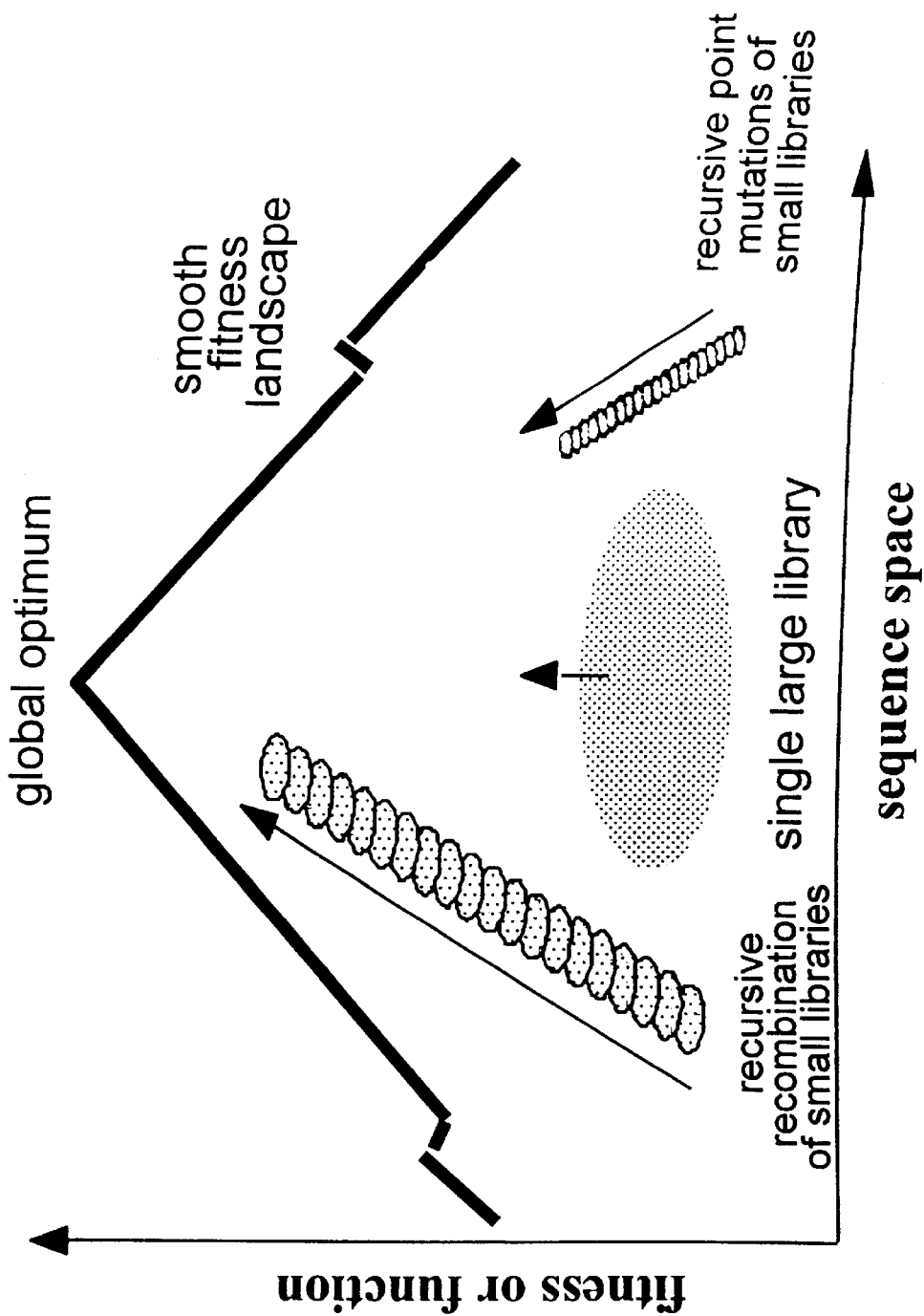
Figure 17:
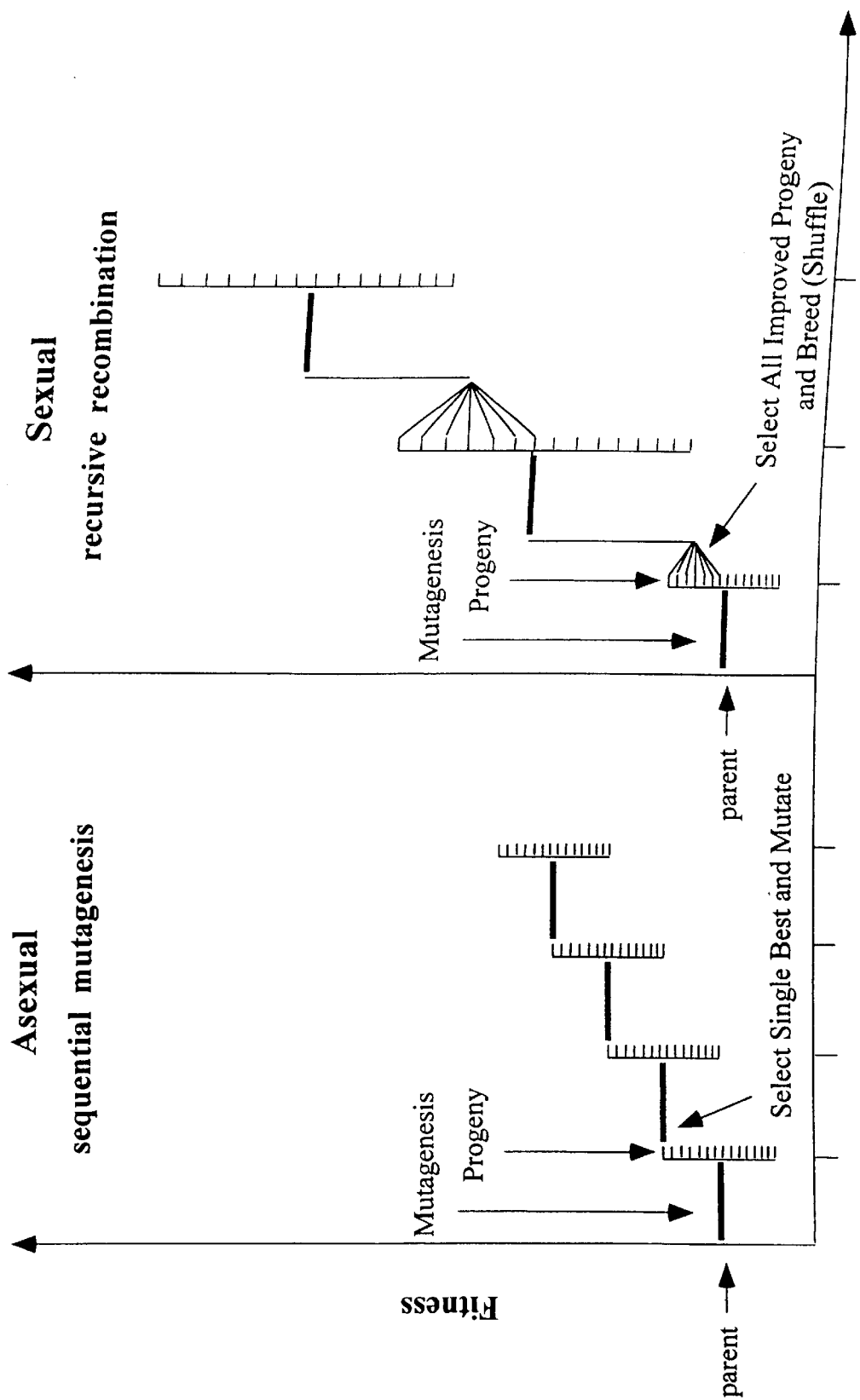
FIG. 17: graphs of asexual sequential mutagenesis and sexual recursive recombination.
Figure 18:
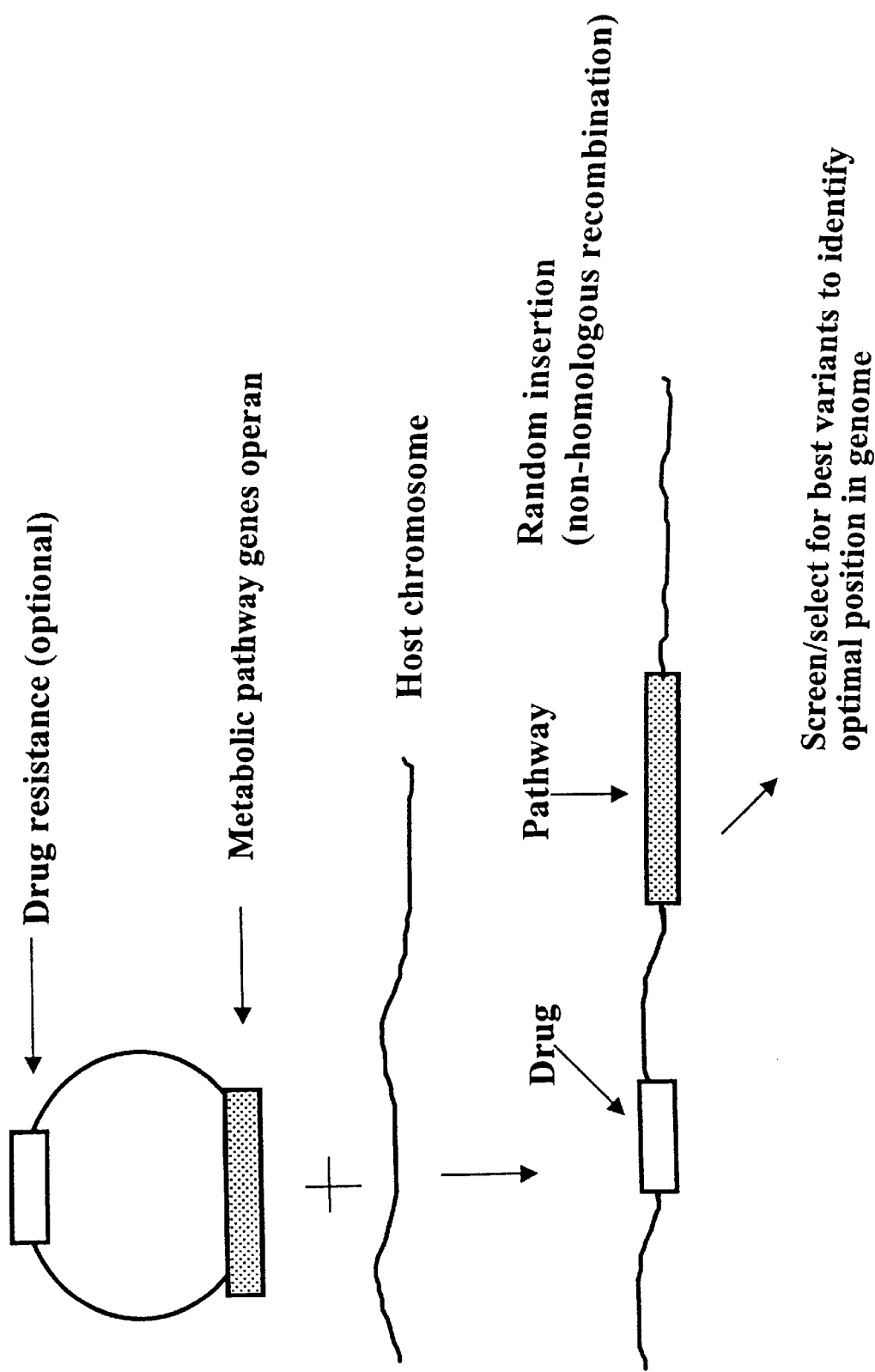
FIG. 18: Schematic for non-homologous recombination.

As shown in FIGS. 16 and 17, DNA Shuffling provides most rapid technology for evolution of complex new functions. As shown in FIG. 16, panel (A), recombination in DNA shuffling achieves accumulation of multiple beneficial mutations in a few cycles. In contrast, because of the high frequency of deleterious mutations relative to beneficial ones, iterative point mutation must build beneficial mutations one at a time, and consequently requires many cycles to reach the same point. As shown in FIG. 16 panel B, rather than a simple linear sequence of mutation accumulation, DNA shuffling is a parallel process where multiple problems may be solved independently, and then combined.

(1) In Vitro Formats

One format for shuffling in vitro is illustrated in FIG. 1. The initial substrates for recombination are a pool of related sequences. The X's in the FIG. 1, panel A, show where the sequences diverge. The sequences can be DNA or RNA and can be of various lengths depending on the size of the gene or DNA fragment to be recombined or reassembled. Preferably the sequences are from 50 bp to 50 kb.

The pool of related substrates are converted into overlapping fragments, e.g., from about 5 bp to 5 kb or more, as shown in FIG. 1, panel B. Often, the size of the fragments is from about 10 bp to 1000 bp, and sometimes the size of the DNA fragments is from about 100 bp to 500 bp. The conversion can be effected by a number of different methods, such as DNaseI or RNase digestion, random shearing or partial restriction enzyme digestion. Alternatively, the conversion of substrates to fragments can be effected by incomplete PCR amplification of substrates or PCR primed from a single primer. Alternatively, appropriate single-stranded fragments can be generated on a nucleic acid synthesizer. The concentration of nucleic acid fragments of a particular length and sequence is often less than 0.1% or 1% by weight of the total nucleic acid. The number of different specific nucleic acid fragments in the mixture is usually at least about 100, 500 or 1000.

The mixed population of nucleic acid fragments are converted to at least partially single-stranded form. Conversion can be effected by heating to about 80° C. to 100° C., more preferably from 90° C. to 96° C., to form single-stranded nucleic acid fragments and then reannealing. Conversion can also be effected by treatment with single-stranded DNA binding protein or recA protein. Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol (PEG), other volume-excluding reagents or salt. The salt concentration is preferably from 0 mM to 200 mM, more preferably the salt concentration is from 10 mM to 100 mM. The salt may be KCl or NaCl. The concentration of PEG is preferably from 0% to 20%, more preferably from 5% to 10%. The fragments that reanneal can be from different substrates as shown in FIG. 1, panel C. The annealed nucleic acid fragments are incubated in the presence of a nucleic acid polymerase, such as Taq or Klenow, or proofreading polymerases, such as pfu or pwo, and dNTP's (i.e. dATP, dCTP, dGTP and dTTP). If regions of sequence identity are large, Taq polymerase can be used with an annealing temperature of between 45–65° C. If the areas of identity are small, Klenow polymerase can be used with an annealing temperature of between 20–30° C. (Stemmer, *Proc. Natl. Acad. Sci. USA* (1994), supra). The polymerase can be added to the random nucleic acid fragments prior to annealing, simultaneously with annealing or after annealing.

The process of denaturation, renaturation and incubation in the presence of polymerase of overlapping fragments to generate a collection of polynucleotides containing different permutations of fragments is sometimes referred to as shuffling of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb, as shown in FIG. 1, panel D. The population represents variants of the starting substrates showing substantial sequence identity thereto but also diverging at several positions. The population has many more members than the starting substrates. The population of fragments resulting from shuffling is used to transform host cells, optionally after cloning into a vector.

In a variation of in vitro shuffling, subsequences of recombination substrates can be generated by amplifying the full-length sequences under conditions which produce a substantial fraction, typically at least 20 percent or more, of incompletely extended amplification products. The amplification products, including the incompletely extended amplification products are denatured and subjected to at least one additional cycle of reannealing and amplification. This variation, in which at least one cycle of reannealing and amplification provides a substantial fraction of incompletely extended products, is termed "stuttering." In the subsequent amplification round, the incompletely extended products reanneal to and prime extension on different sequence-related template species.

In a further variation, a mixture of fragments is spiked with one or more oligonucleotides. The oligonucleotides can be designed to include precharacterized mutations of a wildtype sequence, or sites of natural variations between individuals or species. The oligonucleotides also include sufficient sequence or structural homology flanking such mutations or variations to allow annealing with the wildtype fragments. Some oligonucleotides may be random sequences. Annealing temperatures can be adjusted depending on the length of homology.

In a further variation, recombination occurs in at least one cycle by template switching, such as when a DNA fragment derived from one template primes on the homologous position of a related but different template. Template switching can be induced by addition of recA, rad51, rad55, rad57 or other polymerases (e.g., viral polymerases, reverse transcriptase) to the amplification mixture. Template switching can also be increased by increasing the DNA template concentration.

In a further variation, at least one cycle of amplification can be conducted using a collection of overlapping single-stranded DNA fragments of related sequence, and different lengths. Fragments can be prepared using a single stranded DNA phage, such as M13. Each fragment can hybridize to and prime polynucleotide chain extension of a second fragment from the collection, thus forming sequence-recombined polynucleotides. In a further variation, ssDNA fragments of variable length can be generated from a single primer by Vent or other DNA polymerase on a first DNA template. The single stranded DNA fragments are used as primers for a second, Kunkel-type template, consisting of a uracil-containing circular ssDNA. This results in multiple substitutions of the first template into the second. See Levichkin et al., *Mol. Biology* 29, 572–577 (1995).

(2) In Vivo Formats (a) Plasmid-Plasmid Recombination

The initial substrates for recombination are a collection of polynucleotides comprising variant forms of a gene. The variant forms often show substantial sequence identity to each other sufficient to allow homologous recombination between substrates. The diversity between the polynucleotides can be natural (e.g., allelic or species variants), induced (e.g., error-prone PCR), or the result of in vitro recombination. Diversity can also result from resynthesizing genes encoding natural proteins with alternative and/or mixed codon usage. There should be at least sufficient diversity between substrates that recombination can generate more diverse products than there are starting materials. There must be at least two substrates differing in at least two positions. However, commonly a library of substrates of $10^3$–$10^8$ members is employed. The degree of diversity depends on the length of the substrate being recombined and the extent of the functional change to be evolved. Diversity at between 0.1–50% of positions is typical. The diverse substrates are incorporated into plasmids. The plasmids are often standard cloning vectors, e.g., bacterial multicopy plasmids. However, in some methods to be described below, the plasmids include mobilization functions. The substrates can be incorporated into the same or different plasmids. Often at least two different types of plasmid having different types of selection marker are used to allow selection for cells containing at least two types of vector. Also, where different types of plasmid are employed, the different plasmids can come from two distinct incompatibility groups to allow stable co-existence of two different plasmids within the cell. Nevertheless, plasmids from the same incompatibility group can still co-exist within the same cell for sufficient time to allow homologous recombination to occur.

Plasmids containing diverse substrates are initially introduced into procaryotic or eukaryotic cells by any transfection methods (e.g., chemical transformation, natural competence, electroporation, viral transduction or biolistics). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid.

Having introduced the plasmids into cells, recombination between substrates to generate recombinant genes occurs within cells containing multiple different plasmids merely by propagating in the cells. However, cells that receive only one plasmid are unable to participate in recombination and the potential contribution of substrates on such plasmids to evolution is not fully exploited (although these plasmids may contribute to some extent if they are propagated in mutator cells or otherwise accumulate point mutations (i.e., by ultraviolet radiation treatment). The rate of evolution can be increased by allowing all substrates to participate in recombination. Such can be achieved by subjecting transfected cells to electroporation. The conditions for electroporation are the same as those conventionally used for introducing exogenous DNA into cells (e.g., 1,000–2,500 volts, 400 μF and a 1–2 mM gap). Under these conditions, plasmids are exchanged between cells allowing all substrates to participate in recombination. In addition the products of recombination can undergo further rounds of recombination with each other or with the original substrate. The rate of evolution can also be increased by use of conjugative transfer. Conjugative transfer systems are known in many bacteria (*E. coli, P. aeruginosa, S. pneumoniae,* and *H. influenzae*) and can also be used to transfer DNA between bacteria and yeast or between bacteria and mammalian cells.

To exploit conjugative transfer, substrates are cloned into plasmids having MOB genes, and tra genes are also provided in cis or in trans to the MOB genes. The effect of conjugative transfer is very similar to electroporation in that it allows plasmids to move between cells and allows recombination between any substrate and the products of previous recombination to occur merely by propagating the culture. The details of how conjugative transfer is exploited in these vectors are discussed in more detail below. The rate of evolution can also be increased by fusing protoplasts of cells to induce exchange of plasmids or chromosomes. Fusion can be induced by chemical agents, such as PEG, or viruses or viral proteins, such as influenza virus hemagglutinin, HSV-1 gB and gD. The rate of evolution can also be increased by use of mutator host cells (e.g., Mut L, S, D, T, H and *Ataxia telangiectasia* human cell lines).

The time for which cells are propagated and recombination is allowed to occur, of course, varies with the cell type but is generally not critical, because even a small degree of recombination can substantially increase diversity relative to the starting materials. Cells bearing plasmids containing recombined genes are subject to screening or selection for a desired function. For example, if the substrate being evolved contains a drug resistance gene, one selects for drug resistance. Cells surviving screening or selection can be subjected to one or more rounds of screening/selection followed by recombination or can be subjected directly to an additional round of recombination.

The next round of recombination can be achieved by several different formats independently of the previous round. For example, a further round of recombination can be effected simply by resuming the electroporation or conjugation-mediated intercellular transfer of plasmids described above. Alternatively, a fresh substrate or substrates, the same or different from previous substrates, can be transfected into cells surviving selection/screening. Optionally, the new substrates are included in plasmid vectors bearing a different selective marker and/or from a different incompatibility group than the original plasmids. As a further alternative, cells surviving selection/screening can be subdivided into two subpopulations, and plasmid DNA from one subpopulation transfected into the other, where the substrates from the plasmids from the two subpopulations undergo a further round of recombination. In either of the latter two options, the rate of evolution can be increased by employing DNA extraction, electroporation, conjugation or mutator cells, as described above. In a still further variation, DNA from cells surviving screening/selection can be extracted and subjected to in vitro DNA shuffling.

After the second round of recombination, a second round of screening/selection is performed, preferably under conditions of increased stringency. If desired, further rounds of recombination and selection/screening can be performed using the same strategy as for the second round. With successive rounds of recombination and selection/screening, the surviving recombined substrates evolve toward acquisition of a desired phenotype. Typically, in this and other methods of recursive recombination, the final product of recombination that has acquired the desired phenotype differs from starting substrates at 0.1%–25% of positions and has evolved at a rate orders of magnitude in excess (e.g., by at least 10-fold, 100-fold, 1000-fold, or 10,000 fold) of the rate of naturally acquired mutation of about 1 mutation per $10^{-9}$ positions per generation (see Anderson & Hughes, *Proc. Natl. Acad. Sci. USA* 93, 906–907 (1996)).

(b) Virus-Plasmid Recombination

The strategy used for plasmid-plasmid recombination can also be used for virus-plasmid recombination; usually, phage-plasmid recombination. However, some additional comments particular to the use of viruses are appropriate. The initial substrates for recombination are cloned into both plasmid and viral vectors. It is usually not critical which substrate(s) are inserted into the viral vector and which into the plasmid, although usually the viral vector should contain different substrate(s) from the plasmid. As before, the plasmid (and the virus) typically contains a selective marker. The plasmid and viral vectors can both be introduced into cells by transfection as described above. However, a more efficient procedure is to transform the cells with plasmid, select transformants and infect the transformants with a virus. Because the efficiency of infection of many viruses approaches 100% of cells, most cells transformed and infected by this route contain both a plasmid and virus bearing different substrates.

Homologous recombination occurs between plasmid and virus generating both recombined plasmids and recombined virus. For some viruses, such as filamentous phage, in which intracellular DNA exists in both double-stranded and single-stranded forms, both can participate in recombination. Provided that the virus is not one that rapidly kills cells, recombination can be augmented by use of electroporation or conjugation to transfer plasmids between cells. Recombination can also be augmented for some types of virus by allowing the progeny virus from one cell to reinfect other cells. For some types of virus, virus infected-cells show resistance to superinfection. However, such resistance can be overcome by infecting at high multiplicity and/or using mutant strains of the virus in which resistance to superinfection is reduced.

The result of infecting plasmid-containing cells with virus depends on the nature of the virus. Some viruses, such as filamentous phage, stably exist with a plasmid in the cell and also extrude progeny phage from the cell. Other viruses, such as lambda having a cosmid genome, stably exist in a cell like plasmids without producing progeny virions. Other viruses, such as the T-phage and lytic lambda, undergo recombination with the plasmid but ultimately kill the host cell and destroy plasmid DNA. For viruses that infect cells without killing the host, cells containing recombinant plasmids and virus can be screened/selected using the same approach as for plasmid-plasmid recombination. Progeny virus extruded by cells surviving selection/screening can also be collected and used as substrates in subsequent rounds of recombination. For viruses that kill their host cells, recombinant genes resulting from recombination reside only in the progeny virus. If the screening or selective assay requires expression of recombinant genes in a cell, the recombinant genes should be transferred from the progeny virus to another vector, e.g., a plasmid vector, and retransfected into cells before selection/screening is performed.

For filamentous phage, the products of recombination are present in both cells surviving recombination and in phage extruded from these cells. The dual source of recombinant products provides some additional options relative to the plasmid-plasmid recombination. For example, DNA can be isolated from phage particles for use in a round of in vitro recombination. Alternatively, the progeny phage can be used to transfect or infect cells surviving a previous round of screening/selection, or fresh cells transfected with fresh substrates for recombination.

(c) Virus-Virus Recombination

The principles described for plasmid-plasmid and plasmid-viral recombination can be applied to virus-virus recombination with a few modifications. The initial substrates for recombination are cloned into a viral vector. Usually, the same vector is used for all substrates. Preferably, the virus is one that, naturally or as a result of mutation, does not kill cells. After insertion, some viral genomes can be packaged in vitro. The packaged viruses are used to infect cells at high multiplicity such that there is a high probability that a cell receives multiple viruses bearing different substrates.

After the initial round of infection, subsequent steps depend on the nature of infection as discussed in the previous section. For example, if the viruses have phagemid genomes such as lambda cosmids or M13, F1 or Fd phagemids, the phagemids behave as plasmids within the cell and undergo recombination simply by propagating the cells. Recombination can be augmented by electroporation of cells. Following selection/screening, cosmids containing recombinant genes can be recovered from surviving cells (e.g., by heat induction of a cos$^-$ lysogenic host cell), repackaged in vitro, and used to infect fresh cells at high multiplicity for a further round of recombination.

If the viruses are filamentous phage, recombination of replicating form DNA occurs by propagating the culture of infected cells. Selection/screening identifies colonies of cells containing viral vectors having recombinant genes with improved properties, together with phage extruded from such cells. Subsequent options are essentially the same as for plasmid-viral recombination.

(d) Chromosome-Plasmid Recombination

This format can be used to evolve both the chromosomal and plasmid-borne substrates. The format is particularly useful in situations in which many chromosomal genes contribute to a phenotype or one does not know the exact location of the chromosomal gene(s) to be evolved. The initial substrates for recombination are cloned into a plasmid vector. If the chromosomal gene(s) to be evolved are known, the substrates constitute a family of sequences showing a high degree of sequence identity but some divergence from the chromosomal gene. If the chromosomal genes to be evolved have not been located, the initial substrates usually constitute a library of DNA segments of which only a small number show sequence identity to the gene or gene(s) to be evolved. Divergence between plasmid-borne substrate and the chromosomal gene(s) can be induced by mutagenesis or by obtaining the plasmid-borne substrates from a different species than that of the cells bearing the chromosome.

The plasmids bearing substrates for recombination are transfected into cells having chromosomal gene(s) to be evolved. Evolution can occur simply by propagating the culture, and can be accelerated by transferring plasmids between cells by conjugation, electroporation or protoplast fusion. Evolution can be further accelerated by use of mutator host cells or by seeding a culture of nonmutator host cells being evolved with mutator host cells and inducing intercellular transfer of plasmids by electroporation, conjugation or protoplast fusion. Preferably, mutator host cells used for seeding contain a negative selection marker to facilitate isolation of a pure culture of the nonmutator cells being evolved. Selection/screening identifies cells bearing chromosomes and/or plasmids that have evolved toward acquisition of a desired function.

Subsequent rounds of recombination and selection/screening proceed in similar fashion to those described for plasmid-plasmid recombination. For example, further recombination can be effected by propagating cells surviving recombination in combination with electroporation, conjugative transfer of plasmids, or protoplast fusion. Alternatively, plasmids bearing additional substrates for recombination can be introduced into the surviving cells. Preferably, such plasmids are from a different incompatibility group and bear a different selective marker than the original plasmids to allow selection for cells containing at least two different plasmids. As a further alternative, plasmid and/or chromosomal DNA can be isolated from a subpopulation of surviving cells and transfected into a second subpopulation. Chromosomal DNA can be cloned into a plasmid vector before transfection.

(e) Virus-Chromosome Recombination

As in the other methods described above, the virus is usually one that does not kill the cells, and is often a phage or phagemid. The procedure is substantially the same as for plasmid-chromosome recombination. Substrates for recombination are cloned into the vector. Vectors including the substrates can then be transfected into cells or in vitro packaged and introduced into cells by infection. Viral genomes recombine with host chromosomes merely by propagating a culture. Evolution can be accelerated by allowing intercellular transfer of viral genomes by electroporation, or reinfection of cells by progeny virions. Screening/selection identifies cells having chromosomes and/or viral genomes that have evolved toward acquisition of a desired function.

There are several options for subsequent rounds of recombination. For example, viral genomes can be transferred between cells surviving selection/recombination by electroporation. Alternatively, viruses extruded from cells surviving selection/screening can be pooled and used to superinfect the cells at high multiplicity. Alternatively, fresh substrates for recombination can be introduced into the cells, either on plasmid or viral vectors.

(f) Poolwise Whole Genome Recombination

Asexual evolution is a slow and inefficient process. Populations move as individuals rather than as a group. A diverse population is generated by mutagenesis of a single parent, resulting in a distribution of fit and unfit individuals. In the absence of a sexual cycle, each piece of genetic information for the surviving population remains in the individual mutants. Selection of the fittest results in many fit individuals being discarded, along with the genetically useful information they carry. Asexual evolution proceeds one genetic event at a time, and is thus limited by the intrinsic value of a single genetic event. Sexual evolution moves more quickly and efficiently. Mating within a population consolidates genetic information within the population and results in useful information being combined together. The combining of useful genetic information results in progeny that are much more fit than their parents. Sexual evolution thus proceeds much faster by multiple genetic events. These differences are further illustrated in FIG. 17. In contrast to sexual evolution, DNA shuffling is the recursive mutagenesis, recombination, and selection of DNA sequences (see also, FIG. 25.).

Figure 25A:
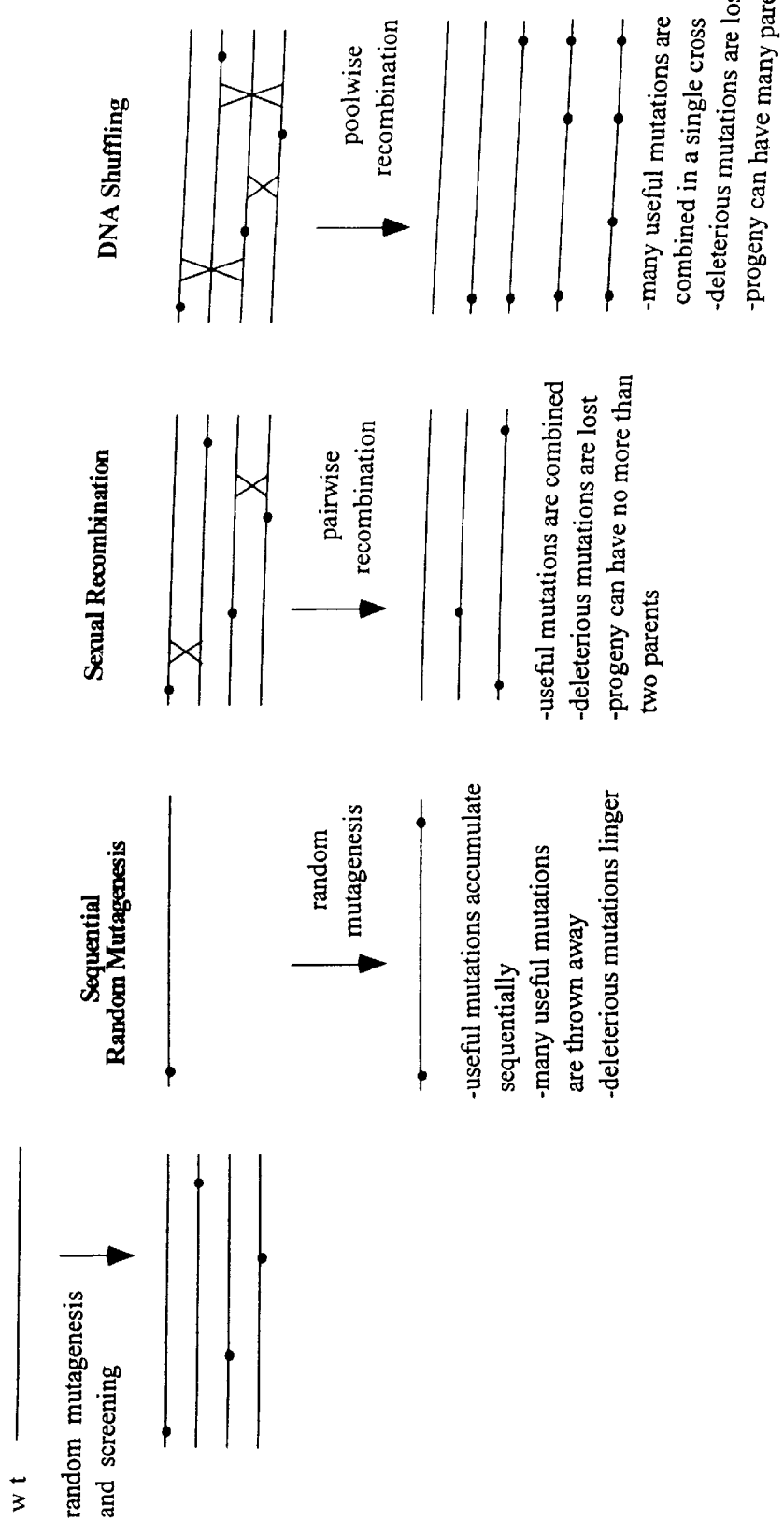
FIG. 25: Schematic and graph of poolwise recombination.
Figure 25B:
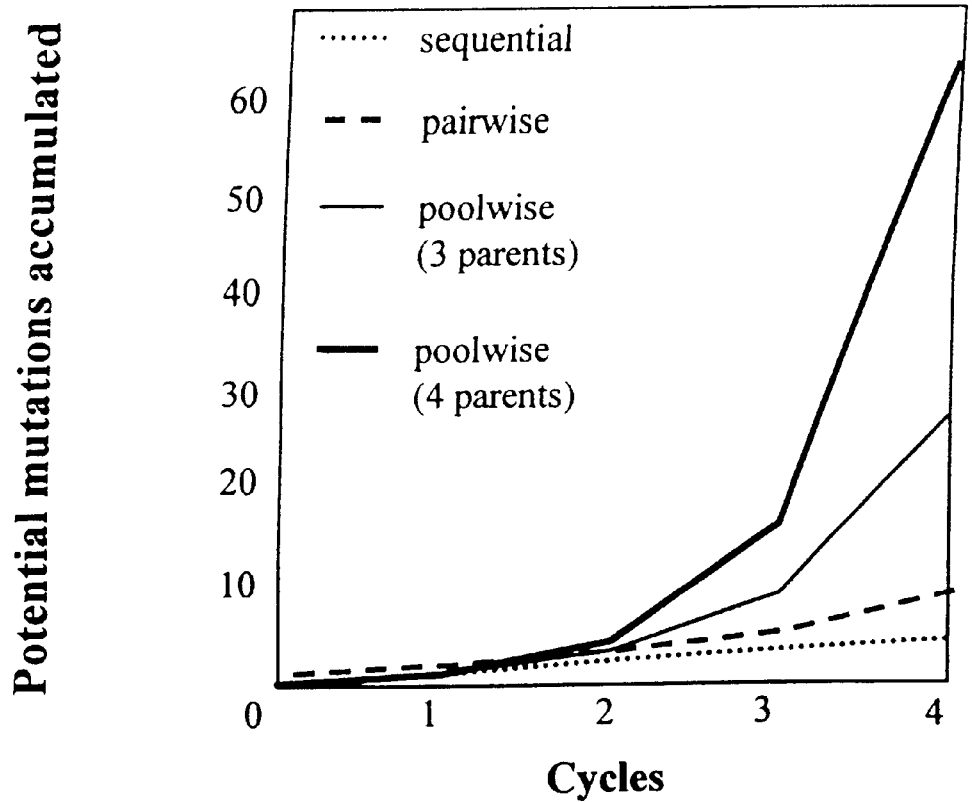

Sexual recombination in nature effects pairwise recombination and results in progeny that are genetic hybrids of two parents. In contrast, DNA shuffling in vitro effects poolwise recombination, in which progeny are hybrids of multiple parental molecules. This is because DNA shuffling effects many individual pairwise recombination events with each thermal cycle. After many cycles the result is a repetitively inbred population, with the "progeny" being the $F_X$ (for X cycles of reassembly) of the original parental molecules. These progeny are potentially descendants of many or all of the original parents. The graph shown in FIG. 25 shows a plot of the potential number of mutations an individual can accumulate by sequential, pairwise and poolwise recombination.

Poolwise recombination is an important feature to DNA shuffling in that it provides a means of generating a greater proportion of the possible combinations of mutations from a single "breeding" experiment. In this way, the "genetic potential" of a population can be readily assessed by screening the progeny of a single DNA shuffling experiment.

Figure 14:
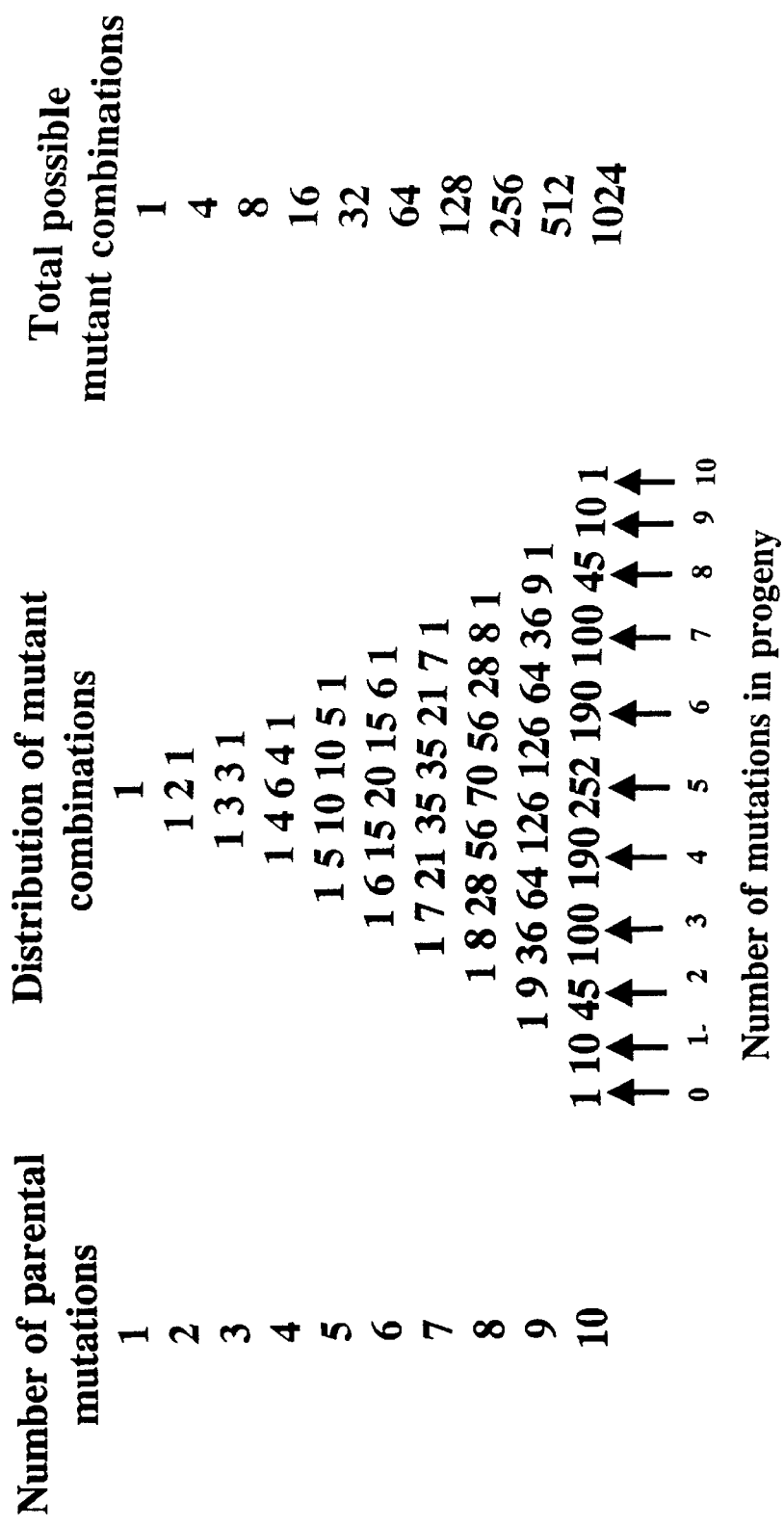
FIG. 14: illustration of combinatoriality.

For example, if a population consists of 10 single mutant parents, there are $2^{10}=1024$ possible combinations of those mutations ranging from progeny having 0–10 mutations. Of these 1024, only 56 will result from a single pairwise cross (FIG. 14) (i.e those having 0, 1, and 2 mutations). In nature the multiparent combinations will eventually arise after multiple random sexual matings, assuming no selection is imparted to remove some mutations from the population. In this way, sex effects the consolidation and sampling of all useful mutant combinations possible within a population. For the purposes of directed evolution, having the greatest number of mutant combinations entering a screen or selection is desirable so that the best progeny (i.e., according to the selection criteria used in the selection screen) is identified in the shortest possible time.

One challenge to in vivo and whole genome shuffling is devising methods for effecting poolwise recombination or multiple repetitive pairwise recombination events. In crosses with a single pairwise cross per cycle before screening, the ability to screen the "genetic potential" of the starting population is limited. For this reason, the rate of in vivo and whole genome shuffling mediated cellular evolution would be facilitated by effecting poolwise recombination. Two strategies for poolwise recombination are described below (protoplast fusion and transduction).

(i.) Protoplast Fusion

Protoplast fusion (discussed supra) mediated whole genome shuffling (WGS) is one format that can directly effect poolwise recombination. Whole gene shuffling is the recursive recombination of whole genomes, in the form of one or more nucleic acid molecule(s) (fragments, chromosomes, episomes, etc), from a population of organisms, resulting in the production of new organisms having distributed genetic information from at least two of the starting population of organisms. The process of protoplast fusion is further illustrated in FIG. 26.

Figure 27A:
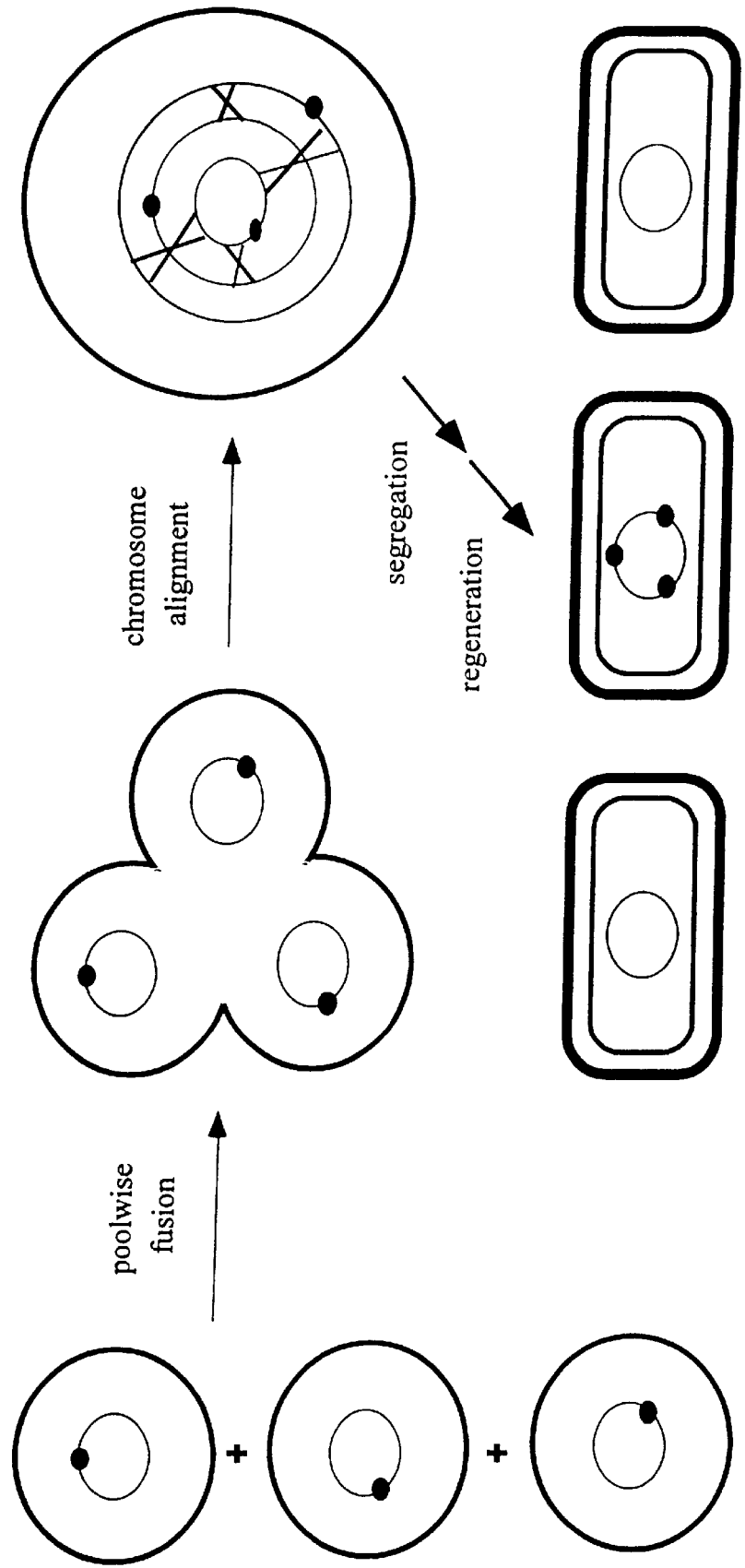
FIG. 27: Schematic assay for poolwise recombination.
Figure 27B:
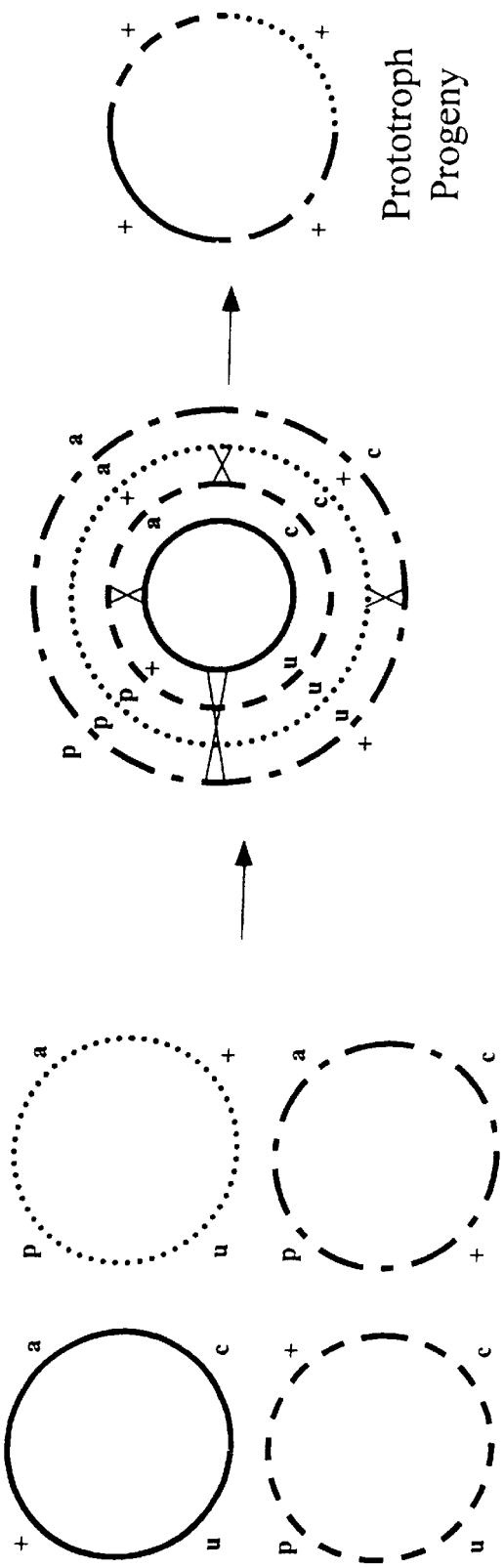

Progeny resulting from the fusion of multiple parent protoplasts have been observed (Hopwood & Wright, 1978), however, these progeny are rare ($10^{-4}$–$10^{-6}$). The low frequency is attributed to the distribution of fusants arising from two, three, four, etc parents and the likelihood of the multiple recombination events (6 crossovers for a four parent cross) that would have to occur for multiparent progeny to arise. Thus, it is useful to enrich for the multiparent progeny. This can be accomplished, e.g., by repetitive fusion or enrichment for multiply fused protoplasts. The process of poolwise fusion and recombination is further illustrated in FIG. 27.

(ii.) Repetitive Fusion

Figure 15:
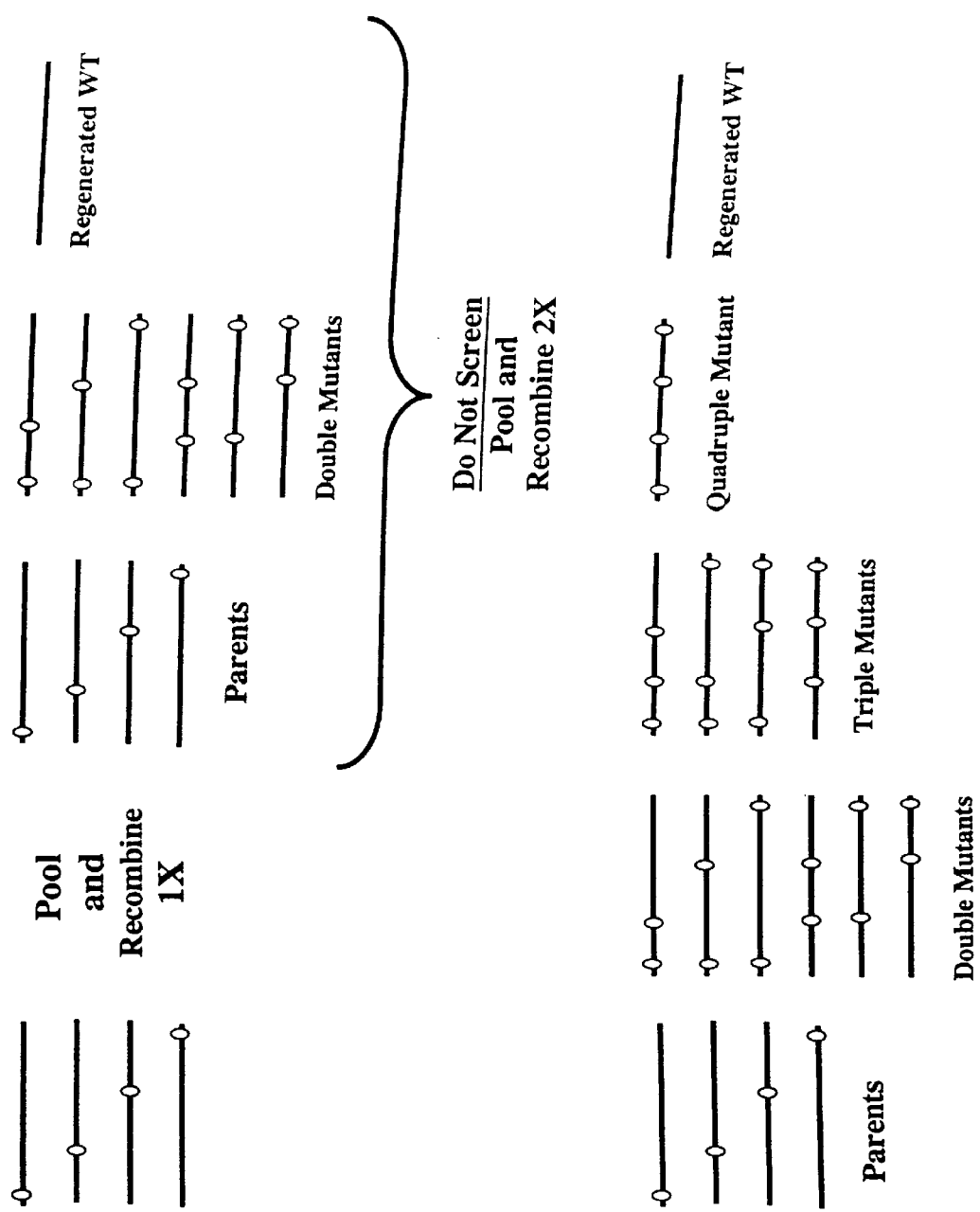
FIG. 15: Repeated pairwise recombination to access multi-mutant progeny.

Protoplasts of identified parental cells are prepared, fused and regenerated. Protoplasts of the regenerated progeny are then, without screening or enrichment, formed, fused and regenerated. This can be carried out for two, three, or more cycles before screening to increase the representation of multiparent progeny. The number of possible mutations/progeny doubles for each cycle. For example, if one cross produces predominantly progeny with 0, 1, and 2 mutations, a breeding of this population with itself will produce progeny with 0, 1, 2, 3, and 4 mutations (FIG. 15), the third cross up to eight, etc. The representation of the multiparent progeny from these subsequent crosses will not be as high as the single and double parent progeny, but it will be detectable and much higher than from a single cross. The repetitive fusion prior to screening is analogous to many sexual crosses within a population, and the individual thermal cycles of in vitro DNA shuffling described supra. A factor effecting the value of this approach is the starting size of the parental population. As the population grows, it becomes more likely that a multiparent fusion will arise from repetitive fusions. For example, if 4 parents are fused twice, the 4 parent progeny will make up approximately 0.2% of the total progeny. This is sufficient to find in a population of 3000 (95% confidence), but better representation is preferable. If ten parents are fused twice >20% of the progeny will be four parent offspring.

(iii.) Enrichment for Multiply Fused Protoplasts

After the fusion of a population of protoplasts, the fusants are typically diluted into hypotonic medium, to dilute out the fusing agent (e.g., 50% PEG). The fused cells can be grown for a short period to regenerate cell walls or separated directly and are then separated on the basis of size. This is carried out, e.g., by cell sorting, using light dispersion as an estimate of size, to isolate the largest fusants. Alternatively the fusants can be sorted by FACS on the basis of DNA content. The large fusants or those containing more DNA result from the fusion of multiple parents and are more likely to segregate to multiparent progeny. The enriched fusants are regenerated and screened directly or the progeny are fused recursively as above to further enrich the population for diverse mutant combinations.

(iv.) Transduction

Transduction can theoretically effect poolwise recombination, if the transducing phage particles contain predominantly host genomic DNA rather than phage DNA. If phage DNA is overly represented, then most cells will receive at least one undesired phage genome. Phage particles generated from locked-in-prophage (supra) are useful for this purpose. A population of cells is infected with an appropriate transducing phage, and the lysate is collected and used to infect the same starting population. A high multiplicity of infection is employed to deliver multiple genomic fragments to each infected cell, thereby increasing the chance of producing recombinants containing mutations from more than two parent genomes. The resulting transductants are recovered under conditions where phage can not propagate e.g., in the presence of citrate. This population is then screened directly or infected again with phage, with the resulting transducing particles being used to transduce the first progeny. This would mimic recursive protoplast fusion, multiple sexual recombination, and in vitro DNA shuffling.

(g) Methods for Whole Genome Shuffling by Blind Family Shuffling of Parsed Genomes and Recursive Cycles of Forced Integration and Excision by Homologous Recombination, and Screening for Improved Phenotypes.

In vitro methods have been developed to shuffle single genes and operons, as set forth, e.g., herein. "Family" shuffling of homologous genes within species and from different species is also an effective methods for accelerating molecular evolution. This section describes additional methods for extending these methods such that they can be applied to whole genomes.

In some cases, the genes that encode rate limiting steps in a biochemical process, or that contribute to a phenotype of interest are known. This method can be used to target family shuffled libraries to such loci, generating libraries of organisms with high quality family shuffled libraries of alleles at the locus of interest. An example of such a gene would be the evolution of a host chaperonin to more efficiently chaperone the folding of an overexpressed protein in E. coli.

The goals of this process are to shuffle homologous genes from two or more species and to then integrate the shuffled genes into the chromosome of a target organism. Integration of multiple shuffled genes at multiple loci can be achieved using recursive cycles of integration (generating duplications), excision (leaving the improved allele in the chromosome) and transfer of additional evolved genes by serially applying the same procedure.

Figure 22:
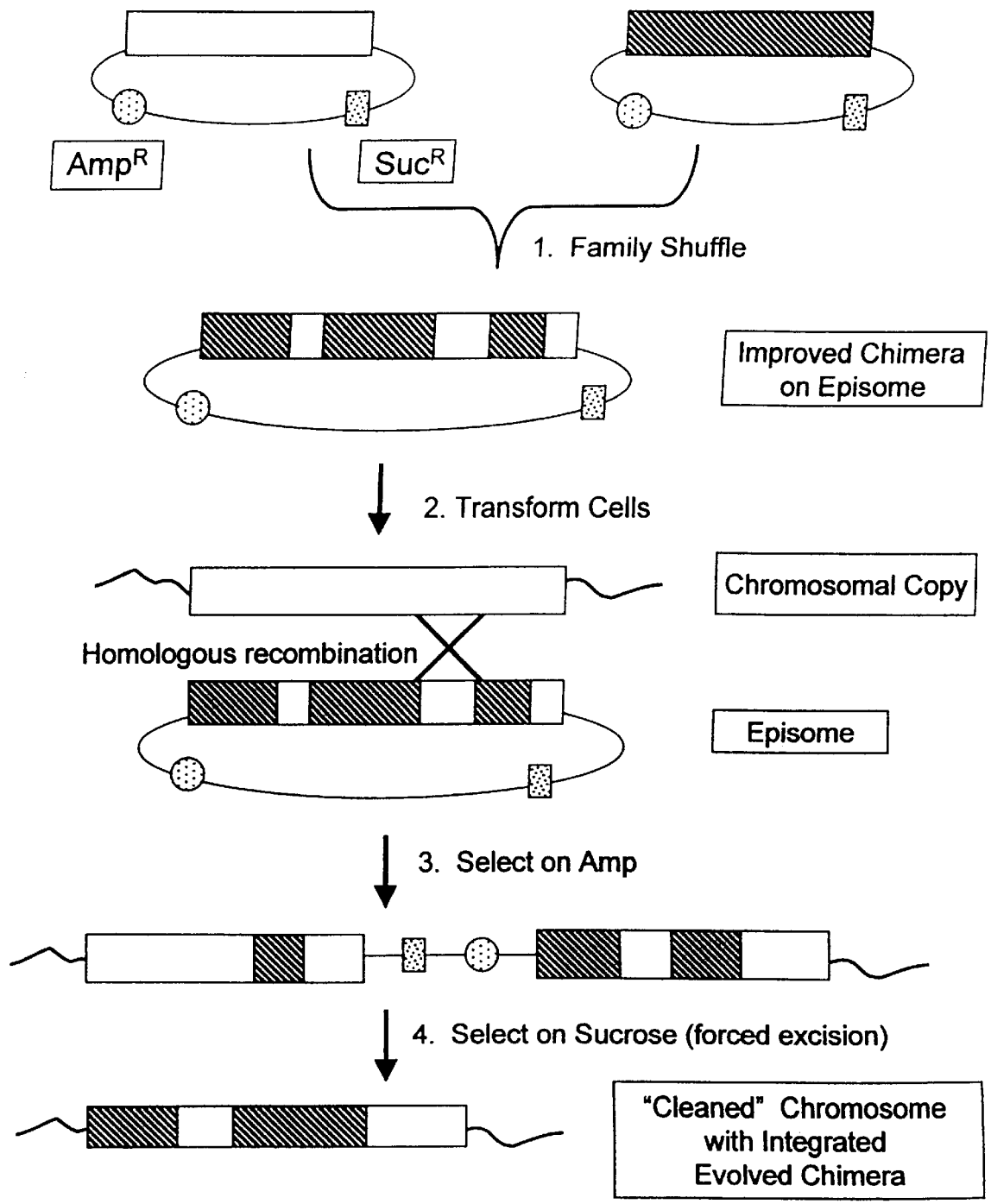
FIG. 22: Whole genome shuffling of parsed (subcloned) genomes.

In the first step, genes to be shuffled into suitable bacterial vectors are subcloned. These vectors can be plasmids, cosmids, BACS or the like. Thus, fragments from 100 bp to 100 kb can be handled. Homologous fragments are then "family shuffled" together (i.e. homologous fragments from different species or chromosomal locations are homologously recombined). As a simple case, homologs from two species (say, E. coli and Salmonella) are cloned, family shuffled in vitro and cloned into an allele replacement vector (e.g., a vector with a positively selectable marker, a negatively selectable marker and conditionally active origin of replication). The basic strategy for whole genome family shuffling of parsed (subcloned) genomes is additionally set forth in FIG. 22.

The vectors are transduced into E. coli and selected, e.g., for drug resistance. Most drug resistant vectors occur only by homologous recombination between a family shuffled insert and a chromosomal copy of the cloned insert. Colonies with improved phenotype are screened (e.g., by mass spectroscopy for enzyme activity or small molecule production, or a chromogenic screen, or the like, depending on the phenotype to be assayed). Negative selection (i.e. sac selection) is imposed to force excision of tandem duplication. Roughly half of the colonies should retain the improved phenotype. Importantly, this process regenerates a 'clean' chromosome in which the wild type locus is replaced with a family shuffled fragment that encodes a beneficial allele. Since the chromosome is "clean" (i.e., has no vector sequences), other improved alleles can also be moved into this point on the chromosome by homologous recombination.

In subsequent rounds, independently identified improved alleles are optionally moved into the improved strain (e.g., by P1 transduction of the drug marked tandem duplication above). Transductants are screened for further improvement in phenotype by virtue of receiving the transduced tandem duplication, which itself contains the family shuffled genetic material. Negative selection is again imposed and the process of shuffling the improved strain is recursively repeated as desired.

Figure 23:
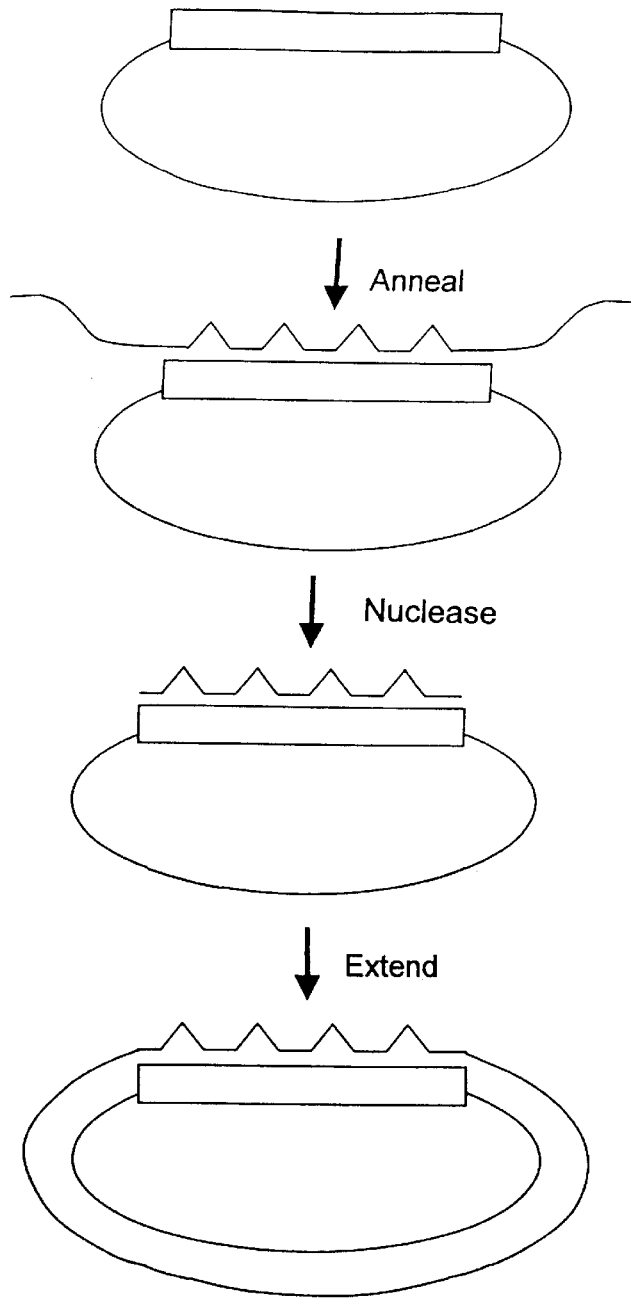
FIG. 23: Schematic for blind cloning of gene homologs.

Although this process was described with reference to targeting a gene or genes of interest, it can be used "blindly," making no assumptions about which locus is to be targeted. This procedure is set forth in FIG. 23. For example, the whole genome of an organism of interest is cloned into manageable fragments (e.g., 10 kb for plasmid-based methods). Homologous fragments are then isolated from related species.

For E. coli., cloning the genome in 10 kb fragments requires about 300 clones. The homologous fragments are isolated, e.g., from Salmonella. This gives roughly three hundred pairs of homologous fragments. Each pair is family shuffled and the shuffled fragments are cloned into an allele replacement vector. The inserts are integrated into the E. coli genome as described above. A global screen is made to identify variants with an improved phenotype. This serves as the basis collection of improvements that are to be shuffled to produce a desired strain. The shuffling of these independently identified variants into one super strain is done as described above.

(h) Methods for High Throughput Family Shuffling of Genes

Family shuffling has been shown to be an efficient method for creating high quality libraries of genetic variants. Given a cloned gene from one species, it is of interest to quickly and rapidly isolate homologs from other species, and this process can be rate limiting. For example, if one wants to perform family shuffling on an entire genome, one may need to construct hundreds to thousands of individual family shuffled libraries.

In this embodiment, a gene of interest is optionally cloned into a vector in which ssDNA can be made. An example of such a vector is a phagemid vector with an M13 origin of replication. Genomic DNA or cDNA from a species of interest is isolated, denatured, annealed to the phagemid, and then enzymatically manipulated to clone it. The cloned DNA is then used to family shuffle with the original gene of interest. PCR based formats are also available. These formats require no intermediate cloning steps, and are, therefore, of particular interest for high throughput applications.

Figure 24:
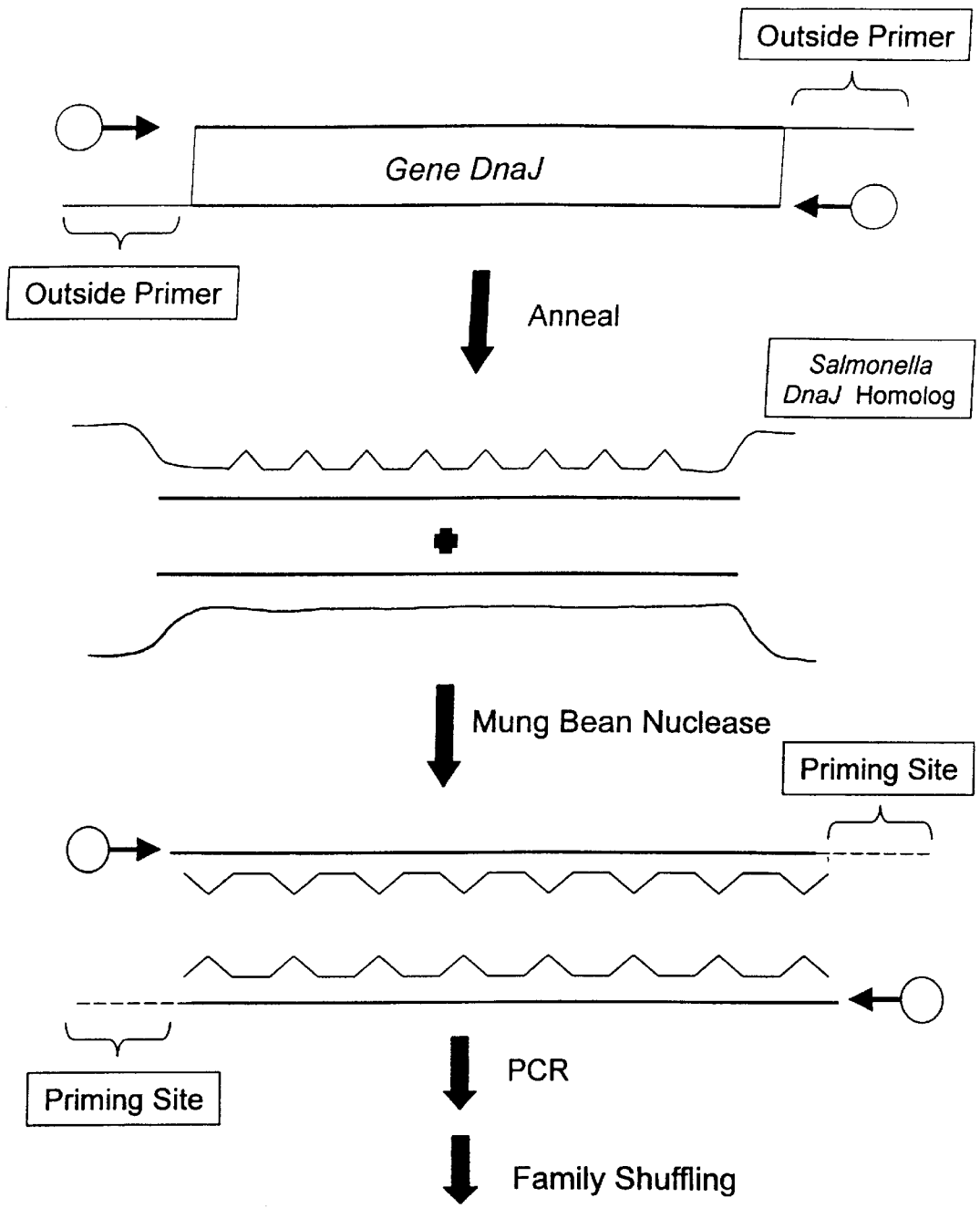
FIG. 24: High throughput family shuffling.

Shuffling the E. coli chaperonin gene DnaJ with other homologs is described below as an example. The example can be generalized to any other gene, including eukaryotic genes such as plant or animal genes (including mammalian genes), by following the format described. FIG. 24 provides a schematic outline of the steps to high throughput family shuffling.

As a first step, the E. coli DnaJ gene is cloned into an M13 phagemid vector. ssDNA is then produced, preferably in a dut(−) ung(−) strain so that Kunkel site directed mutagenesis protocols can be applied. Genomic DNA is then isolated from a non- E. coil source, such as Salmonella and Yersinia Pestis. The bacterial genomic DNAs are denatured and reannealed to the phagemid ssDNA (e.g., about 1 microgram of ssDNA). The reannealed product is treated with an enzyme such as Mung Bean nuclease that degrades ssDNA as an exonuclease but not as an endonuclease (the nuclease does not degrade mismatched DNA that is embedded in a larger annealed fragment). The standard Kunkel site directed mutagenesis protocol is used to extend the fragment and the target cells are transformed with the resulting mutagenized DNA.

In a first variation on the above, the procedure is adapted to the situation where the target gene or genes of interest are unknown. In this variation, the whole genome of the organism of interest is cloned in fragments (e.g., of about 10 kb each) into a phagemid. Single stranded phagemid DNA is then produced. Genomic DNA from the related species is denatured and annealed to the phagemids. Mung bean nuclease is used to trim away unhybridized DNA ends. Polymerase plus ligase is used to fill in the resulting gapped circles. These clones are transformed into a mismatch repair deficient strain. When the mismatched molecules are replicated in the bacteria, most colonies contain both the *E. coli* and the homologous fragment. The two homologous genes are then isolated from the colonies (e.g., either by standard plasmid purification or colony PCR) and shuffled.

Another approach to generating chimeras that requires no in vitro shuffling is simply to clone the Salmonella genome into an allele replacement vector, transform *E. coli,* and select for chromosomal integrants. Homologous recombination between Salmonella genes and *E. coli* homologs generate shuffled chimeras. A global screen is done to screen for improved phenotypes. If colonies with improved phenotypes are obtained, it is verified that the improvement is due to allele replacement by P1 transduction into a fresh strain and counterscreening for improved phenotype. A collection of such improved alleles can then be combined into one strain using the methods for whole genome shuffling by blind family shuffling of parsed genomes as set forth herein. Additionally, once these loci are identified, it is likely that further rounds of shuffling and screening will yield further improvements. This could be done by cloning the chimeric gene and then using the methods described in this disclosure to breed the gene with homologs from many different strains of bacteria.

In general, the transformants contain clones of the homologue of the target gene (e.g., *E. coli* DnaJ in the example above). Mismatch repair in vivo results in a decrease in diversity of the gene. There are at least two solutions to this. First, transduction can be performed into a mismatch repair strain. Alternatively or in addition, the M13 template DNA can be selectively degraded, leaving the cloned homologue. This can be done using methods similar to the standard Eckstein site directed mutagenesis technique (General texts which describe general molecular biological techniques useful herein, including mutagenesis, include Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology,* F. M. Ausubel et al., eds., Current Protocols, a joint venture between Greene Publishing Associates, Inc. and John Wiley & Sons, Inc., (supplemented through 1998) ("Ausubel")).

This method relies on incorporation of alpha thiol modified dNTP's during synthesis of the new strand followed by selective degradation of the template and resynthesis of the template strand. In one embodiment, the template strand is grown in a dut(−) ung(−) strain so that uracil is incorporated into the phagemid DNA. After extension as noted above (and before transformation) the DNA is treated with uracil glycosylate and an apurinic site endonuclease such as Endo III or Endo IV. The treated DNA is then treated with a processive exonuclease that resects from the resulting gaps while leaving the other strand intact (as in Eckstein mutagenesis). The DNA is polymerized and ligated. Target cells are then transformed. This process enriches for clones encoding the homologue which is not derived from the target (i.e., in the example above, the non- *E. coli.* homologue).

An analogous procedure is optionally performed in a PCR format. As applied to the DnaJ illustration above, DnaJ DNA is amplified by PCR with primers that build 30-mer priming sites on each end. The PCR is denatured and annealed with an excess of Salmonella genomic DNA. The Salmonella DnaJ gene hybribidizes with the *E. coli* homologue. After treatment with Mung Bean nuclease, the resulting mismatched hybrid is PCR amplified with the flanking 30-mer primers. This PCR product can be used directly for family shuffling.

As genomics provides an increasing amount of sequence information, it is increasingly possible to directly PCR amplify homologs with designed primers. For example, given the sequence of the *E. coli* genome and of a related genome (i.e. Salmonella), each genome can be PCR amplified with designed primers in, e.g., 5 kb fragments. The homologous fragments can be put together in a pairwise fashion for shuffling. For genome shuffling, the shuffled products are cloned into the allele replacement vector and bred into the genome as described supra.

Hyper-Recombinogenic RecA Clones

The invention further provides hyper-recombinogenic RecA proteins (see, the examples below). Examples of such proteins are from clones 2, 4, 5, 6 and 13 shown in FIG. 13. It is fully expected that one of skill can make a variety of related recombinogenic proteins given the disclosed sequences.

First, clones comprising the sequences in FIGS. 12 and 13 are optionally used as the starting point for any of the shuffling methods herein, providing a starting point for mutation and recombination to improve the clones which are shown.

Second, standard molecular biological techniques can be used to make nucleic acids which comprise the given nucleic acids, e.g., by cloning the nucleic acids into any known vector. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Third, it will be appreciated that conservative substitutions of the given sequences can be used to produce nucleic acids which encode hyperrecombinogenic clones. "Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in any described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company. Finally, the addition of sequences which do not alter the activity of a nucleic acid molecule, such as a non-functional sequence is a conservative modification of the basic nucleic acid.

One of skill will appreciate that many conservative variations of the nucleic acid constructs disclosed yield a functionally identical construct. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence of a packaging or packageable construct are substituted with different amino acids with highly similar properties, are also readily identified as being highly similar to a disclosed construct. Such conservatively substituted variations of each explicitly disclosed sequence are a feature of the present invention.

Fourth, nucleic acids which hybridize under stringent conditions to the nucleic acids in the figures are a feature of the invention. "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Finally, preferred nucleic acids encode hyper-recombinogenic RecA proteins which are at least one order of magnitude (10 times) as active as a wild-type RecA protein.

EXAMPLES

The following examples are offered to illustrate, but not to limit the present invention. Variations upon the exact procedures set forth will be apparent to one of skill upon review of the present disclosure.

Example 1

Evolving Hyper-Recombinogenic RecA

RecA protein is implicated in most *E. coli* homologous recombination pathways. Most mutations in recA inhibit recombination, but some have been reported to increase recombination (Kowalczykowski et al., *Microbiol. Rev.*, 58, 401–465 (1994)). The following example describes evolution of RecA to acquire hyper-recombinogenic activity useful in in vivo shuffling formats.

Hyperrecombinogenic RecA was selected using a modification of a system developed by Shen et al., *Genetics* 112, 441–457 (1986); Shen et al., *Mol. Gen. Genet.* 218, 358–360 (1989)) to measure the effect of substrate length and homology on recombination frequency. Shen & Huang's system used plasmids and bacteriophages with small (31–430 bp) regions of homology at which the two could recombine. In a restrictive host, only phage that had incorporated the plasmid sequence were able to form plaques.

For shuffling of recA, endogenous recA and mutS were deleted from host strain MC1061. In this strain, no recombination was seen between plasmid and phage. *E. coli* recA was then cloned into two of the recombination vectors (Bp221 and πMT631c18). Plasmids containing cloned RecA were able to recombine with homologous phage:λV3 (430 bp identity with Bp221),λV13 (430 bp stretch of 89% identity with Bp221) and λlink H (31bp identity with πMt631c18, except for 1 mismatch at position 18).

The cloned RecA was then shuffled in vitro using the standard DNase-treatment followed by PCR-based reassembly. Shuffled plasmids were transformed into the nonrecombining host strain. These cells were grown up overnight, infected with phage λVc, λV13 or λlink H, and plated onto NZCYM plates in the presence of a 10-fold excess of MC1061 lacking plasmid. The more efficiently a recA allele promotes recombination between plasmid and phage, the more highly the allele is represented in the bacteriophage DNA. Consequently, harvesting all the phage from the plates and recovering the recA genes selects for the most recombinogenic recA alleles.

Recombination frequencies for wild type and a pool of hyperrecombinogenic RecA after 3 rounds of shuffling were as follows:

| Cross | Wild Type | Hyper Recom |
|---|---|---|
| BP221 × V3 | $6.5 \times 10^{-4}$ | $3.3 \times 10^{-2}$ |
| BP221 × V13 | $2.2 \times 10^{-5}$ | $1.0 \times 10^{-3}$ |
| πMT631c18 × link H | $8.7 \times 10^{-6}$ | $4.7 \times 10^{-5}$ |

These results indicate a 50-fold increase in recombination for the 430 bp substrate, and a 5-fold increase for the 31 bp substrate.

The recombination frequency between BP221 and V3 for five individual clonal isolates are shown below, and the DNA and protein sequences and alignments thereof are included in FIGS. 12 and 13.
Wildtype: $1.6 \times 10^{-4}$
Clone 2: $9.8 \times 10^{-3}$ (61×increase)
Clone 4: $9.9 \times 10^{-3}$ (62×increase)
Clone 5: $6.2 \times 10^{-3}$ (39×increase)
Clone 6: $8.5 \times 10^{-3}$ (53×increase)
Clone 13: 0.019(116×increase)
Clones 2, 4, 5, 6 and 13 can be used as the substrates in subsequent rounds of shuffling, if further improvement in recA is desired. Not all of the variations from the wildtype recA sequence necessarily contribute to the hyperrecombinogenic phenotype. Silent variations can be eliminated by backcrossing. Alternatively, variants of recA incorporating individual points of variation from wildtype at codons 5, 18, 156, 190, 236, 268, 271, 283, 304, 312, 317, 345 and 353 can be tested for activity.

Example 2
Whole Organism Evolution for Hyper-Recombination

The possibility of selection for an *E. coli* strain with an increased level of recombination was indicated from phenotypes of wild-type, ΔrecA, mutS and ΔrecA mutS strains following exposure to mitomycin C, an inter-strand cross-linking agent of DNA.

Exposure of *E. coli* to mitomycin C causes inter-strand cross-linking of DNA thereby blocking DNA replication. Repair of the inter-strand DNA cross links in *E. coli* occurs via a RecA-dependent recombinational repair pathway (Friedberg et al., in DNA Repair and Mutagenesis (1995) pp. 191–232). Processing of cross-links during repair results in occasional double-strand DNA breaks, which too are repaired by a RecA-dependent recombinational route. Accordingly, recA⁻ strains are significantly more sensitive than wildtype strains to mitomycin C exposure. In fact, mitomycin C is used in simple disk-sensitivity assays to differentiate between RecA⁺ and RecA⁻ strains.

In addition to its recombinogenic properties, mitomycin C is a mutagen. Exposure to DNA damaging agents, such as mitomycin C, typically results in the induction of the *E. coli* SOS regulon which includes products involved in error-prone repair of DNA damage (Friedberg et al., 1995, supra, at pp. 465–522).

Following phage P1-mediated generalized transduction of the Δ(recA-srl)::Tn10 allele (a nonfunctional allele) into wild-type and mutS *E. coli*, tetracycline-resistant transductants were screened for a recA-phenotype using the mitomycin C-sensitivity assay. It was observed in LB overlays with a ¼ inch filter disk saturated with 10 μg of mitomycin C following 48 hours at 37° C., growth of the wild-type and mutS strains was inhibited within a region with a radius of about 10 mm from the center of the disk. DNA cross-linking at high levels of mitomycin C saturates recombinational repair resulting in lethal blockage of DNA replication. Both strains gave rise to occasional colony forming units within the zone of inhibition, although, the frequency of colonies was ~10–20-fold higher in the mutS strain. This is presumably due to the increased rate of spontaneous mutation of mutS backgrounds. A side-by-side comparison demonstrated that the ΔrecA and ΔrecA mutS strains were significantly more sensitive to mitomycin C with growth inhibited in a region extending about 15 mm from the center of the disk. However, in contrast to the recA⁺ strains, no Mit$^r$ individuals were seen within the region of growth inhibition-not even in the mutS background. The appearance of Mit$^r$ individuals in recA⁺ backgrounds, but not in ΔrecA backgrounds indicates the Mit$^r$ is dependent upon a functional RecA protein and suggests that Mit$^r$ may result from an increased capacity for recombinational repair of mitomycin C-induced damage.

Mutations which lead to increased capacity for RecA-mediated recombinational repair may be diverse, unexpected, unlinked, and potentially synergistic. A recursive protocol alternating selection for Mit$^r$ and chromosomal shuffling evolves individual cells with a dramatically increased capacity for recombination.

The recursive protocol is as follows. Following exposure of a mutS strain to mitomycin C, Mit$^r$ individuals are pooled and cross-bread [e.g., via Hfr-mediated chromosomal shuffling or split-pool generalized transduction, or protoplast fusion). Alleles which result in Mit$^r$ and presumably result in an increased capacity for recombinational repair are shuffled among the population in the absence of mismatch repair. In addition, error-prone repair following exposure to mitomycin C can introduce new mutations for the next round of shuffling. The process is repeated using increasingly more stringent exposures to mitomycin C. A number of parallel selections in the first round as a means of generating a variety of alleles. Optionally, recombinogencity of isolates can be monitored for hyper-recombination using a plasmid×plasmid assay or a chromosome×chromosome assay (e.g., that of Konrad, *J. Bacteriol.* 130, 167–172 (1977)).

Example 3
Whole Genome Shuffling of Streptomyces Coelicolor to Improve the Production of γ-actinorhodin.

To improve the production of the secondary metabolite γ-actinorhodin from *S. coelicolor*, the entire genome of this organism is shuffled either alone or with its close relative *S. lividans*. In the first procedure described below, genetic diversity arises from random mutations generated by chemical or physical means. In the second procedure, genetic diversity arises from the natural diversity existing between the genomes of *S. coelicolor* and *S. lividans*.

Spore suspensions of *S. coelicolor* are resuspended in sterile water and subjected to U.V. mutagenesis such that 1% of the spores survive (~600 "energy" units using a Stratalinker, Stratagene), and the resulting mutants are "grown out" on sporulation agar. Individual spores represent uninucleate cells harboring different mutations within their genome. Spores are collected, washed, and plated on solid medium, preferably soy agar, R5, or other rich medium that results in sporulating colonies. Colonies are then imaged and picked randomly using an automated colony picker, for example the Q-bot (Genetix). Alternatively colonies producing larger or darker halos of blue pigment are picked in addition or preferentially.

The colonies are inoculated into 96 well microtitre plates containing ⅓×YEME medium (170 μl/well). Two sterile 3 mm glass beads are added to each well, and the plates are shaken at 150–250 rpm at 30° C. in a humidified incubator. The plates are incubated up to 7 days and the cell supernatents are assayed for γ-actinorhodin production.

To assay, 50 μL of supernatant is added to 100 μL of distilled water in a 96 well polypropylene microtitre plate, and the plate is centrifuged at 4000 rpm to pellet the mycelia. 50 μL of the cleared supernatant is then removed and added to a flat bottom polystyrene 96 well microtitre plate containing 150 μL 1M KOH in each well. The resulting plates are then read in a microtitre plate reader measuring the absorbance at 654 nm of the individual samples as a measure of the content γ-actinorhodin.

Mycelia from cultures producing γ-actinorhodin at levels significantly higher than that of wildtype *S. coelicolor* are then isolated. These are propagated on solid sporulation medium, and spore preparations of each improved mutant are made. From these preparations protoplasts of each of the improved mutants are generated, pooled together, and fused (as described in *Genetic Manipulation of Streptomyces—A laboratory Manual*, Hopwood, D. A., et al.). The fused protoplasts are regenerated and allowed to sporulate. Spores are collected and either plated on solid medium for further picking and screening, or, to increase the representation of multiparent progeny, are used to generate protoplasts and fused again (or several times as described previously for methods to effect poolwise recombination) before further picking and screening.

Further improved mutants result from the combination of two or more mutations that have additive or synergistic effects on g-actinorhodin production. Further improved mutants can be again mated by protoplast poolwise fusion, or they can be exposed to random mutagenesis to create a new population of cells to be screened and mated for further improvements.

As an alternative to random mutagenesis a source of genetic diversity, natural diversity can be employed. In this case, protoplasts generated from wildtype *S. coelicolor* and *S. lividans* are fused together. Spores from the regenerated progeny of this mating are then either repetitively fused and regenerated to create additional diversity, or they are separated on solid medium, picked, and screened for enhanced production of g-actinorhodin. As before, the improved subpopulation are mated together to identify further improved family shuffled organisms.

Example 4
Whole Genome Shuffling of Rhodococcus for Two-Phase Reaction Catalysis This example provides and example of how to apply the techniques described herein to technologies that allow the generic improvement of biotransformations catalyzed by whole cells. Rhodococcus was selected as an initial target because it is both representative of systems in which molecular biology is rudimentary (as is common in whole cell catalysts which are generally selected by screening environmental isolates), and because it is an organism that can catalyze two-phase reactions.

The goal of whole genome shuffling of Rhodococcus is to obtain an increase in flux through any chosen pathway. The substrate specificity of the pathway can be altered to accept molecules which are not currently substrates. Each of these features can be selected for during whole genome shuffling.

During whole genome shuffling, libraries of shuffled enzymes and pathways are made and transformed into Rhodococcus and screened, preferably by high-throughput assays for improvements in the target phenotype, e.g., by mass spectroscopy for measuring the product.

As noted above, the chromosomal context of genes can have dramatic effects on their activities. Cloning of the target genes onto a small plasmid in Rhodococcus can dramatically reduce the overall pathway activity (by a factor of 5- to 10-fold or more). Thus, the starting point for DNA shuffling of a pathway (on a plasmid) can be 10-fold lower than the activity of wild-type strain. By contrast, integration of the genes into random sites in the Rhodococcus chromosome can result in a significant (5- to 10-fold) increase in activity. A similar phenomenon was observed in the recent directed evolution in *E coli* of an arsenate resistance operon (originally from *Staphylococcus aureus*) by DNA shuffling. Shuffling of this plasmid produced sequence changes that led to efficient integration of the operon into the *E coli* chromosome. Of the total 50-fold increase in arsenate resistance obtained by directed evolution of the three gene pathway, approximately 10-fold resulted from this integration into the chromosome. The position within the chromosome is also likely to be important: for example sequences close to the replication origin have an effectively higher gene dosage and therefore greater expression level.

In order to fully exploit unpredictable chromosomal position effects, and to incorporate them into a directed evolution strategy which utilizes multiple cycles of mutation, recombination and selection, genes are manipulated in vitro and then transferred to an optimal chromosomal position. Recombination between plasmid and chromosome occurs in two different ways. Integration takes place at a position where there is significant sequence homology between plasmid and chromosome, i.e., by homologous recombination. Integration also takes place where there is no apparent sequence identity, i.e., by non-homologous recombination. These two recombination mechanisms are effected by different cellular machineries and have different potential applications in directed evolution.

To combine the increase in activity that resulted from gene duplication and chromosomal integration of the target pathway with the powerful technique of DNA shuffling, libraries of shuffled genes are made in vitro, and integrated into the chromosome in place of the wild-type genes by homologous recombination. Recombinants are then be screened for increased activity. This process is optionally made recursive as discussed herein. The best Rhodococcus variants are pooled, and the pool divided in two. Genes are cloned out of the pool by PCR, shuffled together and re-integrated into the chromosomes of the other half of the pool by homologous recombination. Recombinants are once again be screened, the best taken and pooled and the process optionally repeated.

Sometimes there are complex interactions between enzymes catalyzing successive reactions in a pathway. Sometimes the presence of one enzyme can adversely affect the activities of others in the pathway. This can be the result of protein-protein interactions, or inhibition of one enzyme by the product of another, or an imbalance of primary or secondary metabolism.

This problem is overcome by DNA shuffling, which produces solutions in the target gene cluster that bring about improvements in whatever trait is screened. An alternative approach, which can solve not only this problem, but also anticipated future rate limiting steps such as supply of reducing power and substrate transportation, is complementation by overexpression of other as yet unknown genomic sequences.

A library of Rhodococcus genomic DNA in a multicopy Rhodococcus vector such as pRC1 is first made. This is transformed into Rhodococcus and transformants are screened for increases in the desired phenotype. Genomic fragments which result in increased pathway activity are evolved by DNA shuffling to further increase their beneficial effect on a selected property. This approach requires no sequence information, nor any knowledge or assumptions about the nature of protein or pathway interactions, or even of the rate-limiting step; it relies only on detection of the desired phenotype. This sort of random cloning and subsequent evolution by DNA shuffling of positively interacting genomic sequences is extremely powerful and generic. A variety of sources of genomic DNA are used, from isogenic strains to more distantly related species with potentially desirable properties. In addition, the technique is, in principle, applicable to any microorganism for which the molecular biology basics of transformation and cloning vectors are available, and for any property which can be assayed, preferably in a high-throughput format.

Homologous recombination within the chromosome is used to circumvent the limitations of plasmid-evolution and size restrictions, and is optionally used to alter central metabolism. The strategy is similar to that described above for shuffling genes within their chromosomal context, except that no in vitro shuffling occurs. Instead, the parent strain is treated with mutagens such as ultraviolet light or nitrosoguanidine, and improved mutants are selected. The improved mutants are pooled and split. Half of the pool is used to generate random genomic fragments for cloning into a homologous recombination vector. Additional genomic fragments are derived from related species with desirable properties (in this case higher metabolic rates and the ability to grow on cheaper carbon sources). The cloned genomic fragments are homologous recombined into the genomes of the remaining half of the mutant pool, and variants with improved phenotypes are selected. These are subjected to a further round of mutagenesis, selection and recombination. Again this process is entirely generic for the improvement of any whole cell biocatalyst for which a recombination vector and an assay can be developed.

Efficient homologous recombination is important for the recursivity of the chromosomal evolution strategies outlined above. Non-homologous recombination results in a futile integration (upon selection) followed by excision (following counterselection) of the entire plasmid. Alternatively, if no counter-selection were used, there is integration of more and more copies of plasmid/genomic sequences which is both unstable and also requires an additional selectable marker for each cycle. Furthermore, additional non-homologous recombination will occur at random positions and may or may not lead to good expression of the integrated sequence.

Example 5
Increasing the Rate of Homologous Recombination in Rhodococcus

A genetic approach is used to increase the rate of homologous recombination in Rhodococcus. Both targeted and non-targeted strategies to evolve increases in homologous recombination are used. Rhodococcus recA is evolved by DNA shuffling to increase its ability to promote homologous recombination within the chromosome. The recA gene was chosen because there are variants of recA known to result in increased rates of homologous recombination in *E coli*. as discussed above.

The recA gene from Rhodococcus is DNA shuffled and cloned into a plasmid that carries a selectable marker and a disrupted copy of the Rhodococcus homolog of the *S cerevisiae* URA3 gene (a gene which also confers sensitivity to the uracil precursor analogue 5-fluoroorotic acid). Homologous integration of the plasmid into the chromosome disrupts the host uracil synthesis pathway leading to a strain that carries the selectable marker and is also resistant to 5-fluoroorotic acid. The shuffled recA genes is integrated, and can be amplified from the chromosome, shuffled again and cloned back into the integration-selection vector. At each cycle, the recA genes promoting the greatest degree of homologous recombination are those that are the best represented as integrants in the genome. Thus a Rhodococcus recA with enhanced homologous recombination-promoting activity is evolved.

Many other genes are involved in several different homologous recombination pathways, and mutations in some of these proteins may also lead to cells with an increased level of homologous recombination. For example mutations in *E coli* DNA polymerase III have recently been shown to increase RecA-independent homologous recombination. Resistance to DNA cross-linking agents such as nitrous acid, mitomycin and ultraviolet are dependent on homologous recombination. Thus, increases in the activity of this pathway result in increased resistance to these agents. Rhodococcus cells are mutagenized and selected for increased tolerance to DNA cross-linking agents. These mutants are tested for the rate at which a plasmid will integrate homologous into the chromosome. Genomic libraries are prepared from these mutants, combined as described above, and used to evolve a strain with even higher levels of homologous recombination.

The foregoing description of the preferred embodiments of the present invention has been presented for purposes of illustration and description. They are not intended to be exhaustive or to limit the invention to the precise form disclosed, and many modifications and variations are possible in light of the above teaching. Such modifications and variations which may be apparent to a person skilled in the art are intended to be within the scope of this invention. All patent documents and publications cited above are incorporated by reference in their entirety for all purposes to the same extent as if each item were so individually denoted.

What is claimed is:

1. A method of evolving a cell to acquire a desired function, comprising:
   (1) introducing a library of DNA fragments into a plurality of cells, whereby at least one of the fragments undergoes recombination with a segment in the genome or an episome of the cells to produce modified cells;
   (2) screening the modified cells for modified cells that have evolved toward acquisition of the desired function;
   (3) recombining DNA from the modified cells that have evolved toward the desired function with a further library of DNA fragments, at least one of which undergoes recombination with a segment in the genome or the episome of the modified cells to produce further modified cells, or recombining DNA between the modified cells that have evolved toward the desired function to produce further modified cells;
   (4) screening the further modified cells for further modified cells that have further evolved toward acquisition of the desired function;
   (5) repeating (3) and (4) as required until the further modified cells have acquired the desired function.

2. The method of claim 1, wherein the library is a library of locked in prophage.

3. The method of claim 1, wherein the step of recombining DNA between the modified cells is performed by protoplast fusing the modified cells and allowing fused cells to recombine.

4. The method of claim 1, wherein the step of recombining DNA between the modified cells is performed by protoplast fusing the modified cells and allowing fused cells to recombine, the method further comprising enriching the resulting fused cell population for fused cells comprising more than two cell genomes.

5. The method of claim 1, wherein the library of DNA fragments is a substantially complete genomic library from at least one heterologous cell type.

6. The method of claim 1, wherein the library of fragments comprises natural variants of a gene from different individuals.

7. The method of claim 1, further comprising subdividing the modified cells into first and second pools, isolating the further library of DNA fragments from the second pool and introducing the further library of DNA fragments into the first pool.

8. The method of claim 1, wherein the library of DNA fragments are components of viruses and the introducing occurs by infection of the cells with the viruses.

9. The method of claim 1, wherein the library of DNA fragments is cloned into a suicide vector incapable of permanent episomal existence in the cells.

10. The method of claim 9, wherein the suicide vector further comprises a selective marker.

11. The method of claim 1, further comprising coating the library or further library of DNA fragments with recA protein to stimulate recombination with the segment of the genome.

12. The method of claim 1, further comprising denaturing the library of fragments to produce single-stranded DNA, reannealling the single-stranded DNA to produce duplexes some of which contain mismatches at points of variation in the fragments, and selecting duplexes containing mismatches by affinity chromatography to immobilized MutS.

13. The method of claim 1, further comprising fragmenting the library of fragments to produce subfragments before denaturation, and reassembling duplexes of subfragments containing mismatches into reassembled fragments.

14. The method of claim 13, wherein the average diversity between reassembled fragments is at least five times greater than the average diversity between fragments.

15. The method of claim 1, wherein the desired function is secretion of a protein, and the plurality of cells further comprises a construct encoding the protein.

16. The method of claim 15, wherein the protein is inactive unless secreted, and the modified or further modified cells having evolved toward acquisition of the desired function are screened by propagating the cells and recovering surviving cells.

17. The method of claim 16, wherein the protein is β-lactamase or alkaline phosphatase, and the modified or further modified cells having evolved toward acquisition of the desired function are screened by monitoring metabolism of a chromogenic substrate of the alkaline phosphatase, or by monitoring resistance to a β-lactamase antibiotic.

18. The method of claim 17, wherein the protein is an antibody and the plurality of cells is *E. coli*.

19. The method of claim 18, wherein the construct further encodes a marker which is expressed with the protein as a fusion protein, and the screening comprises propagating the modified or further modified cells and identifying cells secreting the fusion protein by FACS sorting.

20. The method of claim 19, wherein the marker protein is linked to a phospholipid anchoring domain that anchors the marker protein to the cell surface after secretion from the cell.

21. The method of claim 19, wherein the cells are contained in agar drops which confine secreted protein in proximity with the cell secreting the protein.

22. The method of claim 15, wherein at least one fragment in the library encodes a signal sequence, and the at least one fragment is incorporated into a construct operably linked to a sequence encoding a protein to be secreted from the cells.

23. The method of claim 12, wherein at least one fragment in the library encodes a signal processing enzyme and the cells contain a construct encoding a protein to be secreted operably linked to a signal sequence.

24. The method of claim 12, wherein at least one fragment in the library encodes a gene selected from the group consisting of SecA, SecB, SecE, SecD and SecF genes.

25. The method of claim 1, wherein the desired function is enhanced recombination.

26. The method of claim 1, wherein the library of fragments comprises a cluster of genes collectively conferring recombination capacity.

27. The method of claim 1, wherein the library of DNA fragments comprises at least one gene, which at least one gene is selected from the group consisting of recA, recBCD, recBC, recE, recF, recG, recO, recQ, recR, recT, ruvA, ruvB, sbcB, ssb, topA, gyrA and B, lig, polA, uvrD, E, recL, mutU and helD.

28. The method of claim 27, wherein the plurality of cells further comprises a gene encoding a marker whose expression is prevented by a mutation removable by recombination, and the modified or further modified cells are screened by their expression of the marker resulting from removal of the mutation by recombination.

29. The method of claim 27, wherein in the screening steps, the modified or further modified cells are exposed to a mutagen and modified or further modified cells having evolved toward acquisition of the desired function are selected by their survival of the exposure, survival being conferred by the cells' enhanced recombinational capacity to remove damage induced by the mutagen.

30. The method of claim 27, wherein the mutagen is radiation.

31. The method of claim 30, wherein enhanced recombination is conferred by increased genomic copy number of the modified or further modified cells.

32. The method of claim 22, wherein at least one gene is selected from a replication or cell septation gene.

33. The method of claim 32, wherein the modified or further modified cells having evolved toward acquisition of the desired function are selected by their capacity for syncytium formation or cell fusion.

34. The method of claim 1, wherein the plurality of cells are plant cells and the desired property is improved resistance to a chemical or microbe, and in the screening the steps, the modified or further modified cells are exposed to the chemical or microbe and modified or further modified cells having evolved toward the acquisition of the desired function are selected by their capacity to survive the exposure.

35. The method of claim 34, wherein the microorganism is a virus, bacterium, or fungus.

36. The method of claim 35, wherein the chemical is a viricide, fungicide, insecticide, bactericide or herbicide.

37. The method of claim 36, wherein the chemical is BT-toxin.

38. The method of claim 36, wherein the chemical is glyphosate or atrazine.

39. The method of claim 36, further comprising propagating a plant cell having acquired the desired function to produce a transgenic plant.

40. The method of claim 1, wherein the plurality of cells are embryonic cells of an animal, and the method further comprises propagating the transformed cells to transgenic animal.

41. The method of claim 40, wherein the modified cells are screened as components of the transgenic animals.

42. The method of claim 41, further comprising obtaining embryonic cells from the transgenic animals having modified cells evolved toward acquisition of the property and transforming the cells with the further library.

43. The method of claim 40, further comprising isolating DNA from transgenic animals that have evolved toward acquisition of the property and introducing the DNA into fresh embryonic cells.

44. The method of claim 40, wherein the animal is a fish.

45. The method of claim 40, wherein at least one of the fragments encodes a growth hormone and the desired property is increased size of the animal.

46. The method of claim 1, wherein the library of DNA fragments comprises a library of natural variants from different species.

47. The method of claim 1, wherein the library of DNA fragments comprises one or more shuffled nucleic acid.

48. The method of claim 47, wherein the shuffled library is produced by in vitro or in vivo shuffling.

49. The method of claim 1, wherein the further modified cells of step (3) are recombined with at least one additional library of DNA fragments, at least one of which undergoes recombination with a segment in the genome or the episome of the further modified cells to produce additionally modified cells, or recombining DNA between the further modified cells that have evolved toward the desired function to produce additionally modified cells, prior to performing the screening of step (4).

* * * * *

UNITED STATES PATENT AND TRADEMARK OFFICE
CERTIFICATE OF CORRECTION

PATENT NO. : 6,326,204 B1  Page 1 of 1
DATED : December 4, 2001
INVENTOR(S) : Stephen del Cardayre et al.

It is certified that error appears in the above-identified patent and that said Letters Patent is hereby corrected as shown below:

Column 108,
Line 9, "ruvA, ruvB" should read -- ruvA, ruvB, ruvC, --.
Line 57, "animal" should read -- animals --.

Column 109,
Line 9, "fragments comprises one or more shuffled nucleic acid" should read
-- fragments comprises at least one shuffled nucleic acid --.

Signed and Sealed this

Third Day of June, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 1485
<212> TYPE: DNA
<213> ORGANISM: Escherichia coli

<400> SEQUENCE: 1 gggatttttgg tcatgagatt atcaaaaagc ggccgcggcc taagaggcca gagaagcctg    60

| | |
|---|---|
| tcggcacggt ctggtttgct tttgccactg cccgcggtga aggcattacc cggcgggatg | 120 |
| cttcagcggc gaccgtgatg cggtgcgtcg tcaggctact gcgtatgcat tgcagacctt | 180 |
| gtggcaacaa tttctacaaa acacttgata ctgtatgagc atacagtata attgcttcaa | 240 |
| cagaacatat tgactatccg gtattacccg gcatgacagg agtaaaaatg ctatcgacg | 300 |
| aaaacaaaca gaaagcgttg gcggcagcac tgggccagat tgagaaacaa tttggtaaag | 360 |
| gctccatcat gcgcctgggt gaagaccgtt ccatggatgt ggaaaccatc tctaccggtt | 420 |
| cgctttcact ggatatcgcg cttggggcag gtggtctgcc gatgggccgt atcgtcgaaa | 480 |
| tctacggacc ggaatcttcc ggtaaaacca cgctgacgct gcaggtgatc gccgcagcgc | 540 |
| agcgtgaagg taaaacctgt gcgtttatcg atgctgaaca cgcgctggac ccaatctacg | 600 |
| cacgtaaact gggcgtcgat atcgacaacc tgctgtgctc ccagccggac accggcgagc | 660 |
| aggcactgga aatctgtgac gccctggcgc gttctggcgc agtagacgtt atcgtcgttg | 720 |
| actccgtggc ggcactgacg ccgaaagcgg aaatcgaagg cgaaatcggc gactctcaca | 780 |
| tgggccttgc ggcacgtatg atgagccagg cgatgcgtaa gctggcgggt aacctgaagc | 840 |
| agtccaacac gctgctgatc ttcatcaacc agatccgtat gaaaattggt gtgatgttcg | 900 |
| gtaacccgga aaccaccacc ggtggtaacg cgctgaaatt ctacgcctct gttcgtctcg | 960 |
| acatccgtcg tatcggcgcg gtgaaagagg gcgaaaacgt ggtgggtagc gaaacccgcg | 1020 |
| tgaaagtggt gaagaacaaa atcgctgcgc cgtttaaaca ggctgaattc cagatcctct | 1080 |
| acggcgaagg tatcaacttc tacggcgaac tggttgacct gggcgtaaaa gagaagctga | 1140 |
| tcgagaaagc aggcgcgtgg tacagctaca aggtgagaa atcggtcag gtaaagcga | 1200 |
| atgcgactgc ctggctgaaa gataacccgg aaaccgcgaa agagatcgag aagaaagtac | 1260 |
| gtgagttgct gctgagcaac ccgaactcaa cgccggattt ctctgtagat gatagcgaag | 1320 |
| gcgtagcaga aactaacgaa gattttttaat cgtcttgttt gatacacaag ggtcgcatct | 1380 |
| gcggcccttt tgcttttta agttgtaagg atatgccatg acagaatcaa catcccgtcg | 1440 |
| gcctggtagg ccatttttg gatcttcacc tagatccttt taaat | 1485 |

<210> SEQ ID NO 2
<211> LENGTH: 1382
<212> TYPE: DNA
<213> ORGANISM: Escherichia coli

<400> SEQUENCE: 2

| | |
|---|---|
| tgttggcacg gtctggcttg cttttgccac tgcccgcggt gaaggcatta cccggcggga | 60 |
| atgcttcaac ggcgaccgtg atgcggtgcg tcgtcaggct actgcgtatg cattgcagac | 120 |
| cttgtggcaa caatttctac gaaacacctg atactgtatg agcatacagt ataattgctt | 180 |
| caacagaaca tattgactat ccggtattac cggcatgac aggagtgaaa atggctattg | 240 |
| acgaaaacaa acagaaagcg ttggcgacag cactgggcca gattgagaaa caatttggta | 300 |
| aaggctccat catgcgcctg gtgaagacc gttccatgga tgtggaaacc atctctaccg | 360 |
| gttcgctttc actggatatc gcgcttgggg caggtggtct gccgatgggc cgtatcgtcg | 420 |
| aaatctacgg accggaatct tccggtaaaa ccacactgac gctgcaggtg atcgccgcag | 480 |
| cgcagcgtga aggtaaaacc tgtgcgttta tcgatgccga acacgcgctg acccaatct | 540 |
| acgcacgcaa actgggcgtc gatatcgaca acctgctgtg ctcccagccg acaccggcg | 600 |
| agcaggcact ggaaatctgt gacgccctgg cgcgttctgg cgcagtagac gttatcgtcg | 660 |
| ttgactccgt ggcggcactg acgccgaaag cggaaatcga aggcgaaatc ggcgactctc | 720 |

```
acatgggcct tgcggcacgt atgatgagcc aggcgatgcg caagctggcg ggtaacctga      780
agcagtccaa cacgctgctg atcttcatta accagatccg tatgaaaatt ggtgtgatgt      840
tcggtaaccc ggaaaccact accggtggta acgcgctgaa attctacgcc tccgttcgtc      900
tcgacatccg tcgtatcggc gcggtgaaag agggcgaaaa cgtggtgggt agcgaaaccc      960
gcgtgaaagt ggtgaagaac aaaatcgctg cgccgtttaa acaggctgaa ttccaggtcc     1020
tctacggcga aggtatcaac ttctacggcg aactggttga cctgggcgta aagagaagc      1080 tgatcgagaa agcaggcgcg tggtacagct acaaaggaga aagattggt cagggtaaag      1140 cgaacgcgac tgcctggctg aaagataatc cggaaaccgc gaaagagatt gagaagaaag     1200
tacgtgagtt gctgctgagc aacccgaact caacgccgga tttctctgga gatgatagcg     1260
aaggcgtagc agaaactaac gaagatttt aatcgtcttg tttgatacac aagggtcgca     1320
tctgcgaccc ttttgctttt ttaagttgta aggatatgcc atgacagaat caacatcccg     1380
tc                                                                    1382
```

<210> SEQ ID NO 3
<211> LENGTH: 1430
<212> TYPE: DNA
<213> ORGANISM: Escherichia coli

<400> SEQUENCE: 3

```
agaggccaga gaagcctgtc ggcacggtct ggtttgcctt tgccactgcc cgcggtgaag       60
gcattactcg gcgggaatgc ttcagtggcg accgtgatgc ggtgcgtcgt caggctactg      120
cgtatgcatt gcagaccttg tggcaacaat ttctacaaaa cacctgatac tgtatgagca      180
tacagtataa ttgcttcaac agaacatatt gactatccgg tattacccgg catgacagga      240
gtaaacatgg ctatcgacga aacaaacag aaagcgttag cggcagcact gggccagatt       300
gagaaacaat ttggtaaagg ctccatcatg cgcctgggtg aagaccgttc catggatgtg      360
gaaaccatct ccaccggttc gctttcactg gatatcgcac ttggggcagg tggtctgccg      420
atgggccgta tcgtcgaaat ctacggaccg gaatcttccg gtaaaaccac gctgacgctg      480
caggtgatcg ccgcagcgca gcgtgaaggt aaaacctgtg cgtttatcga tgctgaacac      540
gcgctggacc caatctacgc acgtaaactg ggcgtcgata tcgacaacct gctgtgctcc      600
cagcccgaca ccggcgagca ggcactggaa atcgtgacg ccctggcgcg ttctggcgcg       660
gtagacgtta tcgtcgttga ctccgtggcg gcactgacgc cgaaagcgga aatcgaaggc      720
gaaatcggcg actctcacat gggccttgcg gcacgtatga tgagccaggc gatgcgtaag      780
ctggcgggta acctgaagca gtccaacacg ctgctgatct tcatcaacca gatccgtatg      840
aaaattggtg tgatgttcgg taacccggaa accactaccg gtggtaacgc gctgaaattc      900
tacgcctctg ttcgtctcga catccgtcgt atcggcgcgg tgaagagggg cgaaaacgtg      960
gtgggtagcg aaacccgcgt gaaagtggtg aagaacaaaa tcgctgcgcc gtttaaacag     1020
gctgaattcc aaatcctcta cggcgaaggt atcaacttct acggcgaact ggttgacctg     1080
ggcgtaaaag agaagctgat cgagaaagca ggcgcgtggt acagctacaa aggtgagaag     1140
atcggtcagg gtaaagcgaa tgcgactgcc tggctgaaaa taacccggaa accgcgaaa      1200 gagatcgaga agaagtacg tgagttgctg ctgagtaacc cgaactcaac gccggatttc      1260
tctgtagatg atagcgaagg cgtagcagga actaacgaag atttttaatc gtcttgtttg     1320
atacacaagg gtcgcatctg cggccctttt gcttttttaa gttgtaggga tatgccatga     1380
```

```
                      cagaatcaac atcccgtcgg cctggtaggc cattttttgg atcttcacct      1430

<210> SEQ ID NO 4
<211> LENGTH: 1380
<212> TYPE: DNA
<213> ORGANISM: Escherichia coli

<400> SEQUENCE: 4
cggcagggtc tggtttgctt ttgccactgc ccgcggtgaa ggcattatcc ggcgggaatg        60
cttcagcggc ggccgtgatg cggtgcgtcg tcaggctact gcgtatgcat tgcagacctt       120
gtggcaacaa tttctacaaa cacctgata  ctgtatgagc atacagtata attgcttcga       180
cagaacatat tgactatccg gtattacccg gcatgacagg agtaaaaatg gctatcgacg       240
agaacaaaca gaaagcgttg gcggcagcac tgggccagat tgagaaacaa tttggtaaag       300
gctccatcat gcgcctgggt gaagaccgtt ccatggatgt ggaaaccatc tctaccggtt       360
cgctttcact ggatatcgcg cttggggcag gtggtctgcc gatgggccgt atcgtcgaaa       420 tctacgacc  ggaatcttcc ggtaaaacca cactgacgct gcaggtgatc gccgcagcgc       480
agcgtgaagg taaaacctgt tgcgtttatc gatgctgaac acgcgctaga cccaatctac       540
gcacgtaaac tgggcgtcga tatcgacaac ctgctgtgct cccagccgga caccggcgag       600
caggcactgg aaatctgtga cgccctggcg cgttctggcg cagtagacgt tatcgtcgtt       660
gactccgtag cggcactgac gccgaaagcg gaaatcgaag gcgaaatcgg cgactctcac       720
atgggccttg cggcacgtat gatgagccag gcgatgcgta agctggcggg taacctgaag       780
ttgtccaaca cgctgctgat ctttatcaac cagatccgta tgaaaattgg cgtgatgttc       840
ggtaacccgg aaaccaccac cggtggtaac gcgctgaaat tctacgcctc tgttcgtctc       900
gacatccgtc gtatcggtgc ggtgaaagag ggcgaaaacg tggtgggtag cgaaacccgc       960
gtgaaagtgg tgaagaacaa atcgctgcg  ccgtttaaac aggctgaatt ccagatcctc      1020
tacggcgaag gtatcaactt ctacggcgaa ctggttgacc tgggcgtaaa agagaagctg      1080
atcgagaaag caggcgcgtg gtacagctac aaaggtgaga gatcggtca  gggtaaagcg      1140 aatgcggctg cctggctgaa aggtaacccg gaaaccgcga agagatcga  gaagaaagta      1200 cgtgagttgc tgctgagcaa cccgaactca acgccggatt tctctagaga tgatagcgaa      1260
ggcgtagcag aaactaacga agatttttaa tcgtcttgtt taatacacga gggtcgcatc      1320
tgcggccctt ttgcttttt  aagttgtaag gatatgccat gacagaatca acatccagtc      1380

<210> SEQ ID NO 5
<211> LENGTH: 1343
<212> TYPE: DNA
<213> ORGANISM: Escherichia coli

<400> SEQUENCE: 5
agaggccaga gaagccagtt ggcacggtct ggtttgcttt tgccactgcc cggggtgagg        60
gcattacccg gcgggaatgc ttcagcggcg accgtgatgc ggtgcgtcgt caggctactg       120
cgtatgcact gcagaccttg tggcaacaat ttctacaaaa cacctgttac tgtatgagca       180
tgcagtataa ttgcttcaac agaacatatt gactatccgg tattacccgg catgacagga       240
gtaaaaatgg ctattgacga aaacaaacag aaagcgttgg cggcagcact gggccagatt       300
gagaaacaat ttggtaaagg ctccatcatg cgcctgggtg aagaccgttc catggatgtg       360
gaaaccatct ctactggttc gctttcactg gatatcgcgc ttggggcagg tggtctgccg       420
atgggccgta tcgtcgaaat ctatggaccg gaatcttccg gtaaaaccac actgacgctg       480
```

-continued

| | |
|---|---|
| caggtgatcg ccgcagcgca gcgtgagggt aaaacctgtg cgtttatcga tgctgaacac | 540 |
| gcgctggacc caatctacgc acgtaaactg ggcgtcgata tcgacaacct gctgtgctcc | 600 |
| cagccggaca ccggcgagca ggcactggaa atctgtgacg ccctggcgcg ttctggcgct | 660 |
| gtagacgtta tcgtcgttga ctccgtggcg gcactgtcgc cgaaagcgga atcgaaggc | 720 |
| gaaatcggcg actctcacat gggccttgcg gcacgtatga tgagccaggc aatgcgtaag | 780 |
| ctggcgggta acctgaagca gtccaacacg ctgctgatct tcatcaacca gatccgtatg | 840 |
| aaaattggtg tgatgttcgg taacccggaa accaccaccg tggtaacgc gctgaaattc | 900 |
| tacgcctctg ttcgtctcga catccgtcgt atcggcgcag tgaaagaggg cgaaaacgtg | 960 |
| gtgggtagcg aaacccgcgt gaaagtggtg aagaacaaaa tcgctgcgcc gtttaaacag | 1020 |
| gctgaattcc agatcctcta cggcgaaggt atcaacttct acggcgaact ggttgatctg | 1080 |
| ggcgtaaaag agaagctgat cgagaaagca ggcgcgtggt acagctacaa aggtgagaag | 1140 |
| gttggtcagg gtaaagcgaa tgcgactgcc tggctgaaag ataacccgga accgcgaaa | 1200 |
| gagatcgaga agaaagtacg tgagttgctg ctgagcaacc cgaactcaac gccggatttc | 1260 |
| tctgtagatg atagcgaagg cgtagcagaa actaacgaag atttttaatc stcttgtttg | 1320 |
| atacacaagg gtcgcatctg cgg | 1343 |

<210> SEQ ID NO 6
<211> LENGTH: 1379
<212> TYPE: DNA
<213> ORGANISM: Escherichia coli

<400> SEQUENCE: 6

| | |
|---|---|
| gaggccagag aagcctgtcg gcttggtctg gtttgctttt accattgccc gcggtgaagg | 60 |
| cattacccgg cgggaatgct tcagcggcga ccgtgatgcg gtgcgtcgtc aggctactgt | 120 |
| gtatgcactg cagaccttgt ggcaacgatt tctacaaaac actcgatacc gtatgagcac | 180 |
| acagtataat cgcttcgaca gaacttattg actatccggt attacccggc atgacaggag | 240 |
| taaaaatggc tattgacgaa acaaacagaa aagcgttggc ggcagcactg ggccagattg | 300 |
| agaaacagtt tggtaaaggc tccatcatgc gcctggggga agaccgttcc atggatgtgg | 360 |
| aaaccatctc taccggttcg ctttcactgg atatcgcgct tggggcaggt ggtctgccga | 420 |
| tgggccgtat cgtcgaaatc tacgaccgga atcttccgg taaaaccacg ctgacgctgc | 480 |
| aggtgatcgc cgcagcgcag cgtgaaggta aaacctgtgc gtttatcgat gctgaacacg | 540 |
| cgctggaccc gatctacgca cgtaaactgg gcgtcgatat cgacaacctg ctgtgctccc | 600 |
| agccggacac cggcgagcag gcactggaaa tctgtgacgc cctggcgcgc tctggcgcag | 660 |
| tggacgttat cgtcgttgac tccgtggcgg cactgacgcc gaaagcggaa atcgaaggcg | 720 |
| aaatcggcga ctctcacatg ggccttgcag cacgtatgat gagccaggcg atgcgtaagc | 780 |
| tggcgggtaa cctgaagcag tccaacacgc tgctgatctt catcaaccag atccgtatga | 840 |
| aaattggtgt gatgttcggt aacccggaaa ccactaccgg tggtaacgcg ctgaaattct | 900 |
| acgcctctgt tcgtctcgac atccgtcgta tcggcacggt gaaagagggc gaaaacgtgg | 960 |
| tgggtagcga aacccgcgtg aaagtggtga agaacaaaat cgctgcgccg tttaaacagg | 1020 |
| ctgaattcca aatcctctac gacgaaggta tcaacttcta cggcgaactg gttgacatgg | 1080 |
| gcgtaaaaga gaagctgatc gagaaagcag gcgcgtggta cagctacaaa ggtgagaagg | 1140 |
| ccggtcaggg taaagcgaat gcgactgcct ggctgaaaga taacccggaa accgcgaaag | 1200 |

```
agatcgagaa gaaagtacgt gagttgctgc tgagcaaccc gaactcaacg ccggatttct   1260
ctgtagatga tagcgaaggc gtagcagaaa ctaacgaaga ttttaatcg tcttgtttga    1320 tacacaaggg tcgcatctgc ggcccttttg cttttttaag ttgtaaggat atgccatga    1379
```

<210> SEQ ID NO 7
<211> LENGTH: 358
<212> TYPE: PRT
<213> ORGANISM: Escherichia coli

<400> SEQUENCE: 7

```
Met Thr Gly Val Lys Met Ala Ile Asp Glu Asn Lys Gln Lys Ala Leu
 1               5                  10                  15

Ala Ala Ala Leu Gly Gln Ile Glu Lys Gln Phe Gly Lys Gly Ser Ile
            20                  25                  30

Met Arg Leu Gly Glu Asp Arg Ser Met Asp Val Glu Thr Ile Ser Thr
        35                  40                  45

Gly Ser Leu Ser Leu Asp Ile Ala Leu Gly Ala Gly Gly Leu Pro Met
    50                  55                  60

Gly Arg Ile Val Glu Ile Tyr Gly Pro Glu Ser Ser Gly Lys Thr Thr
65                  70                  75                  80

Leu Thr Leu Gln Val Ile Ala Ala Gln Arg Glu Gly Lys Thr Cys
                85                  90                  95

Ala Phe Ile Asp Ala Glu His Ala Leu Asp Pro Ile Tyr Ala Arg Lys
            100                 105                 110

Leu Gly Val Asp Ile Asp Asn Leu Leu Cys Ser Gln Pro Asp Thr Gly
        115                 120                 125

Glu Gln Ala Leu Glu Ile Cys Asp Ala Leu Ala Arg Ser Gly Ala Val
    130                 135                 140

Asp Val Ile Val Val Asp Ser Val Ala Ala Leu Thr Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Gln Ser Asn
            180                 185                 190

Thr Leu Leu Ile Phe Ile Asn Gln Ile Arg Met Lys Ile Gly Val Met
        195                 200                 205

Phe Gly Asn Pro Glu Thr Thr Thr Gly Gly Asn Ala Leu Lys Phe Tyr
    210                 215                 220

Ala Ser Val Arg Leu Asp Ile Arg Arg Ile Gly Ala Val Lys Glu Gly
225                 230                 235                 240

Glu Asn Val Val Gly Ser Glu Thr Arg Val Lys Val Lys Asn Lys
                245                 250                 255

Ile Ala Ala Pro Phe Lys Gln Ala Glu Phe Gln Ile Leu Tyr Gly Glu
            260                 265                 270

Gly Ile Asn Phe Tyr Gly Glu Leu Val Asp Leu Gly Val Lys Glu Lys
        275                 280                 285

Leu Ile Glu Lys Ala Gly Ala Trp Tyr Ser Tyr Lys Gly Glu Lys Ile
    290                 295                 300

Gly Gln Gly Lys Ala Asn Ala Thr Ala Trp Leu Lys Asp Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Val Asp Ser Glu Gly Val Ala
            340                 345                 350
```

-continued

```
Glu Thr Asn Glu Asp Phe
        355

<210> SEQ ID NO 8
<211> LENGTH: 358
<212> TYPE: PRT
<213> ORGANISM: Escherichia coli

<400> SEQUENCE: 8

Met Thr Gly Val Lys Met Ala Ile Asp Glu Asn Lys Gln Lys Ala Leu
  1               5                  10                  15

Ala Thr Ala Leu Gly Gln Ile Glu Lys Gln Phe Gly Lys Gly Ser Ile
             20                  25                  30

Met Arg Leu Gly Glu Asp Arg Ser Met Asp Val Glu Thr Ile Ser Thr
         35                  40                  45

Gly Ser Leu Ser Leu Asp Ile Ala Leu Gly Ala Gly Gly Leu Pro Met
     50                  55                  60

Gly Arg Ile Val Glu Ile Tyr Gly Pro Glu Ser Ser Gly Lys Thr Thr
 65                  70                  75                  80

Leu Thr Leu Gln Val Ile Ala Ala Gln Arg Glu Gly Lys Thr Cys
             85                  90                  95

Ala Phe Ile Asp Ala Glu His Ala Leu Asp Pro Ile Tyr Ala Arg Lys
            100                 105                 110

Leu Gly Val Asp Ile Asp Asn Leu Leu Cys Ser Gln Pro Asp Thr Gly
            115                 120                 125

Glu Gln Ala Leu Glu Ile Cys Asp Ala Leu Ala Arg Ser Gly Ala Val
        130                 135                 140

Asp Val Ile Val Val Asp Ser Val Ala Ala Leu Thr Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Gln Ser Asn
            180                 185                 190

Thr Leu Leu Ile Phe Ile Asn Gln Ile Arg Met Lys Ile Gly Val Met
        195                 200                 205

Phe Gly Asn Pro Glu Thr Thr Thr Gly Gly Asn Ala Leu Lys Phe Tyr
    210                 215                 220

Ala Ser Val Arg Leu Asp Ile Arg Arg Ile Gly Ala Val Lys Glu Gly
225                 230                 235                 240

Glu Asn Val Val Gly Ser Glu Thr Arg Val Lys Val Val Lys Asn Lys
                245                 250                 255

Ile Ala Ala Pro Phe Lys Gln Ala Glu Phe Gln Val Leu Tyr Gly Glu
            260                 265                 270

Gly Ile Asn Phe Tyr Gly Glu Leu Val Asp Leu Gly Val Lys Glu Lys
        275                 280                 285

Leu Ile Glu Lys Ala Gly Ala Trp Tyr Ser Tyr Lys Gly Glu Lys Ile
    290                 295                 300

Gly Gln Gly Lys Ala Asn Ala Thr Ala Trp Leu Lys Asp Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Gly Asp Asp Ser Glu Gly Val Ala
            340                 345                 350

Glu Thr Asn Glu Asp Phe
```

<210> SEQ ID NO 9
<211> LENGTH: 358
<212> TYPE: PRT
<213> ORGANISM: Escherichia coli

<400> SEQUENCE: 9

```
Met Thr Gly Val Asn Met Ala Ile Asp Glu Asn Lys Gln Lys Ala Leu
  1               5                  10                  15

Ala Ala Ala Leu Gly Gln Ile Glu Lys Gln Phe Gly Lys Gly Ser Ile
             20                  25                  30

Met Arg Leu Gly Glu Asp Arg Ser Met Asp Val Glu Thr Ile Ser Thr
         35                  40                  45

Gly Ser Leu Ser Leu Asp Ile Ala Leu Gly Ala Gly Gly Leu Pro Met
 50                  55                  60

Gly Arg Ile Val Glu Ile Tyr Gly Pro Glu Ser Ser Gly Lys Thr Thr
 65                  70                  75                  80

Leu Thr Leu Gln Val Ile Ala Ala Gln Arg Glu Gly Lys Thr Cys
                 85                  90                  95

Ala Phe Ile Asp Ala Glu His Ala Leu Asp Pro Ile Tyr Ala Arg Lys
            100                 105                 110

Leu Gly Val Asp Ile Asp Asn Leu Leu Cys Ser Gln Pro Asp Thr Gly
            115                 120                 125

Glu Gln Ala Leu Glu Ile Cys Asp Ala Leu Ala Arg Ser Gly Ala Val
        130                 135                 140

Asp Val Ile Val Val Asp Ser Val Ala Ala Leu Thr Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Gln Ser Asn
            180                 185                 190

Thr Leu Leu Ile Phe Ile Asn Gln Ile Arg Met Lys Ile Gly Val Met
        195                 200                 205

Phe Gly Asn Pro Glu Thr Thr Thr Gly Gly Asn Ala Leu Lys Phe Tyr
    210                 215                 220

Ala Ser Val Arg Leu Asp Ile Arg Arg Ile Gly Ala Val Lys Glu Gly
225                 230                 235                 240

Glu Asn Val Val Gly Ser Glu Thr Arg Val Lys Val Lys Asn Lys
                245                 250                 255

Ile Ala Ala Pro Phe Lys Gln Ala Glu Phe Gln Ile Leu Tyr Gly Glu
            260                 265                 270

Gly Ile Asn Phe Tyr Gly Glu Leu Val Asp Leu Gly Val Lys Glu Lys
        275                 280                 285

Leu Ile Glu Lys Ala Gly Ala Trp Tyr Ser Tyr Lys Gly Glu Lys Ile
    290                 295                 300

Gly Gln Gly Lys Ala Asn Ala Thr Ala Trp Leu Lys Asp Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Val Asp Ser Glu Gly Val Ala
            340                 345                 350

Gly Thr Asn Glu Asp Phe
        355
```

<210> SEQ ID NO 10
<211> LENGTH: 358
<212> TYPE: PRT
<213> ORGANISM: Escherichia coli

<400> SEQUENCE: 10

Met Thr Gly Val Lys Met Ala Ile Asp Glu Asn Lys Gln Lys Ala Leu
 1               5                  10                  15

Ala Ala Ala Leu Gly Gln Ile Glu Lys Gln Phe Gly Lys Gly Ser Ile
            20                  25                  30

Met Arg Leu Gly Glu Asp Arg Ser Met Asp Val Glu Thr Ile Ser Thr
        35                  40                  45

Gly Ser Leu Ser Leu Asp Ile Ala Leu Gly Ala Gly Gly Leu Pro Met
 50                  55                  60

Gly Arg Ile Val Glu Ile Tyr Gly Pro Glu Ser Ser Gly Lys Thr Thr
 65                  70                  75                  80

Leu Thr Leu Gln Val Ile Ala Ala Gln Arg Gly Lys Thr Cys
                85                  90                  95

Ala Phe Ile Asp Ala Glu His Ala Leu Asp Pro Ile Tyr Ala Arg Lys
            100                 105                 110

Leu Gly Val Asp Ile Asp Asn Leu Leu Cys Ser Gln Pro Asp Thr Gly
        115                 120                 125

Glu Gln Ala Leu Glu Ile Cys Asp Ala Leu Ala Arg Ser Gly Ala Val
130                 135                 140

Asp Val Ile Val Val Asp Ser Val Ala Ala Leu Thr Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Leu Ser Asn
            180                 185                 190

Thr Leu Leu Ile Phe Ile Asn Gln Ile Arg Met Lys Ile Gly Val Met
        195                 200                 205

Phe Gly Asn Pro Glu Thr Thr Thr Gly Gly Asn Ala Leu Lys Phe Tyr
210                 215                 220

Ala Ser Val Arg Leu Asp Ile Arg Arg Ile Gly Ala Val Lys Glu Gly
225                 230                 235                 240

Glu Asn Val Val Gly Ser Glu Thr Arg Val Lys Val Val Lys Asn Lys
                245                 250                 255

Ile Ala Ala Pro Phe Lys Gln Ala Glu Phe Gln Ile Leu Tyr Gly Glu
            260                 265                 270

Gly Ile Asn Phe Tyr Gly Glu Leu Val Asp Leu Gly Val Lys Glu Lys
        275                 280                 285

Leu Ile Glu Lys Ala Gly Ala Trp Tyr Ser Tyr Lys Gly Glu Lys Ile
290                 295                 300

Gly Gln Gly Lys Ala Asn Ala Ala Trp Leu Lys Gly Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Arg Asp Asp Ser Glu Gly Val Ala
            340                 345                 350

Glu Thr Asn Glu Asp Phe
        355

<210> SEQ ID NO 11

```
<211> LENGTH: 358
<212> TYPE: PRT
<213> ORGANISM: Escherichia coli

<400> SEQUENCE: 11

Met Thr Gly Val Lys Met Ala Ile Asp Glu Asn Lys Gln Lys Ala Leu
 1               5                  10                  15

Ala Ala Ala Leu Gly Gln Ile Glu Lys Gln Phe Gly Lys Gly Ser Ile
            20                  25                  30

Met Arg Leu Gly Glu Asp Arg Ser Met Asp Val Glu Thr Ile Ser Thr
        35                  40                  45

Gly Ser Leu Ser Leu Asp Ile Ala Leu Gly Ala Gly Gly Leu Pro Met
 50                  55                  60

Gly Arg Ile Val Glu Ile Tyr Gly Pro Glu Ser Ser Gly Lys Thr Thr
 65                  70                  75                  80

Leu Thr Leu Gln Val Ile Ala Ala Gln Arg Glu Gly Lys Thr Cys
                85                  90                  95

Ala Phe Ile Asp Ala Glu His Ala Leu Asp Pro Ile Tyr Ala Arg Lys
                100                 105                 110

Leu Gly Val Asp Ile Asp Asn Leu Leu Cys Ser Gln Pro Asp Thr Gly
            115                 120                 125

Glu Gln Ala Leu Glu Ile Cys Asp Ala Leu Ala Arg Ser Gly Ala Val
        130                 135                 140

Asp Val Ile Val Val Asp Ser Val Ala Ala Leu Ser Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Gln Ser Asn
            180                 185                 190

Thr Leu Leu Ile Phe Ile Asn Gln Ile Arg Met Lys Ile Gly Val Met
        195                 200                 205

Phe Gly Asn Pro Glu Thr Thr Thr Gly Gly Asn Ala Leu Lys Phe Tyr
    210                 215                 220

Ala Ser Val Arg Leu Asp Ile Arg Arg Ile Gly Ala Val Lys Glu Gly
225                 230                 235                 240

Glu Asn Val Val Gly Ser Glu Thr Arg Val Lys Val Val Lys Asn Lys
                245                 250                 255

Ile Ala Ala Pro Phe Lys Gln Ala Glu Phe Gln Ile Leu Tyr Gly Glu
            260                 265                 270

Gly Ile Asn Phe Tyr Gly Glu Leu Val Asp Leu Gly Val Lys Glu Lys
        275                 280                 285

Leu Ile Glu Lys Ala Gly Ala Trp Tyr Ser Tyr Lys Gly Glu Lys Val
    290                 295                 300

Gly Gln Gly Lys Ala Asn Ala Thr Ala Trp Leu Lys Asp Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Val Asp Asp Ser Glu Gly Val Ala
            340                 345                 350

Glu Thr Asn Glu Asp Phe
        355

<210> SEQ ID NO 12
<211> LENGTH: 358
<212> TYPE: PRT
```

-continued

```
<213> ORGANISM: Escherichia coli

<400> SEQUENCE: 12

Met Thr Gly Val Lys Met Ala Ile Asp Glu Asn Lys Gln Lys Ala Leu
  1               5                  10                  15

Ala Ala Ala Leu Gly Gln Ile Glu Lys Gln Phe Gly Lys Gly Ser Ile
             20                  25                  30

Met Arg Leu Gly Glu Asp Arg Ser Met Asp Val Glu Thr Ile Ser Thr
         35                  40                  45

Gly Ser Leu Ser Leu Asp Ile Ala Leu Gly Ala Gly Leu Pro Met
     50                  55                  60

Gly Arg Ile Val Glu Ile Tyr Gly Pro Glu Ser Ser Gly Lys Thr Thr
 65                  70                  75                  80

Leu Thr Leu Gln Val Ile Ala Ala Gln Arg Glu Gly Lys Thr Cys
                 85                  90                  95

Ala Phe Ile Asp Ala Glu His Ala Leu Asp Pro Ile Tyr Ala Arg Lys
            100                 105                 110

Leu Gly Val Asp Ile Asp Asn Leu Leu Cys Ser Gln Pro Asp Thr Gly
        115                 120                 125

Glu Gln Ala Leu Glu Ile Cys Asp Ala Leu Ala Arg Ser Gly Ala Val
130                 135                 140

Asp Val Ile Val Val Asp Ser Val Ala Ala Leu Thr Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Gln Ser Asn
            180                 185                 190

Thr Leu Leu Ile Phe Ile Asn Gln Ile Arg Met Lys Ile Gly Val Met
        195                 200                 205

Phe Gly Asn Pro Glu Thr Thr Thr Gly Gly Asn Ala Leu Lys Phe Tyr
    210                 215                 220

Ala Ser Val Arg Leu Asp Ile Arg Arg Ile Gly Thr Val Lys Glu Gly
225                 230                 235                 240

Glu Asn Val Val Gly Ser Glu Thr Arg Val Lys Val Lys Asn Lys
                245                 250                 255

Ile Ala Ala Pro Phe Lys Gln Ala Glu Phe Gln Ile Leu Tyr Asp Glu
                260                 265                 270

Gly Ile Asn Phe Tyr Gly Glu Leu Val Asp Met Gly Val Lys Glu Lys
        275                 280                 285

Leu Ile Glu Lys Ala Gly Ala Trp Tyr Ser Tyr Lys Gly Glu Lys Ala
    290                 295                 300

Gly Gln Gly Lys Ala Asn Ala Thr Ala Trp Leu Lys Asp Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Val Asp Asp Ser Glu Gly Val Ala
            340                 345                 350

Glu Thr Asn Glu Asp Phe
        355

<210> SEQ ID NO 13
<211> LENGTH: 1398
<212> TYPE: DNA
<213> ORGANISM: Artificial Sequence
<220> FEATURE:
```

<223> OTHER INFORMATION: Description of Artificial Sequence: consensus
     e. coli sequence

<400> SEQUENCE: 13

```
agaggccaga gaagcctgtc ggcacggtct ggtttgcttt tgccactgcc cgcggtgaag      60
gcattacccg gcgggaatgc ttcagcggcg accgtgatgc ggtgcgtcgt caggctactg     120
cgtatgcatt gcagaccttg tggcaacaat ttctacaaaa cacctgatac tgtatgagca     180
tacagtataa ttgcttcaac agaacatatt gactatccgg tattaccogg catgacagga     240
gtaaaaatgg ctattgacga aaacaaacag aaagcgttgg cggcagcact gggccagatt     300
gagaaacaat ttggtaaagg ctccatcatg cgcctgggtg aagaccgttc catggatgtg     360
gaaaccatct ctaccggttc gctttcactg gatatcgcgc ttggggcagg tggtctgccg     420
atgggccgta tcgtcgaaat ctacggaccg gaatcttccg gtaaaaccac gctgacgctg     480
caggtgatcg ccgcagcgca gcgtgaaggt aaaacctgtg cgtttatcga tgctgaacac     540
gcgctggacc caatctacgc acgtaaactg ggcgtcgata tcgacaacct gctgtgctcc     600
cagccggaca ccggcgagca ggcactggaa atctgtgacg ccctggcgcg ttctggcgca     660
gtagacgtta tcgtcgttga ctccgtggcg gcactgacgc cgaaagcgga atcgaaggc      720
gaaatcggcg actctcacat gggccttgcg gcacgtatga tgagccaggc gatgcgtaag     780
ctggcgggta acctgaagca gtccaacacg ctgctgatct tcatcaacca gatccgtatg     840
aaaattggtg tgatgttcgg taacccggaa accactaccg tggtaacgc gctgaaattc      900
tacgcctctg ttcgtctcga catccgtcgt atcggcgcgg tgaagaggg cgaaaacgtg     960
gtgggtagcg aaacccgcgt gaaagtggtg aagaacaaaa tcgctgcgcc gtttaaacag    1020
gctgaattcc agatcctcta cggcgaaggt atcaacttct acggcgaact ggttgacctg    1080
ggcgtaaaag agaagctgat cgagaaagca ggcgcgtggt acagctacaa aggtgagaag    1140
atcggtcagg gtaaagcgaa tgcgactgcc tggctgaaag ataacccgga aaccgcgaaa    1200
gagatcgaga gaaagtacg tgagttgctg ctgagcaacc cgaactcaac gccggatttc    1260
tctgtagatg atagcgaagg cgtagcagaa actaacgaag atttttaatc gtcttgtttg    1320
atacacaagg gtcgcatctg cggcccttttt gcttttttaa gttgtaagga tatgccatga    1380
cagaatcaac atcccgtc                                                  1398
```

<210> SEQ ID NO 14
<211> LENGTH: 358
<212> TYPE: PRT
<213> ORGANISM: Artificial Sequence
<220> FEATURE:
<223> OTHER INFORMATION: Description of Artificial Sequence: consensus
     e. coli sequence

<400> SEQUENCE: 14

```
Met Thr Gly Val Lys Met Ala Ile Asp Glu Asn Lys Gln Lys Ala Leu
  1               5                  10                  15

Ala Ala Ala Leu Gly Gln Ile Glu Lys Gln Phe Gly Lys Gly Ser Ile
                 20                  25                  30

Met Arg Leu Gly Glu Asp Arg Ser Met Asp Val Glu Thr Ile Ser Thr
             35                  40                  45

Gly Ser Leu Ser Leu Asp Ile Ala Leu Gly Ala Gly Gly Leu Pro Met
         50                  55                  60

Gly Arg Ile Val Glu Ile Tyr Gly Pro Glu Ser Ser Gly Lys Thr Thr
 65                  70                  75                  80
```

-continued

```
Leu Thr Leu Gln Val Ile Ala Ala Ala Gln Arg Glu Gly Lys Thr Cys
             85                  90                  95

Ala Phe Ile Asp Ala Glu His Ala Leu Asp Pro Ile Tyr Ala Arg Lys
            100                 105                 110

Leu Gly Val Asp Ile Asp Asn Leu Leu Cys Ser Gln Pro Asp Thr Gly
            115                 120                 125

Glu Gln Ala Leu Glu Ile Cys Asp Ala Leu Ala Arg Ser Gly Ala Val
            130                 135                 140

Asp Val Ile Val Val Asp Ser Val Ala Ala Leu Thr Pro Lys Ala Glu
145                 150                 155                 160

Ile Glu Gly Glu Ile Gly Asp Ser His Met Gly Leu Ala Ala Arg Met
                165                 170                 175

Met Ser Gln Ala Met Arg Lys Leu Ala Gly Asn Leu Lys Gln Ser Asn
            180                 185                 190

Thr Leu Leu Ile Phe Ile Asn Gln Ile Arg Met Lys Ile Gly Val Met
            195                 200                 205

Phe Gly Asn Pro Glu Thr Thr Thr Gly Gly Asn Ala Leu Lys Phe Tyr
            210                 215                 220

Ala Ser Val Arg Leu Asp Ile Arg Arg Ile Gly Ala Val Lys Glu Gly
225                 230                 235                 240

Glu Asn Val Val Gly Ser Glu Thr Arg Val Lys Val Val Lys Asn Lys
            245                 250                 255

Ile Ala Ala Pro Phe Lys Gln Ala Glu Phe Gln Ile Leu Tyr Gly Glu
            260                 265                 270

Gly Ile Asn Phe Tyr Gly Glu Leu Val Asp Leu Gly Val Lys Glu Lys
            275                 280                 285

Leu Ile Glu Lys Ala Gly Ala Trp Tyr Ser Tyr Lys Gly Glu Lys Ile
    290                 295                 300

Gly Gln Gly Lys Ala Asn Ala Thr Ala Trp Leu Lys Asp Asn Pro Glu
305                 310                 315                 320

Thr Ala Lys Glu Ile Glu Lys Lys Val Arg Glu Leu Leu Leu Ser Asn
                325                 330                 335

Pro Asn Ser Thr Pro Asp Phe Ser Val Asp Asp Ser Glu Gly Val Ala
            340                 345                 350

Glu Thr Asn Glu Asp Phe
            355
```